US006822142B2

(12) United States Patent
Karunanandaa et al.

(10) Patent No.: US 6,822,142 B2
(45) Date of Patent: Nov. 23, 2004

(54) TRANSGENIC PLANTS CONTAINING ALTERED LEVELS OF STEROID COMPOUNDS

(75) Inventors: Balasulojini Karunanandaa, St. Louis, MO (US); Martha Post-Beittenmiller, St. Louis, MO (US); Mylavarapu Venkatramesh, St. Louis, MO (US); Ganesh M. Kishore, St. Louis, MO (US); Gregory M. Thorne, St. Louis, MO (US); John R. LeDeaux, St. Louis, MO (US)

(73) Assignee: Monsanto Company, St. Louis, MO (US)

( * ) Notice: Subject to any disclaimer, the term of this patent is extended or adjusted under 35 U.S.C. 154(b) by 124 days.

(21) Appl. No.: 09/885,723

(22) Filed: Jun. 20, 2001

(65) Prior Publication Data

US 2003/0150008 A1 Aug. 7, 2003

Related U.S. Application Data

(60) Provisional application No. 60/260,114, filed on Jan. 5, 2001.

(51) Int. Cl.$^7$ .................. C12N 15/09; C12N 15/63; C12N 15/82; A01H 5/00; A01H 5/10

(52) U.S. Cl. ............... 800/298; 800/278; 536/23.6; 435/320.1; 435/419

(58) Field of Search .................. 800/278, 288, 800/295, 298; 435/320.1, 410, 419, 183, 468; 536/23.1, 23.2, 23.5, 23.6, 23.7, 23.74

(56) References Cited

U.S. PATENT DOCUMENTS

| | | | |
|---|---|---|---|
| 5,306,862 A | | 4/1994 | Chappell et al. |
| 5,349,126 A | | 9/1994 | Chappell et al. |
| 5,365,017 A | | 11/1994 | Chappell et al. |
| 5,460,949 A | | 10/1995 | Saunders et al. |
| 5,480,805 A | | 1/1996 | Wolf et al. |
| 5,589,619 A | * | 12/1996 | Chappell .................. 800/205 |
| 6,153,815 A | * | 11/2000 | Covello .................. 800/306 |

FOREIGN PATENT DOCUMENTS

| | | |
|---|---|---|
| EP | 0480730 A2 | 4/1992 |
| EP | 0486290 A2 | 5/1992 |
| JP | 09121863 | 5/1997 |
| WO | WO 93/02187 | 2/1993 |
| WO | WO 97/03202 | 1/1997 |
| WO | WO 97/34003 | 9/1997 |
| WO | WO 98/45457 | 10/1998 |
| WO | WO 99/04622 | 2/1999 |
| WO | WO 00/61771 | 10/2000 |
| WO | WO 01/31027 A1 | 3/2001 |

OTHER PUBLICATIONS

Broun P. et al. Science vol. 282; Nov. 13, 1998, pp. 1315–1317.*

Fourgoux–Nicol et al (1999, Plant Molecular Biology 40 : 857–872.*

Devarenne T. Plant Physiology, Jul. 2002; vol. 129, pp. 1095–1106.*

Bak et al., "Cloning and expression in *Escherichia coli* of the obtusifoliol 14–alpha–demethylase of *Sorghum bicolor* (L.) Moench, a cytochrome P450 orthologous to the sterol 14–alpha–demethylases (CYP51) from fungi and mammals," *Plant Journal*, 11(2):191–201, 1997.

Bak et al., "Cloning and expression in *Escherichia coli* of the obtusifoliol 14–alpha–demethylase of *Sorghum bicolor* (L.) Moench, a cytochrome P450 orthologous to the sterol 14–alpha–demethylases (CYP51) from fungi and mammals," *EMBL Online!*, Database Accession No. U74319, abstract, 1996.

Cabello–Hurtado et al., "Cloning and functional expression in yeast of a cDNA coding for an obtusifoliol 14–alpha–demethylase (CYP51) in wheat," *Biochemical and Biophysical Research Communications*, 230(2):381– 385, 1997.

Cabello–Hurtado et al., "Cloning and functional expression in yeast of a cDNA coding for an obtusifoliol 14–alpha–demethylase (CYP51) in wheat," *EMBL Online!*, Database Accession No. Y09291, abstract, 1996.

Colebatch et al., "Lotus faponicus root nodule ESTs: tools for functional genomics," *EMBL Online!*, Database Accession No. AW719774, abstract, 2000.

Covello, "An example of intron junctional sliding in the gene families encoding squalene monooxygenase homologues in *Arabidopsis thaliana* and *Brassica napus*," *EMBL Online!*, Database Accession No. AJ005930, 1998.

(List continued on next page.)

*Primary Examiner*—David T. Fox
*Assistant Examiner*—Russell Kallis
(74) *Attorney, Agent, or Firm*—Fulbright & Jaworski L.L.P.

(57) ABSTRACT

Disclosed are constructs comprising sequences encoding 3-hydroxy-3methylglutaryl-Coenzyme A reductase and at least one other sterol synthesis pathway enzyme. Also disclosed are methods for using such constructs to alter sterol production and content in cells, plants, seeds and storage organs of plants. Also provided are oils and compositions containing altered sterol levels produced by use of the disclosed constructs. Novel nucleotide sequences useful in the alteration of sterol production are also provided. Also provided are cells, plants, seeds and storage organs of plants comprising sequences encoding 3-hydroxy-3methylglutaryl-Coenzyme A reductase, at least one other sterol synthesis pathway enzyme and at least one tocopherol synthesis enzyme.

18 Claims, 78 Drawing Sheets

OTHER PUBLICATIONS

Nakamura et al., "A large scale analysis if cDNA in *Aradopsis thalian*: generation of 12,028 non–redundant expressed sequence tags from normalized size–selected cDNA libraries," *EMBL Online*!, Database Accession No. AV440215, 2000.

Schafer et al., "An example of intron junctional sliding in the gene families encoding sqalene monooxygenase homologues in *Arabidopsis thaliana* and *Brassica napus*", *Plant Molecular Biology*, 39(4):721–728, 1999.

Shintani et al., "Elevating the vitamin E content of plants through metabolic engineering," *Science*, 282(5396):2098–2100, 1998.

Van der Hoeven et al., "Generation of ESTs retrieved from tomato radicule tissue," *EMBL Online*!, Database Accession No. AW625933, abstract, 2000.

Bach and Benveniste, "Cloning of cDNAs or genes encoding enzymes of sterol biosynthesis from plants and other eukaryotes: heterologous expression and complementation analysis of mutations for functional characterization," *Progress in Lipid Research*, 36(2/3): 197–226, 1997.

Jenkins et al., "Plant sterols, health claims and strategies to reduce cardiovascular and strategies to reduce cardiovascular disease risk," *J. of the American College of Nutrition*, 18:559–562, 1999.

Nguyen, "The cholesterol–lowering action of plant stanol esters," *J. of Nutrition*, 129:2109–2112, 1999.

Schaller et al., "Overexpression of an arabidopsis cDNA encoding a sterol–C24(1)–methyltransferase in tobacco modifies the ration of 24–methyl cholesterol to sitosterol and is associated with growth reduction," *Plant Physiol.*, 118:461–469, 1998.

Mikiro Tada and Masahide Shiroishi, Mechanism of Photoregulated Carotenogenesis in *Rhodotorul minuta* v. Photoinduction of 3–Hydroxy–3–Methyl Glutaryl Coenzyme A Reductase, Plant & Cell Physiol. 23(4):615–621, 1982, Okayama, Japan.

Yoder, John I., et al., "Transformation Systems for Generating Marker–Free Transgenic Plants," Bio/Technology, vol. 12, Mar., 1994, pp. 263–267.

Gil, Gregorio, et al., "Membrane–Bound Domain of HMG CoA Reductase is Required for Sterol–Enhanced Degradation of the Enzyme," Cell, vo. 41, May, 1985, pp. 249–258.

Schaller, Hubert, et. al., "Expression of the *Hevea brasiliensis* (H.B.K.) Müll. Arg. 3–Hydroxy–3–Methylglutaryl–Coenzyme A Reductase 1 in Tobacco Results in Sterol Overproduction," Plant Physiol., vol. 109, 1995, pp. 761–770.

Gonzalez, et al., Abstract of Poster at Third Terpnet Meeting of the European Network on Plant Isoprenoids, May 29–30, 1997, Poitiers, France.

Dale, Susan, et al., "Bacterial Expression of the Catalytic Domain of 3–hydroxy–3–methylglutaryl–CoA Reductase (Isoform HMGR1) from *Arabidopsis thaliana*, and its Inactivation by Phosphorylation at Ser577 by *Brassica oleracea* 3–hydroxy–3–methylglutaryl–CoA reductase Kinase," Eur. J. Biochem, vol. 233, 1995, pp. 506–513.

Downing, James, F., et al., "The Isolation of two Mutants of *Saccharomyces cerevisiae* which Demonstrate Increased Activity of 3–Hydroxy–3–Methylglutaryl Coenzyme a Reductase," Biochemical and Biophysical Research Communications, vol. 94, No. 3, Jun. 16, 1980, pp. 974–979.

Chin, Daniel J., et al., "Nucleotide Sequence of 3–hydroxy–3–methyl–glutaryl Coenzyme A Reductase, a Glycoprotein of Endloplasmic Reticulum," Nature, vol. 308, No. 5960, Apr. 12–18, 1984, pp. 613–617.

Basson, Michael E., et al., "Structural and Functional Conservation between Yeast and Human 3–Hydroxy–3–Methylglutaryl Coenzyme A Reductases, the Rate–Limiting Enzyme of Sterol Biosynthesis," Molecular and Cellular Biology, vol. 8, No. 9, Sep. 1998, pp. 3797–3808.

Register, James, C., et al., "Structure and Function of Selectable and non–selectable Transgenes in Maize after Introduction by Particle Bombardment," Plant Mol. Biol. vol. 25:, 1994, pp., 951–961.

Bard, et al., Genetic and Biochemical Aspects of Yeast Sterol Regulation Involving 3–Hydroxy–3–methylglutaryl Coenzyme A Reductase, Journal of General Microbiology, 1981, 125:415–420.

* cited by examiner

Figure 3: Construct pMON29920

Figure 4: Construct pMON43800

Figure 5: Construct pMON23616

Figure 6: Construct pMON43818

Figure 7: Construct pMON43052

Figure 8: Construct pMON51850

Figure 9: Construct pMON43057

Figure 10: Construct pMON43058

Figure 11: Sterol composition of R1 transgenic soybean seeds when *Arabidopsis* truncated HMGR (catalytic domain without linker) was overexpressed using seed-specific 7S promoter ( data from pMON43057: p7s::*At* HMGR truncated).

Figure 12: Sterol composition of R1 transgenic soybean seeds when *Arabidopsis* truncated HMGR (catalytic domain without linker) and *Arabidopsis* SMTII were overexpressed (data from pMON43058: p7S::*At* HMGR truncated & p7S::*At* SMTII). The expression of the genes is controlled by the seed-specific 7S promoter.

Figure 13: Construct pMON53733

Figure 14: Construct pMON53734

Figure 15: Construct pMON53735

Figure 16: Construct pMON53736

Figure 17: Construct pMON53737

Figure 18: Construct pMON53738

Figure 19: Construct pMON53739

Figure 20: Construct pMON53740

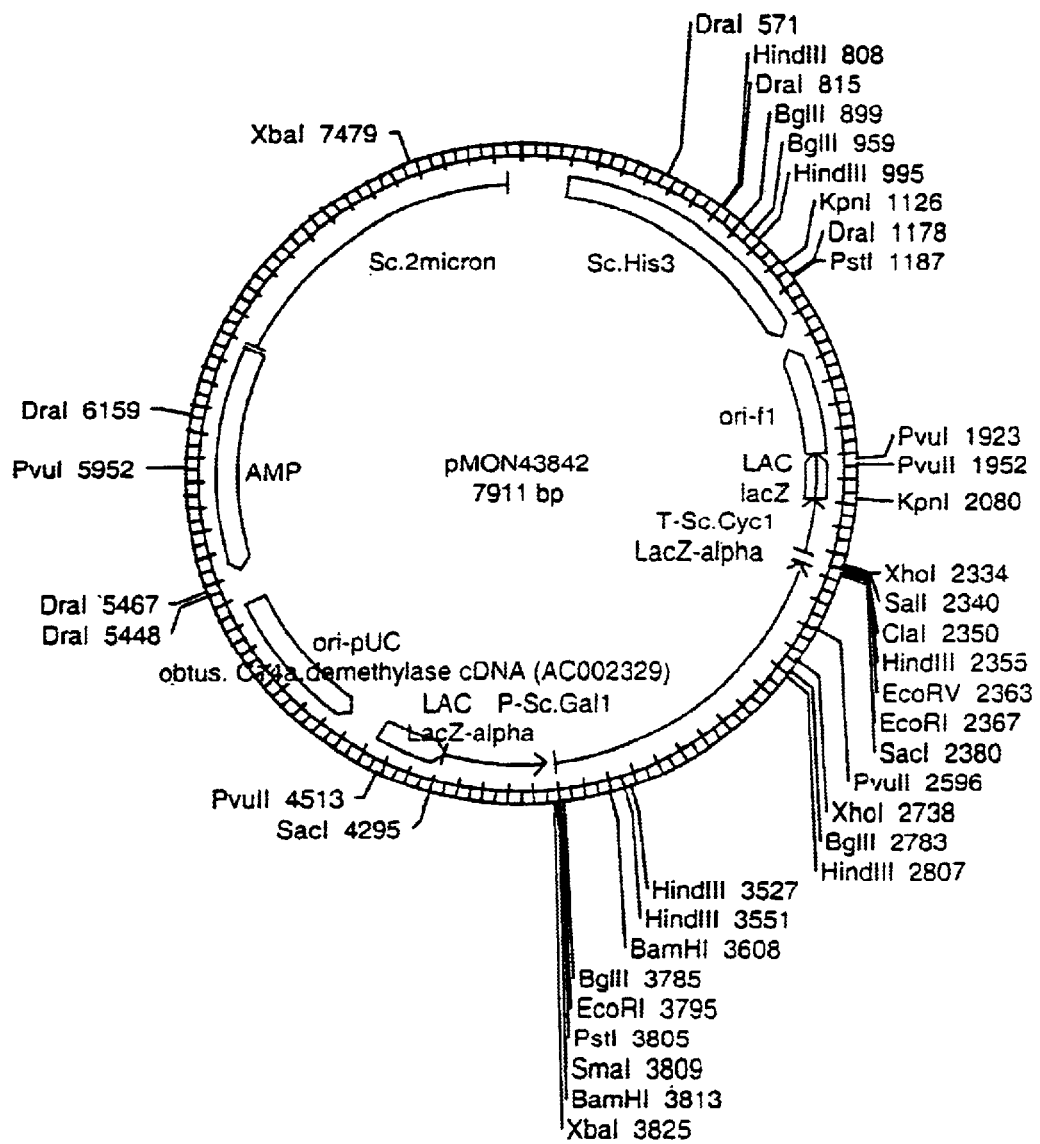
Figure 29: Construct pMON43842

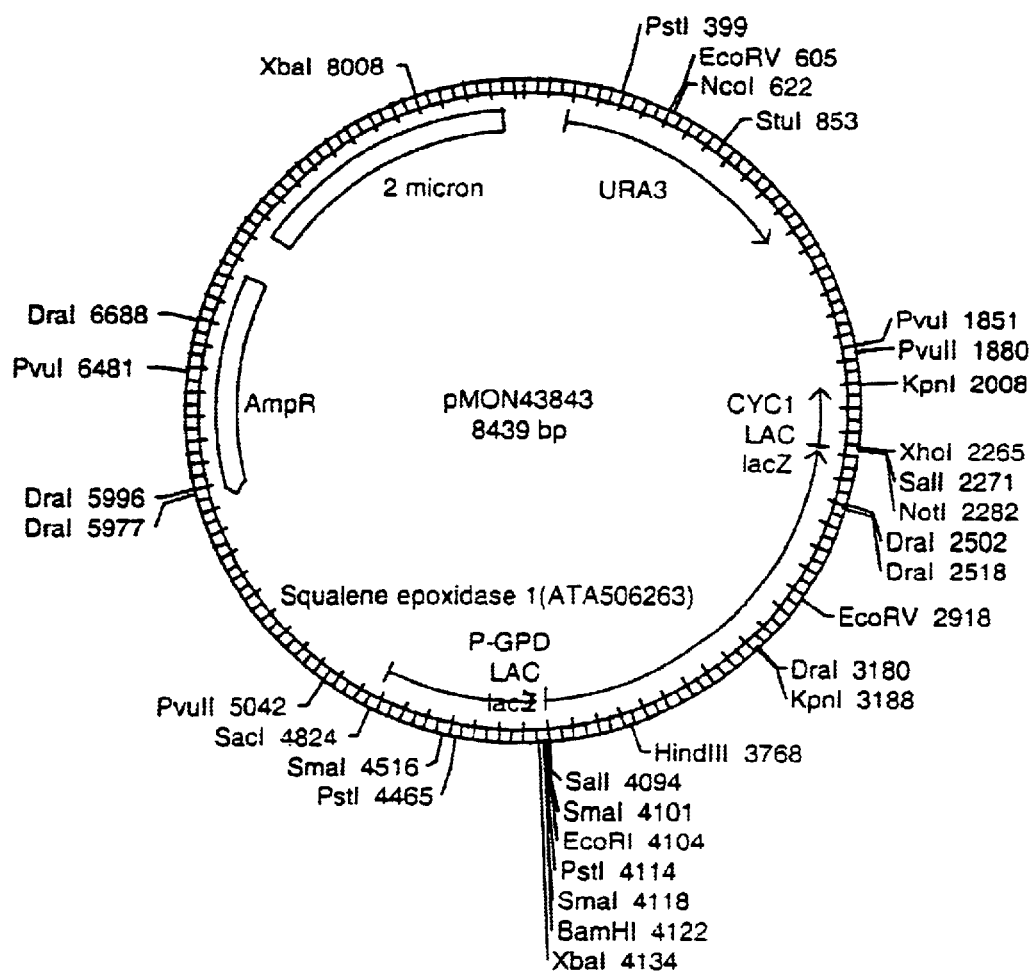
Figure 30: Construct pMON43843

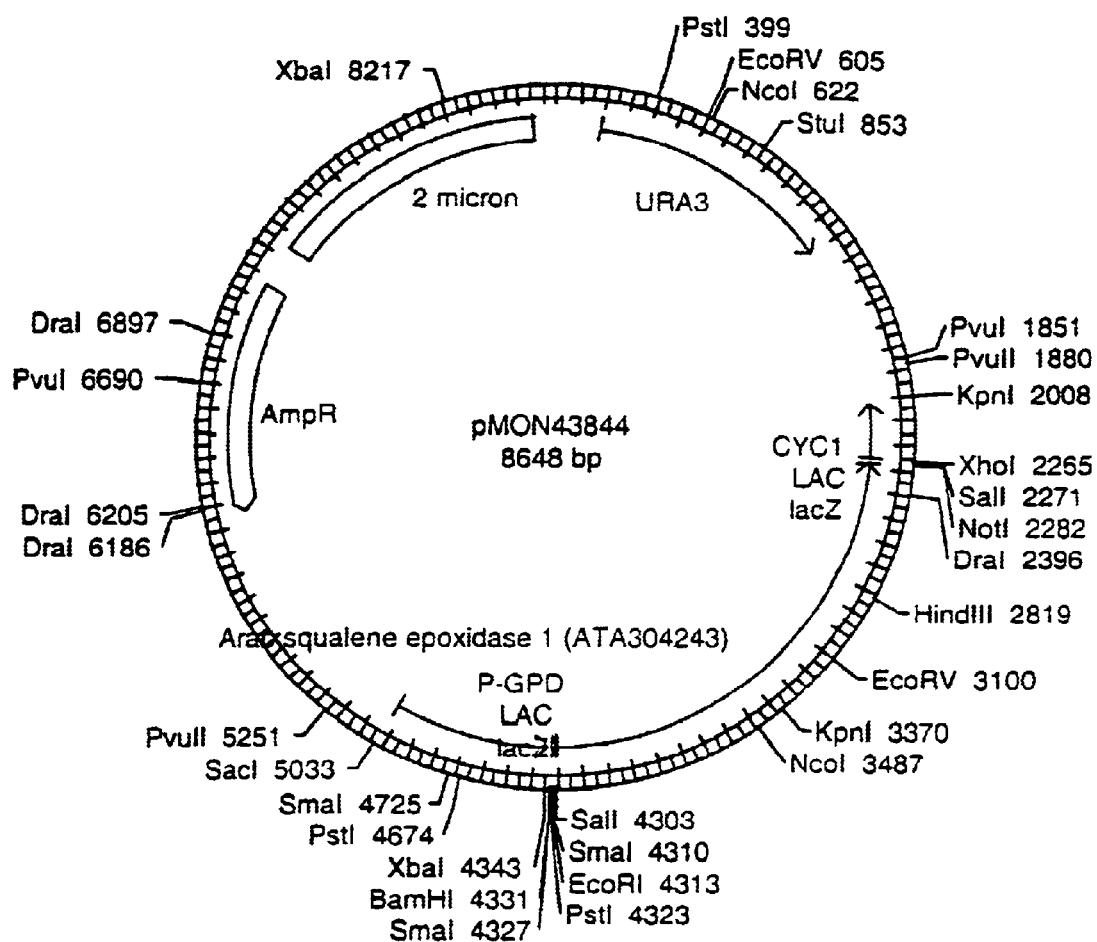
Figure 31: Construct pMON43844

FIG. 32A

```
Plurality: 5.00  Threshold: 4   AveWeight 1.00   AveMatch 2.91   AvMisMatch -2.00
                              1
50
  HMGRclustalW{methanobac}   .......... .......... .......... ..........
..........
  HMGRclustalW{methanococ}   .......... .......... .......... ..........
..........
  HMGRclustalW{halobacter}   .......... .......... .......... ..........
..........
  HMGRclustalW{sulfolobus}   .......... .......... .......... ..........
..........
  HMGRclustalW{    yeast2}   MSLPLKTIVH LVKPFACTAR FSARYPIHVI VVAVLLSAAA
YLSVTQSYLN
  HMGRclustalW{    yeast1}   MPPLFKGLKQ MAKPIAYVSR FSAKRPIHII LFSLIISAFA
YLSVIQYYFN
  HMGRclustalW{phycomyces}   .......... .......... .......... ..........
..........
  HMGRclustalW{  fusarium}   .......... .......... .......... ..........
..........
  HMGRclustalW{   candida}   .......... .......... .......... ..........
..........
  HMGRclustalW{dictyoste2}   .......... .......... .......... ..........
..........
       HMGRclustalW{wheat1}  .......... .......... .......... ..........
..........
  HMGRclustalW{      rice}   .......... .......... .......... ..........
..........
       HMGRclustalW{  corn}  .......... .......... .......... ..........
..........
       HMGRclustalW{wheat3}  .......... .......... .......... ..........
..........
       HMGRclustalW{wheat2}  .......... .......... .......... ..........
..........
HMGRclustalW{     soybean}   .......... .......... .......... ..........
..........
  HMGRclustalW{rubbertre3}   .......... .......... .......... ..........
..........
  HMGRclustalW{rosyperiwi}   .......... .......... .......... ..........
..........
  HMGRclustalW{    tomato}   .......... .......... .......... ..........
..........
  HMGRclustalW{woodtobacc}   .......... .......... .......... ..........
..........
  HMGRclustalW{    potato}   .......... .......... .......... ..........
..........
       HMGRclustalW{radish}  .......... .......... .......... ..........
..........
HMGRclustalW{arabadopsis1}   .......... .......... .......... ..........
..........
  HMGRclustalW{cucumisme1}   .......... .......... .......... ..........
..........
  HMGRclustalW{rubbertre2}   .......... .......... .......... ..........
..........
  HMGRclustalW{rubbertre1}   .......... .......... .......... ..........
..........
  HMGRclustalW{camptothec}   .......... .......... .......... ..........
..........
  HMGRclustalW{arabadops2}   .......... .......... .......... ..........
..........
  HMGRclustalW{chineseham}   .......... .......... .......... ..........
..........
```

FIG. 32B

```
HMGRclustalW{chineseha2}   .......... .......... .......... ..........
..........
HMGRclustalW{syrianhamst}  .......... .......... .......... ..........
..........
    HMGRclustalW{    rat}  .......... .......... .......... ..........
..........
   HMGRclustalW{  rabbit}  .......... .......... .......... ..........
..........
   HMGRclustalW{   human}  .......... .......... .......... ..........
..........
   HMGRclustalW{   mouse}  .......... .......... .......... ..........
..........
   HMGRclustalW{ xenopus}  .......... .......... .......... ..........
..........
HMGRclustalW{sea urchin}   .......... .......... .......... ..........
..........
HMGRclustalW{ cockroach}   .......... .......... .......... ..........
..........
HMGRclustalW{drosophila}   .......... .......... .......... ..........
..........
HMGRclustalW{dictyostel}   .......... .......... .......... ..........
..........
HMGRclustalW{schistoscm}   .......... .......... .......... ..........
..........
HMGRclustalW{archaeoglo}   .......... .......... .......... ..........
..........
HMGRclustalW{pseudomonas}  .......... .......... .......... ..........
..........
              Consensus    ---------- ---------- ---------- ---------- ------
----
```

FIG. 32C

```
                                       51                                          100
  HMGRclustalW{methanobac}    .......... .......... .......... ..........
                              ..........
  HMGRclustalW{methanococ}    .......... .......... .......... ..........
  ..........
  HMGRclustalW{halobacter}    .......... .......... .......... ..........
  HMGRclustalW{sulfolobus}    .......... .......... .......... ..........
  ..........
  HMGRclustalW(      yeast2}  EWKLDSN.QY STYLSIKPDE LFEKCTHYYR SPVSDTWKLL
SSKEAADIYT
  HMGRclustalW{      yeast1}  GWQLDSNSVF ETAPNKDSNT LFQECSHYYR DSSLDGWVSI
TAHEASELPA
  HMGRclustalW{phycomyces}    .......... .......... .......... ..........
  HMGRclustalW{   fusarium}   .......... .......... ......MDH EGCQGQHPQQ
CCQWVSNAWS
  HMGRclustalW{    candida}   .......... .......... ......MFYH GASANQHWIA
VDDLSKVPVD
  HMGRclustalW{dictyoste2}    .......... .......... .......... ..........
  HMGRclustalW{     wheat1}   .......... .......... .......... ..........
  ..........
  HMGRclustalW(       rice}   .......... .......... .......... ..........
  ..........
  HMGRclustalW(       corn}   .......... .......... .......... ..........
  ..........
  HMGRclustalW{     wheat3}   .......... .......... .......... ..........
  ..........
  HMGRclustalW{     wheat2}   .......... .......... .......... ..........
  ..........
HMGRclustalW{     soybean}    .......... .......... .......... ..........
  HMGRclustalW{rubbertre3}    .......... .......... .......... ..........
  HMGRclustalW{rosyperiwi}    .......... .......... .......... ..........
  HMGRclustalW{     tomato}   .......... .......... .......... ..........
  HMGRclustalW{woodtobacc}    .......... .......... .......... ..........
  HMGRclustalW{     potato}   .......... .......... .......... ..........
  HMGRclustalW{     radish}   .......... .......... .......... ..........
HMGRclustalW{arabadopsis1}    .......... .......... .......... ..........
  HMGRclustalW{cucumismel}    .......... .......... .......... ..........
  HMGRclustalW{rubbertre2}    .......... .......... .......... ..........
  HMGRclustalW{rubbertre1}    .......... .......... .......... ..........
  HMGRclustalW{camptothec}    .......... .......... .......... ..........
  HMGRclustalW{arabadops2}    .......... .......... .......... ..........
  HMGRclustalW{chineseham}    .......... .......... .......... .MLSRLFRMH
GLFVASHPWE
  HMGRclustalW{chineseha2}    .......... .......... .......... .MLSRLFRMH
```

FIG. 32D

```
GLFVASHPWE
  HMGRclustalW{syrianhamst}    ..........  ..........  ..........  .MLSRLFRMH
GLFVASHPWE
    HMGRclustalW{      rat}    ..........  ..........  ..........  .MLSRLFRMH
GLFVASHPWE
  HMGRclustalW{     rabbit}    ..........  ..........  ..........  .MLSRLFRMH
GLFVASHPWE
  HMGRclustalW{      human}    ..........  ..........  ..........  .MLSRLFRMH
GLFVASHPWE
  HMGRclustalW{      mouse}    ..........  ..........  ..........  ..........
..........
    HMGRclustalW{    xenopus}  ..........  ..........  ..........  .MLSRLFRMH
GQFVASHPWE
  HMGRclustalW{sea urchin}     ..........  ..........  ..........  .MLSRLFLAQ
GRFCSSHPWE
  HMGRclustalW{  cockroach}    ..........  ..........  ..........  .MVGRLFRAH
GQFCASHPWE
  HMGRclustalW{drosophila}     ..........  ..........  ..........  .MIGPLFRAT
.QFCASHPWE
    HMGRclustalW{dictyostel}   ..........  ..........  ..........  ..........
..........
    HMGRclustalW{schistosom}   ..........  ..........  ..........  ..........
..........
    HMGRclustalW{archaeoglo}   ..........  ..........  ..........  ..........
..........
    HMGRclustalW{pseudomonas}  ..........  ..........  ..........  ..........
..........

Consensus        ----------  ----------  ----------  -MLSRLFRMH
GLFVASHPWE
```

FIG. 32E

```
                                        101                                        150
    HMGRclustalW{methanobac}   .......... .......... .......... ..........
    HMGRclustalW{methanococ}   .......... .......... .......... ..........
    HMGRclustalW{halobacter}   .......... .......... .......... ..........
    HMGRclustalW{sulfolobus}   .......... .......... .......... ..........
    HMGRclustalW{    yeast2}   PFHYYLSTIS FQSKDNSTTL PSLDDVIYSV DHTRYLLSEE
PKIPTELVSE
    HMGRclustalW{    yeast1}   PHHYYLLNLN FNSPNETDSI PELANTVFEK DNTKYILQED
LSVSKEISST
    HMGRclustalW{phycomyces}   .......... .......... .......... ..........
    HMGRclustalW{   fusarium}  EFLDLLKNAE TLDIVIMLLG YIAMHLTFVS LFLSMRKMGS
KFWLGICTLF
    HMGRclustalW{    candida}  VDHYNVVPFQ FRRAGEYKEP VLSGIVELDE VKFVVSQSDA
AEQWQQLTAE
    HMGRclustalW{dictyoste2}   .......... .......... .......... ..........
    HMGRclustalW{    wheat1}   .......... .......... .......... ..........
    HMGRclustalW{      rice}   .......... .......... .......... ..........
    HMGRclustalW{      corn}   .......... .......... .......... ..........
    HMGRclustalW{    wheat3}   .......... .......... .......... ..........
    HMGRclustalW{    wheat2}   .......... .......... .......... ..........
HMGRclustalW{     soybean}     .......... .......... .......... ..........
    HMGRclustalW{rubbertre3}   .......... .......... .......... ..........
    HMGRclustalW{rosyperiwi}   .......... .......... .......... ..........
    HMGRclustalW{    tomato}   .......... .......... .......... ..........
    HMGRclustalW{woodtobacc}   .......... .......... .......... ..........
    HMGRclustalW{    potato}   .......... .......... .......... ..........
    HMGRclustalW{    radish}   .......... .......... .......... ..........
HMGRclustalW{arabadopsis1}     .......... .......... .......... ..........
    HMGRclustalW{cucumismel}   .......... .......... .......... ..........
    HMGRclustalW{rubbertre2}   .......... .......... .......... ..........
    HMGRclustalW{rubbertre1}   .......... .......... .......... ..........
    HMGRclustalW{camptothec}   .......... .......... .......... ..........
    HMGRclustalW{arabadops2}   .......... .......... .......... ..........
    HMGRclustalW{chineseham}   VIVGTVT..L TICMMSMN.. MFTGNNK... ..........
```

FIG. 32F

```
HMGRclustalW(chineseha2)    VIVGTVT..L  TICMMSMN..  MFTGNNK...  ..........
..........
HMGRclustalW(syrianhamst)   VIVGTVT..L  TICMMSMN..  MFTGNNK...  ..........
..........
     HMGRclustalW(    rat)  VIVGTVT..L  TICMMSMN..  MFTGNNK...  ..........
..........
   HMGRclustalW(    rabbit) VIVGTVT..L  TICMMSMN..  MFTGNDK...  ..........
..........
HMGRclustalW(        human) VIVGTVT..L  TICMMSMN..  MFTGNNK...  ..........
..........
HMGRclustalW(        mouse) ..........  ..........  ..........  ..........
..........
HMGRclustalW(      xenopus) VIVGTVT..L  TICMMSMN..  MFTGNDK...  ..........
..........
HMGRclustalW(sea urchin)    VIVCTLT..L  TICMLSMN..  YFTGLPR...  ..........
..........
HMGRclustalW( cockroach)    VIVATLT..L  TVCMLTVDQ.  RPLGLP....  ..........
..........
HMGRclustalW(drosophila)    VIVALLT..I  TACMLNGGQE  QYPGCEQRIG  HSTASAAAAG
SGSGAGSGAS
HMGRclustalW(dictyostel)    ..........  ..........  ..........  ..........
..........
HMGRclustalW(schistosom)    ..........  ..........  ..........  ..........
..........
HMGRclustalW(archaeoglo)    ..........  ..........  ..........  ..........
..........
HMGRclustalW(pseudomonas)   ..........  ..........  ..........  ..........
..........

Consensus      VIVGTVT--L  TICMMSMN--  MFTGNNK---  ----------
----
```

FIG. 32G

```
                                    151                                         200
    HMGRclustalW{methanobac}    .......... .......... .......... ..........
    HMGRclustalW{methanococ}    .......... .......... .......... ..........
    HMGRclustalW{halobacter}    .......... .......... .......... ..........
    HMGRclustalW{sulfolobus}    .......... .......... .......... ..........
    HMGRclustalW{    yeast2}    NGTKWRLRNN SNFILDLHNI YRNMVKQFSN KTSEFDQFDL
FIILAAYLTL
    HMGRclustalW{    yeast1}    DGTKWRLRSD RKSLFDVKTL AYSLYDVFSE NVTQADPFDV
LIMVTAYLMM
    HMGRclustalW{phycomyces}    .......... .......... .......... ..........
    HMGRclustalW{  fusarium}    SSVFAFLFGL VVTTKLGVPI SVILLSEGLP FLVVTIGFEK
NIVLTRAVMS
    HMGRclustalW{   candida}    DGTVWRSRAY HGKLGKYSDM AVGAFNKVLN LVRGAETFDI
ALVTCAYIAM
    HMGRclustalW{dictyoste2}    .......... .......... .......... ..........
    HMGRclustalW{    wheat1}    .......... .......... .......... ..........
    HMGRclustalW{      rice}    .......... .......... .......... ..........
    HMGRclustalW{      corn}    .......... .......... .......... ..........
    HMGRclustalW{    wheat3}    .......... .......... .......... ..........
    HMGRclustalW{    wheat2}    .......... .......... .......... ..........
    HMGRclustalW{   soybean}    .......... .......... .......... ..........
    HMGRclustalW{rubbertre3}    .......... .......... .......... ..........
    HMGRclustalW{rosyperiwi}    .......... .......... .......... ..........
    HMGRclustalW{    tomato}    .......... .......... .......... ..........
    HMGRclustalW{woodtobacc}    .......... .......... .......... ..........
    HMGRclustalW{    potato}    .......... .......... .......... ..........
    HMGRclustalW{    radish}    .......... .......... .......... ..........
    HMGRclustalW{arabadopsis1}  .......... .......... .......... ..........
    HMGRclustalW{cucumismel}    .......... .......... .......... ..........
    HMGRclustalW{rubbertre2}    .......... .......... .......... ..........
    HMGRclustalW{rubbertre1}    .......... .......... .......... ..........
    HMGRclustalW{camptothec}    .......... .......... .......... ..........
    HMGRclustalW{arabadops2}    .......... .......... .......... ..........
    HMGRclustalW{chineseham}    .......... ........I CGWNYEC.PK FEEDVLSSDI
IILTITRCIA
```

FIG. 32H

```
HMGRclustalW{chineseha2}   ..........  .........I CGWNYEC.PK FEEDVLSSDI
IILTITRCIA
HMGRclustalW{syrianhamst}  ..........  .........I CGWNYEC.PK FEEDVLSSDI
IILTITRCIA
    HMGRclustalW{    rat}  ..........  .........I CGWNYEC.PK FEEDVLSSDI
IILTITRCIA
 HMGRclustalW{     rabbit} ..........  .........I CGWNYEC.PK FEEDVLSSDI
IILTITRCIA
 HMGRclustalW{      human} ..........  .........I CGWNYEC.PK FEEDVLSSDI
IILTITRCIA
 HMGRclustalW{      mouse} ..........  ..........  ..........  ..........
..........
   HMGRclustalW{   xenopus} ..........  .........I CGWNYAC.PK FEEDVLSSDI
IILTITRCIA
 HMGRclustalW{sea urchin}  ..........  .........I CGWNYECAPQ VKESSLSSDV
LVMCIMRTLA
 HMGRclustalW{ cockroach}  ..........  .......... PGWGHNC..I TLEEYNAADM
IVMTLIRCVA
 HMGRclustalW{drosophila}  GTIPPSSMGG SATSSRHRPC HGWSQSC.DG LEAEYNAADV
ILMTIVRCTA
 HMGRclustalW{dictyostel}  ..........  ..........  ..........  ..........
..........
 HMGRclustalW{schistosom}  ..........  ..........M LKILNTVLLF FDCFSTGTFF
VLLIYLFTRL
 HMGRclustalW{archaeoglo}  ..........  ..........  ..........  ..........
..........
 HMGRclustalW{pseudomonas} ..........  ..........  ..........  ..........
..........

Consensus        ----------  ---------I CGWNYEC-PK FEEDVLSSDI
IILTITRCIA
```

FIG. 32I

```
                                            201                                          250
    HMGRclustalW{methanobac}     ..........  ..........  ..........  ..........  ..........
    HMGRclustalW{methanococ}     ..........  ..........  ..........  ..........  ..........
    HMGRclustalW{halobacter}     ..........  ..........  ..........  ..........  ..........
    HMGRclustalW{sulfolobus}     ..........  ..........  ..........  ..........  ..........
    HMGRclustalW{    yeast2}     FYTLCCLFND  MRKIGSKFWL  SFSALSNSAC  ALYLSLYTTH  SLLKKPASLL
    HMGRclustalW{    yeast1}     FYTIFGLFND  MRKTGSNFWL  SASTVVNSAS  SLFLALYVTQ  CILGKEVSAL
    HMGRclustalW{phycomyces}     ..........  ..........  ..........  ..........  ..........
    HMGRclustalW{  fusarium}     HAIEHRRIQA  QNSKSGKRSP  DGSTQNMIQY  AVQAAIKEKG  FEIIRDYAIE
    HMGRclustalW{   candida}     FYTLFNLFAR  MRAVGSKVWL  GLSTLVSSFF  AFLFALYITT  RVLDLSIPFL
    HMGRclustalW{dictyoste2}     ..........  ..........  ..........  ..........  ..........
    HMGRclustalW{    wheat1}     ..........  ..........  ..........  ..........  ..........
    HMGRclustalW{      rice}     ..........  ..........  ..........  ..........  ..........
    HMGRclustalW{      corn}     ..........  ..........  ..........  ..........  ..........
    HMGRclustalW{    wheat3}     ..........  ..........  ..........  ..........  ..........
    HMGRclustalW{    wheat2}     ..........  ..........  ..........  ..........  ..........
    HMGRclustalW{   soybean}     ..........  ..........  ..........  ..........  ..........
    HMGRclustalW{rubbertre3}     ..........  ..........  ..........  ..........  ..........
    HMGRclustalW{rosyperiwi}     ..........  ..........  ..........  ..........  ..........
    HMGRclustalW{    tomato}     ..........  ..........  ..........  ..........  ..........
    HMGRclustalW{woodtobacc}     ..........  ..........  ..........  ..........  ..........
    HMGRclustalW{    potato}     ..........  ..........  ..........  ..........  ..........
    HMGRclustalW{    radish}     ..........  ..........  ..........  ..........  ..........
    HMGRclustalW{arabadopsis1}   ..........  ..........  ..........  ..........  ..........
    HMGRclustalW{cucumismel}     ..........  ..........  ..........  ..........  ..........
    HMGRclustalW{rubbertre2}     ..........  ..........  ..........  ..........  ..........
    HMGRclustalW{rubbertre1}     ..........  ..........  ..........  ..........  ..........
    HMGRclustalW{camptothec}     ..........  ..........  ..........  ..........  ..........
    HMGRclustalW{arabadops2}     ..........  ..........  ..........  ..........  ..........
    HMGRclustalW{chineseham}     ILYIYFQFQN  LRQLGSKYIL  GIAGLFTIFS  SFVFSTVVIH  ..........
```

FIG. 32J

```
HMGRclustalW{chineseha2}   ILYIYFQFQN  LRQLGSKYIL  GIAGLFTIFS  SFVFSTVVIH
..........
HMGRclustalW{syrianhamst}  ILYIYFQFQN  LRQLGSKYIL  GIAGLFTIFS  SFVFSTVVIH
..........
HMGRclustalW{      rat}    ILYIYFQFQN  LRQLGSKYIL  GIAGLFTIFS  SFVFSTVVIH
..........
HMGRclustalW{   rabbit}    ILYIYFQFQN  LRQLGSKYIL  GIAGLFTIFS  SFVFSTVVIH
..........
HMGRclustalW{    human}    ILYIYFQFQN  LRQLGSKYIL  GIAGLFTIFS  SFVFSTVVIH
..........
HMGRclustalW{    mouse}    ..........  ..........  ..........  ..........
..........
HMGRclustalW{  xenopus}    ILYIYFQFQN  LRQLGSKYIL  GIAGLFTIFS  SFVFSTVVIH
..........
HMGRclustalW{sea urchin}   VAYLYLQFTK  LRTTGSKYIL  GIAGLFTIFS  SFLFSSAVIH
..........
HMGRclustalW{ cockroach}   VLYSYYQFCH  LQKLGSKYIL  GIAGLFTVFS  SFVFSSSVIN
..........
HMGRclustalW{drosophila}   VLYCYYQFCS  LHRLGSKYVL  GIAGLFTVFS  SFIFTTAIIK
..........
HMGRclustalW{dictyostel}   ..........  ..........  ..........  ..........
..........
HMGRclustalW{schistosom}   RTHLLHFSSS  NCHLDVIIYQ  SRAVIIFLVV  FVYFIGVLTC
KINDKILVHT
HMGRclustalW{archaeoglo}   ..........  ..........  ..........  ..........
..........
HMGRclustalW{pseudomonas}  ..........  ..........  ..........  ..........
..........
              Consensus    ILYIYFQFQN  LRQLGSKYIL  GIAGLFTIFS  SFVFSTVVIH  ------
    ----
```

FIG. 32K

```
                                251
300
   HMGRclustalW(methanobac)    ..........  ..........  ..........  ..........
..........
    HMGRclustalW(methanococ)   ..........  ..........  ..........  ..........
..........
    HMGRclustalW(halobacter)   ..........  ..........  ..........  ..........
..........
    HMGRclustalW(sulfolobus)   ..........  ..........  ..........  ..........
..........
    HMGRclustalW(      yeast2) SLVIGLPFIV  VIIG.FKHKV  RLAAFSLQKF  HRISIDKKIT
VSNIIYEAMF
    HMGRclustalW(      yeast1) TLFEGLPFIV  VVVG.FKHKI  KIAQYALEKF  ERVGLSKRIT
TDEIVFESVS
    HMGRclustalW(phycomyces)   ..........  ..........  ..........  ..........
..........
    HMGRclustalW(    fusarium) IVILVIGAAS  GVQGGLQQFC  FLAAWTLF.F  DFILLFTFYT
AILSIKLRST
    HMGRclustalW(    .candida) SLSEGIPFFV  AVVG.FNNKI  LLAEKVLQ.N  QLNAQSSKND
APTVLYQALR
    HMGRclustalW(dictyoste2)   ..........  ..........  ..........  ..........
..........
    HMGRclustalW(wheat1)       ..........  ..........  ..........  ..........
..........
    HMGRclustalW(        rice) ..........  ..........  ..........  ..........
..........
    HMGRclustalW(        corn) ..........  ..........  .........M  EVRG......
.GVGQGSAAR
......HPPA
    HMGRclustalW(wheat3)       ..........  ..........  ..........  ..........
..........
    HMGRclustalW(wheat2)       ..........  ..........  ..........  ..........
..........
    HMGRclustalW(     soybean) ..........  ..........  ..........  ..........
..........
    HMGRclustalW(rubbertre3)   ..........  ..........  .........M  DEVRRRPP.K
HIVRKDHDGE
VLNSFSHG..
    HMGRclustalW(rosyperiwi)   ..........  ..........  .........M  DSRRRSP...
TVTAKAAAGE
LPLAPHEGQ.
    HMGRclustalW(      tomato) ..........  ..........  .........M  DVRRRSEEPV
YPSKVFAADE
KPLKPHKKQQ
    HMGRclustalW(woodtobacc)   ..........  ..........  .........M  DVRRRSEKPA
YPTKEFAAGE
KPLKPHK...
    HMGRclustalW(      potato) ..........  ..........  .........M  DVRRRPVKPL
YTSKDASAG.
EPLKQQE...
    HMGRclustalW(      radish) ..........  ..........  .........M  DIRR..RPPK
PPVNSN....
...RFLDNRS
    HMGRclustalW(arabadopsis1) ..........  ..........  .........M  DLRR..RPPK
PPVTNNNNSN
GSFRSYQPRT
    HMGRclustalW(cucumismel)   ..........  ..........  .........M  DRRRSLRPPR
PNAVQDADAT
CTFRRDEQDA
    HMGRclustalW(rubbertre2)   ..........  ..........  ..........  ..........
..........
    HMGRclustalW(rubbertre1)   ..........  ..........  .........M  DTTG..RLH.
....HR....
......KHAT
    HMGRclustalW(camptothec)   ..........  ..........  .........M  DVRRRSINSI
HQIPSVGGTA
PPMLKPKQPT
    HMGRclustalW(arabadops2)   ..........  ..........  .........M  EDLRRRFPTK
KNGEEISN..
..........
    HMGRclustalW(chineseham)   FLDKELTGLN  EALPFFLLLI  DLSRASALAK  FALSSNSQDE
VRENIARGMA
```

FIG. 32L

```
HMGRclustalW{chineseha2}   FLDKELTGLN  EALPFFLLLI  DLSRASALAK  FALSSNSQDE
VRENIARGMA
HMGRclustalW{syrianhamst}  FLDKELTGLN  EALPFFLLLI  DLSRASALAK  FALSSNSQDE
VRENIARGMA
    HMGRclustalW{    rat}  FLDKELTGLN  EALPFFLLLI  DLSRASALAK  FALSSNSQDE
VRENIARGMA
  HMGRclustalW{   rabbit}  FLDKELTGLN  EALPFFLLLI  DLSRASALAK  FALSSNSQDE
VRENIARGMA
  HMGRclustalW{    human}  FLDKELTGLN  EALPFFLLLI  DLSRASTLAK  FALSSNSQDE
VRENIARGMA
  HMGRclustalW{    mouse}  ..........  ..........  ..........  ..........
..........
  HMGRclustalW{   xenopus}  FLDKELTGLN  EALPFFLLLI  DLSKASALAK  FALSSNSQDE
VRDNIARGMA
 HMGRclustalW{sea urchin}  LFGLELTGLN  EALPFFLLLI  DLTKASALTK  FALSSTTQNE
VVDNIARGMA
  HMGRclustalW{ cockroach}  FLGSDVSDLK  DALFFFLLLI  DLSKATVLAQ  FALSSRSQDE
VKENIARGIA
 HMGRclustalW{drosophila}  FLGSDISELK  DALFFLLLVI  DLSNSGRLRS  GAMGSN.QAE
VTQNIARGLE
  HMGRclustalW{dictyostel}  ..........  ..........  ..........  ..........
..........
  HMGRclustalW{schistosom}  MLRNKRQLNT  LFYTLILFTF  ALCSLSSVLF  VPYTSFAIFL
LSTSVFLLFS
  HMGRclustalW{archaeoglo}  ..........  ..........  ..........  ..........
..........
  HMGRclustalW{pseudomonas}  ..........  ..........  ..........  ..........
..........

Consensus    FLDKELTGLN  EALPFFLLL-  DL-RASALAK  FALSSNSQDE
VRENIARGMA
```

FIG. 32M

```
                                       301                                              350
  HMGRclustalW(methanobac)     .......... .......... .......... ..........  ..........
  HMGRclustalW(methanococ)    .......... .......... .......... ..........  ..........
  HMGRclustalW(halobacter)    .......... .......... .......... ..........  ..........
  HMGRclustalW(sulfolobus)    .......... .......... .......... ..........  ..........
  HMGRclustalW(     yeast2)   QEGAYLIRDY LFYISSFIGC AIYARHLPGL VNFCILSTFM  LVFDLLLSAT
  HMGRclustalW(     yeast1)   EEGGRLIQDH LLCIFAFIGC SMYAHQLKTL TNFCILSAFI  LIFELILTPT
  HMGRclustalW(phycomyces)    .......... .......... .......... ..........  ..........
  HMGRclustalW(   fusarium)   VSSVMSICVW PLRMMASRRV AENVAKGDDE LNRVRGDAPL  FGRKSSSIPK
  HMGRclustalW(    candida)   EQGPLLLRDH LFMITAFLGC SFYASYLDGL KNFCILAALI  LAFDILTTST
  HMGRclustalW(dictyoste2)    .......... .......... .......... ..........  ..........
  HMGRclustalW(    wheat1)    .......... .......... .......... ..........  ..........
  HMGRclustalW(       rice)   .......... .......... .......... .MRIT.....  ...NGLAMVS
  HMGRclustalW(       corn)   PE....PSRA ........AA RVQAGDALPL PIRHT.....  ...NLIFSAL
  HMGRclustalW(    wheat3)    .......... .......... .......... ..........  ..........
  HMGRclustalW(    wheat2)    .......... .......... .......... ..........  ..........
  HMGRclustalW(    soybean)   .......... .......... .......... ..........  ..........
  HMGRclustalW(rubbertre3)    ........HH L.......PP LKPSDYSLPL SLYLA.....  ...NALVFSL
  HMGRclustalW(rosyperiwi)    ........NQ Q.......PS IPRSSDVLPL PLYLA.....  ...NGVFFTL
  HMGRclustalW(     tomato)   QQ....QEDK N.......TL LIDASDALPL PLYLTT....  ...NGLFFTM
  HMGRclustalW(woodtobacc)    QQ....QEQD N.......SL LI.ASDALPL PLYLT.....  ...NGLFFTM
  HMGRclustalW(     potato)   .......... ........VS SPKASDALPL PLYLT....:  ...NGLFFTM
  HMGRclustalW(     radish)   DD....DDRR K.....TLTS PPKASDALPL PLYLT.....  ...NAVFFTL
  HMGRclustalW(arabadopsis1)  SD....DDHR RR..ATTIAP PPKASDALPL PLYLT.....  ...NAVFFTL
  HMGRclustalW(cucumisme1)    SA....ADHL KR.......A SPKASDALPL PLYLT.....  ...NTIFFTL
  HMGRclustalW(rubbertre2)    .......... .......... .......... ..........  ..........
  HMGRclustalW(rubbertre1)    PV....EDRS P.......T TPKASDALPL PLYLT.....  ...NAVFFTL
  HMGRclustalW(camptothec)    KV....DAVD L.......PD SPKASDALPL PLYIT.....  ...NGVFFTL
  HMGRclustalW(arabadops2)    ......VAVD ........PP LRKASDALPL PLYLT.....  ...NTFFLSL
  HMGRclustalW(chineseham)    ILGPTFTLDA LV..ECLVIG VGTMSGVRQL EIMCCFGCMS  VLANYFVFMT
```

FIG. 32N

```
  HMGRclustalW(chineseha2)   ILGPTFTLDA  LV..ECLVIG  VGTMSGVRQL  EIMCCFGCMS
VLANYFVFMT
  HMGRclustalW(syrianhamst)  ILGPTFTLDA  LV..ECLVIG  VGTMSGVRQL  EIMCCFGCMS
VLANYFVFMT
  HMGRclustalW(       rat)  ILGPTFTLDA  LV..ECLVIG  VGTMSGVRQL  EIMCCFGCMS
VLANYFVFMT
  HMGRclustalW(    rabbit)  ILGPTFTLDA  LV..ECLVIG  VGTMSGVRQL  EIMCCFGCMS
VLANYFVFMT
  HMGRclustalW(     human)  ILGPTFTLDA  LV..ECLVIG  VGTMSGVRQL  EIMCCFGCMS
VLANYFVFMT
  HMGRclustalW(     mouse)  ..........  ..........  ..........  ..........
..........
  HMGRclustalW(   xenopus)  ILGPTFTLEA  LV..ECLVIG  VGTMSGVRQL  EIMCCFGCMS
VLANYFAFMT
  HMGRclustalW(sea urchin)  ILGPTITLDT  VV..TTLVIS  IGTMSSIRKM  EVFCCFGILS
LIANYFVFMT
  HMGRclustalW( cockroach)  MLGPTITLDT  VV..ETLVIG  VGMLSGVRRL  EVLCCFACMS
VIVNYVVFMT
  HMGRclustalW(drosophila)  LLGPAISLDT  IV..VVLLVG  VGTLSGVQRL  EVLCMFAVLS
VLVNYVVFMT
  HMGRclustalW(dictyostel)  ..........  .........M  LFAPPNLETK  ELFWIIY.IL
ILIPKVFAKV
  HMGRclustalW(schistosom)  DLSVFFIVLE  YYLLEIELVN  YEHAKRHCLL  SHLFSNQLFV
DHMLGMFLKT
  HMGRclustalW(archaeoglo)  ..........  ..........  ..........  ..........
..........
  HMGRclustalW(pseudomonas) ..........  ..........  ..........  ..........
..........

Consensus      ILGPTFTLDA  LV--ECLVIG  VGTASD-LPL  -LYCTFGCMS
VLANYFFFMT
```

FIG. 320

```
                                              351
400
    HMGRclustalW{methanobac}   ..........  ..........  ..........  ..........
..........
    HMGRclustalW{methanococ}   ..........  ..........  ..........  ..........
    HMGRclustalW{halobacter}   ..........  ..........  ..........  ..........
..........
    HMGRclustalW{sulfolobus}   ..........  ..........  ..........  ..........
..........
    HMGRclustalW{     yeast2}  FYSAILSMKL  EINIIHRSTV  IRQTL..EED  GVVPTTADII
YKDETASEPH
    HMGRclustalW{     yeast1}  FYSAILALRL  EMNVIHRSTI  IKQTL..EED  GVVPSTARII
SKAEKKSVSS
    HMGRclustalW{phycomyces}   ..........  ..........  ..........  ..........
..........
    HMGRclustalW{   fusarium}  FKVLMILGFI  FVNIVNICSI  PFRNP..SSM  STIRTWASSL
GGVIAPLSVD
    HMGRclustalW{    candida}  FLSAILSLKL  EINQIHRSTL  LREQL..EDD  GLTETTVDDV
LKSNSLAGTK
    HMGRclustalW{dictyoste2}   ..........  ..........  ..........  ..........
..........
    HMGRclustalW{    wheat1}   ..........  ..........  ..........  ..........
    HMGRclustalW{       rice}  LVLSSCDLVR  LCSDRER...  PL........  ....GGREFA
TVVCQLASVV
    HMGRclustalW{       corn}  FAASLAYLMR  RWREKIRSST  PLHA......  ...VGLAEML
AIFGLVASLI
    HMGRclustalW{    wheat3}   ..........  ..........  ..........  ..........
..........
    HMGRclustalW{    wheat2}   ..........  ..........  ..........  ..........
    HMGRclustalW{    soybean}  ..........  ..........  ..........  ..........
..........
    HMGRclustalW{rubbertre3}   FFSVAYFLLH  RWREKIRKST  PLHI......  ...VTFPEIA
ALICLVASVI
    HMGRclustalW{rosyperiwi}   FFSVMYFLLT  RWREKIRNAT  PLHV......  ...VTLSELA
ALASLIASVI
    HMGRclustalW{     tomato}  FFSVMYFLLS  RWREKIRNST  PLHV......  ...VTLSELG
AIVSLIASVI
    HMGRclustalW{woodtobacc}   FFSVMYYLLS  RWREKIRNST  PLHV......  ...VTFSELV
AIASLIASVI
    HMGRclustalW{     potato}  FFSVMYFLLV  RWREKIRNSI  PLHV......  ...VTLSELL
AMVSLIASVI
    HMGRclustalW{     radish}  FFSVAYYLLH  RWRDKIRYNT  PLHV......  ...VTVTELG
AIVALIASFI
HMGRclustalW{arabadopsis1}     FFSVAYYLLH  RWRDKIRYNT  PLHV......  ...VTITELG
AIIALIASFI
    HMGRclustalW{cucumisme1}   FFSVAYYLLH  RWRDKIRNST  PLHV......  ...VTLSEIA
AIVSLMASFI
    HMGRclustalW{rubbertre2}   ..........  ..........  ..........  ..........
..........
    HMGRclustalW{rubbertre1}   FFSVAYYLLH  RWRDKIRNST  PLHI......  ...VTLSEIV
AIVSLIASFI
    HMGRclustalW{ camptothec}  FFTVVYYLLV  RWREKIRNST  PLHV......  ...VTLSEIA
AIFTFVASFI
    HMGRclustalW{ arabadops2}  FFATVYFLLS  RWREKIRNST  PLHV......  ...VDLSEIC
ALIGFVASFI
    HMGRclustalW{chineseham}   FFPACVSLVL  ELSRESREGR  PIWQ...LSH  FARVLEEEE.
NKPNPVTQRV
```

FIG. 32P

```
HMGRclustalW(chineseha2)   FFPACVSLVL  ELSRESREGR  PIWQ...LSH  FARVLEEEE.
NKPNPVTQRV
HMGRclustalW(syrianhamst)  FFPACVSLVL  ELSRESREGR  PIWQ...LSH  FARVLEEEE.
NKPNPVTQRV
   HMGRclustalW(    rat)   FFPACVSLVL  ELSRESREGR  PIWQ...LSH  FARVLEEEE.
NKPNPVTQRV
   HMGRclustalW( rabbit)   FFPACVSLVL  ELSRESREGR  PIWQ...LSH  FARVLEEEE.
NKPNPVTQRV
   HMGRclustalW(  human)   FFPACVSLVL  ELSRESREGR  PIWQ...LSH  FARVLEEEE.
NKPNPVTQRV
   HMGRclustalW(  mouse)   ..........  ..........  ..........  ..........
..........
   HMGRclustalW(xenopus)   FFPACVSLVL  ELSRESREGR  PIWQ...LSQ  FASVLEEEED
NKPNPVTQRV
HMGRclustalW(sea urchin)   FFPACLSLVL  ELSNSNKYGR  PVWH...LGR  FAEVLEEEED
RKPNPVVQRV
HMGRclustalW( cockroach)   FYPACLSLIL  ELSRSGESGR  PAWHD..KSL  IIKALHEED.
QKPNPVVQRV
HMGRclustalW(drosophila)   FYPACLSLIF  DLSRSGVDMS  VVREKAKGSL  PLKSLTEEE.
QKANPVLQRV
HMGRclustalW(dictyostel)   MSVRELFPFF  KWGFNIRRSN  FLVP......  ...ILSNNVI
VTGEEAVQYE
HMGRclustalW(schistosom)   SLFSISTTSK  YAYLESIFKC  TLMEQIIYIM  IVFVFLPSFM
RIFASYAKRM
HMGRclustalW(archaeoglo)   ..........  ..........  ..........  ..........
..........
HMGRclustalW(pseudomonas)  ..........  ..........  ..........  ..........
..........
              Consensus    FFSACYSLLL  -WRRKIRNST  PLHV---LSH  FARVTLEEEA  AKPN-
VASRI
```

FIG. 32Q

```
                                        401                              450
    HMGRclustalW{methanobac}    ..........  ..........  ..........  ..........
    HMGRclustalW{methanococ}    ..........  ..........  ..........  ..........
    HMGRclustalW{halobacter}    ..........  ..........  ..........  ..........
    HMGRclustalW{sulfolobus}    ..........  ..........  ..........  ..........
    HMGRclustalW{    yeast2}    FLRSNVAIIL  GKASVIGLLL  LINLYVF...  .TDKLNATIL
NTVYFDSTIY
    HMGRclustalW{    yeast1}    FLNLSVVVII  MKLSVILLFV  FINFYNF...  GANWVN.DAF
NSLYFDKERV
    HMGRclustalW{phycomyces}    ..........  ..........  ..........  ..........
    HMGRclustalW{  fusarium}    PFKVASNGLD  AILPTAKSNN  RPTLVTV...  LTPIKYELEY
PSIHYALGSA
    HMGRclustalW{   candida}    TFTDAPSTLV  TVAKVAGVSV  FFGLHFY...  GFGSAWLSDL
SAGNETNDTF
    HMGRclustalW{dictyoste2}    ..........  ..........  ..........  ..........
    HMGRclustalW{    wheat1}    ..........  ..........  ..........  ..........
    HMGRclustalW{      rice}    YLLSLFAHPD  APATTTGDDD  ..........  ..........
    HMGRclustalW{      corn}    YLLSFFGIAF  VQSIVSSGDD  ..........  ..........
    HMGRclustalW{    wheat3}    ..........  ..........  ..........  ..........
    HMGRclustalW{    wheat2}    ..........  ..........  ..........  ..........
    HMGRclustalW{   soybean}    ..........  ..........  ..........  ..........
    HMGRclustalW{rubbertre3}    YLLGFFGIGF  VHSFS.RAST  ..........  ..........
    HMGRclustalW{rosyperiwi}    YLVSFFGLDF  VQSLIYKPNN  ..........  ..........
    HMGRclustalW{    tomato}    YLLGFFGIGF  VQTFVSRGNN  ..........  ..........
    HMGRclustalW{woodtobacc}    YLLGFFGIGF  VQSFVSRDNN  ..........  ..........
    HMGRclustalW{    potato}    YLLGFFGIGF  VQSFVSRSNS  ..........  ..........
    HMGRclustalW{    radish}    YLLGFFGIDF  VQSFISRP..  ..........  ..........
    HMGRclustalW{arabadopsis1} YLLGFFGIDF  VQSFISRASG  ..........  ..........
    HMGRclustalW{cucumismel}   YLLGFFGIDF  VQSFIARSSP  ..........  ..........
    HMGRclustalW{rubbertre2}    ..........  ..........  ..........  ..........
    HMGRclustalW{rubbertre1}    YLLGFFGIDF  VQSFIARASH  ..........  ..........
    HMGRclustalW{camptothec}   YLLGFFGIGL  VQPFTSRSSH  ..........  ..........
    HMGRclustalW{arabadops2}   YLLGFCGIDL  IFRSS..SD.  ..........  ..........
    HMGRclustalW{chineseham}   KMIMSLGLVL  VHAESRWIAD  PSPQNST...  TE.HSKVSLG
LDEDVSKRIE
```

FIG. 32R

```
  HMGRclustalW(chineseha2)   KMIMSLGLVL  VHAHSRWIAD  PSPQNST...  TE.HSKVSLG
LDEDVSKRIE
  HMGRclustalW(syrianhamst)  KMIMSLGLVL  VHAHSRWIAD  PSPQNST...  TE.HSKVSLG
LDEDVSKRIE
  HMGRclustalW(      rat)    KMIMSLGLVL  VHAHSRWIAD  PSPQNST...  AE.QSKVSLG
LAEDVSKRIE
  HMGRclustalW(      rabbit) KMIMSLGLVL  VHAHSRWIAD  PSPQNST...  AD.NSKVSLG
LDENVSKRIE
  HMGRclustalW(      human)  KMIMSLGLVL  VHAHSRWIAD  PSPQNST...  AD.TSKVSLG
LDENVSKRIE
  HMGRclustalW(      mouse)  ..........  ..........  ..........  ..........
..........
  HMGRclustalW(    xenopus)  KMIMSLGLVL  VHAHSRWISE  PSSQNST...  SISDHEVTTM
LDDMMPKRVE
  HMGRclustalW(sea urchin)   KMIMRTGLVL  VHAHSYWLAS  ....NDT...  ELMSRDMLYD
GNLLTDKKID
  HMGRclustalW( cockroach)   KVIMSAGLML  VHAH.RWVRC  ..........  ........L.
..........
  HMGRclustalW(drosophila)   KLIMTTGLMA  VHIYSREVSP  ....AAT...  TMVDKTLTPT
LSLNVSNNRT
  HMGRclustalW(dictyostel)   KPLPYIPQHN  QQQQQKQQPS  ..........  ..........
..........
  HMGRclustalW(schistosom)   YGEQKKCLVS  NKGVSSSTRK  RRHSYSSGHS  YVEYRRMSVH
NLIGYVVNPN
  HMGRclustalW(archaeoglo)   ..........  ..........  ..........  ..........
..........
  HMGRclustalW(pseudomonas)  ..........  ..........  ..........  ..........
..........
           Consensus         YLL-FFG-VL  V-A-SR-ISD  PSPQNST---  ----SKVSLG LDE-
VSKRIE
```

FIG. 32S

```
                                         451                                              500
  HMGRclustalW{methanobac}      ..........  ..........  ..........  ..........  ..........
  HMGRclustalW{methanococ}      ..........  ..........  ..........  ..........  ..........
  HMGRclustalW{halobacter}      ..........  ..........  ..........  ..........  ..........
  HMGRclustalW{sulfolobus}      ..........  ..........  ..........  ..........  ..........
  HMGRclustalW{     yeast2}     SLPNFINYKD  IGNLSNQVII  SVLPKQYYTP  LKKYHQIEDS  VLLIIDSVSN
  HMGRclustalW{     yeast1}     SLPDFITSNA  SENFKEQAIV  SVTPLLYYKP  IKSYQRIEDM  VLLLLRNVSV
  HMGRclustalW{phycomyces}      ..........  ..........  ..........  ..........  ..........
  HMGRclustalW{   fusarium}     ASNPAYN.DA  FHHHFQGYGV  GGRMVGGILK  SLEDPVLSKW  IVIALALSVA
  HMGRclustalW{    candida}     TLYDAVA.DQ  IPIGSNGTLV  TLFPTRFFLP  EKLSTQIEAV  VLSFIGLIST
  HMGRclustalW{dictyoste2}      ..........  ..........  ..........  ..........  ..........
  HMGRclustalW{     wheat1}     ..........  ..........  ..........  ..........  ..........
  HMGRclustalW{       rice}     ..D.......  ..........  ..........  ..........  ..........
  HMGRclustalW{       corn}     ..DEDFLVGS  G.........  ..........  ..........  ..........
  HMGRclustalW{     wheat3}     ..........  ..........  ..........  ..........  ..........
  HMGRclustalW{     wheat2}     ..........  ..........  ..........  ..........  ..........
  HMGRclustalW{    soybean}     ..........  ..........  ..........  ..........  ..........
  HMGRclustalW{ rubbertre3}     ..D.SWDVEE  Y.........  ..........  D DDNIIIKEDT  R.........
  HMGRclustalW{ rosyperiwi}     ..E.GWEIEE  ..........  ..........  ...EILMVEDS  RN........
  HMGRclustalW{     tomato}     ..D.SWDE..  ..........  ..........  N DEEFLLKEDS  RC........
  HMGRclustalW{ woodtobacc}     ..DECWDEED  E.........  ..........  N DEQFLLEEDS  RR........
  HMGRclustalW{     potato}     ..D.SWDIED  E.........  ..........  N AEQLIIEEDS  RR........
  HMGRclustalW{     radish}     ..D.SGDSER  ..........  ..........  .....DFDDH   R.........
  HMGRclustalW{arabadopsis1}    ..D.AWDLAD  T.........  ..........  I .....DDDDH
  HMGRclustalW{ cucumismel}     ..D.AWDLED  ..........  ..........  .....EIDRT   L.........
  HMGRclustalW{ rubbertre2}     ..........  ..........  ..........  ..........  ..........
  HMGRclustalW{ rubbertre1}     ..D.VWDLED  T.........  ..........  D P.NYLIDEDH  R.........
  HMGRclustalW{ camptothec}     ..DDVWGVDD  DE........  ..........  D VDEIVLKEDT  R.........
  HMGRclustalW{ arabadops2}     ..DDVWVNDG  ..........  ..........  ..........
  HMGRclustalW{ chineseham}     PSVSLWQFYL  SKMISMDIEQ  VVTLSLAFLL  AVKYIFFEQA  ET..ESTLSL
```

FIG. 32T

```
  HMGRclustalW(chineseha2)    PSVSLWQFYL  SKMISMDIEQ  VVTLSLAFLL  AVKYIFFEQA
ET..ESTLSL
  HMGRclustalW(syrianhamst)   PSVSLWQFYL  SKMISMDIEQ  VVTLSLAFLL  AVKYIFFEQA
ET..ESTLSL
      HMGRclustalW(      rat) PSVSLWQFYL  SKMISMDIEQ  VITLSLALLL  AVKYIFFEQA
ET..ESTLSL
    HMGRclustalW(    rabbit)  PSVSLWQFYL  SKMISMDIEQ  VITLSLALLL  AVKYIFFEQA
ET..ESTLSL
   HMGRclustalW(      human)  PSVSLWQFYL  SKMISMDIEQ  VITLSLALLL  AVKYIFFEQT
ET..ESTLSL
   HMGRclustalW(      mouse)  ..........  ..........  ..........  ..........
..........
    HMGRclustalW(   xenopus)  PSMPLWQFYL  SRMVTMDVEQ  IITLGLALLL  AVKYIFFEQT
ET..ESTFSM
   HMGRclustalW(sea urchin)   PTMPLWEFYA  TRLWPPTLDY  ILTAILATVL  ASHYIFFSDL
ATYPEKRVSI
   HMGRclustalW( cockroach)   .SIALWPDLT  S......LRY  FCTHCDTGVS  YSRWSFASEG
EE..LPTVKL
   HMGRclustalW(drosophila)   ESGEIADIII  KWLT.MSADH  IVISIVLIAL  VVKFICFDNR
DP...LPDQL
   HMGRclustalW(dictyostel)   ..QDYIQQPQ  ..........  ..........  ..N....DNN
IN........
   HMGRclustalW(schistosom)   CHYKCWSTTF  VIFVSLIILH  LNNRYSERIS  SFKHNSSENE
VFPVLYHITA
   HMGRclustalW(archaeoglo)   ..........  ..........  ..........  ..........
..........
  HMGRclustalW(pseudomonas)   ..........  ..........  ..........  ..........
..........
                 Consensus    PSDSLWDFY-  SKMISMDIEQ  VVTLSLA-LL  AVKYIFFED-  RT--
ESTLSL
```

FIG. 32U

```
                                     501
550
  HMGRclustalW(methanobac)     ..........  ..........  ..........  ..........
..........
  HMGRclustalW(methanococ)     ..........  ..........  ..........  ..........
..........
  HMGRclustalW(halobacter)     ..........  ..........  ..........  ..........
..........
  HMGRclustalW(sulfolobus)     ..........  ..........  ..........  ..........
..........
  HMGRclustalW(      yeast2)   AIRDQFISKL  LFFAFAVSIS  INVYLLNAAK  IHTGYMNFQ.
..PQSNKIDD
  HMGRclustalW(      yeast1)   AIRDRFVSKL  VLSALVCSAV  INVYLLNAAR  IHTSYTADQL
VKTEVTKKSF
  HMGRclustalW(phycomyces)     ..........  ..........  ..........  ..........
..........
  HMGRclustalW(    fusarium)   LNGYLFNVAR  WGIKDPNVPE  HNIDRNELAR  AREFNDTGS.
.........AT
  HMGRclustalW(     candida)   AARDKYISKF  ILFAFAVSAS  INVYLLNVAR  IHTTRLEDA.
.........IE
  HMGRclustalW(dictyoste2)     ..........  ..........  ..........  ..........
..........
  HMGRclustalW(      wheat1)   ..........  ..........  ..........  ..........
..........
  HMGRclustalW(        rice)   ..........  ..........  ..........  ..........
..........
  HMGRclustalW(        corn)   ..........  ..........  ..........  ..........
..........
  HMGRclustalW(      wheat3)   ..........  ..........  ..........  ..........
..........
  HMGRclustalW(      wheat2)   ..........  ..........  ..........  ..........
..........
HMGRclustalW(       soybean)   ..........  ..........  ..........  ..........
..........
  HMGRclustalW(rubbertre3)     ..........  ..........  ..........  ..........
..........
  HMGRclustalW(rosyperiwi)     ..........  ..........  ..........  ....G.....
..........
  HMGRclustalW(      tomato)   ..........  ..........  ..........  ....G.....
..........
  HMGRclustalW(woodtobacc)     ..........  ..........  ..........  ....G.....
..........
  HMGRclustalW(      potato)   ..........  ..........  ..........  ....G.....
..........
  HMGRclustalW(      radish)   ..........  ..........  ..........  ..........
..........
HMGRclustalW(arabadopsis1)     ..........  ..........  ..........  ..........
..........
  HMGRclustalW(cucumisme1)     ..........  ..........  ..........  ..........
..........
  HMGRclustalW(rubbertre2)     ..........  ..........  ..........  ..........
..........
  HMGRclustalW(rubbertre1)     ..........  ..........  ..........  ..........
..........
  HMGRclustalW(camptothec)     ..........  ..........  ..........  ..........
..........
  HMGRclustalW(arabadops2)     ..........  ..........  ..........  ..........
..........
  HMGRclustalW(chineseham)     KN..PITSPV  VTPKKAPDNC  CRREPLLVRR  SEKLSSVEEE
PGVSQDRKVE
```

FIG. 32V

```
HMGRclustalW(chineseha2)   KN..PITSPV VTPKKAPDNC CRREPLLVRR SEKLSSVEEE PGVSQDRKVE
HMGRclustalW(syrianhamst)  KN..PITSPV ATPKKAPDNC CRREPVLSRR NEKLSSVEEE PGVNQDRKVE
HMGRclustalW(       rat)   KN..PITSPV VTPKKAQDNC CRREPLLVRR NQKLSSVEED PGVNQDRKVE
HMGRclustalW(    rabbit)   KN..PITSPV VTQKKVPDSC CRREPVVVRN NQKFCSVEEE AGMSQDRKVE
HMGRclustalW(     human)   KN..PITSPV VTQKKVPDNC CRREPMLVRN NQKCDSVEEE TGINRERKVE
HMGRclustalW(     mouse)   .......... .......... .......... .......... ..........
HMGRclustalW(   xenopus)   KN..PIISPV AVQKKQIESC CRREPEQ.EK TVHVSTTEEA S..SKEETEA
HMGRclustalW(sea urchin)   MEGHEVVNPG SDHEDASEVE TIGTLSSSPS TSDVRVIESM TSRTQACQTD
HMGRclustalW( cockroach)   VTGDSVVNSN STDDAQLHYY IMRWLTV..S ADHIVILILL LALAVKFVFF
HMGRclustalW(drosophila)   RQ....SGPV AIEAKASQTT PIDEEHVE.. .......QEKD TENSAAVRTL
HMGRclustalW(dictyostel)   .......... .......... .......... .......... ..........
HMGRclustalW(schistosom)   YEVTSIFHFI YNIFHVINAN LVVYLFLGLF LFKRIRLNKP INSQLRNLNI
HMGRclustalW(archaeoglo)   .......... .......... .......... .......... ..........
HMGRclustalW(pseudomonas) .......... .......... .......... .......... ..........

Consensus   KN--PITSPV VT-KKAPDNC CRREPLLVRR --K-SSVEEE.-G-SQDRKVE
```

FIG. 32W

```
                                    551                                600
  HMGRclustalW{methanobac}   ..........  ..........  ..........  ..........
  ..........
  HMGRclustalW{methanococ}   ..........  ..........  ..........  ..........
  ..........
  HMGRclustalW{halobacter}   ..........  ..........  ..........  ..........
  ..........
  HMGRclustalW{sulfolobus}   ..........  ..........  ..........  ..........
  ..........
  HMGRclustalW{    yeast2}   LVVQQKSATI  EFSET.....  ......RSMPA  SSGLETPVTA
KDIIISEEIQ
  HMGRclustalW{    yeast1}   TAPVQKASTP  VLTN......  ......KTVIS  GSKVKSLSSA
QSSSSGPSSS
  HMGRclustalW{phycomyces}   ..........  ..........  ..........  ..........
  HMGRclustalW{  fusarium}   LPLGEYVPPT  PMRTQ.....  ......PSTPA  ITDDEAEG..
..LHMTKARP
  HMGRclustalW{   candida}   LKKPKKKASK  TAVSV.....  ......PKAVV  VKDSETTKSS
EILHSSSESE
  HMGRclustalW{dictyoste2}   ..KGKSVNVE  DLKDQ.....  ......EIIAL  VDKGEIQP..
...HNLETRL
  HMGRclustalW{    wheat1}   ..........  ..........  ..........  ..........
  HMGRclustalW{      rice}   .......GQG  GSR.......  ..........  ...RA.....A
PPEPAPMHGH
  HMGRclustalW{      corn}   ......SSGS  AAA.......  ..........  ...PSRQHAQA
PAPCELLGSP
  HMGRclustalW{    wheat3}   ..........  ..........  ..........  ..........
  HMGRclustalW{    wheat2}   ..........  ..........  ..........  ..........
  HMGRclustalW{   soybean}   ..........  ..........  ..........  ..........
  HMGRclustalW{rubbertre3}   .......PTG  AC........  ..........  ..AAPSLDCS
LSLPTKIHAP
  HMGRclustalW{rosyperiwi}   ..T..NCTTL  GC........  ..........  ..AVPPPSVP
KIAPVVPQQP
  HMGRclustalW{    tomato}   ..P...ATTL  GC........  ..........  ..AVPAPPAR
QIAPMAPPQP
  HMGRclustalW{woodtobacc}   ..P...ATTL  GCT.......  ..........  ..AVPPPPAL
QIVPMVPPQP
  HMGRclustalW{    potato}   ..PCAAATTL  GC........  ..........  ..VVPPPPVR
KIAPMVPQQP
  HMGRclustalW{    radish}   ......LVTC  PPP.......  ..........  ..PPP....S
QIVAAKLPNP
  HMGRclustalW{arabadopsis1} ......LVTC  SPP.......  ..........  ..TP......
IVSVAKLPNP
  HMGRclustalW{cucumisme1}   ......LIDN  NRY.......  ..........  ..AAPRSASA
VALPSKVVDA
  HMGRclustalW{rubbertre2}   ..........  ..........  ..........  ..........
  HMGRclustalW{rubbertre1}   ......LVTC  PPA.......  ..........  ..NISTKTTI
IAAPTKLPTS
  HMGRclustalW{camptothec}   .......TVP  CAA.......  ..........  ..APVDCPLP
PIKPKVVDPV
  HMGRclustalW{arabadops2}   ......MIPC  NQ........  ..........  ..SLDCREVL
PIKPNSVDPP
  HMGRclustalW{chineseham}   VIKPLVVETE  SAS.......  .RATFVLG.A  .SGTSPPVAA
RTQELEIELP
```

FIG. 32X

```
HMGRclustalW{chineseha2}   VIKPLVVETE  SAS.......  .RATFVLG.A  .SGTSPPVAA
RTQELEIELP
HMGRclustalW{syrianhamst}  VIKPLVAETE  STS.......  .RATFVLG.A  .SGGCSPVAL
GTQEPEIELP
   HMGRclustalW{     rat}  VIKPLVAEAE  TSG.......  .RATFVLG.A  .SAASPPLAL
GAQEPGIELP
   HMGRclustalW{  rabbit}  VIKPLVAETD  SPH.......  .RAAFVVGGS  .SFPDTSLVL
ETKEPEIELP
   HMGRclustalW{   human}  VIKPLVAETD  TPN.......  .RATFVVGNS  .SLLDTSSVL
VTQEPEIELP
   HMGRclustalW{   mouse}  ..........  ..........  ..........  ..........
..........
   HMGRclustalW{ xenopus}  VIKPLPLETS  P.........  .KAKFIVG..  .DSSPLELSP
EDKNTMFDLP
HMGRclustalW{sea urchin}   PVTASPRNSR  SSSPVSSHSV  KPARFTIGSS  GSGSEDEEEE
VIKEEEVEWV
HMGRclustalW{ cockroach}   ETRDELTTTR  GMDG.....W  VEVSSPVEHK  YVQTEQPSCS
APEQPLEEPP
HMGRclustalW{drosophila}   LFTIEDQSSA  N.........  ..........  ..ASTQTDLL
PLRHRLVGPI
HMGRclustalW{dictyostel}   .....SGKEQ  EQ........  ..........  ..QQQQQQQQ
QQTPDITNQP
HMGRclustalW{schistosom}   PKIKETLISD  QVKQSPVLPK  FSKKLNDIPL  QSRKRIYCLH
KDDDYIDRND
HMGRclustalW{archaeoglo}   ..........  ..........  ..........  ..........
..........
HMGRclustalW(pseudomonas}  ..........  ..........  ..........  ..........
..........
             Consensus     VIKPLVAETE  --S-------  -RATFV-G-A  -SA-PPPPA-  -I-
PPEIELP
```

FIG. 32Y

```
                                   601                                              650
  HMGRclustalW{methanobac}    .......... ..........  ..........  .......MS.
...IMDDLME
  HMGRclustalW{methanococ}    .......... ..........  ..........  .......MEN
YNDILEKMLN
  HMGRclustalW{halobacter}    .......... ..........  ..........  .......MTD
AASLADRVRE
  HMGRclustalW{sulfolobus}    .......... ..........  ..........  .......MK.
IDEVVEKLVK
  HMGRclustalW{    yeast2}    NNE.CVYALS SQDEPIRP.L  SNLVELME..  ...KEQLKNMN
NTEVSNLVVN
  HMGRclustalW{    yeast1}    SEEDDSRDIE SLDKKIRP.L  EELEALLS..  ...SGNTKQLK
NKEVAALVIH
  HMGRclustalW{phycomyces}    .......... ..........  ..........  ..........
..........
  HMGRclustalW{  fusarium}    ANL....... ....PNRS.N  EELEKLLS..  ...ENALREMT
DEEVISLSMR
  HMGRclustalW{   candida}    SEQ....... ....SSRP.L  EQVIELYK..  ...DGKVKTLV
DDEVVSLVTA
  HMGRclustalW{dictyoste2}    PNN....... ........F   QRAVHIRR..  ...KLLARDLQ
KEHQRALHAQ
  HMGRclustalW{    wheat1}    .......... ..........  ..........  ..........
..........
  HMGRclustalW{      rice}    G......... ..........  ..........  ...GGMMEGD
DEEIVAAVAS
  HMGRclustalW{      corn}    AA........ ..........  .......A..  ...PEKMPED
DEEIVASVVA
  HMGRclustalW{    wheat3}    .......... ..........  ..........  ..........
..........
  HMGRclustalW{    wheat2}    .......... ..........  ..........  ..........
..........
  HMGRclustalW{   soybean}    .......... ..........  ..........  ..........
..........
  HMGRclustalW{rubbertre3}    .......... ..........I  VSTTT.....  ...TSTLSDD
DEQIIKSVVS
  HMGRclustalW{rosyperiwi}    SK........ ......MV.I  IEKPAPLI..  ...TPQNSEE
DEDIIKAVVA
  HMGRclustalW{    tomato}    S......... ......MS.M  VEKPAPLI..  ...TSASSGE
DEEIIKSVVQ
  HMGRclustalW{woodtobacc}    SKV....... ......AA.M  SEKPAPLV..  ...TPAASEE
DEEIIKSVVQ
  HMGRclustalW{    potato}    AKV....... .....ALS.Q  TEKPSPII..  ...MPALSED
DEEIIQSVVQ
  HMGRclustalW{    radish}    E......... ..........  ..........  ...QPPLPKE
DEEIVKSVLD
  HMGRclustalW{arabadopsis1}  EP........ ..........  .......IV..  ...TESLPEE
DEEIVKSVID
  HMGRclustalW{cucumismel}    EA........ ..........  .......LN..  ...TIPLPEE
DEEVVKMVVD
  HMGRclustalW{rubbertre2}    .......... ..........  ..........  ..........
..........
  HMGRclustalW{rubbertre1}    EP........ ..........  .......LI..  ...APLVSEE
DEMIVNSVVD
  HMGRclustalW{camptothec}    P......... ..........  .......I..  ...SPPSSEE
DEEIIKSVVE
  HMGRclustalW{arabadops2}    RE........ ..........  ..........  ...SELDSVE
DEEIVKLVID
  HMGRclustalW{chineseham}    SE........ ......PRP.N  EECLQILE..  SAEKGAKFLS
DAEIIQLVNA
```

FIG. 32Z

```
HMGRclustalW{chineseha2}    SE........  .....PRP.N  EECLQILE..  SAEKGAKFLS
DAEIIQLVNA
HMGRclustalW{syrianhamst}   SE........  .....PRP.N  EECLQILE..  SAEKGAKFLS
DAEIIQLVNA
    HMGRclustalW{     rat}  SE........  .....PRP.N  EECLQILE..  SAEKGAKFLS
DAEIIQLVNA
    HMGRclustalW{  rabbit}  KE........  .....PRP.N  EECLQILG..  NAEKGAKFLS
DAEIIQLVNA
    HMGRclustalW{   human}  RE........  .....PRP.N  EECLQILG..  NAEKGAKFLS
DAEIIQLVNA
    HMGRclustalW{   mouse}  ..........  ..........  ..........  ..........
..........
    HMGRclustalW{ xenopus}  EE........  .....PRP.L  DECVRILK..  NPDKGAQYLT
DAEVISLVNA
    HMGRclustalW{sea urchin} LET.......  .ELKAPRP.M  PELLEIL...  NVGKGPNALT
DDEVQLLVGA
    HMGRclustalW{cockroach}  AS........  .....NRS.I  DECLSVC...  KSDVGAQALS
DCEVMALVTS
    HMGRclustalW{drosophila} KP........  .....PRP.V  QECLDILNST  EEGSGPAALS
DEEIVSIVHA
    HMGRclustalW{dictyostel} TKTN......  ..........  ..........  .KKIPIKELS
NEEILIKLEK
    HMGRclustalW{schistosom} SSSVSTFSNT  CKNSNERPSN  VLDLDMLTEK  IKQGLGHELS
DTEILQLLSH
    HMGRclustalW{archaeoglo} ..........  ..........  ..........  ..........
.MQVLRLDRR
    HMGRclustalW{pseudomonas} ..........  ..........  ..........  ..........
..........
              Consensus     SE--------  -----PRP-N  EECLQIL---  -AEKGAKSLS
DEEIKLVVA
```

FIG. 32AA

```
                                        651
700
    HMGRclustalW(methanobac)   GR..IKLYEI  E.RHVPVDEA  VRIRREFIE.  ....RTCGVK
..LEHVSNYS
    HMGRclustalW(methanococ)   GE..IKPYQL  D.KMFGSKIA  TEIRRKFIE.  ....KKVGIE
..FKHICNYS
    HMGRclustalW(halobacter)   GD..LRLHEL  E.AHADADTA  AEARRLLVE.  ....SQSGAS
..LDAVGNYG
    HMGRclustalW(sulfolobus)   GE..ISFHEV  D.NLLEANAA  MVARRLALE.  ....KIVGVG
..LPSIGSTV
    HMGRclustalW(    yeast2)   G..KLPLYSL  EKCLEDTTRA  VLVRRKALST  LAESPILVS.
...EKLPFRN
    HMGRclustalW(    yeast1)   G..KLPLYAL  EKKLGDTTRA  VAVRRKALSI  LAEAPVLAS.
...DRLPYKN
    HMGRclustalW(phycomyces)   .........  ..........  ..........  ..........
..........
    HMGRclustalW(   fusarium)  G..KIPGYAL  EKTLGDFTRA  VKIRRSIIAR  NKAAADITHS
LDRSKLPYEN
    HMGRclustalW(    candida)  G..KLPLYAL  EKQLGDNLRA  VAIRRKAISD  LADAPVLRS.
...NKLPYLH
    HMGRclustalW(dictyoste2)   A..VVAAAEK  AATSGEDPSS  IQPVVPPTSN  LDFEGSLTN.
.....LPVDH
    HMGRclustalW(wheat1)       .........  ..........  ..........  ..........
..........
    HMGRclustalW(      rice)   G..ALPSHRL  ESRLGDCRRA  ARLRREALR.  ....RVTGRG
..VEGLPFDG
    HMGRclustalW(      corn)   G..KVPSYAL  EARLGDCRRA  AGIRREALR.  ....RITGRD
..IEGLPLDG
    HMGRclustalW(wheat3)       .........  ..........  ..........  ..........
..........
    HMGRclustalW(wheat2)       .........  ..........  ..........  ..........
..........
HMGRclustalW(      soybean)    .........  ..........  ..........  ..........
..........
    HMGRclustalW(rubbertre3)   G..SIPSYSL  ESKLGNCKRA  ALIRRETLQ.  ....RMSGRS
..LEGLPLDG
    HMGRclustalW(rosyperiwi)   G..KIPSYSL  ESKLGDCKRA  AGIRREALQ.  ....RITGKS
..LEGLPLEG
    HMGRclustalW(    .tomato)  G..KIPSYSL  ESKLGDCKRA  ASIRKEVMQ.  ....RITGKS
..LEGLPLEG
    HMGRclustalW(woodtobacc)   G..KMPSYSL  ESKLGDCKRA  ASIRKEALQ.  ....RITGKS
..LEGLPLEG
    HMGRclustalW(    potato)   G..KTPSYSL  ESKLGDCMRA  ASIRKEALQ.  ....RITGKS
..LEGLPLEG
    HMGRclustalW(radish)       G..VVPSYSL  ESRLGDCKRA  ASIRREALQ.  ....RLTGRS
..IEGLPLDG
HMGRclustalW(arabadopsis1)     G..VIPSYSL  ESRLGDCKRA  ASIRREALQ.  ....RVTGRS
..IEGLPLDG
    HMGRclustalW(cucumismel)   G..SVPSYSL  ESKLGDPKRA  ASIRREALQ.  ....RTTGRS
..IHGLPFEG
    HMGRclustalW(rubbertre2)   .........  ..........  ..........  ..........
..........
    HMGRclustalW(rubbertre1)   G..KIPSYSL  ESKLGDCKRA  AAIRREALQ.  ....RMTRRS
..LEGLPVEG
    HMGRclustalW(camptothec)   G..TTPSYAL  ESKLGDSHRA  AAIRREALQ.  ....RMTKKS
..LAGLPLDG
    HMGRclustalW(arabadops2)   G..TIPSYSL  ETKLGDCKRA  AAIRREAVQ.  ....RITGKS
..LTGLPLEG
    HMGRclustalW(chineseham)   K..HIPAYKL  ETLMETHERG  VSIRRQLLST  K..LPEPSS.
..LQYLPYRD
```

FIG. 32BB

```
HMGRclustalW(chineseha2)   K..HIPAYKL ETLMETHERG VSIRRQLLST K..LPEPSS.
..LQYLPYRD
HMGRclustalW(syrianhamst)  K..HIPAYKL ETLMETHERG VSIRRQLLST K..LPEPSS.
..LQYLPYRD
HMGRclustalW(       rat)   K..HIPAYKL ETLMETHERG VSIRRQLLSA K..LAEPSS.
..LQYLPYRD
HMGRclustalW(    rabbit)   K..HIPAYKL ETLMETHERG VSIRRQLLSK K..LPEPSS.
..LQYLPYRD
HMGRclustalW(     human)   K..HIPAYKL ETLMETHERG VSIRRQLLSK K..LSEPSS.
..LQYLPYRD
HMGRclustalW(     mouse)   .......... .......... .......... ..........
..........
HMGRclustalW(   xenopus)   K..HIPAYKL ETMMESPREG VAIRRQMLSD K..LPQRSA.
..LQSLPYKN
HMGRclustalW(sea urchin)   K..HIPAYKL ENILDNPERG VAVRRQIISK L..LPITDA.
..LEKLPYAS
HMGRclustalW( cockroach)   G..HIAGYQL EKVVRNPERG VGIRRQILTK T..ADLKDA.
..LDNLPYKN
HMGRclustalW(drosophila)   GGTHCPLHKI ESVLDDPERG VRIRRQIIGS R..AKMPVGR
..LDVLPYEH
HMGRclustalW(dictyostel)   G..EVLAYRL ENELGDCSRA VEIRRMLLEK ....QLSKK.
..IEPIPHEG
HMGRclustalW(schistosom)   G..RLKTREL ESVVRNPFRA VELRRLDLS. ....TFLNNP
HIIERIPYKD
HMGRclustalW(archaeoglo)   HYKSGKIRRA MSSRIPGFYK LSVEERLKKV AEFAGLSDEE
..VKAVLSQG
HMGRclustalW(pseudomonas)  ........MS LDSRLPAFRN LSPAARLDHI GQLLGLSHDD
..VSLLANAG Consensus    G---IPSYSL ESKLGDCKRA VSIRREALSK K--LRITGSS --
LEGLPYEG
```

FIG. 32CC

```
                                                       701
750
  HMGRclustalW{methanobac}    IDMERASRRN  IENPIGVVQI  PLGVAGPLRV  RGEHADGEYY
VPLATSEGAL
  HMGRclustalW{methanococ}    IDEEMAMKKN  IENMIGAIQI  PLGFAGPLKI  NGEYAKGEFY
IPLATTEGAL
  HMGRclustalW{halobacter}    FPAEAAES.A  IENMVGSIQV  PMGVAGPVSV  DGGSVAGEKY
LPLATTEGAL
  HMGRclustalW{sulfolobus}    IDYSEIKNKN  AENVIGAIQI  PLGIVGPIRV  NGDYAKGDFY
VPMATTEGAL
 HMGRclustalW{      yeast2}   YDYDRVFGAC  CENVIGYMPI  PVGVIGPLII  DGT....SYH
IPMATTEGCL
 HMGRclustalW{      yeast1}   YDYDRVFGAC  CENVIGYMPL  PVGVIGPLVI  DGT....SYH
```

FIG. 32DD

```
IPMATTEGCL
    HMGRclustalW(phycomyces}   .........   .........   .........   .........
.PMATTEGCL
    HMGRclustalW(  fusarium}   YNWERFFGAC CENVIGYMPL PVGVAGPLVI DGQ....SYF
IPMATTEGVL
    HMGRclustalW(   candida}   YDYDRVFGAC CENVIGYMPL PVGVAGPLII DGK....PYH
IPMATTEGCL
    HMGRclustalW(dictyoste2}   FDYTKVLGAC CENVIGYIPI PVGVAGPILL DGK....LVS
IPMATTEGCL
        HMGRclustalW(wheat1}   .........   .........   .........   .........
..........
        HMGRclustalW(   rice}  MDYQAILGQC CEMPVGYVQL PVGVAGPLLL DGR....EYH
VPMATTEGCL
        HMGRclustalW(   corn}  FDYASILGQC CELPVGYVQL PVGVAGPLLL DGR....RFY
LPMATTEGCL
        HMGRclustalW(wheat3}   .........   .........   .........   .........
..........
        HMGRclustalW(wheat2}   .........   .........   .........   .........
..........
HMGRclustalW(       soybean}   .........   .........   .........   .........
..........
    HMGRclustalW(rubbertre3)   FDYESILGQC CEMAIGYVQI PVGIAGPLLL DGK....EYT
VPMATTEGCL
    HMGRclustalW(rosyperiwi)   FDYASILGQC CEMPVGYVQL PVGIAGPLLL DGR....EYM
LPMATTEGCL
    HMGRclustalW(    tomato}   FNYESILGQC CEMPIGYVQI PVGIAGPLLL NGK....EFS
VPMATTEGCL
    HMGRclustalW(woodtobacc}   FDYESILGQC CEMPIGYVQI PVGIAGPLLL DGR....EYS
VPMATTEGCL
    HMGRclustalW(    potato}   FDYSSILGQC CEMPVGYVQI PVGIAGPLLL DGR....EYS
VPMATTEGCL
        HMGRclustalW(radish}   FDYDSILGQC CEMPVGYIQI PVGIAGPLLL DGY....EYS
VPMATTEGCL
HMGRclustalW(arabadopsis1)     FDYESILGQC CEMPVGYIQI PVGIAGPLLL DGY....EYS
VPMATTEGCL
    HMGRclustalW(cucumismel}   FDYESILGQC CEMPVGYVQI PVGIAGPLLL DGF....EYT
VPMATTEGCL
    HMGRclustalW(rubbertre2}   .........   .........   .........   .........
..........
    HMGRclustalW(rubbertre1)   FDYESILGQC CEMPVGYVQI PVGIAGPLLL NGR....EYS
VPMATTEGCL
    HMGRclustalW(camptothec}   FDYDSILGQC CEMPVGYVQI PVGIAGPLLL DGR....EYS
VPMATTEGCL
    HMGRclustalW(arabadops2}   FDYNSILGQC CEMPVGYVQI PVGIAGPLLL DGV....EYS
VPMATTEGCL
    HMGRclustalW(chineseham}   YNYSLVMGAC CENVIGYMPI PVGVAGPLCL DGK....EYQ
VPMATTEGCL
    HMGRclustalW(chineseha2}   YNYSLVMGAC CENVIGYMPI PVGVAGPLCL DGK....EYQ
VPMATTEGCL
    HMGRclustalW(syrianhamst}  YNYSLVMGAC CENVIGYMPI PVGVAGPLCL DGK....EYQ
VPMATTEGCL
        HMGRclustalW(    rat}  YNYSLVMGAC CENVIGYMPI PVGVAGPLCL DGK....EYQ
VPMATTEGCL
        HMGRclustalW( rabbit}  YNYSLVLGAC CENVIGYMPI PVGVVGPLCL DGK....EFQ
VPMATTEGCL
        HMGRclustalW(  human}  YNYSLVMGAC CENVIGYMPI PVGVAGPLCL DEK....EFQ
VPMATTEGCL
        HMGRclustalW(  mouse}  .........   .........   .........   .........
..........
        HMGRclustalW( xenopus} YNYSLVMGAC CENVIGYMPI PVGVAGPLLL NNK....EYQ
```

FIG. 32EE

```
VPMATTEGCL
    HMGRclustalW(sea urchin)      YDYSFVSGAC  CENVIGYMPV  PVGVAGPLLL  DGQ....EFQ
VPMATTEGCL
    HMGRclustalW( cockroach)      YDYLKVMGAC  CENVIGYMPV  PVGVAGPLNL  DGR....LVH
VPLATTEGCL
    HMGRclustalW(drosophila)      FDYRKVLNAC  CENVLGYVPI  PVGYAGPLLL  DGE....TYY
VPMATTEGAL
    HMGRclustalW(dictyostel)      FDFAKVQGQC  CENVIGYVPI  PVGTAGPIQL  NGQ....LVT
IPMATTEGCL
    HMGRclustalW(schistosom)      YDYRLVYGQC  CEEVIGYMPI  PVGKIGPLLL  DGR....SHY
IPLATTEGCL
    HMGRclustalW(archaeoglo)      .LPLDVADRM  IENVIGTFEL  PLGIATNFLI  DGK....DYL
IPMAIREPSV
    HMGRclustalW(pseudomonas)     ALPMDIANGM  IENVIGTFEL  PYAVASNFQI  NGR....DVL
VPLVVEEPSI Consensus           FDY-SVLG-C  CENVIGY--I  PVGVAGPLLL  DGK----EYS
VPMATTEGCL
                                         HMGCoA binding
E
```

FIG. 32FF

```
                                            751
800
    HMGRclustalW{methanobac}    VASVNRGCSV  ITRAGGATVR  VTGDSMT.RA  PVIRTGSVVE
ALQLREWIYE
    HMGRclustalW{methanococ}    VASVNRGCSI  ITKCGGATVR  VIDDKMT.RA  PCLKTKSVVD
AIKVRDWIRE
    HMGRclustalW{halobacter}    LASVNRGCSV  INSAGGATAR  VLKSGMT.RA  PVFRVADVAE
AEALVSWTRD
    HMGRclustalW{sulfolobus}    IASVNRGIKA  VTLSGGVRAK  VLKDEMT.RA  PVFKFDSIEQ
IPNFLKFIEE
    HMGRclustalW{      yeast2}  VASAMRGCKA  INAGGGATTV  LTKDGMT.RG  PVVRFPTLIR
SGACKIWLDS
    HMGRclustalW{      yeast1}  VASAMRGCKA  INAGGGATTV  LTKDGMT.RG  PVVRFPTLKR
SGACKIWLDS
    HMGRclustalW{phycomyces}    VASTARGCKA  INAGGGASTI  VIADGMT.RG  PCVEFPTILR
AAACKLWIEN
    HMGRclustalW{    fusarium}  VASASRGCKA  INSGGGAITV  LTADGMT.RG  PCVAFETLER
AGAAKLWLDS
    HMGRclustalW{     candida}  VASAMRGCKA  INLGGGVTTV  LTKDGMT.RG  PCVKFPSLKR
AGQCKLWLDS
    HMGRclustalW{dictyoste2}    VASTHRGAKA  ITKSGGAKTV  LLQSGMT.RA  PVCRLPSSIR
AGELKQWIEN
        HMGRclustalW{wheat1}    ..........  ..........  ..........  ..........
..........
    HMGRclustalW{        rice}  VASVNRRVQG  HLVSGGAFSV  LLRDAMS.RA  PAVKLPCPMR
AAELKAFAEA
    HMGRclustalW{        corn}  VASTNRGCKA  IAESGGATSV  VLRDAMT.RA  PVARFPTARR
AAELKAFLED
        HMGRclustalW{wheat3}    ..........  ..........  ..........  ..........
..........
        HMGRclustalW{wheat2}    ..........  ..........  ..........  ..........
..........
HMGRclustalW{      soybean}     ..........  ..........  ..........  ..........
..........
    HMGRclustalW{rubbertre3}    VASANRGCKA  IYASGGATSV  LLRDGMT.RA  PVVRFPTAKR
AADLKFFMED
    HMGRclustalW{rosyperiwi}    VASTNRGCKA  ILASGGANSV  LLRDGMT.RA  PVVRFGTAKR
AAELKFYMED
    HMGRclustalW{      tomato}  VASTNRGCKA  IYASGGATCI  LLRDGMT.RA  PCVRFGTAKR
AAELKFFVED
    HMGRclustalW{woodtobacc}    VASTNRGCKA  IYASGGATSV  LLRDGMT.RA  PCVRFGTAKR
AAELKFFVED
    HMGRclustalW{      potato}  VASTNRGCKA  IFVSGGADSV  LLRDGMT.RA  PVVRFTTAKR
AAELKFFVED
        HMGRclustalW{radish}    VASTNRGCKA  MYVSGGATST  VLKDGMT.RA  PVVRFASARR
ASELKFFLES
HMGRclustalW{arabadopsis1}      VASTNRGCKA  MFISGGATST  VLKDGMT.RA  PVVRFASARR
ASELKFFLEN
    HMGRclustalW{cucumisme1}    VASTNRGCKA  IYASGGATSM  LLKDGMT.RA  PVVRFGSAKR
ASELKFFLED
        HMGRclustalW{rubbertre2} ..........  ..........  ..........  ..........
..........
    HMGRclustalW{rubbertre1}    VASTNRGCKA  IYLSGGATSV  LLKDGMT.RA  PVVRFASATR
AAELKFFLED
    HMGRclustalW{camptothec}    VASTNRGCKA  IFACGGATSV  LLRDAMT.RA  PVVRFGSAKR
AADLKFFLEN
    HMGRclustalW{arabadops2}    VASTNRGFKA  IHLSGGAFSV  LVKDAMT.RA  PVVRFPSARR
AALVMFYLQD
    HMGRclustalW{chineseham}    VASTNRGCRA  IGLGGGASSR  VLADGMT.RG  PVVRLPRACD
SAEVKAWLET
```

FIG. 32GG

```
HMGRclustalW(chineseha2)   VASTNRGCRA  IGLGGGASSR  VLADGMT.RG  PVVRLPRACD  SAEVKAWLET
HMGRclustalW(syrianhamst)  VASTNRGCRA  IGLGGGASSR  VLADGMT.RG  PVVRLPRACD  SAEVKAWLET
HMGRclustalW(      rat)    VASTNRGCRA  ISLGGGASSR  VLADGMS.RG  PVVRLPRACD  SAEVKSWLET
HMGRclustalW(   rabbit)    VASTNRGCRA  ICLGGGASSR  VLADGMT.RG  PVVRLPRACD  SAEVKAWLET
HMGRclustalW(    human)    VASTNRGCRA  IGLGGGASSR  VLADGMT.RG  PVVRLPRACD  SAEVKAWLET
HMGRclustalW(    mouse)    .........   .........   .........   .........   .........
HMGRclustalW(  xenopus)    VASTNRGCRA  IMLGGGAKSR  VLADGMT.RG  PVVRLPTACD  AAEVKAWLDS
HMGRclustalW(sea urchin)   VASTNRGCRA  LRSAGGIHSV  LIGDGMT.RG  PLVRLPSAQE  AGAIKQWLEV
HMGRclustalW( cockroach)   VASTNRGMRA  LMRCG.VTSR  IVADGMT.RG  PVVRFPNIDR  ASEAMLWMQV
HMGRclustalW(drosophila)   VASTNRGCKA  LSVRG.VRSV  VEDVGMT.RA  PCVRFPSVAR  AAEAKSWIEN
HMGRclustalW(dictyostel)   VASTHRGCKA  ITESGGAKCT  ITSRGMT.RA  PVVRFSDIVK  ASEFVSWIND
HMGRclustalW(schistosom)   VASTNRGCRA  IFLAGGIKSV  VYRDQMT.RA  PVVWFPSIID  SVKCIAWIDS
HMGRclustalW(archaeoglo)   VAAASNAARM  ARESGGFTTD  YTGSLMIGQI  QVTKLLNPNA  AKFEVLRQKD
HMGRclustalW(pseudomonas)  VAAASYMAKL  ARANGGFTTS  SSAPLMHAQV  QIVGIQDPLN  ARLSLLRRKD Consensus   VASTNRGCKA  I-LSGGATSV  VLADGMT-RA  PVVRFPSAKR  AAELKFWLED
```

FIG. 32HH

```
                              801
850
  HMGRclustalW{methanobac}   NM..DALREE  AESTTRHGKL  VKIDPI.....  IVAGSYVYPR
FVYTTGDSMG
  HMGRclustalW{methanococ}   NF..ERIKEV  AESTTRHGKL  IKIEPI.....  LIVGRNLYPR
FVFKTGDAMG
  HMGRclustalW{halobacter}   NF..AALKEA  AESTTNHGEL  LDVTP......  YVVGNSVYLR
FRYDTKDAMG
  HMGRclustalW{sulfolobus}   NL..EKIRNI  ANSTSHHGKL  KSITP......  FVLGNNVWLR
FSFETGDAMG
  HMGRclustalW{     yeast2}  EEGQNSIKKA  FNSTSRFARL  QHIQT......  CLAGDLLFMR
PRTTTGDAMG
  HMGRclustalW{     yeast1}  EEGQNAIKKA  FNSTSRFARL  QHIQT......  CLAGDLLFMR
FRTTTGDAMG
  HMGRclustalW{phycomyces}   EG.NDIVTNA  FNSTSRFARL  RKLKI......  ALAGKLVFIR
FSTTTGDAMG
  HMGRclustalW{   fusarium}  EAGQDMMKKA  FNSTSRFARL  QSMKT......  ALAGTNLYIR
FKTTTGDAMG
  HMGRclustalW{    candida}  DEGQEEMKKA  FNSTSRFARL  QHLQT......  ALAGDLLFIR
FRTVTGDAMG
  HMGRclustalW{dictyoste2}   QENFYQVASA  FNSTSRFARL  KSIKV......  VIAGRLVYLR
FKSSTGDAMG
     HMGRclustalW{wheat1}    ..........  ..........  ..........  ..........
.....GDAMG
  HMGRclustalW{       rice}  PANFELLAAV  FNRSSRFGRL  QDIRC......  ALAGRNLYMR
FSCITGDAMG
      HMGRclustalW{   corn}  PANFDTLSVV  FNRSSRFARL  QGVQC......  AMAGRNLYMR
FSCSTGDAMG
     HMGRclustalW{wheat3}    ..........  ..........  ..........  ..........
.....GDAMG
     HMGRclustalW{wheat2}    ..........  ..........  ..........  ..........
.....GDAMG
HMGRclustalW{    soybean}    ..........  ..........  ..........  ..........
..........
  HMGRclustalW{rubbertre3}   PDNFDTIAVV  FNKSSRFARL  QSVQC......  AIAGKNLYMR
FSCSTGDAMG
  HMGRclustalW{rosyperiwi}   TQNFETISVV  FNKSSRFAKL  QSVQC......  AIAGKNLYIR
FSCSTGDAMG
  HMGRclustalW{     tomato}  PIKFESLANV  FNQSSRFARL  QRIQC......  AIAGKNLYMR
LCCSTGDAMG
  HMGRclustalW{woodtobacc}   PVKFETLAAV  FNQSSRFARL  QRIQC......  AIAGKNLYMR
FVCSTGDAMG
  HMGRclustalW{     potato}  PLNFETLSLM  FNKSSRFARL  QGIQC......  AIAGKNLYIT
FSCSTGDAMG
     HMGRclustalW{radish}    PENFETLAVV  FNRSSRFARL  QSVMC......  TLAGKNAYVR
FSCSTGDAMG
HMGRclustalW{arabadopsis1}   PENFDTLAVV  FNRSSRFARL  QSVKC......  TIAGKNAYVR
FCCSTGDAMG
  HMGRclustalW{cucumismel}   PSNFDTLAVV  FNRSSRFARL  QSIRC......  SIAGKNLYVR
FCCSTGDAMG
    HMGRclustalW{rubbertre2} ..........  ..........  ..........  ..........
..........
  HMGRclustalW{rubbertre1}   PDNFDTLAVV  FNKSSRFARL  QGIKC......  SIAGKNLYIR
FSCSTGDAMG
  HMGRclustalW{camptothec}   PLNFETLAAV  FNSSSRFGKL  QNIKC......  AIAGKNLYMR
YSCSTGDAMG
  HMGRclustalW{arabadops2}   PSNFERLSLI  FNKSSRFARL  QSITC......  TIAGRNLYPR
FACSTGDAMG
  HMGRclustalW{chineseham}   PEGFAVIKDA  FDSTSRFARL  QKLHV......  TMAGRNLYIR
FQSKTGDAMG
```

FIG. 32II

```
HMGRclustalW{chinseha2}    PEGFAVIKDA  FDSTSRFARL  QKLHV.....  TMAGRNLYIR
FQSKTGDAMG
HMGRclustalW{syrianhamst}  PEGFAVIKDA  FDSTSRFARL  QKLHV.....  TMAGRNLYIR
FQSKTGDAMG
     HMGRclustalW{   rat}  PEGFAVVKEA  FDSTSRFARL  QKLHV.....  TLAGRNLYIR
LQSKTGDAMG
     HMGRclustalW{rabbit}  PEGFAVIKEA  FDSTSRFARL  QKLHI.....  SMAGRNLYIR
FQSRTGDAMG
     HMGRclustalW{ human}  SEGFAVIKEA  FDSTSRFARL  QKLHT.....  SIAGRNLYIR
FQSRSGDAMG
     HMGRclustalW{ mouse}  ..........  ..........  ..........  ..........
..........
     HMGRclustalW{xenopus} AEGFKVIKDA  FDSTSRFARL  GRLQN.....  CVAGRNLYIR
FQSKTGDAMG
HMGRclustalW{sea urchin}   PENFAAIKER  FESTSRFAKL  KSIQT.....  ALAGRYMFLR
FKALTGDAMG
HMGRclustalW{ cockroach}   PYNFEQIKKN  FDSTSRFARL  SKIHI.....  RVAGRHLFIR
FIATTGDAMG
HMGRclustalW{drosophila}   DENYRVVKTE  FDSTSRFGRL  KDCHI.....  AMDGPQLYIR
FVAITGDRMG
HMGRclustalW{dictyostel}   TDNYQALKAV  FDSTSRFARL  SAIKC.....  TIAGRSVYIR
FKCDTGDAMG
HMGRclustalW{schistosom}   EEGFQTLKSA  FDKTSAHVNL  LSVFA.....  CPAGRYIHIR
FAARTGDAMG
HMGRclustalW{archaeoglo}   EIIERANECD  PMLVNLGGGC  KDIEAR.VID  TIMGKMLIVH
LIVDVKDAMG
HMGRclustalW{pseudomonas}  EIIELANRKD  QLLNSLGGGC  RDIEVHTFAD  TPRGPMLVAH
LIVDVRDAMG Consensus      PENFETLK-A  FNSTSRFARL  QSIQC-----  AIAGRNLYIR
FSCSTGDAMG
                                                              NADH binding domain 1
(continued)
```

FIG. 32JJ

```
                                    851
900
    HMGRclustalW(methanobac)   MNMVTIATER ALELLT...R ETGAHV..IA LSGNLCTDKK
PAAVNLIEGR
    HMGRclustalW(methanococ)   MNMVTIATEK ACNFIEGELK KEGIFVKTVA VSGNACVDKK
PSGMNLINGR
    HMGRclustalW(halobacter)   MNMATIATEA VCGVVE...A ETAASL..VA LSGNLCSDKK
PAAINAVEGR
    HMGRclustalW(sulfolobus)   MNMVTIAVEK VCEFIE.... ENFPSADCLA VSGNMCSDKK
QTNVNSLFGR
    HMGRclustalW(    yeast2)   MNMISKGVEY SLKQMVEEY. .GWEDMEVVS VSGNYCTDKK
PAAINWIEGR
    HMGRclustalW(    yeast1)   MNMISKGVEY SLKQMVEEY. .GWEDMEVVS VSGNYCTDKK
PAAINWIEGR
    HMGRclustalW(phycomyces)   MNM....... .......... .......... ..........
..........
    HMGRclustalW(   fusarium)  MNMISKGVEH ALSVMANDG. .GFDDMQIIS VSGNYCTDKK
AAALNWIDGR
    HMGRclustalW(    candida)  MNMISKGVEY ALKQMTEVF. .GWDDMMVVS VSGNYCTDKK
PAAVNWINGR
    HMGRclustalW(dictyoste2)   MNMVSKGVEK ALEVITEY.. ..FPEMEVLS LSGNVCTDKK
PSSINWLEGR
        HMGRclustalW(wheat1)   MNMVSKGVEN VLGYIRNN.. ..FPDMDVIS ISGNYCSDKK
ATAVNWIDGR
    HMGRclustalW(      rice)   MNMVSKGVEN VLGYLQNV.. ..FPDMDVIS VSGNYCSDKK
PTAVNWIEGR
        HMGRclustalW(  corn)   MNMVSKGVQN VLDFLQDD.. ..FHDMDVIS ISGNFCSDKK
PSAVNWIEGR
        HMGRclustalW(wheat3)   MNMISKGVQN VLDYLQDD.. ..FPDMDVIS ISGNFCSDKK
PAAVNWIEGR
        HMGRclustalW(wheat2)   MNMISKGVQH VLDYLEED.. ..FPDMDVVS ISGNFCSDKK
SAAVNWIEGR
HMGRclustalW(       soybean)   .......... .......... .......... ..........
..........
        HMGRclustalW(rubbertre3) MNMVSKAVQN VIDYLQND.. ..FPDMDVIG LTGNFCADKK
AAAVNWIEGR
    HMGRclustalW(rosyperiwi)   MNMVSKGVQN VLEFLQTD.. ..YPDMDVLG ISGNFCADKK
PAAVNWIEGR
    HMGRclustalW(     tomato)  MNMVSKGVQN VLDYLQNE.. ..YPDMDVIG ISGNFCSDKK
PAAVNWIEGR
    HMGRclustalW(woodtobacc)   MNMVSKGVQN VLDYLQNE.. ..YPDMDVIG ISGNFCSDKK
PAAVNWIEGR
    HMGRclustalW(     potato)  MNMVSKGVQN VLDYLQSE.. ..YPDMDVIG ISGNFCSDKK
PAAVNWIEGR
        HMGRclustalW(radish)   MNMVSKGVQN VLEFLTED.. ..FPDMDVIG ISGNFCSDKK
PAAVNWIEGR
HMGRclustalW(arabadopsis1)     MNMVSKGVQN VLEYLTDD.. ..FPDMDVIG ISGNFCSDKK
PAAVNWIEGR
    HMGRclustalW(cucumismel)   MNMVSKGVQN VLEFLQHD.. ..FSDMEVIG ISGNFCADKK
PAAVNWIEGR
    HMGRclustalW(rubbertre2)   .......... ....LESD.. ..FADMDVIG ISGNFCSDKK
PAAVNWIEGR
    HMGRclustalW(rubbertre1)   MNMVSKGVQN VLEFLQSD.. ..FSDMDVIG ISGNFCSDKK
PAAVNWIEGR
    HMGRclustalW(camptothec)   MNMISKGVQN VLDFLQDD.. ..FPDMDVIG ISGNYCSDKK
PAAVNWIEGR
    HMGRclustalW(arabadops2)   MNMVSKGVQN VLDFVKSE.. ..FPDMDVIG ISGNYCSDKK
ASAVNWIEGR
    HMGRclustalW(chineseham)   MNMISKGTEK ALLKLQEF.. ..FPEMQILA VSGNYCTDKK
PAAINWIEGR
```

FIG. 32KK

```
HMGRclustalW{chineseha2}   MNMISKGTEK ALLKLQEF.. ..FPEMQILA VSGNYCTDKK
PAAINWIEGR
HMGRclustalW{syrianhamst}  MNMISKGTEK ALVKLQEF.. ..FPEMQILA VSGNYCTDKK
PAAVNWIEGR
    HMGRclustalW{     rat}  MNMISKGTEK ALLKLQEG.. ..VPELQILA VSGNYCTDKK
PAAINWIEGR
   HMGRclustalW{   rabbit}  MNMISKGTEK ALSKLHEY.. ..FPEMQILA VSGNYCTDKK
PAAVNWIEGR
   HMGRclustalW{    human}  MNMISKGTEK ALSKLHEY.. ..FPEMQILA VSGNYCTDKK
PAAINWIEGR
   HMGRclustalW{    mouse}  ........EK ALLKLQEF.. ..FPDMQILA VSGNYCTDKK
PAAINWIEGR
   HMGRclustalW{   xenopus} MNMISKVTEQ ALARLQEE.. ..FPDLHVLA VSGNYCTDKK
PAAINWIEGR
   HMGRclustalW{sea urchin} MNMISKGTEQ ALHALQTM.. ..FPNIEIMS LSGNYCTDKK
VAAINWIEGR
   HMGRclustalW{ cockroach} MNMLSKGTEV ALAYVQQV.. ..YPDMEILS LSGNFCTDKK
PAAVNWIEGR
   HMGRclustalW{drosophila} MNMVSKALRW PFAEFTLH.. ..FPDMQIIS LSGNFCCDKK
PAAINWIKGR
   HMGRclustalW{dictyostel} MNMVSKGVEA VLEHLKII.. ..FDDMTLLS ISGNMCTDKK
PSSINWTEGR
   HMGRclustalW{schistosom} MNMVSKATDS ALHCLKKY.. ..FSNMQVIS LSGNMCTDKK
PATINTILGR
   HMGRclustalW{archaeoglo} ANAVNTMCEK VAPFIERITG .GKVYLRIIS NLAAYRLARA
KAVFDKDVIG
   HMGRclustalW{pseudomonas} ANTVNTMAEA VAPLMEAITG .GQVRLRILS NLADLRLARA
QVRITPQQLE
              Consensus    MNMVSKGVEN VL--LQED-- -GFPDMDVIS ISGNYCTDKK
PAAVNWIEGR
           NADH binding domain 1 (concluded)
```

FIG. 32LL

```
                                      901                                      950
   HMGRclustalW{methanobac}     GKSITAEITV PGEMVESVLK TTPEAVVEVN TAKVLIGSAA
AG..SMG.FN
   HMGRclustalW{methanococ}    GKSIVAEVFL TEKEVNKYLK TTSQAIAEVN RLKVYIGSAI
SN..SMG.FN
   HMGRclustalW{halobacter}    GRSVTADVRI PREVVEERLH TTPERGRELN TRKVLVGSAK
AA..SLG.FN
   HMGRclustalW{sulfolobus}    GKTVLAEALI KKDVIRNILH SNAQLIHDIN LRKVWLGTAR
AG..SLSQFN
   HMGRclustalW{     yeast2}   GKSVVAEATI PGDVVKSVLK SDVSALVELN ISKVLVGSAM
AG..SVGGFN
   HMGRclustalW{     yeast1}   GKSVVAEATI PGDVVRKVLK SDVSALVELN IAKVLVGSAM
AG..SVGGFN
   HMGRclustalW{phycomyces}    .......... .......... .......... ..........
..........
   HMGRclustalW{   fusarium}   GKGVVAEAII PGEVVRSVLK SDVDSLVELN VAKVLIGSAM
AG..SVGGFN
   HMGRclustalW{    candida}   GKSVVAEASI PKDAVVKVLK SSVKAVVDVN VNKVLIGSAM
AG..SVGGFN
   HMGRclustalW{dictyoste2}    GKSVVAEAVI SGDIVRDVLK TTVEALVSLN IDKVLIGSAM
AG..SIGGFN
       HMGRclustalW{wheat1}    GKSVVCEATI KGRVVQSVID TTVEKLVELN IIKVLAGSAV
AG..ALGGFN
       HMGRclustalW{    rice}  GKSVVCEAII KGDVVQKVLK TTVEKLVELN IIKVLAGSAV
AG..ALGGFN
       HMGRclustalW{    corn}  GKSVVCEAVI GEEVVKKVLK TDVQSLVELN TIKVLAGSAV
AG..ALGGFN
       HMGRclustalW{wheat3}    GKSVVCEAVI REELLKKVLK TNVQSLVELN VIKVLAGSAV
AG..ALGGFN
       HMGRclustalW{wheat2}    GKSVVCEAII REVVEKVLD TNVQSLVELN VIKVLAGSAV
AG..ALGGFN
HMGRclustalW{     soybean}     .......... ........LK TNVSALVELN MLKVLAGSAV
AG..ALGGFN
   HMGRclustalW{rubbertre3}    GKSVVCEAII KEEVVKKVLK TNVAALVELN MIKVLTGSAV
AG..SLGGFN
   HMGRclustalW{rosyperiwi}    GKSVVCEAII KEEIVKTVLK TEVAALIELN MVKVLAGSAI
AG..ALGGFN
   HMGRclustalW{     tomato}   GKSVVCEAII TEEVVKKVLK TEVAALVELN MLKVLTGSAM
AG..ALGGFN
   HMGRclustalW{woodtobacc}    GKSVVCEAII TEEVVKKVLK TEVAALVELN MLKVLTGSAM
AG..ALGGFN
   HMGRclustalW{     potato}   GKSVVCEAII KEVVVKKVLK TEVAALVELN MLKVLTGSAM
AG..ALGGFN
       HMGRclustalW{radish}    GKSVVCEAVI RGETVNKVLK TSVASLVELN MLKVLTGSAI
AG..SLGGFN
HMGRclustalW{arabadopsis1}     GKSVVCEAVI RGEIVNKVLK TSVAALVELN MLKVLAGSAV
AG..SLGGFN
   HMGRclustalW{cucumismel}    GKSVVCEAVI KDEVVRKVLK TSVASLVELN MLKVLTGSAM
AG..ALGGFN
   HMGRclustalW{rubbertre2}    GKSVVCEAII KEEVVKKVLK TDVALLVELN MLKVLAGSAV
AG..ALGGFN
   HMGRclustalW{rubbertre1}    GKSVVCEAII KEEVVKKVLK TNVASLVELN MLKVLAGSAV
AG..ALGGFN
   HMGRclustalW{ camptothec}   GKSVVCEAVI KEEVVKKVLK TNVASLVELN MLKVLTGSAM
AG..ALGGFN
   HMGRclustalW{ arabadops2}   GKHVVCEAFI KAEIVEKVLK TSVEALVELN TLKVLVGSAM
AG..SLGGFN
   HMGRclustalW{chineseham}    GKTVVCEAVI PAKVVREVLK TTTEAMIDVN INKVLVGSAM
```

FIG. 32MM

```
AG..SIGGYN
   HMGRclustalW{chineseha2}   GKTVVCEAVI  PAKVVREVLK  TTTEAMIDVN  INKNLVGSAM
AG..SIGGYN
   HMGRclustalW{syrianhamst}  GKTVVCEAVI  PARVVREVLK  TTTEAMIDVN  INKNLVGSAM
AG..SIGGYN
       HMGRclustalW{     rat} GKTVVCEAVI  PAKVVREVLK  TTTEAMVDVN  INKNLVGSAM
AG..SIGGYN
    HMGRclustalW{    rabbit}  GKTVVCEAVI  PAKVVREVLK  TTTEAMIDVN  INKNLVGSAM
AG..SIGGYN
    HMGRclustalW{     human}  GKSVVCEAVI  PAKVVREVLK  TTTEAMIEVN  INKNLVGSAM
AG..SIGGYN
    HMGRclustalW{     mouse}  GKTVVCEAVI  PAKVVREVLK  TTTEAMVDVN  INKNLVGSAM
AG..SIGGYN
    HMGRclustalW{   xenopus}  GKSVVCEAII  PAKVVREVLK  SSTEALVEVN  INKNFIGSAM
AG..SIGGYN
   HMGRclustalW{sea urchin}   GKSVVCEATV  PAHIVQQVLK  TSASALVDLN  IHKNLVGSAM
AG..SIGGFN
    HMGRclustalW{ cockroach}  GKSVVCEAIV  PADIIKSVLK  TSVQALMDVN  ITKNLIGSAV
AG..SIGGFN
   HMGRclustalW{drosophila}   GKRVVTECTI  SAATLRSVLK  TDAKTLVECN  KLKNMGGSAM
AG..SIGGNN
   HMGRclustalW{dictyostel}   GRSVVCEAMI  TGDVVQRVLK  TNVQALVDLN  IAKNLIGSAM
AG..SIGGFN
   HMGRclustalW{schistosom}   GKSVIAEAHL  SADVLAQVLH  TNAQRLARLT  HSKNWIGSAM
AGCPGMMGCN
   HMGRclustalW{archaeoglo}   .....GEEVV  EGIMLAYAFA  AADPFRCATH  NKGIMNGISA
LM........
   HMGRclustalW{pseudomonas}  TAEFSGEAVI  EGILDAYAFA  AVDPYRAATH  NKGIMNGIDP
LI........
                Consensus     GKSVVCEAVI  PAEVVRKVLK  TTVEALVELN  ILKNLVGSAM  AG--
SLGGFN
                                                                                 K
```

FIG. 32NN

```
                                     951
1000
  HMGRclustalW{methanobac}   AHYANIIGAI FLATGQDEAH IVEGSLGVTI AEERK.....
.....GDLYF
  HMGRclustalW{methanococ}   AHYANIIGAI FLATGQDEAH IVEGSLGITM AEVED.....
.....DGLYF
  HMGRclustalW{halobacter}   AHVANVVAAM FLATGQDEAQ VVEGANAITT AEVQD.....
.....GDLYV
  HMGRclustalW{sulfolobus}   AHFANIVTAI FIATGQDVAQ IVESSSGYTW TEVRG.....
.....EDLYI
  HMGRclustalW{     yeast2}  AHAANLVTAL FLALGQDPAQ NVESSNCITL MKEVD.....
.....GDLRI
  HMGRclustalW{     yeast1}  AHAANLVTAV FLALGQDPAQ NVESSNCITL MKEVD.....
.....GDLRI
  HMGRclustalW{phycomyces}   .......... .......... .......... ..........
..........
  HMGRclustalW{   fusarium}  AHAANIVAAI FLATGQDPAQ VVESANCITI MKNLN.....
.....GALQI
  HMGRclustalW{    candida}  AQAANMVTAV YLALGQDPAQ NVESSNCITL MTETED....
.....GDLKV
  HMGRclustalW{dictyoste2}   AHASNIVTAL YIATGQDPAQ NVESSNCITL MESINGG...
.....KDLYI
  HMGRclustalW{    wheat1}   AHASNIATAL FIATGQDPAQ NVESSQCITM LEAVNEG...
.....KDLHI
  HMGRclustalW{       rice}  AHASNIVTAL FIATGQDPAQ NVESSQCITM LEEVNDG...
.....DDLHI
  HMGRclustalW{       corn}  AHASNIVTAI FIATGQDPAQ NVESSHCITM LEPVNAG...
.....RDLHI
  HMGRclustalW{    wheat3}   AHASNIVTAI FIATGQDPAQ NVESSQCIAM LEAVNDG...
.....KDLHI
  HMGRclustalW{    wheat2}   AHASNIVSAI FIATGQDPAQ NVESSQCITM LEAVNGG...
.....RDLHI
HMGRclustalW{     soybean}   AHASNIVSAI FIATGQDPAQ NVESSHCITM MEAINDG...
.....RDLHI
  HMGRclustalW{rubbertre3}   AHASNMVTAV YIATGQDPAQ NVESSHCITM MEAVNDG...
.....KDLHI
  HMGRclustalW{rosyperiwi}   AHASNIVSAI FIATGQDPAQ NVESSQCITM MEAVNDG...
.....KDLHI
  HMGRclustalW{     tomato}  AHASNIVSAV FIATGQDPAQ NIESSHCITM MEAVNDG...
.....KDLHI
  HMGRclustalW{woodtobacc}   AHASNIVSAV YIATGQDPAQ NIESSHCITM MEAVNDG...
.....KDLHV
  HMGRclustalW{     potato}  AHASNIVSAV YLATGQDPAQ NVESSHCITM MEAVNDG...
.....KDLHV
  HMGRclustalW{     radish}  RHASNIVSAV FLATGQDPAQ NVESSQCITM MEAINDG...
.....KDIHI
HMGRclustalW{arabadopsis1}   AHASNIVSAV FIATGQDPAQ NVESSQCITM MEAINDG...
.....KDIHI
  HMGRclustalW{cucumismel}   AHSSNIVSAI FLATGQDPAQ NVESSHCITM MEPVNNG...
.....RDLHI
  HMGRclustalW{rubbertre2}   AHAGNIVSAI FIATGQDPAQ NVESSHCITM MEAVNDG...
.....KDLHI
  HMGRclustalW{rubbertre1}   AHAGNIVSAI FIATGQDPAQ NVESSHCITM MEAVNDG...
.....KDLHI
  HMGRclustalW{camptothec}   AHASNIVSAV YLATGQDPAQ NVESSHCITM MEAINDG...
.....KDLHV
  HMGRclustalW{arabadops2}   AHSSNIVSAV FIATGQDPAQ NVESSHCMTM ILPDGD....
.....DLHI
  HMGRclustalW{chineseham}   AHAANIVTAI YIACGQDAAQ NVGSSNCITL MEASGPTN..
```

FIG. 3200

```
.....EDLYI
  HMGRclustalW(chineseha2)   AHAANIVTAI YIACGQDAAQ NVGSSNCITL MEASGPTN..
.....EDLYI
  HMGRclustalW(syrianhamst)  AHAANIVTAI YIACGQDAAQ NVGSSNCITL MEASGPTN..
.....EDLYI
     HMGRclustalW(     rat)  LHAANIVTAI YIACGQDAAQ NVGSSNCITL MEASGPTN..
.....EDLYI
   HMGRclustalW(    rabbit)  AHAANYVTAI YIACGQDAAQ NVGSSNCITL MEASGPPN..
.....EDLYI
  HMGRclustalW(       human) AHAANIVTAI YIACGQDAAQ NVGSSNCITL MEASGPTN..
.....EDLYI
  HMGRclustalW(       mouse) AHAANIVTAI YIACGQDAAQ NVGSSNCITL MEASGPTN..
.....EDLYI
   HMGRclustalW(   xenopus)  AHAANIVTAI YIACGQDAAQ NVGSSNCITI MEATGPTY..
.....EDLYI
  HMGRclustalW(sea urchin)   AHAANIVTAI YIATGQDAAQ NIASSNCMTL METRGPKG..
.....GDLYL
  HMGRclustalW( cockroach)   AHAANIVTAI FIATGQDPAQ NVGSSNCMTL MEPWGEDG..
.....KDLYV
   HMGRclustalW(drosophila)  AHAANMVTAV FLATGQDPAQ NVTSSNCSTA MECWAENS..
.....EDLYM
   HMGRclustalW(dictyostel)  AHASNIVTAI FLATGQDCAQ NVESSNCITQ MEACNDG...
.....QDLYI
   HMGRclustalW(schistosom)  AHAANIIAGM FAATGQDLAQ VVDSSSCLTQ LEVDLSD...
.....DSLVA
   HMGRclustalW(archaeoglo)  ...........IATGNDFRA IEAGAHSYAA IGG.YKPLTT
YEVDRKGNLV
  HMGRclustalW(pseudomonas)  ...........VATGNDWRA VEAGAHAYAC RSGHYGSLTT
WEKDNNGHLV
              Consensus      AHAANIVTAI FIATGQDPAQ NVESSNCITM MEAVNDGN-- -----
KDLHI
                                                            D
```

FIG. 32PP

```
                                           1001
1050
   HMGRclustalW{methanobac}      AVNLPDVPLA  TVGGGTGLET  ASECLDIMGV  RGGG......
RVHAFAEIVG
   HMGRclustalW{methanococ}      SVTLPDVPIG  TVGGGTRVET  QKECLEMLGC  YGDN......
KALKFAEIVG
   HMGRclustalW{halobacter}      SVSIASLEVG  TVGGGTKLPT  QSEGLDILGV  SGGGDP.AGS
NADALAECIA
   HMGRclustalW{sulfolobus}      SVTLPSLEVG  TVGGGTRLPT  QKEALSIMGV  YGSGNP.PGS
NAKKLAEIIA
   HMGRclustalW{     yeast2}     SVSMPSIEVG  TIGGGTVLEP  QGAMLDLLGV  RGPHPTEPGA
NARQLARIIA
   HMGRclustalW{     yeast1}     SVSMPSIEVG  TIGGGTVLEP  QGAMLDLLGV  RGPHATAPGT
NARQLARIVA
   HMGRclustalW{phycomyces}      ..........  ..........  ..........  ..........
..........
   HMGRclustalW{   fusarium}     SVSMPSLEVG  TLGGGTILEP  QGAMLDILGV  RGSHPTNPGD
NARRLARIIG
   HMGRclustalW{    candida}     SVSMPSIEVG  TIGGGTILDP  QGSMLELLGV  RG.PADVPGE
NARQLAKIVA
   HMGRclustalW{dictyoste2}      SVTMPSIEVG  TVGGGTHLPA  QSACLDLLKI  RGANLERPGA
NSEQLARVVA
       HMGRclustalW{wheat1}      SVTMPPIEV.  ..........  ..........  ..........
..........
       HMGRclustalW{     rice}   SVTMPSIEVG  TIGGGTCLAS  QAACLNLLGV  KGSNHGSPGA
NAGRLATIVA
           HMGRclustalW{  corn}  SVTMPSIEVG  TVGGGTQLAS  QSACLDLLGV  RGASRDRPGS
NARLLATVVA
       HMGRclustalW{wheat3}      SVTMPPIEV.  ..........  ..........  ..........
..........
       HMGRclustalW{wheat2}      SVTMPPIEV.  ..........  ..........  ..........
..........
   HMGRclustalW{    soybean}     SVTMPSIEVG  TVGGGTQLAS  QSACLNLLGV  KGASKESPGS
NSRLLATIVA
   HMGRclustalW{rubbertre3}      SVSMPSIELG  TVGGGTQLAS  QSACLNLLGV  KGASKDSPGS
NSRLLATIVA
   HMGRclustalW{rosyperiwi}      SVTMPSIEVG  TVGGGTQLAS  QSACLNLLGV  KGASKDSPGA
NSRLLATIVA
   HMGRclustalW{    tomato}      SVTMPSIEVG  TVGGGTQLAS  QSACLNLLGV  KGANREAPGS
NARLLATVVA
   HMGRclustalW{woodtobacc}      SVTMPSIEVG  TVGGGTQLAS  QSACLNLLGV  KGANREVPGS
NARLLATIVA
   HMGRclustalW{    potato}      SVTMPSIEVG  TVGGGTQLAS  QSACLNLLGV  KGANRDAPGS
NARLLATIVA
       HMGRclustalW{radish}      SVTMPSIEVG  TVGGGTQLAS  QSACLNLLGV  KGASKESPGM
NSRRLATIVA
HMGRclustalW{arabadopsis1}       SVTMPSIEVG  TVGGGTQLAS  QSACLNLLGV  KGASTESPGM
NARRLATIVA
   HMGRclustalW{cucumismel}      SVTMPSIEVG  TVGGGTQLAS  QSACLNLLGV  KGASKESPGA
NSRLLATIVA
   HMGRclustalW{rubbertre2}      SVTLPSIEVG  TVGGGTQLAS  QSACLNLLGV  MGACKESPGS
YSRLLATIVA
   HMGRclustalW{rubbertre1}      SVTMPSIEVG  TVGGGTQLAS  QSACLNLLGV  KGANKESPGS
NSRLLAAIVA
   HMGRclustalW{camptothec}      SVTMPSIEVG  TVGGGTQLAS  QSACLNLLGV  KGASKEAPGS
NARLLATIVA
   HMGRclustalW{arabadops2}      SVSMPCIEVG  TVGGGTQLAS  QAACLNLLGV  KGSNNEKPGS
NAQQLARIVA
   HMGRclustalW{chineseham}      SCTMPSIEIG  TVGGGTNLLP  QQACLQMLGV  QGACKDNPGE
NARQLARIVC
```

FIG. 32QQ

```
  HMGRclustalW{chineseha2}    SCTMPSIEIG TVGGGTNLLP QQACLQMLGV QGACKDNPGE
NARQLARIVC
  HMGRclustalW{syrianhamst}   SCTMPSIEIG TVGGGTNLLP QQACLQMLGV QGACKDNPGE
NARQLARIVC
  HMGRclustalW{      rat}     SCTMPSIEIG TVGGGTNLLP QQACLQMLGV QGACKDNPGE
NARQLARIVC
  HMGRclustalW{    rabbit}    SCTMPSIEIG TVGGGTNLLP QQACLQMLGV QGACKDSPGE
NARQLARIVC
  HMGRclustalW{     human}    SCTMPSIEIG TVGGGTNLLP QQACLQMLGV QGACKDNPGE
NARQLARIVC
  HMGRclustalW{     mouse}    SCTMPSIEIG TVGGGTNLLP QQACLQMLGV QGACKDNPGE
NARQLARIVC
  HMGRclustalW{   xenopus}    SCTMPSIEIG TVGGGTNLAP QQACLQMLGV QGASTETPGK
NACQLAQIVC
  HMGRclustalW{sea urchin}    SCTMPSIELG TVGGGTVLPP QSACLQMMDV KGSNIHGSGL
NASQLARIVC
  HMGRclustalW{ cockroach}    SCTMPSIEIG TIGGGTVLPP QAACLDMLGV RGANEMCPGE
NANTLARIVC
  HMGRclustalW{drosophila}    TCTMPSLEVG TVGGGTGLPG QSACLEMLGV RGAHATRPGD
NAKKLAQIVC
  HMGRclustalW{dictyostel}    TVTMPSIEVG TVGGGTSLPA QSACLDIIGV KGSSSSKPGA
NADQLAKTIA
  HMGRclustalW{schistosom}    SVTMPCLEVG TVGGGTRLSG QRACLDLLDL SV.....D.R
PTEHLSRIIA
  HMGRclustalW{archaeoglo}    GTIEIPMAVG VIGGATKVNP LAKISLKILG VNTAEELARV AAAL
  HMGRclustalW{pseudomonas}   GTLEMPMPVG LVGGATKTHP LAQLSLRILG VKTAQALAEI AVAV Consensus       SVTMPSIEVG TVGGGTQLAP QSACLNLLGV KGA-KESPGS
NARQLARIVA
                                     NADH binding domain 2
```

FIG. 32RR

```
                                       1051
1100
    HMGRclustalW(methanobac)   GAVLAGELSL MGALAAGHLA RAHSELGRG. ..........
    HMGRclustalW(methanococ)   AAVLAGELSL LGALAAGHLG KAHQELGR.. ..........
    HMGRclustalW(halobacter)   VGSLAGELSL LSALASRHLS SAHAELGR.. ..........
    HMGRclustalW(sulfolobus)   STVLSGELNL LAALSNKELG KAHAKLGRAM KV........
    HMGRclustalW(    yeast2)   CAVLAGELSL CSALAAGHLV QSHMTHNRK. ..TNKANELP
QPS.......
    HMGRclustalW(    yeast1)   CAVLAGELSL CAALAAGHLV QSHMTHNRKP AEPTKPNNLD
ATDI......
    HMGRclustalW(phycomyces)   .......... .......... .......... ..........
    HMGRclustalW(  fusarium)   AAVLAGELSL CSALAAGHLV RAHMQHNRSA APSRSTTPGS
SHDARLTGHD
    HMGRclustalW(   candida)   SIVLSGELSL VSALAAGHLV QSHMQHNRAA AKK.......
    HMGRclustalW(dictyoste2)   AAVLSGELSL MSALAAGHLV RSHLKHNRKT EAPAPQADTI
SMTHNLPHSD
    HMGRclustalW(    wheat1)   .......... .......... .......... ..........
    HMGRclustalW(      rice)   GSVVAGRALL LAALASGHLV KSHMMYNRSS KDVAK.....
    HMGRclustalW(      corn)   GGVLAGELSL LSALAAGQLV KSHMKYNRSS KDVSS.....
    HMGRclustalW(    wheat3)   .......... .......... .......... ..........
    HMGRclustalW(    wheat2)   .......... .......... .......... ..........
    HMGRclustalW(   soybean)   GSVLAGELSL MSAIAAGQLV NSHMKYNRSS KDVTK.....
    HMGRclustalW(rubbertre3)   GSVLAGELSL MSAIAAGQLV NSHMKYNRSA KDVSK.....
    HMGRclustalW(rosyperiwi)   GSVLAGELSL MSAISAGQLV RSHMKYNRSS KDITN.....
    HMGRclustalW(    tomato)   GSVLAGELSL MSAISSGQLV NSHMKYNRST KDVTK.....
    HMGRclustalW(woodtobacc)   GSVLAGELSL MSAISAGQLV KSHMKYNRST KDVTK.....
    HMGRclustalW(    potato)   GSVLAGELSL MSAISAGQLV KSHMKYNRSI KDISK.....
    HMGRclustalW(    radish)   GAVLAGELSL MSAIAAGQLV RSHMKYNRSS RDISG.....
    HMGRclustalW(arabadopsis1) GAVLAGELSL MSAIAAGQLV RSHMKYNRSS RDISG.....
    HMGRclustalW(cucumismel)   GSVLAGELSL MSAIAAGQLV RSHMKYNRSS RDVSK.....
    HMGRclustalW(rubbertre2)   GSVLAGELSL MSAIAAGQLV KSHMKYNRSS KDVSK.....
    HMGRclustalW(rubbertre1)   GSVLAGELSL MSAIAAGQLV KSHMKYNRSS KDMSK.....
    HMGRclustalW(camptothec)   GSVLAGELSL MSAIAAGQLV NSHMKYNRSN KDVTK.....
    HMGRclustalW(arabadops2)   GSVLAGELSL MSAIAAGQLV KSHMKYNRSS RDIGP.....
    HMGRclustalW(chineseham)   GTVMAGELSL MAALAAGHLV RSHMVHNRSK INLQD.....
```

FIG. 32SS

```
HMGRclustalW{chineseha2}  GTVMAGELSL MAALAAGHLV RSHMVHNRSK INLQD.....
HMGRclustalW{syrianhamst} GTVMAGELSL MAALAAGHLV RSHMVHNRSK INLQD.....
HMGRclustalW{      rat}   GTVMAGELSL MAALAAGHLV RSHMVHNRSK INLQD.....
HMGRclustalW{   rabbit}   GTVMAGELSL MAALAAGHLV KSHMIHNRSK INLQD.....
HMGRclustalW{    human}   GTVMAGELSL MAALAAGHLV KSHMIHNRSK INLQD.....
HMGRclustalW{    mouse}   GTVMAGELSL MAALAAGHLV RSHMVHNRSK INLQD.....
HMGRclustalW{  xenopus}   STVMAGELSL MAALAAGHLV KSHMVHNRSK INLQD.....
HMGRclustalW{sea urchin}  ATVMAGELSL MSALAAGHLV KSHMKHNRSA LNIASPLPSI
DEVATHRRSK
HMGRclustalW{ cockroach}  GTVLAGELSL MSALAAGHLV KSHMRHNRSS VSTSG.....
HMGRclustalW{drosophila}  ATVMAGELSL MAALVNSDLV KSHMRHNRSS IAVNSAN...
HMGRclustalW{dictyostel}  SAVMAGELSL MSALSAGHLM KSHLQYNRAK TN........
HMGRclustalW{schistosom}  GTVLAAELSL MAALDTDDLV KAHMHFNRAK QSTNSHSCSH
STTTDNNDNI
HMGRclustalW{archaeoglo}  ..GLAQNFAA LRALATEGIQ RGHMELHARN LAIMAGATGD
EVDRVVEIMV
HMGRclustalW{pseudomonas} ..GLAQNLGA MRALATEGIQ RGHMALHARN IAVVAGARGD
EVDWVARQLV
             Consensus   GTVLAGELSL MSALAAGHLV KSHMK-NRSS KDVSK----- ------
----
                                                      *      †††
```

FIG. 32TT

```
                                    1101
1152
  HMGRclustalW(methanobac)   ..........  ..........  ..........
  ..........
    HMGRclustalW(methanococ)  ..........  ..........  ..........
  ..........
    HMGRclustalW(halobacter)  ..........  ..........  ..........
  ..........
    HMGRclustalW(sulfolobus)  ..........  ..........  ..........
  ..........
    HMGRclustalW(    yeast2)  ..........  ..NKGPPCKT  SALL......  ..........
  ..........
    HMGRclustalW(    yeast1)  ..........  ..NRLKDGSV  TCIKS.....  ..........
  ..........
    HMGRclustalW(phycomyces)  ..........  ..........  ..........  ..........
  ..........
    HMGRclustalW(   fusarium) QCPRALSVNN  VDERRRYSEV  KAIDE.....  ..........
    HMGRclustalW(    candida) ..........  ..........  ..........  ..........
  ..........
    HMGRclustalW(dictyoste2)  ..........  ..........  ..........  ..........
  ..........
     HMGRclustalW(   wheat1)  ..........  ..........  ..........  ..........
  ..........
     HMGRclustalW(     rice)  .........A  .....AS...  ..........  ..........
  ..........
     HMGRclustalW(     corn)  .........T  .....TATEK  TRQREVDV..  ..........
  ..........
     HMGRclustalW(   wheat3)  ..........  ..........  ..........  ..........
  ..........
     HMGRclustalW(   wheat2)  ..........  ..........  ..........  ..........
  HMGRclustalW(     soybean)  .........I  .....S....  ..........  ..........
    HMGRclustalW(rubbertre3)  .........I  .....TF...  ..........  ..........
  ..........
    HMGRclustalW(rosyperiwi)  .........I  .....ASSQL  ESDS......  ..........
    HMGRclustalW(    tomato)  .........A  .....SS...  ..........  ..........
  ..........
    HMGRclustalW(woodtobacc)  .........A  .....SS...  ..........  ..........
  ..........
    HMGRclustalW(    potato)  ..........  ..........  ..........  ..........
  ..........
     HMGRclustalW(   radish)  .........A  .....TTTT.  ..........  ..........
  ..........
  HMGRclustalW(arabadopsis1)  .........A  .....TTTTT  TTT.......  ..........
  ..........
    HMGRclustalW(cucumismel)  .........L  .....ES...  ..........  ..........
  ..........
    HMGRclustalW(rubbertre2)  .........A  .....AS...  ..........  ..........
  ..........
    HMGRclustalW(rubbertre1)  .........A  .....AS...  ..........  ..........
    HMGRclustalW(camptothec)  .........A  .....SS...  ..........  ..........
  ..........
    HMGRclustalW(arabadops2)  .........S  .....SQVNR  ..........  ..........
  ..........
    HMGRclustalW(chineseham)  ..........  ...LQGTCTK  KSA.......  ..........
  ..........
```

FIG. 32UU

```
HMGRclustalW{chineseha2}    ........... ...LQGTCTK KSA....... ..........
HMGRclustalW{syrianhamst}   ........... ...LQGTCTK KAA....... ..........
HMGRclustalW{       rat}    ........... ...LQGTCTK KAA....... ..........
HMGRclustalW{    rabbit}    ........... ...LEGACTK KAA....... ..........
HMGRclustalW{     human}    ........... ...LQGACTK KTA....... ..........
HMGRclustalW{     mouse}    ........... ...LQGTCTK KAA....... ..........
HMGRclustalW{   xenopus}    ........... ...LPGTCTK KAA....... ..........
HMGRclustalW{sea urchin}    SVDFSALKES SAAAPGTCTA NAS....... ..........
HMGRclustalW{ cockroach}    .........S ...EPSTPAC KS........ ..........
HMGRclustalW{drosophila}    ........NP LNVTVSSCST IS........ ..........
HMGRclustalW{dictyostel}    ........... .......... .......... ..........
HMGRclustalW{schistosom}    SNIYDNHNVA LSSKIPVTDN SDIRESVHSL HVKPFPVKSD
LSVNPEISHY TM
HMGRclustalW{archaeoglo}    RDGKIRLDYA KEVLERLRS. .......... ..........
HMGRclustalW{pseudomonas}   EYHDVRADRA VALLKQKRGQ .......... ..........

Consensus       ----------A ---LQGTCTK KAA------- ----------
----
```

TRANSGENIC PLANTS CONTAINING ALTERED LEVELS OF STEROID COMPOUNDS

TECHNICAL FIELD

The present invention relates to biotechnology with an emphasis on plant biotechnology, and particularly biotechnology affecting the biosynthesis of steroid compounds.

BACKGROUND

Enhancement of the nutritional or health benefits of oils through genetic engineering is being addressed throughout the agricultural community. Several approaches involve manipulation of already present cellular biosynthetic pathways. Steroid biosynthetic pathways are of current interest, particularly for the enhancement of health benefits from food oils.

Several related U.S. patents address increasing sterol accumulation in higher plants. Those patents include U.S. Pat. No. 5,589,619 "Process and Composition for increasing squalene and sterol accumulation in higher plants" (accumulation of squalene in transgenic plants by increasing HMGR activity) and U.S. Pat. No. 5,306,862 "Method and composition for increasing sterol accumulation in higher plants" (increasing HMGR activity to increase plant sterol accumulation—including sterol and cycloartenol, which affects insect resistance—in tobacco, tomato, corn, carrot, soybean, cotton, barley, arabidopsis, guayule and petunia; seeds with elevated sterol/cycloartenol, 7S promoter and CaMV promoters), U.S. Pat. No. 5,365,017 "Method and composition for increasing sterol accumulation in higher plants" (DNA construct with HMGR-CaMV 35S, transgenic plants, hybrid plants, corn, soy, barley, tomato, Arabidopsis), U.S. Pat. No. 5,349,126 "Process and composition for increasing squalene and sterol accumulation in higher plants" (increase in squalene and sterol accumulation by increasing HMGR activity in transgenic tobacco, cotton, soybean, tomato, alfalfa, Arabidopsis, corn, barley, carrot and guayule plants), and EP 486290 (enhancement of squalene and specific sterol.[squalene zymosterol, cholest-7,24-dienol, cholest-5,7,24-trienol] accumulation in yeast by increasing HMGR activity in yeast deficient in enzymes that convert squalene to ergosterol).

In those patents, the amount of a protein exhibiting 3-hydroxy-3-methylglutaryl Coenzyme-A reductase (HMGR) activity is typically increased. HMGR widens a "bottleneck" near the beginning of a biosynthetic path to steroid production, permitting a higher carbon flux through steroid biosynthetic pathways and resulting in increased sterol accumulation.

U.S. Pat. No. 5,480,805 "Composition for modulating sterols in yeast" (enhancement of delta 8-7 isomerase activity-ERG2 enhances accumulation of specific sterols in yeast).

U.S. Pat. No. 5,460,949 "Method and composition for increasing the accumulation of squalene and specific sterols in yeast" (increasing squalene, zymosterol and specific sterols in yeast by increasing HMGR in yeast having decreased erg5 and erg6 activity—Sc and hamster HMGR).

WO 9845457 (SMTI, Erg6 from A.t., corn, yeast; transgenic plants with altered sterol levels_using DNA encoding an enzyme binding a first sterol and producing a second sterol—altered carotenoid, tocopherol, modified FA levels—HMGR, 5α-reductase, geranylgeranyl pyrophosphate synthase, phytoene synthase, phytoene desaturase, isopentenyl diphosphate isomerase).

Acetate is the metabolic precursor of a vast array of compounds vital for cell and organism viability. Acetyl coenzyme A (CoA) reacts with acetoacetyl CoA to form 3-hydroxy-3 methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through the sequential steps of isomerization, condensation and dehydrogenation, IPP is converted to geranyl pyrophosphate (GPP). GPP combines with IPP to form farnesyl pyrophosphate (FPP), two molecules of which are reductively condensed to form squalene, a 30-carbon precursor of sterols.

A key enzyme in sterol biosynthesis is 3-hydroxy-3-methylglutaryl-Coenzyme A reductase (HMG-CoA reductase or HMGR). Schaller et al. (Plant Physiol. 109: 761–770, 1995) found that over-expression of rubber HMGR (hmg1) genomic DNA in tobacco leads to the overproduction of sterol end-products (sitosterol, campesterol and stigmasterol) up to 6-fold in leaves. Further, the excess sterol was stored as steryl-esters in lipid bodies. HMGR activity was increased by 4- to 8-fold.

Sterols are derivatives of a fused, reduced ring system, cyclopenta-[a]-phenanthrene, comprising three fused cyclohexane rings (A, B, and C) in a phenanthrene arrangement, and a terminal cyclopentane ring (D) having the formula (I) and carbon atom position numbering shown below:

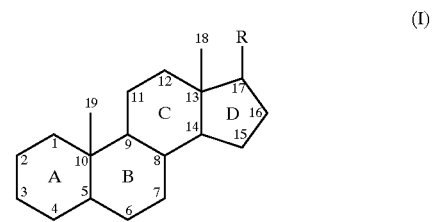

(I)

where R is an 8 to 10 carbon-atom side chain.

In plants, squalene is converted to squalene epoxide, which is then cyclized to form cycloartenol (4,4,14α-trimethyl-9β,19-cyclo-5α-cholest-24-en-3β-ol). Cycloartenol has two methyl groups at position 4, a methyl group at position 14, a methylene bridge between the carbon atoms at positions 9 and 19 that forms a disubstituted cyclopropyl group at those positions, and includes an 8-carbon sidechain of the formula: $CH_3CH(CH_2)_2CH=C(CH_3)_2$. Squalene epoxide can alternatively be converted into pentacyclic sterols, containing five instead of four rings. Exemplary pentacyclic sterols include the phytoalexins and saponins.

Being one of the first sterols in the higher plant biosynthetic pathway, cycloartenol serves as a precursor for the production of numerous other sterols. In normal plants, cycloartenol is converted to predominantly 24-methylene cycloartenol (4,4,14α-dimethyl-9β, 19-cyclo-22,23-dihydro-ergosta-24(28)-en-3-β-ol), cycloeucalenol, (4,14α-trimethyl-9β,19 cyclo-5α-ergosta-24(28)-en-3β-ol), isofucosterol (5α-stigmasta-5-24(28)-dien-3β-ol), sitosterol (5α-stigmasta-5-en-3β-ol), stigmasterol-(stigmasta-5,-22-dien-3β-ol), campesterol (5α-ergosta-5-en-3β-ol), and cholesterol (5α-cholesta-5-en-3β-ol). These transformations are illustrated in FIG. 1.

Although sterols produced by plants, and particularly higher (vascular) plants, can be grouped by the presence or absence of one or more of several functionalities, plant sterols are classified into two general groups herein; i.e., those containing a double bond between the carbon atoms at positions 5 and 6 (delta-5 or Δ5 sterols) and those not containing a double bond between the carbon atoms at positions 5 and 6 (non-delta-5 sterols).

Exemplary naturally-occurring delta-5 plant sterols are isofucosterol, sitosterol, stigmasterol, campesterol, cholesterol, and dihydrobrassicasterol. Exemplary naturally occurring non-delta-5 plant sterols are cycloartenol, 24-methylene cycloartenol, cycloeucalenol, and obtusifoliol. The most abundant sterols of vascular plants are campesterol, sitosterol, and stigmasterol, all of which contain a double bond between the carbon atoms at positions 5 and 6 are classified as delta-5 sterols.

The HMG-CoA reductase enzymes of animals and yeasts are integral membrane glycoproteins of the endoplasmic reticulum. The intact enzyme comprises three regions: a catalytic region containing the active site of the enzyme; a membrane binding region anchoring the enzyme to the endoplasmic reticulum; and a linker region joining the catalytic and membrane binding regions of the enzymes. The membrane binding region occupies the amino-terminal (N-terminal) portion of the intact protein, whereas the catalytic region occupies the carboxy-terminal (C-terminal) portion of the protein, with the linker region constituting the remaining portion. M.E. Basson et al., *Mol. Cell Biol.*, 8(9):3797–3808 (1988).

The activity of HMG-CoA reductase in animals and yeasts is known to be subject to feedback inhibition by sterols. Such feedback inhibition requires the presence of the membrane binding region of the enzyme. See, e.g., G. Gil et al, *Cell*, 41:249–258 (1985); M. Bard and J. F. Downing, *J. Gen. Microbiol.*, 124:415–420 (1981).

Given that mevalonate is the precursor for sterols and other isoprenoids, it might be expected that increases in the amount or activity of HMG-CoA reductase would lead to increases in the accumulation of both sterols and other isoprenoids.

In mutant strains of the yeast *Saccharomyces cerevisiae* (*S. cerevisiae*) having abnormally high levels of HMG-CoA reductase activity, the production of two sterols, 4,14-dimethylzymosterol and 14-methylfucosterol is markedly increased above normal. Downing, et al., *Biochem. Biophys. Res. Comm.*, 94(3): 874–979 (1980).

When HMG-CoA reductase activity was increased by illumination in non-photosynthetic microorganisms, isoprenoid (carotenoid), but not sterol (ergosterol), synthesis was enhanced. Tada, et al., *Plant and Cell Physiology*, 23(4):615–621 (1982).

WO 9703202 discloses a method for identifying agents modulating sterol biosynthesis using a yeast acetoacetyl CoA thiolase (ERG10) gene linked to a reporter system to evaluate compounds, such as lovastatin and other HMG-CoA synthase inhibitors, that affect cholesterol biosynthesis.

U.S. Pat. No. 5,668,001 teaches a recombinant avian HMG-CoA synthase preparation useful for evaluating drugs that inhibit cholesterol biosythesis.

JP 09121863 discloses a plant with increased 3-hydroxy-3-methyl glutaryl coenzyme A reductase (HMGR) activity as a result of increasing the expression of a mutant protein kinase gene that regulates expression of the HMGR gene. The increased HMGR activity increases squalene, zymosterol, cholesta-7,24-dienol and cholest-5,7,24-trenol accumulation in yeast with ERG5 and ERG6 mutants.

EP 480730 "Plant-sterol accumulation and pest resistance-by increasing copy number of 3-hydroxy-3-methyl glutaryl coenzyme-A reductase gene in tobacco, tomato and corn.

WO 9913086 "Human Delta 7-sterol reductase polypeptide-useful for diagnosis or treatment of genetic defects e.g. hereditary Smith-Lemli-Opitz syndrome" teaches making and using the recombinant polypeptide with humans.

Chappell et al. U.S. Pat. No. 5,589,619 teaches that transformation of higher plants with truncated HMG-CoA reductase enhanced the production of squalene, cycloartenol and certain sterols, particularly compounds having unsaturations at the 5-position. Several intermediate sterols as are shown in FIG. 1 were also produced. It would be beneficial if the production of sitosterol and stigmasterol could be enhanced while lessening the accumulation of the intermediate sterols. The present invention provides avenues for enhancing production of sitosterol and stigmasterol and lessening the accumulation of the intermediate sterols.

Gonzalez et al. (Abstract of poster at Third Terpnet Meeting of the European Network on Plant Isoprenoids, May 29–30, 1997, Poitiers, France) over-expressed the Arabidopsis HMGR cDNA (hmg1 and hmg2) and found sterol overproduction with hmg1 only. They used two forms of the hmg1 gene, a full-length form and a truncated form containing only the catalytic domain. HMGRs have three domains, an N-terminal membrane spanning domain, a short linker domain, and a C-terminal catalytic domain. In this case the transgenic plants were also Arabidopsis. The difference between the full-length and truncated forms was a greater accumulation of pathway intermediates in the case of the truncated form. More importantly, the intermediates demonstrated as accumulating were cycloartenol, 24-methylenecycloartanol and obtusifoliol.

Finally, U.S. Pat. Nos. 5,365,017 and 5,306,862, both assigned to Amoco Corp., disclose a method for increasing sterol accumulation in plants by increasing the copy number of a gene having HMG-CoA reductase activity. These inventions disclose a method using hamster truncated HMGR that consisted of the catalytic domain and the linker domain. According to the claims the linker domain was essential for activity. They also demonstrated a greater accumulation of pathway intermediates such as cycloartenol.

BRIEF SUMMARY

The present invention relates to transgenic plants and their progeny having improved nutritional characteristics. More particularly, the present invention relates to transgenic plants and their progeny, the storage organs (e.g. seed, fruit and vegetable parts) of which contain modified levels of steroid compounds, such as (i) elevated levels of beneficial phytosterols (e.g., sitosterol), phytostanols (e.g., sitostanol), and esters thereof, relative to an otherwise identical plant transformed only with a truncated HMG-CoA reductase gene or a wild-type plant, and (ii) reduced levels of steroid pathway intermediate compounds (e.g. one or more of squalene, cycloartenol, 24-methylene cycloartenol, obtusifoliol, stigmasta-7-enol and campesterol) in their storage organs relative to an otherwise identical transgenic plant transformed only with a truncated HMG-CoA reductase gene. Nucleic acid sequences encoding enzymes that affect the biosynthesis and accumulation of steroid compounds in plants (HMG-CoA reductase and a steroid pathway enzyme), and methods for using these sequences to produce such transgenic plants, are also provided. These methods comprise, for example, introducing into cells nucleic acid sequences encoding enzymes that affect the levels of accumulated steroid pathway end products.

The present invention contemplates a recombinant construct or a recombinant vector that contains 2 DNA sequences. The first encodes a polypeptide exhibiting 3-hydroxy-3-methylglutaryl-Coenzyme A (HMG-CoA) reductase activity. The second DNA sequence encodes a polypeptide exhibiting the activity of another steroid pathway enzyme. Each polypeptide-encoding DNA sequence is operably linked in the 5' to 3' direction to a promoter and a transcription termination signal sequence independent of the other sequence. The promoter is located upstream and the termination sequence downstream of each polypeptide-encoding DNA sequence. The second DNA sequence encoding a steroid pathway enzyme can code for a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. It is contemplated that HMG-CoA reductase and the steroid pathway enzyme activity comes from a mutant or truncated form of those enzymes, such as a truncated HMG-CoA reductase lacking the transmembrane region while retaining a functional catalytic domain. Examples of such preferred HMG CoA reductases include the truncated rubber and Arabidopsis HMG CoA reductases disclosed herein.

Preferably, the regulatory function of a promoter is substantially unaffected by cellular levels of squalene such as the CaMV 35S promoter. In one aspect, a promoter is seed-specific. In another aspect, a promoter is derived from a species in a different order from a host cell. In another aspect, the HMG-CoA reductase or steroid pathway enzymes is from a species in a different order from the order that of the host cell. The invention contemplates a construct or recombinant vector having more than one DNA sequence encoding a steroid pathway enzyme that do not have to be under the control of the same promoter. Preferably, a recombinant vector is a plant expression vector.

In another aspect of the invention, a transformed host cell comprises a recombinant construct or vector as described above. Preferably, a host cell is plant cell, preferably that plant cell is from canola, soybean, corn, maize, tobacco, cotton, rape, tomato or alfalfa. The invention contemplates a host cell in a cell culture, plants derived from transformed host cells, and storage organs (seeds, fruits and vegetable parts) from transgenic plants.

In addition to contemplating transgenic plants and seeds, the invention contemplates transgenic plant seeds capable of germinating into a transgenic plant and mutants, recombinants, genetically engineered derivatives thereof and hybrids derived therefrom. The plant over-accumulates steroid pathway products relative to a native, non-transgenic plant of the same strain, wherein said mutants, recombinants, genetically engineered derivatives thereof and hybrids derived therefrom maintain the ability to over-accumulate steroid pathway products.

The invention contemplates a process of increasing the formation of steroid pathway products in a transformed host cell as compared to an otherwise identical non-transformed host cell. Contemplated processes use the described recombinant constructs and vectors to transform host cells, then growing the host cells or regenerating transgenic plants therefrom.

In one aspect of the invention, the genome of a contemplated plant, its progeny, seeds or cell culture, comprises introduced DNA encoding an HMG-CoA reductase activity and introduced DNA encoding a steroid pathway enzyme that is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. The storage organs of such a plant contain an elevated level of total accumulated sterol, compared to storage organs of an otherwise identical plant, the genome of which does not comprise said introduced DNA. Further, the storage organs of the plant contain a reduced level of squalene, cycloartenol, 24-methylene cycloartenol, obtusifoliol, stigmasta-7-enol, or campesterol compared to the seeds of an otherwise identical plant or a plant comprising an introduced DNA encoding an HMG-CoA reductase enzyme.

The invention contemplates a method of producing a plant that accumulates an elevated level of sterol pathway products compared to a corresponding plant comprising no introduced DNA encoding a peptide, polypeptide, or protein that affects the biosynthesis and accumulation of a sterol pathway product, comprising sexually crossing plants to arrive at a plant comprising nucleic acid encoding an HMG CoA reductase and a steroid pathway enzyme, including crosses with a nurse cultivar. The plants, including apomictic plants, uniform populations of the plants and their seeds and parts other than seeds are contemplated.

Another aspect of the invention is oils containing at least one sterol pathway product, extracted from the seeds of a contemplated plant. Preferably sitosterol, at least one sitosterol ester, or mixtures thereof, comprise at least about 57% by weight of the total sterol compounds of a contemplated oil. Preferably sitosterol, that at least one sitosterol ester, or mixtures thereof, comprise at least about 0.08% of the dry weight of a contemplated seed. Preferably, the oil has a reduced amount of squalene, cycloartenol, 24-methylene cycloartenol, obtusifoliol, stigmasta-7-enol, campesterol, or combinations thereof, compared to oil from a corresponding transgenic plant that does not contain introduced DNA encoding a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixture thereof; wherein the reduction is in the range of from about 10% to about 100%.

Sitosterol ester compositions derived from transgenic plants of the present invention, their progeny or their seeds are also contemplated, preferably wherein an esterifying fatty acid has 2 to 22 carbon atoms in the main chain.

A further aspect of the invention is cholesterol-lowering compositions comprising contemplated oils and sitosterol ester compositions. Another further aspect of the invention is foods, food ingredients, or food compositions comprising contemplated oils.

Still further, the invention contemplates pharmaceutical compositions comprising a cholesterol-lowering effective amount of a contemplated oil, and a pharmaceutically acceptable carrier, excipient, or diluent.

A method of lowering the plasma concentration of low density lipoprotein cholesterol is contemplated, comprising orally administering to a human or animal subject an effective amount of an above composition. Also contemplated is a method of treating or preventing an elevated plasma concentration of low-density lipoprotein cholesterol, comprising orally administering to a human or animal subject an effective amount of a contemplated composition.

A related aspect of the invention is a method of making a food additive composition, comprising obtaining oil containing a sterol pathway product compound from seed of a contemplated transgenic plant and mixing the oil with an edible solubilizing agent, an effective amount of a dispersant, and optionally, an effective amount of an antioxidant.

Novel forms of two sterol pathway enzymes and the nucleic acids that encode them are disclosed: an Arabidopsis enzyme having nucleic acid similarity to a squalene epoxidase, and an Arabidopsis enzyme having nucleic acid similarity to an obtusifoliol C14α-demethylase enzyme. Thus, the invention contemplates an isolated DNA molecule having a nucleotide sequence of disclosure SEQ ID NO: 4, 6, 8, 10, 14, 15, 17 or the complements thereof. Also contemplated is a nucleotide sequence that hybridizes to the nucleotide sequence of SEQ ID NO:4, 6, 8, 10, 14, 15, 17 or their complements under a wash stringency equivalent to 0.5X SSC to 2X SSC, 0.1% SDS, at 55–65° C., and that encode a polypeptide having squalene epoxidase or obtusifoliol C14α-demthylase enzymatic activity. Preferably, that enzymatic activity is substantially similar to that of a disclosed squalene epoxidase or obtusifoliol C14α-demethylase, respectively. By substantially similiar is meant having enzymatic activity differing from that of the disclosed enzymes by about 30% or less, preferably by about 20% or less, and more preferably by about 10% or less when assayed by standard enzymatic assays. Also contemplated is a nucleotide sequence encoding the same genetic information as said nucleotide sequence of SEQ ID NO: 4, 6, 8, 10, 14, 15, 17 or their complements or that hybridize as described above, but which is degenerate in accordance with the degeneracy of the genetic code. Recombinant constructs, vectors and transformed host cells comprising the novel isolated and purified nucleic acid sequences are also contemplated. In one embodiment, the vector is a plant vector and the host cell is a plant cell. Methods of producing the disclosed squalene epoxidase or obtusifoliol C14α-demethylase enzymes are also contemplated comprising culturing a transformed host cell for a time and under conditions conductive to the production of the squalene epoxidase or obtusifoliol C14α-demethylase enzyme, and recovering the produced squalene epoxidase or obtusifoliol C14α-demethylase enzyme.

Yet another aspect provides any of the above described transformed host cells, further comprising a recombinant construct or expression vector encoding a tocopheral synthesis pathway enzyme, and in particular, S-adenosylmethionine-dependent α-tocopherol methyltransferase. Also included are plants, seeds and storage organs comprising the transformed host cells.

Another aspect provides, a process of increasing the formation of steroid pathway products and tocopherols in a transformed host cell as compared to an otherwise identical non-transformed host cell comprising (1) transforming a host cell with a recombinant vector comprising (a) as operably linked components in the 5' to 3' direction, a promoter, a DNA sequence encoding a first polypeptide having 3-hydroxy-3-methylglutaryl-Coenzyme A reductase enzyme activity, and a transcription termination signal sequence; and (b) as operably linked components in the 5' to 3' direction, a promoter, a DNA sequence encoding at least one polypeptide having steroid pathway enzyme activity selected from the group consisting of squalene epoxidase enzyme activity, sterol methyl transferase I enzyme activity, sterol C4-demethylase enzyme activity, obtusifoliol C14α-demethylase enzyme activity, sterol C5-desaturase enzyme activity, and sterol methyl transferase II enzyme activity, and a transcription termination signal sequence; (2) transforming the host cell of (1) with a recombinant vector comprising as operably linked components, a promoter, a DNA sequence encoding a tocopherol synthesis pathway enzyme, and a transcription termination sequence; and (3) regenerating said transformed plant cell into said transgenic plant.

BRIEF DESCRIPTION OF THE DRAWINGS

These and other features, aspects, and advantages of the present invention will become better understood with regard to the following description, appended claims and accompanying figures where:

confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD (3")) conferring resistance to spectinomycin and streptomycin; Right Border: right border sequence of T-DNA essential for integration into Agrobacterium; P-e35S: enhanced cauliflower mosaic virus promoter; rubber cHMGR1: cDNA sequence encoding catalytic domain without linker region of rubber HMGR1; E9 3': 3' end of pea rbcS E9 gene.

Figure 21:
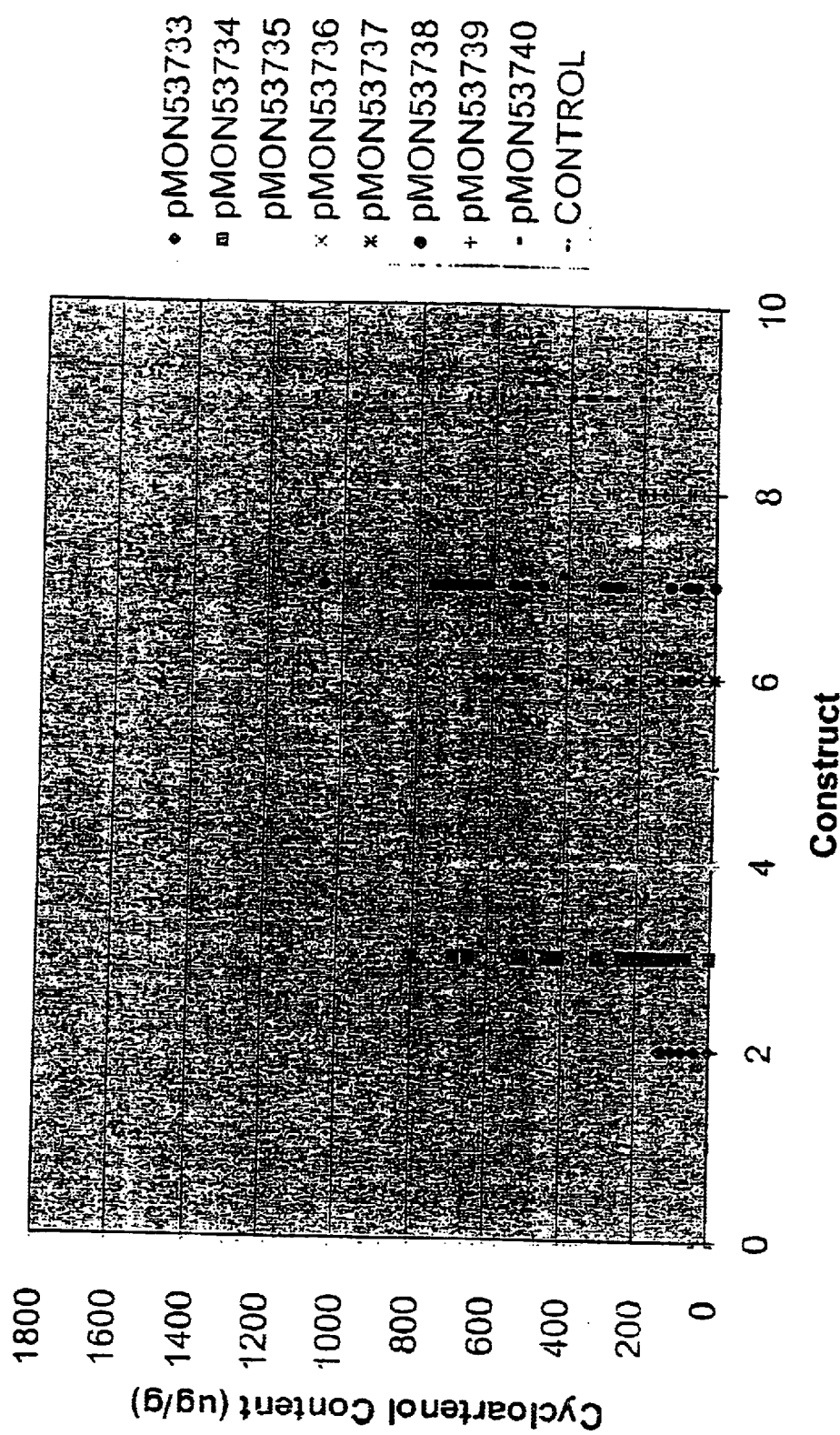

FIG. 21 is a graph comparing the cycloartenol content in micrograms of steroid compound per gram of seeds analyzed in transgenic Arabidopsis plants transformed with pMON53733 through pMON53740 compared to control plants.

Figure 22:
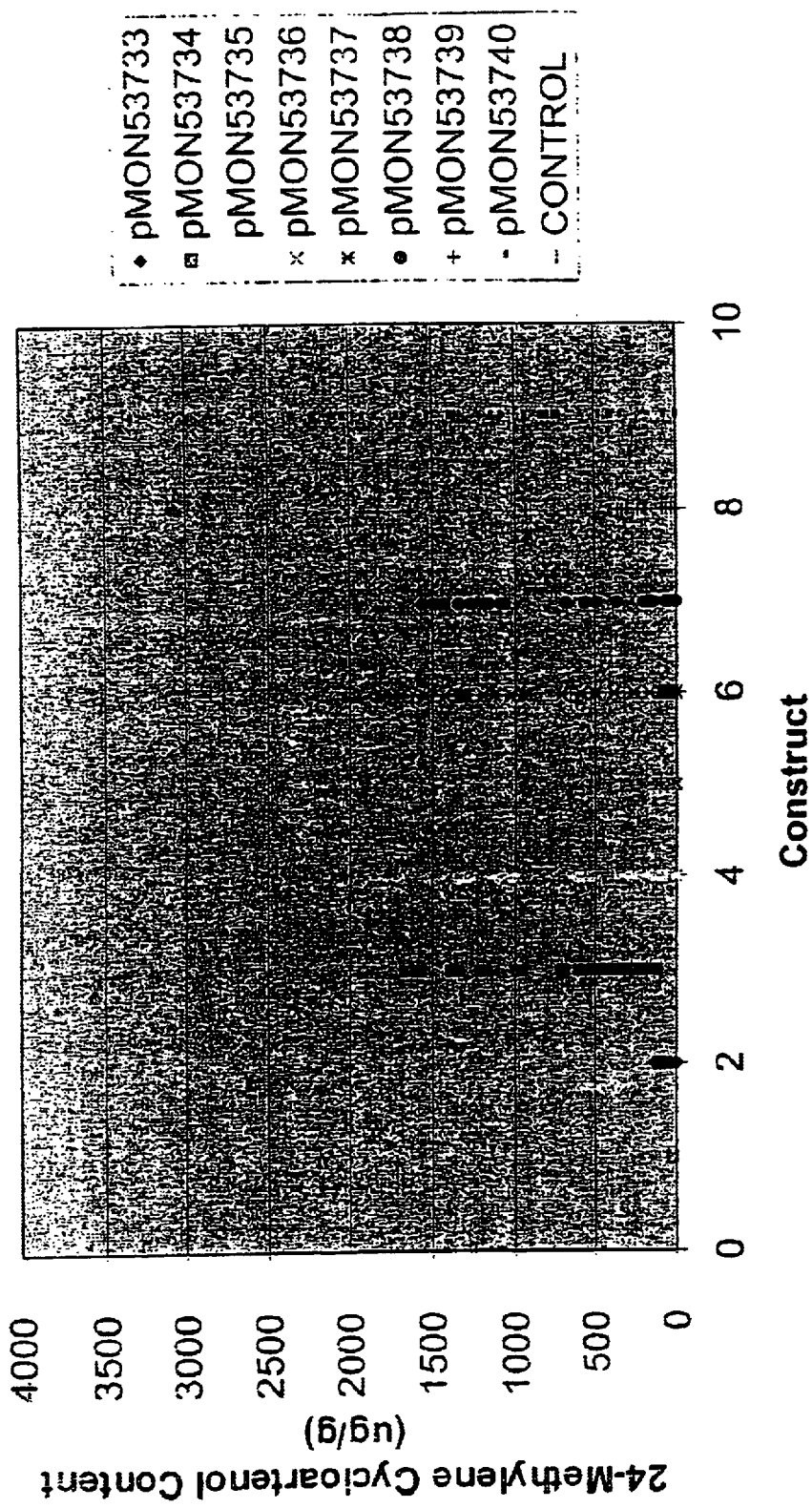

FIG. 22 is a graph comparing the 24-methylene cycloartenol content in micrograms of steroid compound per gram of seeds analyzed in transgenic Arabidopsis plants transformed with pMON53733 through pMON53740 compared to control plants.

Figure 23:
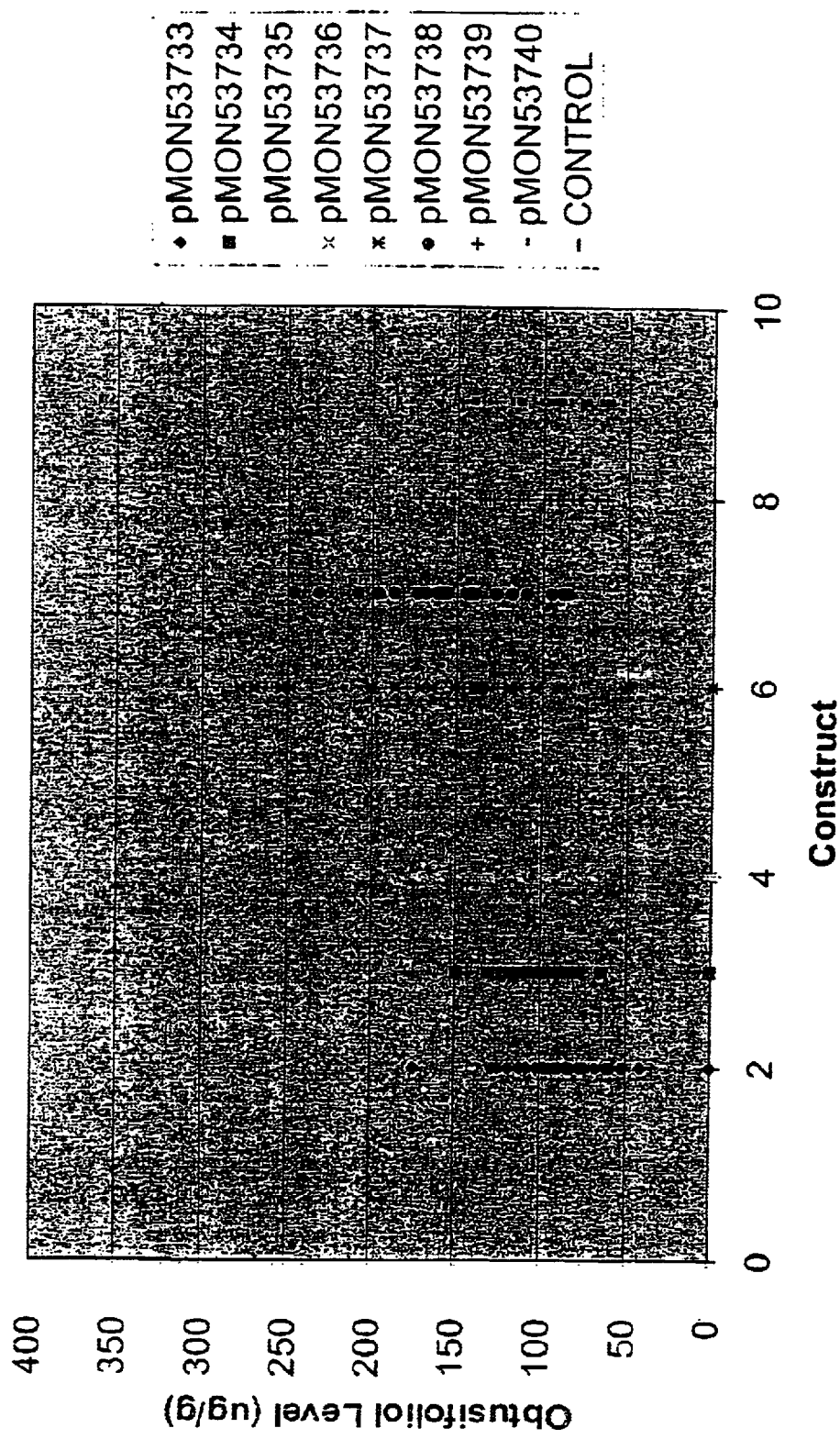

FIG. 23 is a graph comparing the obtusifoliol content in micrograms of steroid compound per gram of seeds analyzed in transgenic Arabidopsis plants transformed with pMON53733 through pMON53740 compared to control plants.

Figure 24:
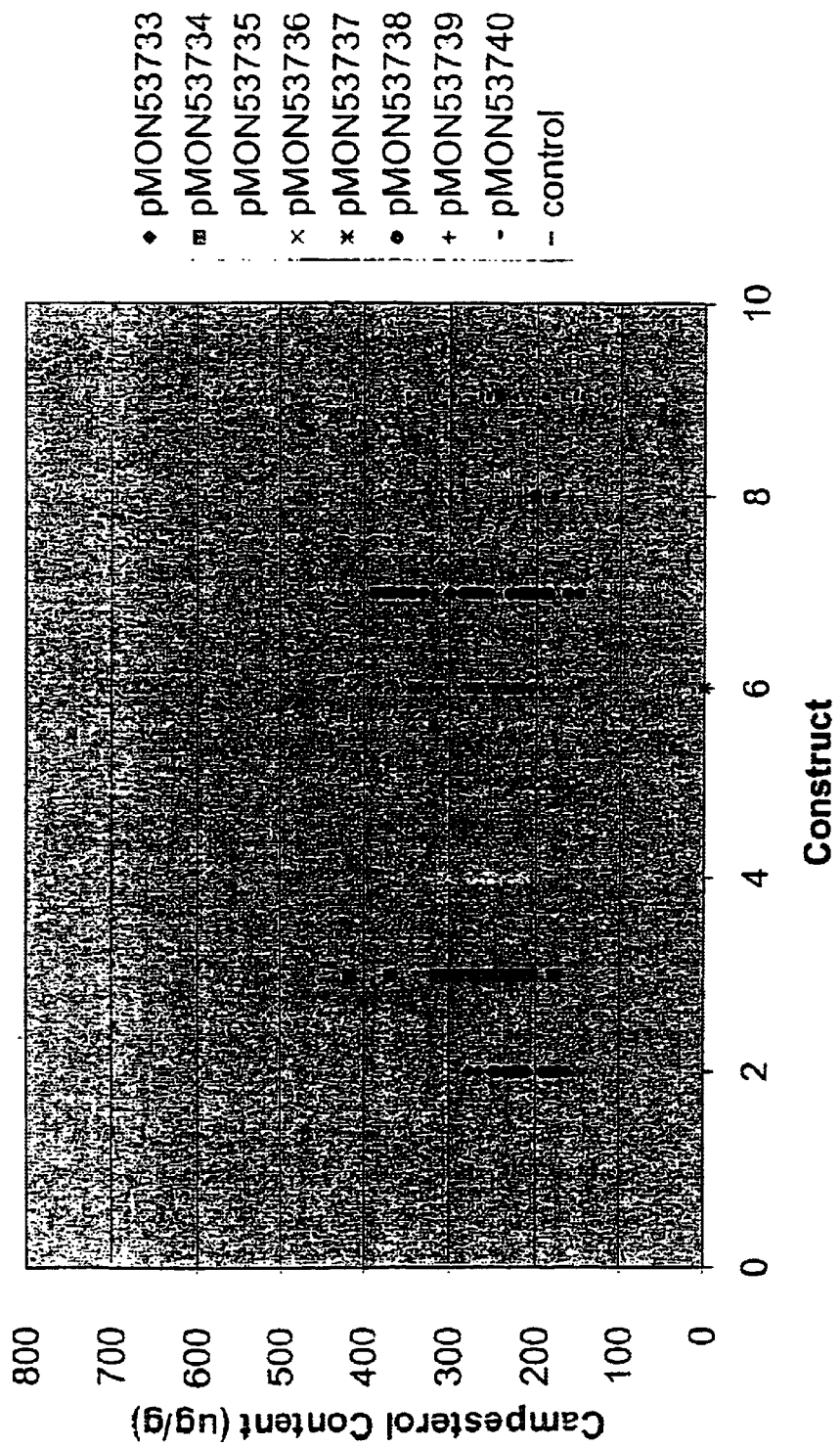

FIG. 24 is a graph comparing the campesterol content in micrograms of steroid compound per gram of seeds analyzed in transgenic Arabidopsis plants transformed with pMON53733 through pMON53740 compared to control plants.

Figure 25:
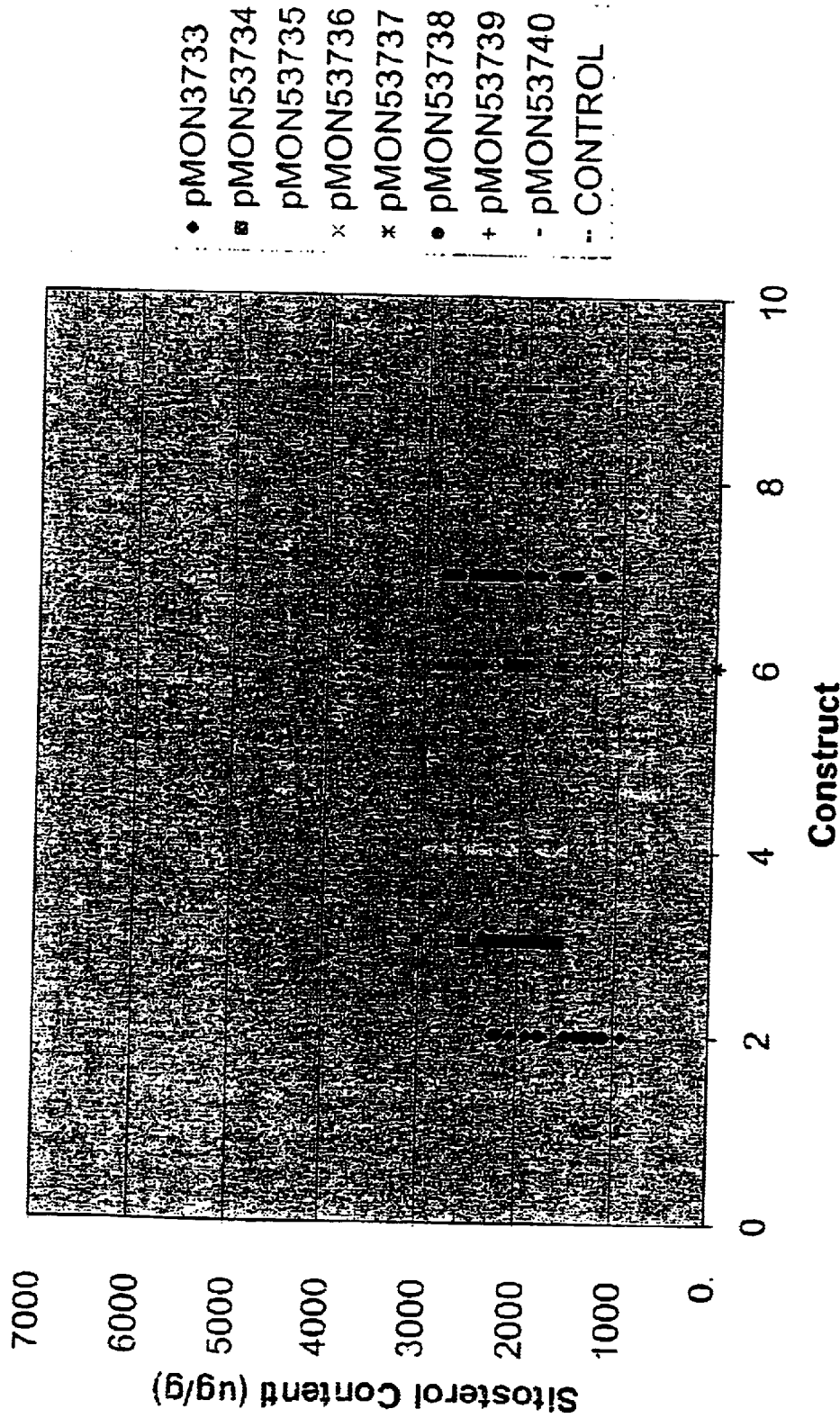

FIG. 25 is a graph comparing the sitosterol content in micrograms of steroid compound per gram of seeds analyzed in transgenic Arabidopsis plants transformed with pMON53733 through pMON53740 compared to control plants.

Figure 26:
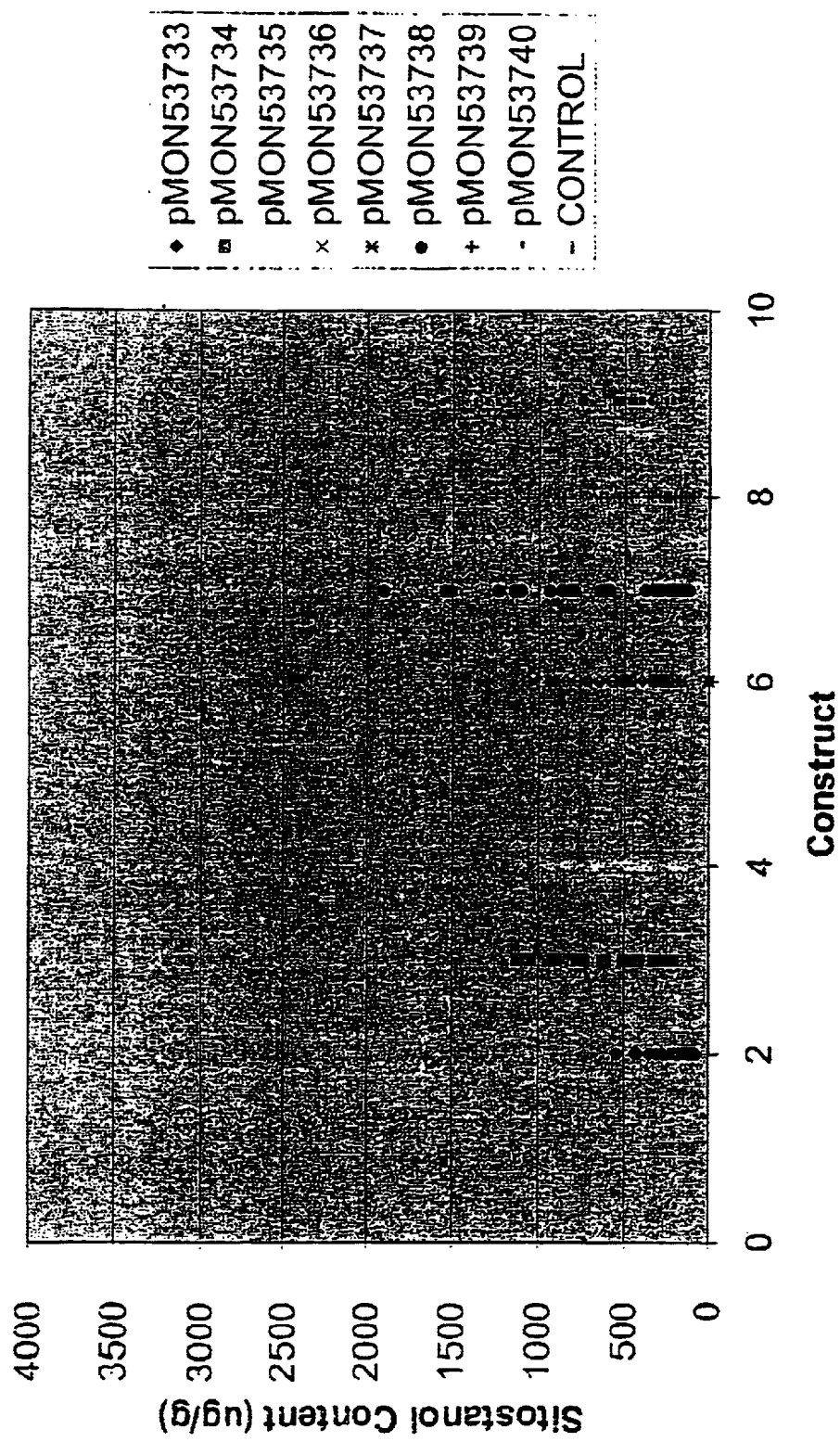

FIG. 26 is a graph comparing the sitostanol content in micrograms of steroid compound per gram of seeds analyzed in transgenic Arabidopsis plants transformed with pMON53733 through pMON53740 compared to control plants.

Figure 27:
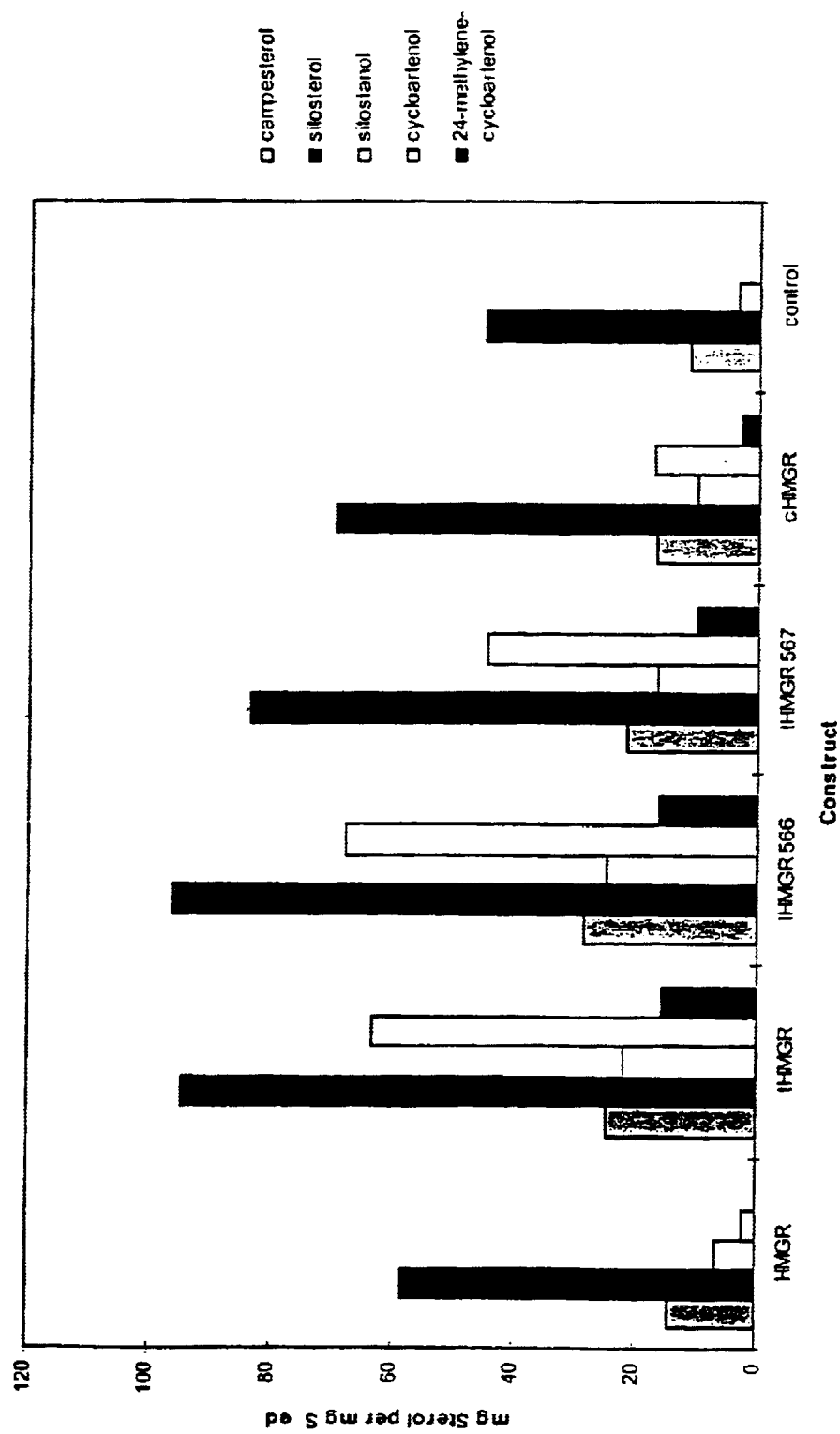

FIG. 27 is a sterol profile (histogram) of transgenic Arabidopsis harboring different forms of rubber HMGR.

Figure 28:
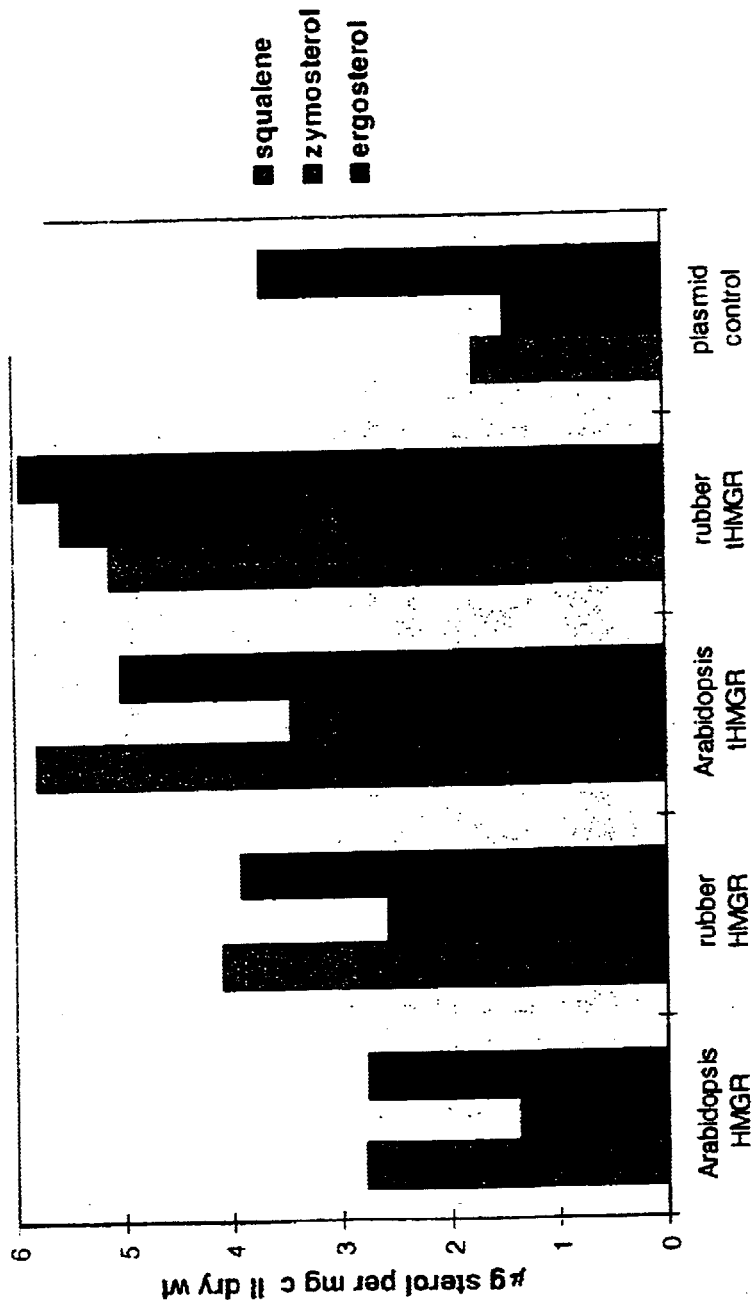

FIG. 28 is a graph of the squalene, zymosterol and erogosterol content in micrograms of sterol per milligram of cell dry weight from HMGR constructs in yeast HMGR1 knockout mutants for constructs having full length and truncated HMG CoA reductase (HMGR) sequences. The truncated sequences contain substantial portions of the catalytic region but lack the linker region and the transmembrane region of HMGR. These sequences are derived from Arabidopsis and rubber plants.

FIG. 29 is a map showing the structure of construct pMON43842. pMON43842 is a yeast expression vector carrying cDNA encoding Arabidopsis putative obtusifoliol C14α-demethylase (AC002329) in sense orientation driven by the p423Gal1 promoter. Sc.His3: HIS3 region from *Saccharomyces cerevisiae* encoding imidazoleglycerol-phosphate dehydratase for histidine synthesis; Ori-f1: bacteriophage f1 origin of replication; LAC: contains partial lacI coding sequence, promoter Plac, promoter Pt7, promoter Pt3, KS polylinker, and partial lacZ coding sequence; lacZ: partial coding sequence for beta-d-galactosidase or lacZ protein; T-Sc.Cyc1: a terminator from Cyc1- iso-1-cytochrome c from *Saccharomyces cerevisiae* to terminate transcription; obtus. C14α.demethylase (AC002329): cDNA encoding Arabidopsis putative obtusifoliol C14α-demethylase; P-Sc.Gal1: a promoter from Gal1- galactokinase of *Saccharomyces cerevisiae* to direct expression with galactose induction; LacZ-alpha: partial coding sequence for beta-d-galactosidase or lacZ protein; Ori-pUC: minimum sequence required for a functional origin of replication, sequence downstream of this region is known to affect copy number when expressed in bacteria; AMP: contains the P3 promoter and the beta-lactamase coding sequence, conferring resistance to ampicillin, penicillin, and carbenicillin; Sc.2 micron: 2 micron origin of replication.

FIG. 30 is a map showing the structure of construct pMON43843. pMON43843 is a yeast expression vector carrying cDNA encoding Arabidopsis putative squalene epoxidase 1 (ATA506263) in sense orientation driven by the p423Gal1 promoter. Sc.His3: HIS3 region from *Saccharomyces cerevisiae* encoding imidazoleglycerol-phosphate dehydratase for histidine synthesis; Ori-f1: bacteriophage f1 origin of replication; LAC: contains partial lacI coding sequence, promoter Plac, promoter Pt7, promoter Pt3, KS polylinker, and partial lacZ coding sequence; lacZ: partial coding sequence for beta-d-galactosidase or lacZ protein; T-Sc.Cyc1: a terminator from Cyc1- iso-1-cytochrome c from *Saccharomyces cerevisiae* to terminates transcription; Squalene epoxidase 1 (ATA506263): cDNA encoding Arabidopsis putative squalene epoxidase 1 (ATA506263); P-Sc.Gal1: a promoter from Gal1- galactokinase of *Saccharomyces cerevisiae* to direct expression with galactose induction; LacZ-alpha: partial coding sequence for beta-d-galactosidase or lacZ protein; Ori-pUC: minimum sequence required for a functional origin of replication, sequence downstream of this region is known to affect copy number when expressed in bacteria; AMP: contains the P3 promoter and the beta-lactamase coding sequence, conferring resistance to ampicillin, penicillin, and carbenicillin; Sc.2 micron: 2 micron origin of replication.

FIG. 31 is a map showing the structure of construct pMON43844. pMON43844 is a yeast expression vector carrying cDNA encoding Arabidopsis putative squalene epoxidase 1 (ATA304243) in sense orientation driven by the p423Gal1 promoter. Sc.His3: HIS3 region from *Saccharomyces cerevisiae* encoding imidazoleglycerol-phosphate dehydratase for histidine synthesis; Ori-f1: bacteriophage f1 origin of replication; LAC: contains partial lacI coding sequence, promoter Plac, promoter Pt7, promoter Pt3, KS polylinker, and partial lacZ coding sequence; lacZ: partial coding sequence for beta-d-galactosidase or lacZ protein; T-Sc.Cyc1: a terminator from Cyc1- iso-1-cytochrome c from *Saccharomyces cerevisiae* to terminate transcription; Arab. squalene epoxidase 1 (ATA304243): cDNA encoding Arabidopsis putative squalene epoxidase 1 (ATA304243); P-Sc.Gal1: a promoter from Gal1- galactokinase of *Saccharomyces cerevisiae* to direct expression with galactose induction; LacZ-alpha: partial coding sequence for beta-d-galactosidase or lacZ protein; Ori-pUC: minimum sequence required for a functional origin of replication, sequence downstream of this region is known to affect copy number when expressed in bacteria; AMP: contains the P3 promoter and the beta-lactamase coding sequence, conferring resistance to ampicillin, penicillin, and carbenicillin; Sc.2 micron: 2 micron origin of replication.

FIG. 32 is a comparision of known HMG CoA reductase amino acid sequences. ClustalW alignment of forty-three non-redundant HMG-CoA reductase sequences to represent archaebacterial, eubacterial, fungal, plant and animal groups. The putative functional domains in the alignment marked as described below are based on the three dimnensional structure of *Pseudomonas mevalonii* HMGR (Lawrence et al., 1995, Science 268:1758): boxed-HMGCoA binding domain, light shade-NAD(H) binding domain, underlined consensus-domains involved in catalysis, * underneath consensus and boldface-key histidine residue involved in catalysis. The putative phosphorylation site residues are marked with ‡ and boldface, and are located at the C-terminal region of the protein, adjacent to a highly conserved arginine, marked with † and boldface. Also indicated are the conserved Glu (E), Lys (K), and Asp (D) residues, marked by E, K, and D, respectively. These residues are thought to be critical in catalysis, based on the crystal structure (Tabernero et al., 1999; PNAS 96(13): 7167–71).

Appendices A through C show SEQ ID Nos: 1 through 3, respectively. Appendices D through G show SEQ ID Nos 20 thorough 23, respectively.

DETAILED DESCRIPTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

We have expressed the full-length forms of the rubber and Arabidopsis HMGRs driven by seed-specific promoters in transgenic canola and soybean. We have demonstrated sterol over-production up to 2–4 fold higher in seeds from these transgenic plants. We also demonstrated a higher accumulation of pathway intermediates in soybean than canola. These results were disclosed in PCT publication WO 00/61771. However, we have expressed a truncated form of the Arabidopsis hmg1 without the linker and membrane spanning domains in Arabidopsis and soybean. The results in Arabidopsis were similar to that demonstrated by Gonzalez et al. (1997) and we compared the sterol profiles of our transgenic plants with those produced by Gonzalez et al., using our methods to show they are comparable. We found the same types of pathway intermediates accumulating. However, in soybean seeds we have demonstrated the accumulation of squalene to a very high level (~3 mg/g seed which is around 100-fold higher than in nontransgenic controls). This is an unexpected result not disclosed or suggested in the prior art. Squalene is a precursor for sterols and in soybean it appears that there is a "bottleneck" in the further conversion of this precursor to sterols. Thus, it appears that there could be additional ways of over-producing sterols in soybean to levels greater than 10-fold which would include combining a truncated form of HMGR with other genes coding for enzymes down-stream of squalene.

This opens the potential to combine other genes such as squalene epoxidase for further enhancing the levels of desirable sterols. Such a combination has not been disclosed or suggested in the prior art. Squalene expoxidase catalyzes the addition of oxygen to squalene which is a 30-carbon linear isoprenoid chain thus allowing for cyclization to form cycloartenol. Additional enzymes downstream that can be also be manipulated are sterol methyltransferase 1, C-4 demethylase, C-14 demethylase, sterol methytransferase 2, and C-5 desaturase that would all deplete other pathway intermediates shown to accumulate in soybeans. By using such strategies it is possible to convert all of the squalene and other intermediates to end sterols such as sitosterol, stigmasterol and campesterol. Thus, sterol level in soybean oils can be elevated from 0.3% up to 3.5%. Expression of the full-length rubber HMGR in soybeans results in a sterol level increase up to 2.7%.

Enhancement of 3-hydroxy-3-methylglutaryl-CoA reductase (HMG Co-A reductase) activity in certain cells results in increased sterol biosynthesis. See, e.g. Chappell, U.S. Pat. No. 5,589,619. The present discovery further contemplates an increase of steroid pathway end products such as Δ5 sterols and their stanol counterparts with a decreased accumulation of certain steroid pathway intermediates by also enhancing various specific steroid pathway enzyme activities, such that more of the steroid pathway intermediate compounds are converted to steroid pathway end products.

DNA sequences encoding squalene epoxidases are useful for removal of squalene accumulation, genes encoding sterol methyl transferase I enzymes are useful for removal of cylcoartenol accumulation, genes encoding sterol C4-demethylase are useful for removal of 24-methylene cycloartenol accumulation, genes encoding obtusifoliol C14α-demethylases are useful for removal of accumulation of obtusifoliol, genes encoding sterol C5-desaturases are useful for removal of stigmasta-7-enol accumulation, and genes encoding sterol methyl transferase II enzymes are useful for the reduction of accumulated campesterol and concomitant increase of sitosterol.

Levels of sitostanol and sitostanol esters can be elevated further by approximately 2- to 40-fold over the transgenic plants of the art having only added genes for HMG CoA reductase by introducing additional genes encoding one or more of the following sterol pathway enzymes: a squalene epoxidase, a sterol methyl transferase I, a sterol C4-demethylase, an obtusifoliol C14α-demethylase, a sterol C5-desaturase, a sterol methyl transferase II.

As used herein, the term "structural coding sequence" means a DNA sequence which encodes for a peptide, polypeptide, or protein which may be made by a cell following transcription of the DNA to mRNA, followed by translation to the desired peptide, polypeptide, or protein.

The term "sterol" as applied to plants refers to any chiral tetracyclic isopentenoid which may be formed by cyclization of squalene oxide through the transition state possessing stereochemistry similar to the trans-syn-trans-anti-trans-anti configuration, i.e., protosteroid cation, and which retains a polar group at C-3 (hydroxyl or keto), an all-trans-anti stereochemistry in the ring system, and a side-chain 20R-configuration (Parker et al. (1992) In Nes et al., Eds., Regulation of Isopentenoid Metabolism, ACS Symposium Series No. 497, p. 110; American Chemical Society, Washington, D.C.). The numbering of the carbon atoms of a representative sterol (cholesterol) is shown in the following structure (FORMULA II):

As used herein, the term "sterol" refers to unsaturated hydroxyl group-containing derivatives of a fused, reduced ring system, cyclopenta [α]-phenanthrene, comprising three fused cyclohexane rings (A, B and C) in a phenanthrene arrangement, and a terminal cyclopentane ring (D). The exemplary steroid below (FORMULA II) illustrates the numbering system employed herein in describing the location of groups and substituents.

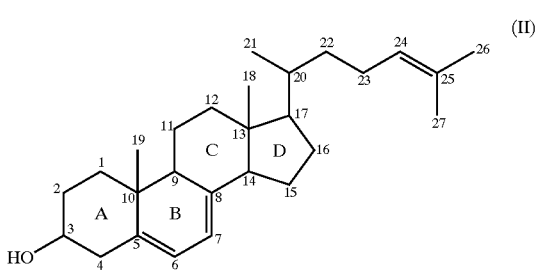

(II)

Sterols may or may not contain a C-5 to C-6 double bond, as this is a feature introduced late in the biosynthetic pathway (note Scheme 1, below). Sterols contain a $C_8$–$C_{10}$ side chain at the C-17 position, as shown above.

The term "phytosterol," which applies to sterols found uniquely in plants, refers to a sterol containing a C-5, and in some cases a C-22, double bond. Phytosterols are further characterized by alkylation of the C-17 side-chain with a methyl or ethyl substituent at the C-24 position. Major phytosterols include, but are not limited to, sitosterol, stigmasterol, campesterol, brassicasterol, etc. Cholesterol, which lacks a C-24 methyl or ethyl side chain, is found in plants but is not unique thereto, and is not a "phytosterol"

"Phytostanols" are saturated forms of phytosterols wherein the C-5 and, when present, C-22 double bond(s) is(are) reduced, and include, but are not limited to, sitostanol, campestanol, and 22-dihydrobrassicastanol.

"Phytosterol esters" and "phytostanol esters" are further characterized by the presence of a fatty acid or phenolic acid moiety rather than a hydroxyl group at the C-3 position.

The term "steroid compounds" includes sterols, phytosterols, phytosterol esters, phytostanols, and phytostanol esters.

The term "phytosterol compound" refers to at least one phytosterol, at least one phytosterol ester, or a mixture thereof.

The term "phytostanol compound" refers to at least one phytostanol, at least one phytostanol ester, or a mixture thereof.

The term "constitutive promoter" refers to a promoter that operates continuously in a cell, and which is not subject to quantitative regulation. The gene with which such a promoter is associated is always "turned on."

The terms "seed-specific," "fruit-specific," "plastid-specific," etc., as they apply to promoters refer to preferential or exclusive activity of these promoters in these organs or organelles, respectively. "Preferential expression" refers to promoter activity greater in the indicated organs or organelles than elsewhere in the plant. "Seed-specific" comprehends expression in the aleurone layer, endosperm, and/or embryo of the seed.

As used herein "isolated polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

The alternative nucleotide sequences described above are considered to possess substantially similar enzymatic activity to that of the polypeptide-encoding polynucleotide sequences of the present invention if they encode polypeptides having enzymatic activity differing from that of any of the polypeptides encoded by the polynucleotide sequences of the present invention by about 30% or less, preferably by about 20% or less, and more preferably by about 10% or less when assayed by standard enzymatic assays.

As used herein "effective amount" is intended to qualify the amount of an agent which will achieve the goal of a lessening in the severity and/or the frequency of incidence of a disease condition or disorder, over no treatment.

The phrase "steroid pathway products" refers to the products of steroid biosynthesis produced by the action of one or more of squalene epoxidase enzyme, sterol methyl transferase I enzyme, sterol C4-demethylase enzyme, obtusifoliol C14α-demethylase enzyme, sterol C5-desaturase enzyme, and sterol methyl transferase II enzyme. Specific examples of steroid pathway products include, but are not limited to, sitosterol, sitostanol, stigmasterol and stigmastanol.

In the context of the present disclosure, a "non-transformed" plant or cell refers to a plant or cells which does not comprise introduced polynucleotides encoding a polypeptide having 3-hydroxy-3-methylglutaryl-Coenzyme A reductase enzyme activity and at least one polypeptide having squalene epoxidase enzyme activity, sterol methyl transferase I enzyme activity, sterol C4-demethylase enzyme activity, obtusifoliol C14α-demethylase enzyme activity, sterol C5-desaturase enzyme activity, or sterol methyl transferase II enzyme activity. Thus, a plant or cell that contains introduced polynucleotide sequences other than those above, would still be considered "non-transformed." As used herein, "peptide" and "protein" are used interchangeably and mean a compound that consists of two or more amino acids that are linked by means of peptide bonds.

I. Plant Steroid Biosynthesis

To aid the reader in understanding the present invention, descriptions of the sterol compound biosynthetic pathway are presented below. These descriptions identify enzymes useful in achieving the modifications to the biosynthesis and accumulation of sterol compounds described herein, and identify sources of nucleic acid sequences encoding these enzymes.

Various steps in the steroid compound biosynthetic pathway in plants are shown in Scheme 1, below. The numbers over the arrows refer to plant sterol compound biosynthetic pathway enzymes and genes as indicated in Table 1.

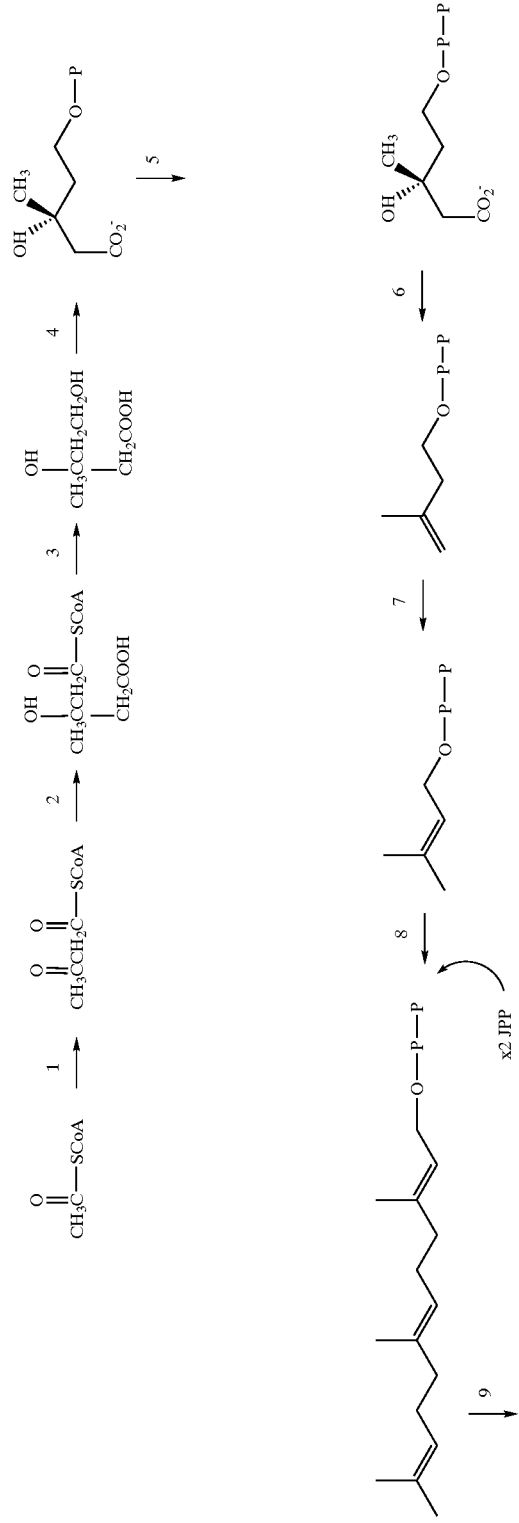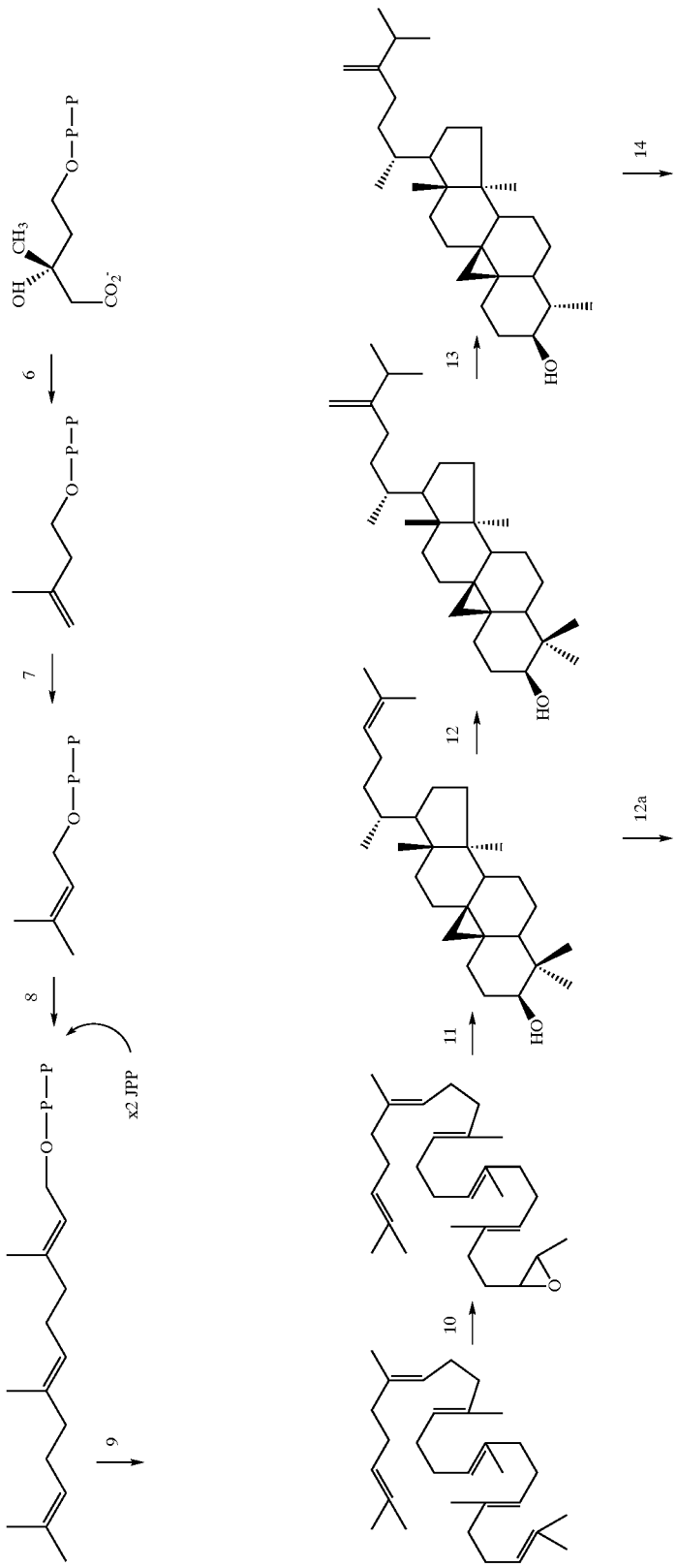

-continued
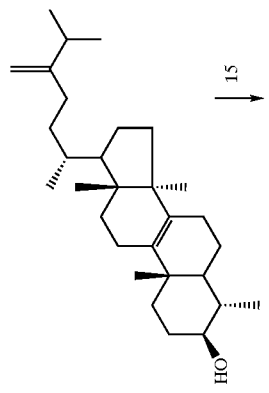
↓ 15
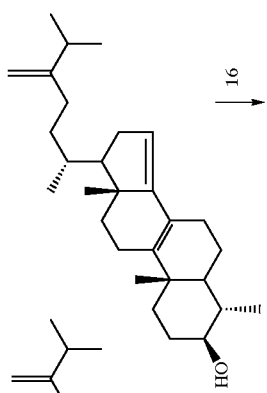
↓ 16
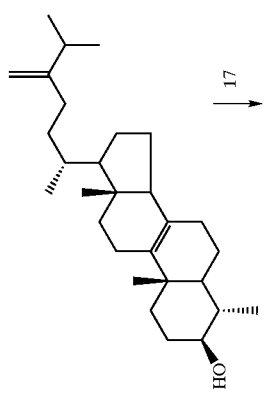
↓ 17
↓ 20a
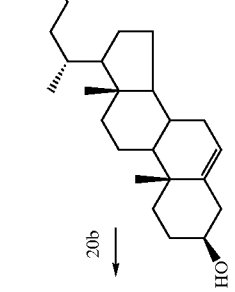
↓ 20b
↑ 19b
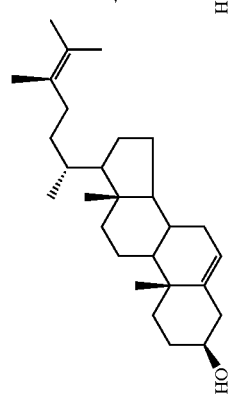
↓ 21b
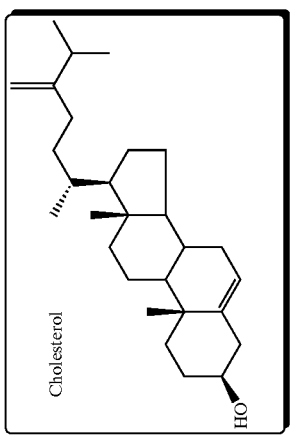
Cholesterol
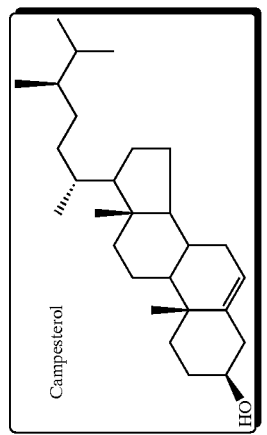
Campesterol -continued
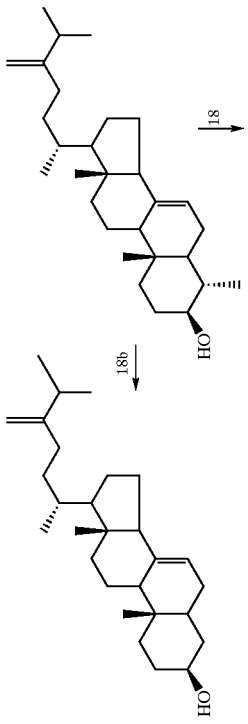
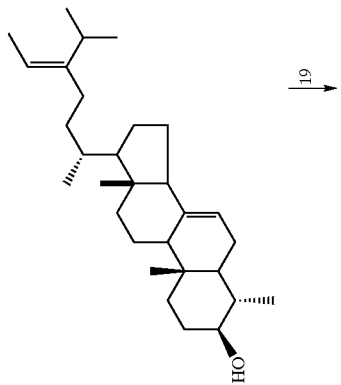
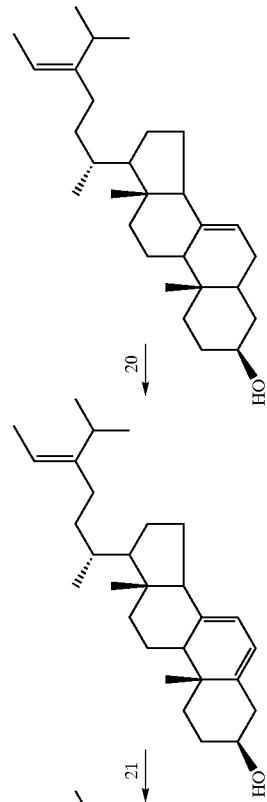
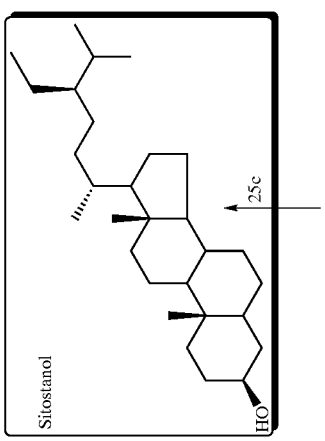
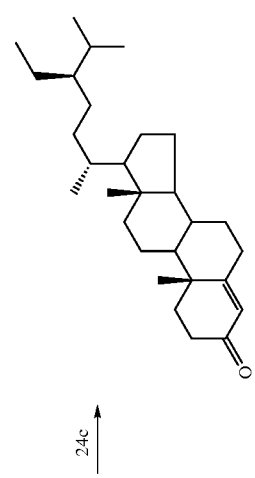
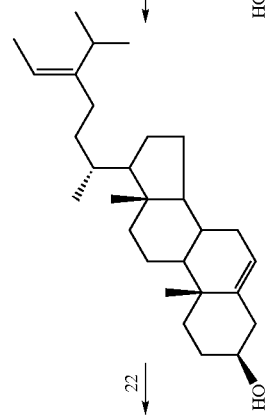
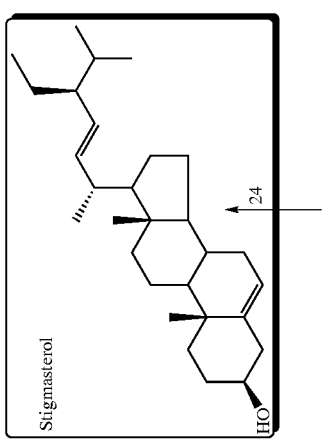
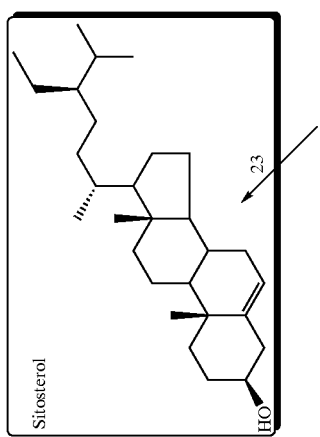
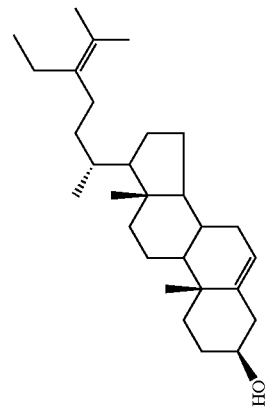
Stigmasterol
Sitosterol
Sitostanol

TABLE 1

Plant Sterol Compound Pathway Enzymes and Genes

| Enzyme | Step in Pathway | GenBank Gene ID |
|---|---|---|
| Acetoacetyl-CoA thiolase | 1 | X78116 |
| HMG-CoA synthase | 2 | X83882 |
| HMG-CoA reductase | 3 | X15032 |
|  |  | L19262 |
| Mevalonate kinase | 4 | X77793 |
| Phosphomevalonate kinase | 5 | Not available |
| Mevalonate pyrophosphate decarboxylase | 6 | Y14325 |
| Isopentenyl diphosphate isomerase | 7 | U49259 |
|  |  | U47324 |
| Farnesyl pyrophosphate synthase | 8 | X75789 |
| Squalene synthase | 9 | AF004560 |
| Squalene epoxidase | 10 | AB016883 |
| Squalene cyclase | 11 | U87266 |
| Sterol C-24 methyltransferase | 12, 18 | U71400 |
| Sterol C-4 demethylase | 13, 19 | Not available |
| Cycloeucalenol-obtusifoliol isomerase | 14 | Not available |
| Sterol C-14 demethylase | 15 | U74319 |
| Sterol C-14 reductase | 16 | PCT WO97/48793 |
| Sterol C-8 isomerase | 17 | AF030357 |
| Sterol C-5 desaturase | 20 | X90454 |
| Sterol C-7 reductase | 21 | U49398 |
| Sterol C-24 isomerase | 22 | Klahre et al. (1998) Plant Cell 10: 1677–1690 |
| Sterol C-24 reductase | 23 | Same as 22 |
| Sterol C-22 desaturase | 24 | Not available |
| Sterol C-5 reductase | 25 | WO00/61771 |

The plant sterol compound biosynthesis pathway has two distinct components. The early pathway reactions, leading from acetyl-CoA to squalene via mevalonic acid, are common to other isoprenoids. The later pathway reactions, leading from squalene to the major plant sterol compounds such as sitosterol, campesterol and stigmasterol, are committed biosynthetic reactions.

The early pathway reactions have been studied in fungi and plants (Lees et al., *Biochemistry and Function of Sterols*, Nes and Parish, Eds., CRC Press, 85–99 (1997); Newman and Chappell, *Biochemistry and Function of Sterols*, Nes and Parish, Eds., CRC Press, 123–134 (1997); Bach et al., *Biochemistry and Function of Sterols*, Nes and Parish, Eds., CRC Press, 135–150 (1997)).

Acetoacetyl CoA thiolase (EC 2.3.1.9) catalyzes the first reported reaction, which consists of the formation of acetoacetyl CoA from two molecules of acetyl CoA (Dixon et al., *J. Steroid Biochem. Mol. Biol.* 62: 165–171 (1997)). This enzyme has been purified from radish. A radish cDNA has been isolated by functional complementation in *Saccharomyces cerevisiae* (GeneBank Accession #X78116). A radish cDNA has also been screened against a cDNA library of Arabidopsis thaliana (Vollack and Bach, *Plant Physiology* 111: 1097–1107 (1996)).

HMGCoA synthase (EC 4.1.3.5) catalyzes the production of HMGCoA. This reaction condenses acetyl CoA with acetoacetyl CoA to yield HMGCoA. HMGCoA synthase has been purified from yeast. A plant HMGCOA synthase cDNA has also been isolated from *Arabidopsis thaliana* (Montamat et al., *Gene* 167: 197–201 (1995)).

HMGCoA reductase, also referred to as 3-hydroxy-3-methyglutaryl-coenzyme A (EC 1.1.1.34), catalyzes the reductive conversion of HMGCoA to mevalonic acid (MVA). This reaction is reported to play a role in controlling plant isoprenoid biosynthesis (Gray, *Adv. Bot. Res.* 14: 25–91 (1987); Bach et al., *Lipids* 26: 637–648 (1991); Stermer et al., *J. Lipid Res.* 35: 1133–1140 (1994). Plant HMGCOA reductase genes are often encoded by multigene families. The number of genes comprising each multigene family varies, depending on the species, ranging from two in *Arabidopsis thaliana* to at least seven in potato. Overexpression of plant HMGCOA reductase genes in transgenic tobacco plants has been reported to result in the overproduction of phytosterols (Schaller et al., *Plant Physiol.* 109: 761–770 (1995)).

Mevalonate kinase (EC 2.7.1.36) catalyzes the phosphorylation of mevalonate to produce mevalonate 5-phosphate. It has been reported that mevalonate kinase plays a role in the control of isoprenoid biosynthesis (Lalitha et al., *Indian. J. Biochem. Biophys.* 23: 249–253 (1986)). A mevalonate kinase gene from *Arabidopsis thaliana* has been cloned (GeneBank accession number X77793; Riou et al., *Gene* 148: 293–297 (1994)).

Phosphomevalonate kinase (EC 2.7.4.2) (MVAP kinase) is an enzyme associated with isoprene and ergosterol biosynthesis that converts mevalonate-5-phosphate to mevalonate-5-pyrophosphate utilizing ATP (Tsay et al., *Mol. Cell. Biol.* 11: 620–631 (1991)).

Mevalonate pyrophosphate decarboxylase ("MVAPP decarboxylase") (EC 4.1.1.33) catalyzes the conversion of mevalonate pyrophosphate to isopentenyl diphosphate ("IPP"). The reaction is reported to be a decarboxylation/dehydration reaction which hydrolyzes ATP and requires $Mg^{2+}$. A cDNA encoding *Arabidopsis thaliana* MVAPP decarboxylase has been isolated (Toth et al., *J. Biol. Chem.* 271: 7895–7898 (1996)). An isolated *Arabidopsis thaliana* MVAPP decarboxylase gene was reported to be able to complement the yeast MVAPP decarboxylase.

Isopentenyl diphosphate isomerase ("IPP:DMAPP") (EC 5.3.3.2) catalyzes the formation of dimethylallyl pyrophosphate (DMAPP) from isopentenyl pyrophosphate (IPP). Plant IPP:DMAPP isomerase gene sequences have been reported for this enzyme. It has also been reported that IPP:DMAPP isomerase is involved in rubber biosynthesis in a latex extract from Hevea (Tangpakdee et al., *Phytochemistry* 45: 261–267 (1997).

Farnesyl pyrophosphate synthase (EC 2.5.1.1) is a prenyltransferase which has been reported to play a role in providing polyisoprenoids for sterol compound biosynthesis as well as a number of other pathways (Li et al., *Gene* 17: 193–196 (1996)). Farnesyl pyrophosphate synthase combines DMAPP with IPP to yield geranyl pyrophosphate ("GPP"). The same enzyme condenses GPP with a second molecule of IPP to produce farnesyl pyrophosphate ("FPP"). FPP is a molecule that can proceed down the pathway to sterol compound synthesis, or that can be shuttled through other pathways leading to the synthesis of quinones or sesquiterpenes.

Squalene synthase (EC 2.5.1.21) reductively condenses two molecules of FPP in the presence of $Mg^{2+}$ and NADPH to form squalene. The reaction involves a head-to-head condensation, and forms a stable intermediate, presqualene diphosphate. The enzyme is subject to sterol demand regulation similar to that of HMGCOA reductase. The activity of squalene synthase has been reported to have a regulatory effect on the incorporation of FPP into sterol and other compounds for which it serves as a precursor (Devarenne et al., *Arch. Biochem. Biophys.* 349: 205–215 (1998)).

Squalene epoxidase (EC 1.14.99.7) (also called squalene monooxygenase) catalyzes the conversion of squalene to squalene epoxide (2,3-oxidosqualene), a precursor to the initial sterol molecule in the sterol compound biosynthetic pathway, cycloartenol. This is the first reported step in the pathway where oxygen is required for activity. The formation of squalene epoxide is also the last common reported step in sterol biosynthesis of animals, fungi, and plants.

The later pathway of sterol compound biosynthetic steps starts with the cyclization of squalene epoxide and ends with the formation of 5 –24-alkyl sterols in plants.

2,3-oxidosqualene cycloartenol cyclase (EC 5.4.99.8) (also called cycloartenol synthase) is the first step in the sterol compound pathway that is plant-specific. The cyclization of 2,3-oxidosqualene leads to lanosterol in animals and fungi, while in plants the product is cycloartenol. Cycloartenol contains a 9,19-cyclopropyl ring. The cyclization is reported to proceed from the epoxy end in a chair-boat-chair-boat sequence that is mediated by a transient C-20 carbocationic intermediate.

S-adenosyl-L-methionine:sterol C-24 methyl transferase ("SMT1") (EC 2.1.1.41) catalyzes the transfer of a methyl group from S-adenosyl-L-methionine to the C-24 center of the sterol side chain (Nes et al. (1991) *J. Biol. Chem.* 266(23):15202–15212). This is the first of two methyl transfer reactions that have been reported to be an obligatory and rate-limiting step of the sterol compound-producing pathway in plants. The second methyl transfer reaction occurs later in the pathway after the $\Delta^{8-7}$ isomerase. The enzyme responsible for the second methyl transfer reaction is named SMTII (Bouvier-Nave, P. et al., (1997) *Eur. J. Biochem.*, 246: 518–529). An isoform, SMTII, catalyzes the conversion of cycloartenol to a $\Delta^{23(24)}$24-alkyl sterol, cyclosadol (Guo et al. (1996) *Tetrahed. Lett.* 37(38):6823–6826).

Sterol C-4 demethylase catalyzes the first of several demethylation reactions, which results in the removal of the two methyl groups at C-4. While in animals and fungi the removal of the two C-4 methyl groups occurs consecutively, in plants it has been reported that there are other steps between the first and second C-4 demethylations. The C-4 demethylation is catalyzed by a complex of microsomal enzymes consisting of a monooxygenase, an NAD$^+$-dependent sterol 4-decarboxylase, and an NADPH-dependent 3-ketosteroid reductase.

Cycloeucalenol-obtusifoliol isomerase ("COI") catalyzes the opening of the cyclopropyl ring at C-9. The opening of the cyclopropyl ring at C-9 creates a double bond at C-8.

Sterol C-14 demethylase catalyzes demethylation at C-14, which removes the methyl group at C-14 and creates a double bond at that position. In both fungi and animals, this is the first step in the sterol synthesis pathway. Sterol 14-demethylation is mediated by a cytochrome P-450 complex.

Sterol C-14 reductase catalyzes a C-14 demethylation that results in the formation of a double bond at C-14 (Ellis et al., *Gen. Microbiol.* 137: 2627–2630 (1991)). This double bond is removed by a $\Delta^{14}$ reductase. The normal substrate is 4-methyl-8,14,24 (24$^1$)-trien-3β-ol. NADPH is the normal reductant.

Sterol C-8 isomerase catalyzes a reaction that involves further modification of the tetracyclic rings or the side chain (Duratti et al., *Biochem. Pharmacol.* 34: 2765–2777 (1985)). The kinetics of the sterol isomerase-catalyzed reaction favor a $\Delta^8$ 6 $\Delta^7$ isomerase reaction that produces a $\Delta^7$ group.

Sterol C-5 desaturase catalyzes the insertion of the $\Delta^5$-double bond that normally occurs at the $\Delta^7$-sterol level, thereby forming a $\Delta^{5,7}$-sterol (Parks et al., *Lipids* 30: 227–230 (1995)). The reaction has been reported to involve the stereospecific removal of the 5α and 6α hydrogen atoms, biosynthetically derived from the 4 pro-R and 5 pro-S hydrogens of the (+) and (−) R-mevalonic acid, respectively. The reaction is obligatorily aerobic, and requires NADPH or NADH. The desaturase has been reported to be a multienzyme complex present in microsomes. It consists of the desaturase itself, cytochrome b$_5$, and a pyridine nucleotide-dependent flavoprotein. The $\Delta^5$-desaturase is reported to be a mono-oxygenase that utilizes electrons derived from a reduced pyridine nucleotide via cytochrome b$_5$.

Sterol C-7 reductase catalyzes the reduction of a $\Delta^7$-double bond in $\Delta^{5,7}$-sterols to generate the corresponding $\Delta^5$-sterol. It has been reported that the mechanism involves, like many other sterol enzymes, the formation of a carbocationic intermediate via electrophilic "attack" by a proton.

Sterol C-24(28) isomerase catalyzes the reduction of a $\Delta^{24(28)}$-$\Delta^{24}$, a conversion that modifies the side chain. The product is a $\Delta^{24(25)}$-24-alkyl sterol. Sterol C-24 reductase catalyzes the reduction of the $^{24(25)}$double bond at C-24, which produces sitosterol. Recently, Klahre et al. ((1998) *Plant Cell* 10:1677–1690) discovered that both the isomerization and reduction steps are catalyzed by an enzyme coded by the same gene, i.e., DIM/DWF1.

Sterol C-22 desaturase (EC 2.7.3.9) catalyzes the formation of a double bond at C-22 on the side chain. This formation of a double bond at C-22 on the side chain marks the end of the sterol compound biosynthetic pathway, and results in the formation of stigmasterol (Benveniste (1986) *Annu. Rev. Plant Physiol.* 37:275–308). The C-22 desaturase in yeast, which is the reported final step in the biosynthesis of ergosterol in that organism, requires NADPH and molecular oxygen. In addition, the reaction is also reported to involve a cytochrome P450 that is distinct from a cytochrome P450 participating in demethylation reactions (Lees et al. (1995) *Lipids* 30: 221–226).

Phytosterols are biogenetic precursors of brassinosteroids, steroid alkaloids, steroid sapogenins, ecdysteroids, and steroid hormones. This precursor role of phytosterols is often described as a "metabolic" function. A common transformation of free sterols in tissues of vascular plants is the conjugation at the 3-hydroxy group of sterols with long-chain fatty acids to form steryl esters, or with a sugar, usually with a single molecule of β-D-glucose, to form steryl glycosides. Some of the steryl glycosides are additionally esterified, at the 6-hydroxy group of the sugar moiety, with long-chain fatty acids to form acylated steryl glycosides.

The existence of several enzymes that are specifically associated with the synthesis and breakdown of conjugated sterols has been reported (Wojciechowski, *Physiology and Biochemistry of Sterols*, eds. Patterson, Nes, AOCS Press, 361 (1991)). Enzymes involved in this process include: UDPGlc:Sterol glucosyltransferase, phospho(galacto)glyceride steryl glucoside acyltransferase, and sterylglycoside and sterylester hydrolases.

UDPGlc:sterol glucosyltransferase (EC 2.4.1.173) catalyzes glucosylation of phytosterols by glucose transfer from UDP-glucose ("UDPGl"). The formation of steryl glycosides can be measured using UDP-[$^{14}$C] glucose as the substrate. Despite certain differences in their specificity patterns, all reported UDPGlc:sterol glucosyltransferases preferentially glucosylate only sterols or sterol-like molecules that contain a C-3 hydroxy group, a β-configuration, and which exhibit a planar ring. It has been reported that UDPGlc:sterol glucosyltransferases are localized in the microsomes.

Phospho(galacto)glyceride steryl glucoside acyltransferase catalyzes the formation of acylated steryl glycosides from the substrate steryl glycoside by transfer of acyl groups from some membranous polar acyllipids to steryl glycoside molecules.

Acylglycerol:sterol acyltransferase (EC 2.3.1.26) catalyzes the reaction wherein certain acylglycerols act as acyl donors in a phytosterol esterification. In plants, the activity of acylglycerol:sterol acyltransferase is reported to be associated with membranous fractions. A pronounced specificity for shorter chain unsaturated fatty acids was reported for all acyltransferase preparations studied in plants. For example, acylglycerol:sterol acyltransferases from spinach leaves and mustard roots can esterify a number of phytosterols.

Sterylglycoside and sterylester hydrolases ("SG-hydrolases") catalyze the enzymatic hydrolysis of sterylglycosides to form free sterols. The SG-hydrolase activity is not found in mature, ungerminated seeds, is reported to emerge only after the third day of germination, and is found mainly in the cotyledons. It has been reported that phospho(galacto)glyceride:SG acyltranaferase may catalyze a reversible reaction. Enzymatic hydrolysis of sterylesters in germinating seeds of mustard, barley and corn is reported to be low in dormant seeds, but increases during the first ten days of germination. This activity is consistent with a decrease in sterylesters and an increase in free sterols over the same temporal period.

II. Processes for Modifying Steroid Compound Biosynthesis and Accumulation

In order to obtain seed producing oil containing elevated levels of phytostanols and phytostanol esters such as sitostanol and sitostanol esters, these recombinant constructs or expression cassettes can be introduced into plant cells by any number of conventional means known in the art and regenerated into fertile transgenic plants. The genome of such plants can then comprise introduced DNA encoding various steroid pathway enzymes, alone or in combination, that achieves the desirable effect of enhancing the levels of phytostanols, phytostanol esters, mixtures thereof in the oil of seed thereof.

Preferably, the genome can comprise introduced DNA encoding a HMG CoA reductase enzyme and an introduced DNA encoding one or more of a squalene epoxidase, a sterol methyl transferase I, a sterol C4-demethylase, an obtusifoliol C14α-demethylase, a sterol C5-desaturase, a sterol methyl transferase II. In each case, the foregoing introduced DNAs can be operatively linked to regulatory signals that cause seed-specific expression thereof.

The present invention encompasses not only such transgenic plants, but also transformed plant cells, including cells and seed of such plants, as well as progeny of such plants, for example produced from the seed. Transformed plant cells and cells of the transgenic plants encompassed herein can be grown in culture for a time and under appropriate conditions to produce oil containing elevated levels of phytosterols and/or phytostanols and their corresponding esters. Alternatively, the phytosterols, phytostanols, and their corresponding esters can be isolated directly from the cultures.

In addition, of course, seed obtained from the transgenic, progeny, hybrid, etc., plants disclosed herein can be used in methods for obtaining oil containing phytosterols, phytosterol esters, phytostanols, phytostanol esters, or mixtures thereof employing extraction and processing procedures known in the art. Note, in this regard, Kochhar (1983) *Prog. Lipid Res.* 22: 161–188.

The present invention also encompasses a method of producing a plant that accumulates an elevated level of sitosterol, at least one sitosterol ester, sitostanol, at least one sitostanol ester, or mixtures thereof, in seeds thereof compared to seeds of a corresponding plant comprising no introduced DNA encoding a polypeptide or protein that affects the biosynthesis of sterols, phytosterols, phytosterol esters, phytostanols, phytostanol esters, or combinations thereof, comprising sexually crossing a transgenic plant of the present invention with such a corresponding plant. The latter can be a non-transgenic plant, or a transgenic plant containing introduced DNA encoding a trait other than one affecting sterol, phytosterol, etc., biosynthesis. For example, such trait may be insect or herbicide resistance. Plants produced by this method also form part of the present invention.

Also included are plants that accumulate an elevated level of sitosterol, at least one sitosterol ester, sitostanol, at least one sitostanol ester, or mixtures thereof, in seeds thereof compared to seeds of a corresponding plant comprising no introduced DNA encoding a polypeptide or protein that affects the biosynthesis of sterols, phytosterols, phytosterol esters, phytostanols, phytostanol esters, or combinations thereof, which are apomictic.

A process of increasing the formation of steroid pathway products in a transformed host cell as compared to an otherwise identical non-transformed host cell comprising the following steps. A host cell is transformed with a recombinant vector comprising (a) as operably linked components in the 5' to 3' direction, a promoter, a DNA sequence encoding a polypeptide exhibiting 3-hydroxy-3-methylglutaryl-Coenzyme A reductase enzyme activity, and a transcription termination signal sequence; and (b) as operably linked components in the 5' to 3' direction, a promoter, a DNA sequence encoding a steroid pathway enzyme, and a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, and a sterol methyl transferase II enzyme. The transformed plant cell is regenerated into a transgenic plant.

A plant contemplated by this invention is a vascular, multicellular higher plant. Such higher plants will hereinafter by usually referred to simply as "plants". Such "plants" include both complete entities having leaves, stems, seeds, roots and the like as well as callus and cell cultures that are monocotyledonous and dicotyledonous. Dicotyledonous plants are a preferred embodiment of the present invention.

Preferred plants are members of the Solanaceae, Leguminosae, Ammiaceae, Brassicaceae, Gramineae, Carduaceae and Malvaceae families. Exemplary plant members of those families are tobacco, petunia and tomato (Solanaceae), soybean and alfalfa (Leguminosae), carrot (Ammiaceae), corn, maize and barley (Gramineae), Arabidopsis (Brassicaceae), guayule (Carduaceae), and cotton (Malvaceae). A preferred plant is tobacco of the strain *Nicotiana tabacum* (*N. Tabacum*), cotton of the strain Coker line 312-5A, soybean of the strain *Glycine max*, alfalfa of the strain RYSI or tomato of the strain *Lycopersicon esculentium*. Other plants include canola, maize and rape.

A transgenic plant contemplated by this invention is produced by transforming a plant cell or protoplast with an added, exogenous structural gene that encodes a polypeptide having HMG-CoA reductase activity and an exogenous structural gene that encodes at least one polypeptide have a steroid pathway enzyme activity to produce a transformed plant cell, and regenerating a transgenic plant form the transformed plant cell. The encoded polypeptide is expressed both in the transformed plant cell or protoplast and the resulting transgenic plant. (The phrase "plant cell" will hereinafter be used to include a plant protoplast, except where plant protoplasts are specifically discussed).

A non-transgenic plant that serves as the source of the plant cell that is transformed, i.e. the precursor cell, is referred to herein as a "native, non-transgenic" plant. The native, non-transgenic plant is of the same strain as the formed transgenic plant.

Sterol production in a transgenic plant of the present invention is increased by increasing the activity of the enzyme HMG-CoA reductase, which enzyme catalyzes the conversion of 3-hydroxy-3-methylglutaryl Coenzyme A (HMG-CoA) to mevalonate and the activity of at least one other steroid pathway enzyme. As used herein, the term "specific activity" means the activity normalized to cellular protein content.

HMG-CoA reductase activity is increased by increasing the amount (copy number) of a gene encoding a polypeptide having HMG-CoA reductase catalytic activity. Expression of the increased amount of that encoded structural gene enhances the activity of that enzyme.

The amount of the expressed gene is increased by transforming a plant cell with a recombinant DNA molecule comprising a vector operatively linked to a DNA segment that encodes a polypeptide having HMG-CoA reductase activitiy, and a promoter suitable for driving the expression of that polypeptide in that plant cell, and culturing the transformed plant cell into a transgenic plant. Such a polypeptide includes intact as well as a catalytically active, truncated HMG-CoA reductase proteins.

Thus, a transformed plant cell and a transgenic plant have one or more added, exogenous genes that encode a polypeptide having HMG-CoA reductase activity and at least one other steroid pathway enzyme activty relative to a native, non-transgenic plant or untransformed plant cell of the same type. As such, a transformed plant cell or transgenic plant can be distinguished from an untransformed plant cell or native, nontransgenic plant by standard technology such as agarose separation of DNA fragments or mRNAs followed by transfer and appropriate blotting with DNA or RNA, e.g., Southern or Northern blotting, or by use of polymerase chain reaction technology, as are well known. Relative HMG-CoA reductase activity of the transformed cell or transgenic plant with untransformed cells and native, non-transgenic plants or cell cultures therefrom can also be compared, with a relative activity for that enzyme of about 1.5:1 for transgenic (transformed) to native (untransformed) showing transformation. Higher relative activity ratios such as about 15:1 have also been observed.

Sterol accumulation can also be used to distinguish between native, non-transgenic and transgenic plants. A transgenic plant has at least about twice the total sterol content as a native, non-transgenic plant where a single added gene is present. Greater differences up to about forty-fold have also been observed.

Sitostanol, sitostanol ester, and tocopherol biosynthesis and accumulation in plants can be modified in accordance with the present invention by variously expressing the nucleic acid coding sequences discussed above, alone or in combination, as described herein. The expression of sequences encoding sterol methyltransferase II enzymes facilitates the production of plants in which the biosynthesis and accumulation of campesterol, campestanol, and their esters can be reduced as these enzymes shunt sterol intermediates away from campesterol, and toward sitosterol and sitostanol.

III. DNA Encoding Useful Polypeptides

The present invention contemplates a recombinant construct or a recombinant vector that contains a DNA sequence encoding a polypeptide exhibiting 3-hydroxy-3-methylglutaryl-Coenzyme A (HMG-CoA) reductase activity and a DNA sequence encoding a polypeptide exhibiting the activity of a steroid pathway enzyme. Each polypeptide-encoding DNA sequence is operably linked in the 5' to 3' direction independent of the other sequence. Each DNA sequence in the 5' to 3' direction comprises a promoter, then the DNA sequence encoding the polypeptide then a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. It is contemplated that HMG-CoA reductase and steroid pathway enzyme activities come from a mutant or truncated form of those enzymes, such as a truncated HMG-CoA reductase lacking the transmembrane region while retaining a functional catalytic domain. Several HMG CoA reductase sequences are known in the art. An amino acid alignment for these is shown in FIG. 32. The sources of the sequences used in building the multiple alignment are listed in Table 5.

TABLE 5

Sources of Sequences Used In Building The Multiple Alignment

| | | | | |
|---|---|---|---|---|
| methanobac | swissprot:hmdh__metth | Begin:1 | End:397 | O26662 |
| methanococ | swissprot:hmdh__metja | Begin:1 | End:405 | Q58116 |
| halobacter | swissprot:hmdh__halvo | Begin:1 | End:403 | Q59468 |
| sulfolobus | swissprot:hmdh__sulso | Begin:1 | End:409 | O08424 |
| yeast2 | gp__pln1:yschmgcr2__1 | Begin:1 | End:1045 | M22255 |
| yeast1 | gp__pln1:yschmgcr1__1 | Begin:1 | End:1054 | M22002 |
| phycomyces | swissprot:hmdh__phybl | Begin:1 | End:105 | Q12649 |
| fusarium | swissprot:hmdh__fusmo | Begin:1 | End:976 | Q12577 |
| candida | gp__pln1:ab012603__1 | Begin:1 | End:934 | AB012603 |
| dictyoste2 | swissprot:hmd2__dicdi | Begin:1 | End:481 | P34136 |
| wheat1 | pir2:pq0761 | Begin:1 | End:150 | hydroxymethylglutaryl-CoA reductase (NADPH) |
| rice | swissprot:hmdh__orysa | Begin:1 | End:509 | P48019 |
| corn | sp__plant:o24594 | Begin:1 | End:579 | O24594 |

TABLE 5-continued

Sources of Sequences Used In Building The Multiple Alignment

| | | | | |
|---|---|---|---|---|
| wheat3 | pir2:pq0763 | Begin:1 | End:150 | hydroxymethylglutaryl-CoA reductase (NADPH) |
| wheat2 | pir2:pq0762 | Begin:1 | End:150 | hydroxymethylglutaryl-CoA reductase (NADPH) |
| soybean | gmtx6:30820__1r59f1 | Begin:101 | End:259 | from proprietary soy sequence database |
| rubbertre3 | swissprot:hmd3__hevbr | Begin:1 | End:586 | Q00583 |
| rosyperiwi | swissprot:hmdh__catro | Begin:1 | End:601 | Q03163 |
| tomato | swissprot:hmd2__lyces | Begin:1 | End:602 | P48022 |
| woodtobacc | swissprot:hmdh__nicsy | Begin:1 | End:604 | Q01559 |
| potato | gp__pln1:pothmgri__1 | Begin:1 | End:596 | L01400 |
| radish | sp__plant:q43826 | Begin:1 | End:573 | Q43826 |
| arabadopsis1 | gp__pln1:athhmgcoar__1 | Begin:1 | End:592 | L19261 |
| cucumismel | gp__pln1:ab021862__1 | Begin:1 | End:587 | AB021862 |
| rubbertre2 | swissprot:hmd2__hevbr | Begin:1 | End:210 | P29058 |
| rubbertre1 | swissprot:hmd1__hevbr | Begin:1 | End:575 | P29057 |
| camptothec | swissprot:hmdh__camac | Begin:1 | End:593 | P48021 |
| arabadops2 | swissprot:hmd2__arath | Begin:1 | End:562 | P43256 |
| chineseham | swissprot:hmdh__crigr | Begin:1 | End:887 | P00347 |
| chineseha2 | gp__rod:cruhmg14__1 | Begin:1 | End:887 | L00183 |
| syrianhamst | gp__rod:hamhmgcob__1 | Begin:1 | End:887 | M12705 |
| rat | swissprot:hmdh__rat | Begin:1 | End:887 | P51639 |
| rabbit | swissprot:hmdh__rabit | Begin:1 | End:888 | Q29512 |
| human | gp__pri2:humhmgcoa__1 | Begin:1 | End:888 | M11058 |
| mouse | gp__rod:mushmgcoa__1 | Begin:1 | End:224 | M62766 |
| xenopus | swissprot:hmdh__xenla | Begin:1 | End:883 | P20715 |
| seaurchin | swissprot:hmdh__strpu | Begin:1 | End:932 | P16393 |
| cockroach | swissprot:hmdh__blage | Begin:1 | End:856 | P54960 |
| drosophila | swissprot:hmdh__drome | Begin:1 | End:916 | P14773 |
| dictyoste1 | swissprot:hmd1__dicdi | Begin:1 | End:552 | P34135 |
| schistosom | swissprot:hmdh__schma | Begin:1 | End:948 | P16237 |
| archaeoglo | swissprot:hmdh__arcfu | Begin:1 | End:436 | O28538 |
| pseudomonas | gp__bct1:psehmgcoa__1 | Begin:1 | End:428 | M24015 |

These sequences, and their truncated counterparts, are useful in the present invention. Examples of such preferred HMG CoA reductases include the truncated rubber and Arabidopsis HMG CoA reductases disclosed herein.

Other enzyme-encoding DNAs can be introduced into plants to elevate even further the levels of desirable Δ5 sterols and their reduced stanol counterparts as well as other phytosterols and tocopherols. Thus, the DNA sequences contemplated for use in the present invention, which can be used alone or in various combinations as discussed below, include, but are not limited to, those encoding the following enzymes: 3-hydroxysteroid oxidases; steroid 5reductases; sterol methyltransferases; sterol acyltransferases; and S-adenosylmethionine-dependent α-tocopherol methyltransferases.

In each case, the sequences encoding these enzymes can comprise an expression cassette comprising, operably linked in the 5' to 3' direction, a seed-specific promoter, the enzyme coding sequence, and a transcriptional termination signal sequence functional in a plant cell such that the enzyme is successfully expressed. For use in the methods disclosed herein, the recombinant constructs or expression cassettes can be incorporated in a vector, for example a plant expression vector. Such vectors can be transformed into host cells such as bacterial cells, for example during the preparation or modification of the recombinant constructs, and plant cells. Thus, the invention encompasses plants and seeds comprising such transformed plant cells.

It will be apparent to those of skill in the art that the nucleic acid sequences set forth herein, either explicitly, as in the case of the sequences set forth above, or implicitly with respect to nucleic acid sequences generally known and not present herein, can be modified due to the built-in redundancy of the genetic code and noncritical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall length. That minimal length defines the length of a DNA segment having a sequence that encodes a particular polypeptide having HMG-CoA reductase activity. As is well known in the art, as long as the required DNA sequence is present (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, as long as the DNA segment is free of such interfering DNA sequences, a DNA segment of the invention can be up to 15,000 base pairs in length. The maximum size of a recombinant DNA molecule, particularly a plant integrating vector, is governed mostly by convenience and the vector size that can be accommodated by a host cell, once all of the minimal DNA sequences required for replication and expression, when desired, are present. Minimal vector sizes are well known.

Also encompassed by the present invention are nucleotide sequences biologically functionally equivalent to those disclosed herein, that encode conservative amino acid changes within the amino acid sequences of the presently disclosed enzymes, producing "silent" changes therein. Such nucleotide sequences contain corresponding base substitutions based upon the genetic code compared to the nucleotide sequences encoding the presently disclosed enzymes. Substitutes for an amino acid within the enzyme sequences disclosed herein is selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

A. HMG-CoA Reductase

The introduction of an HMG CoA reductase gene into a cell results in a higher carbon throughput through the steroid synthesis pathway. The introduction of a truncated HMG CoA reductase gene (lacking the transmembrane region, resulting in a soluble HMG CoA reductase enzyme) provides higher HMG CoA reductase activity and thus increased delta-5 steroid compound production over the same case with an introduced full-length HMG CoA reductase gene. A useful truncated HMG CoA reductase nucleic acid encodes at least the catalytic domain.

Hydroxymethylglutaryl-CoA reductase is enzyme number 1.1.1.88, using the recommended nomenclature of the International Union of Biochemistry and Molecular Biology on the Nomenclature and Classification of Enzymes, *Enzyme Nomenclature* 1992, Edwin C. Webb, ed., Academic Press, Inc. (San Diego, Calif.: 1992), page 35.

The present invention contemplates transforming a plant cell with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane-binding region and the linker region.

The catalytic region contains the active site of the HMG-CoA reductase enzyme and comprises about forty percent of the COOH-terminal portion of intact HMG-CoA reductase enzyme.

The membrane-binding region contains hydrophobic amino acid residues and comprises about fifty percent of the NH$_2$-terminal portion of intact HMG-CoA reductase enzyme.

The linker region connects the catalytic and membrane-binding regions, and constitutes the remaining about ten percent of the intact enzyme.

As discussed in greater detail below, only the catalytic region of HMG-CoA reductase is needed herein to provide the desired enzyme activity. Thus, an exogenous structural gene that encodes a polypeptide corresponding to that catalytic region is the minimal HMG Co A reductase gene required for transforming plant cells in addition to one of the steroid pathway enzymes discussed below. The present invention therefore contemplates use of both intact and truncated structural genes that encode a polypeptide having HMG-CoA reductase activity.

A structural gene encoding a polypeptide having HMG-CoA reductase activity can be obtained or constructed from a variety of sources and by a variety of methodologies. See, e.g. Carlson et al., *Cell*, 28:145 (1982); Rine et al., *Proc. Natl. Acad. Sci. USA*, 80:6750 (1983). Exemplary of such structural genes are the mammalian and yeast genes encoding HMG-CoA reductase or the catalytic region thereof.

Figure 1:
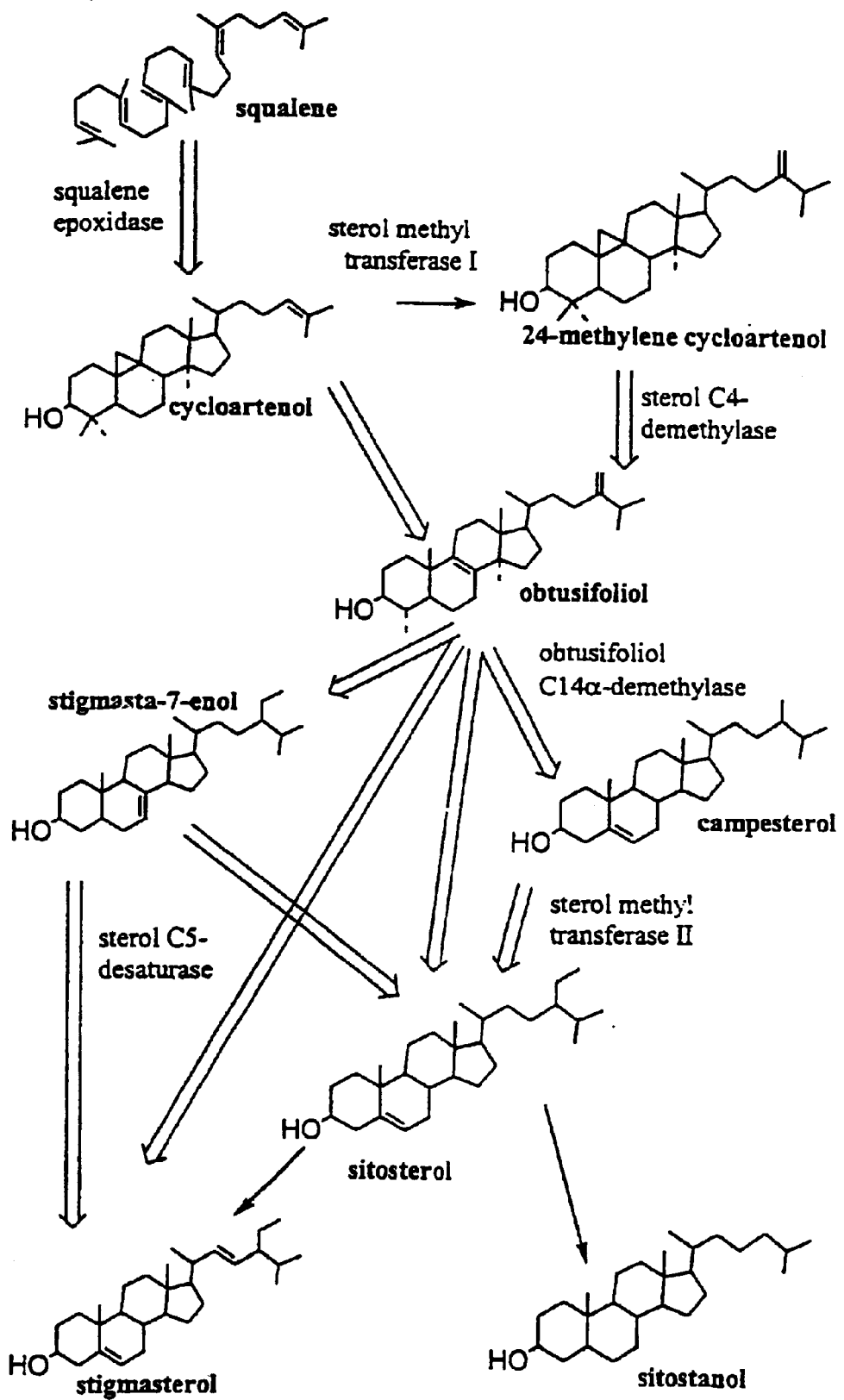
FIG. 1 is an abbreviated version of a plant steroid compound biosynthetic pathway that shows the enzymes affecting steroid compound biosynthesis and accumulation. These include: HMG-CoA reductase, squalene epoxidase, sterol methyl transferase I, sterol C4-demethylase, obtusifoliol C14α-demethylase, sterol C5 desaturase and sterol methyl transferase II.
Figure 2:
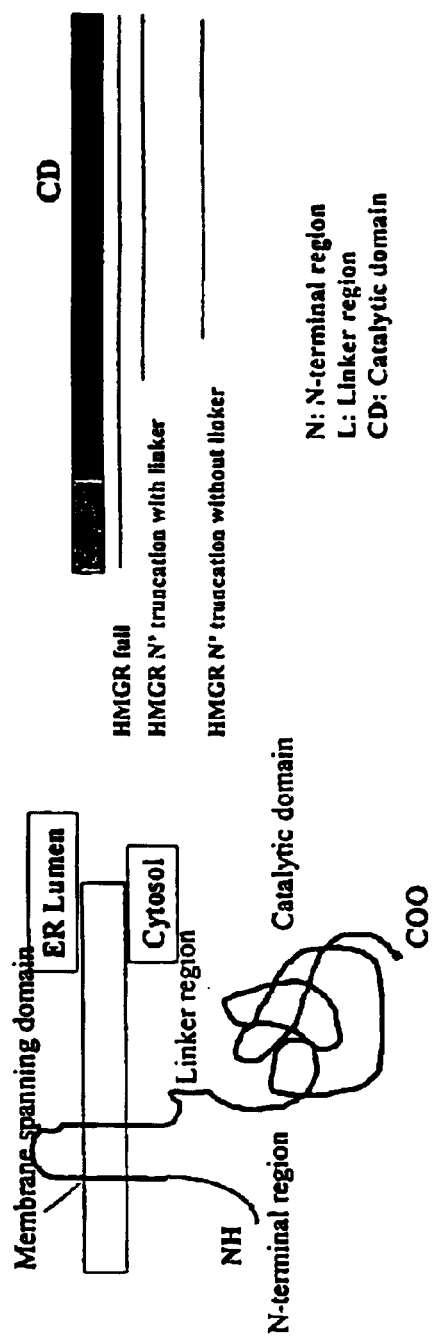
FIG. 2 depicts the forms of Arabidopsis and rubber HMGR1 tested in Arabidopsis and yeast to compare expression, activity and sterol production.

The disclosures of Chappell, et al., U.S. Pat. No. 5,349,126, are incorporated in full herein by reference. The mammalian genome contains a single gene encoding HMG-CoA reductase. The nucleotide sequence of the hamster and human gene for HMG-CoA reductase have been described in Chappell et al. A composite nucleotide sequence of DNA corresponds to the mRNA SEQ ID NO:1 of Chappell et al., as well as the derived amino acid residue sequence SEQ ID NO:2 of Chappell et al., for hamster HMG-CoA reductase is provided in FIG. 2 of Chappell et al, reprinted from Chin et al., *Nature*, 308:613 (1984). The composite nucleotide sequence of FIG. 2, SEQ ID NO:1 of Chappell et al., comprising about 4768 base pairs, includes the nucleotide sequence encoding the intact hamster HMG-CoA reductase enzyme.

Intact hamster HMG-CoA reductase comprises about 887 amino acid residues (SEQ ID NO:2 of Chappell et al.). A structural gene encoding an intact hamster HMG-CoA reductase enzyme of 887 amino acid residues comprises base pairs from about nucleotide position 164 to about nucleotide position 2824 of SEQ ID NO:1 of Chappell et al.

A preferred structural gene is one that encodes a polypeptide corresponding to only the catalytic region of the enzyme. Two catalytically active segments of hamster HMG-CoA reductase have been defined. Liscum et al., *J. Biol. Chem.*, 260(1): 522 (1985). One segment containing a catalytic region has an apparent molecular weight of 62 kDa and comprises amino acid residues from about position 373 to about position 887. A second segment containing a catalytic region has an apparent molecular weight of 53 kDa segment and comprises amino acid residues from about position 460 to about position 887. The 62 kDa catalytically active segment is encoded by base pairs from about nucleotide position 1280 to about nucleotide position 2824 of SEQ ID NO:1 of Chappell et al. The 53 kDa catalytically active segment is encoded by base pairs from about nucleotide position 1541 to about nucleotide position 2824 of SEQ ID NO:1 of Chappell et al.

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1180 to about nucleotide position 1283 or from about position 1180 to about position 1540, respectively of SEQ ID NO:1 of Chappell et al. The structural gene encoding the linker region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme.

A structural gene encoding a polypeptide comprising a catalytically active, truncated or intact HMG-CoA reductase enzyme from other organisms such as yeast can also be used in accordance with the present invention.

Figure 3:
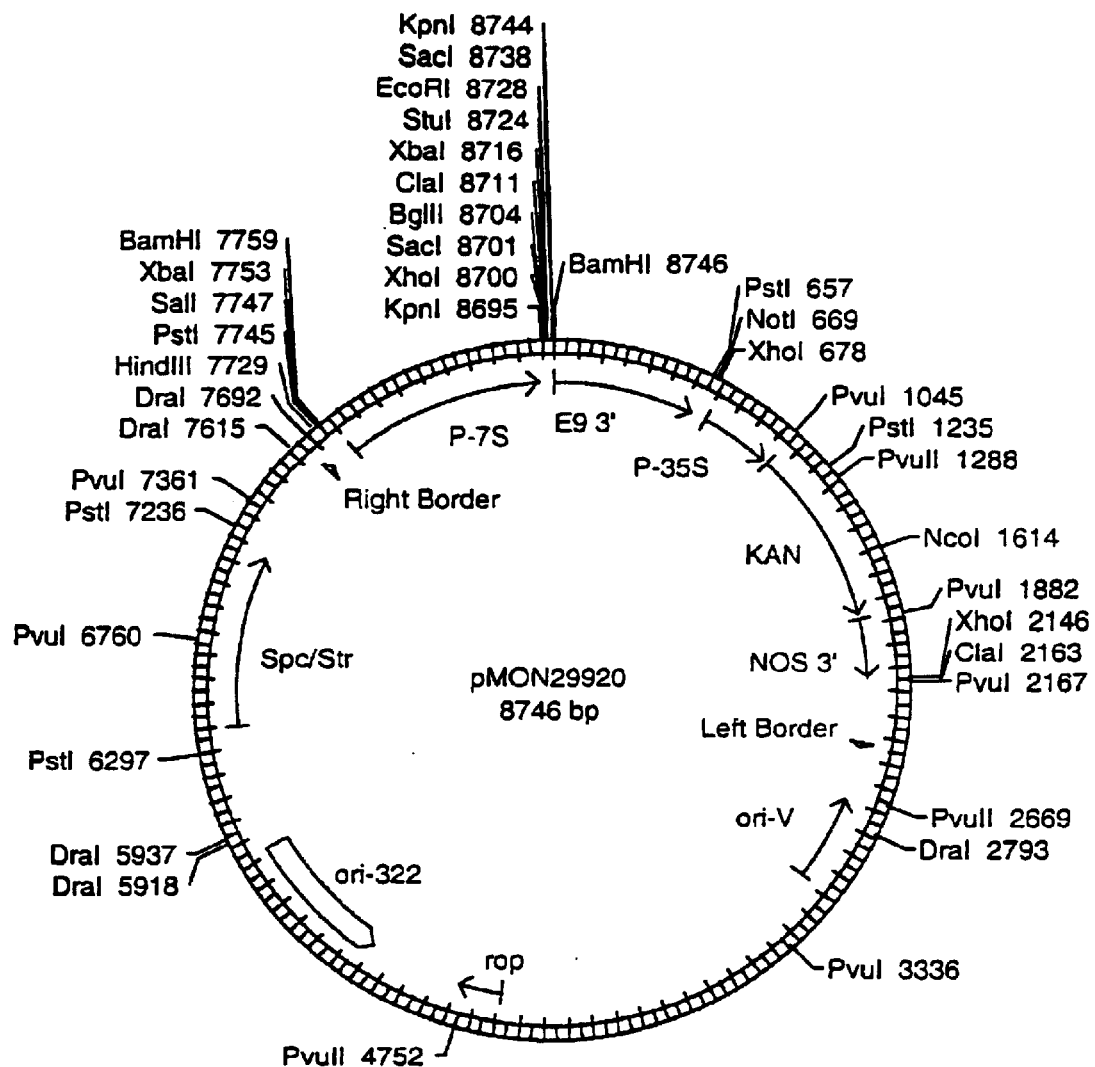
FIG. 3 is a map showing the structure of construct pMON29920. pMON29920 is a binary transformation vector with P-7S/E9 3' cassette and the KAN gene flanked by the two borders where P-7S is the promoter of alpha' beta conglycinin protein from soybean, E9 3' is the 3' end of pea rbc E9 gene and KAN is the coding sequence for NPTII that confers resistance to kanamycin. The NPTII gene is driven by the 35S promoter from cauliflower mosaic virus. Spc.Str is the coding region for Tn7 adenylyltransferase conferring resistance to spectinomycin and streptomycin; ori-V: the vegetative origin of replication; rop: coding region for repressor of primer; ori-322: minimum known sequence required for a functional origin of replication; NOS 3': the 3' termination end of nopaline synthase coding region.

Yeast cells contain two genes encoding HMG-CoA reductase. The two yeast genes, designated HMG1 and HMG2, encode two distinct forms of HMG-CoA reductase, designated HMG-CoA reductase 1 SEQ ID NO:3 of Chappell et al. are presented in FIG. 3 of Chappell et al., are taken from Basson et al. *Mol. Cell Biol.*, 8(9): 3797 (1988). The nucleotide base sequences of HMG2 SEQ ID NO:5 of Chappell et al. as well as the amino acid residue sequence of HMG-CoA reductase 2 SEQ ID NO:6 of Chappell et al. are set forth therein in the Sequence Listing.

The entire HMG1 gene comprises about 3360 base pairs SEQ ID NO:3 of Chappell et al. Intact HMG-CoA reductase 1 comprises an amino acid sequence of about 1054 amino acid residues SEQ ID NO:4 of Chappell et al. Thus, the minimal portion of the HMG1 gene that encodes an intact enzyme comprises base pairs from about nucleotide position 121 to about position 3282 of FIG. 3, SEQ ID NO:3 of Chappell et al.

The entire HMG2 gene comprises about 3348 base pairs SEQ ID NO:5 of Chappell et al. Intact HMG-CoA reductase 2 comprises about 1045 amino acid residues SEQ ID NO:6 of Chappell et al. Thus, the minimal portion of HMG2 gene that encodes intact HMG-CoA reductase 2 comprises base pairs from about nucleotide position 121 to about position 3255 of SEQ ID NO:5 of Chappell et al.

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about reside 1054: i.e., the COOH-terminus. A structural gene that encodes the catalytic region comprises base pairs from about nucleotide position 1974 to about position 3282 of FIG. 3 of Chappell et al.

The linker region of HMG-CoA reductase 1 comprises an amino acid sequence from about residue 525 to about residue 617. A structural gene that encodes the linker region comprises nucleotides from about position 1695 to about position 1973 of FIG. 3 of Chappell et al. A structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane-binding region of the enzyme. Such a structural gene preferably comprises base pairs from about nucleotide position 121 to about position 147 and from about position 1695 to about position 3282 of FIG. 3 of Chappell et al.

A construct similar to those above from an analogous portion of yeast HMG-CoA reductase 2 can also be utilized.

A nucleic acid sequence encoding HMG-CoA reductase from *Hevea brasiliensis* has been disclosed by Chye et al. (1991) *Plant Mol. Biol.* 16: 567–577. A nucleic acid sequence encoding an *Arabidopsis thaliana* HMG-CoA reductase has been published by Caelles et al. (1989) *Plant Mol. Biol.* 13: 627–638, and is also available as GenBank accession number L19261. U.S. Pat. Nos. 5,306,862 and 5,365,017 disclose additional DNA sequences encoding HMG-CoA reductases.

The following sequences are listed by Genbank Accession numbers:

O026662 *methanobacterium thermoautotrophicum*. 3-hydroxy-3-methylglutaryl-coenzyme a reductase (ec 1.1.1.34) (hmg-coa reductase). December/1998

Q58116 *methanococcus jannaschii*. 3-hydroxy-3-methylglutaryl-coenzyme a reductase (ec 1.1.1.34) (hmg-coa reductase). July/1998

Q59468 *halobacterium volcanii* (*haloferax volcanii*). 3-hydroxy-3-methylglutaryl-coenzyme a reductase (ec 1.1.1.34) (hmg-coa reductase). July/1998

O08424 *sulfolobus solfataricus*. 3-hydroxy-3-methylglutaryl-coenzyme a reductase (ec 1.1.1.34) (hmg-coa reductase). December/1998

M22255 *Saccharomyces cerevisiae* Yeast HMG-COA reductase (HGM2) gene, complete cds; 3-hydroxy-3-methyl glutaryl coenzyme A reductase. April/1993

M22002 *Saccharomyces cerevisiae* Yeast HMG-CoA reductase (HGM1) gene, complete cds; 3-hydroxy-3-methyl-glutaryl coenzyme A reductase. April/1993

Q12649 *phycomyces blakesleeanus*. 3-hydroxy-3-methylglutaryl-coenzyme a reductase (ec 1.1.1.34) (hmg-coa reductase) (fragment). November/1997

Q12577 *fusarium moniliforme* (*gibberella fujikuroi*). 3-hydroxy-3-methylglutaryl-coenzyme a reductase (ec 1.1.1.34) (hmg- coa reductase). November/1997

AB012603 *Candida utilis Candida utilis* HMG mRNA for HMG-COA reductase, complete cds. July/1998

P34136 *dictyostelium discoideum* (slime mold). 3-hydroxy-3-methylglutaryl-coenzyme a reductase 2 (ec 1.1.1.34) (hmg- coa reductase 2) (fragment).35735

PQ0761 hydroxymethylglutaryl-CoA reductase (NADPH) (EC 1.1.1.34) (HMGR 10)—wheat (fragment)

P48019 *oryza sativa* (rice). 3-hydroxy-3-methylglutaryl-coenzyme a reductase (ec 1.1.1.34) (hmg-coa reductase) (fragment). February/1996

O24594 *zea mays* (maize). 3-hydroxy-3-methylglutaryl coenzyme a reductase (ec 1.1.1.88). May/1999

PQ0763 hydroxymethylglutaryl-CoA reductase (NADPH) (EC 1.1.1.34) (HMGR 23)—wheat (fragment)

PQ0762 hydroxymethylglutaryl-CoA reductase (NADPH) (EC 1.1.1.34) (HMGR 18)—wheat (fragment)

from proprietary soy sequence database

Q00583 *hevea brasiliensis* (para rubber tree). 3-hydroxy-3-methylglutaryl-coenzyme a reductase 3 (ec 1.1.1.34) (hmg-coa reductase 3). July/1998

Q03163 *catharanthus roseus* (rosy periwinkle) (madagascar periwinkle). 3-hydroxy-3-methylglutaryl-coenzyme a reductase (ec 1.1.1.34) (hmg-coa reductase). July/1998

P48022 *lycopersicon esculentum* (tomato). 3-hydroxy-3-methylglutaryl-coenzyme a reductase 2 (ec 1.1.1.34) (hmg- coa reductase 2). July/1998

Q01559 *nicotiana sylvestris* (wood tobacco). 3-hydroxy-3-methylglutaryl-coenzyme a reductase (ec 1.1.1.34) (hmg-coa reductase). July/1998

L01400 *Solanum tuberosum* Potato hydroxymethylglutaryl coenzyme A reductase (hmgr) mRNA, complete cds; putative. April/1996

Q43826 *raphanus sativus* (radish). hydroxymethylglutaryl-coa reductase (ec 1.1.1.34) (hydroxymethylglutaryl-coa reductase (nadph)) (3-hydroxy-3-methylglutaryl-coenzyme a red L19261 *Arabidopsis thaliana Arabidopsis thaliana* HMG-cOA reductase gene, complete cds. April/1994

AB021862 *Cucumis melo Cucumis melo* mRNA for HMG-CoA reductase, complete cds; putative. January/1999

P29058 *hevea brasiliensis* (para rubber tree). 3-hydroxy-3-methylglutaryl-coenzyme a reductase 2 (ec 1.1.1.34) (hmg- coa reductase 2) (fragment).35735

P29057 *hevea brasiliensis* (para rubber tree). 3-hydroxy-3-methylglutaryl-coenzyme a reductase 1 (ec 1.1.1.34) (hmg-coa reductase 1). July/1998

P48021 *camptotheca acuminata*. 3-hydroxy-3-methylglutaryl-coenzyme a reductase (ec 1.1.1.34) (hmg-coa reductase). November/1997

P43256 *arabidopsis thaliana* (mouse-ear cress). 3-hydroxy-3-methylglutaryl-coenzyme a reductase 2 (ec 1.1.1.34) (hmg-coa reductase 2) (hmgr2). July/1998

P00347 *cricetulus griseus* (chinese hamster). 3-hydroxy-3-methylglutaryl-coenzyme A reductase (ec 1.1.1.34) (hmg-coA reductase). November/1997

L00183 *Cricetulus sp.* Hamster 3-hydroxy-3-methylglutaryl coenzyme A (HMG CoA) reductase gene, exons 19 and 20; 3-hydroxy-3-methylglutaryl coenzyme A (HMG CoA). April/1993

M12705 *Mesocricetus auratus* Syrian hamster 3-hydroxy-3-methylglutaral coenzyme A reductase (HMG-COA reductase) mRNA, complete cds; 3-hydroxy-3-methylglutaral coenzyme A red P51639 *rattus norvegicus* (rat). 3-hydroxy-3-methylglutaryl-coenzyme a reductase (ec 1.1.1.34) (hmg-coa reductase). December/1998

Q29512 *oryctolagus cuniculus* (rabbit). 3-hydroxy-3-methylglutaryl-coenzyme a reductase (ec 1.1.1.34) (hmg-coa reductase). July/1999

M11058 *Homo sapiens* Human 3-hydroxy-3-methylglutaryl coenzyme A reductase mRNA, complete cds; 3-hydroxy-3-methylglutaryl coenzyme A reductase. November/1994

M62766 *Mus musculus* Mouse HMG-CoA reductase mRNA, 3' end. April/1993

P20715 *xenopus laevis* (african clawed frog). 3-hydroxy-3-methylglutaryl-coenzyme a reductase (ec 1.1.1.34) (hmg-coa reductase). November/1997

P16393 *strongylocentrotus purpuratus* (purple sea urchin). 3-hydroxy-3-methylglutaryl-coenzyme a reductase (ec 1.1.1.34) (hmg-coa reductase). November/1997

P54960 *blattella germanica* (german cockroach). 3-hydroxy-3-methylglutaryl-coenzyme a reductase (ec 1.1.1.34) (hmg-coa reductase). November/1997

P14773 *drosophila melanogaster* (fruit fly). 3-hydroxy-3-methylglutaryl-coenzyme a reductase (ec 1.1.1.34) (hmg-coa reductase). December/1998

P34135 *dictyostelium discoideum* (slime mold). 3-hydroxy-3-methylglutaryl-coenzyme a reductase 1 (ec 1.1.1.34) (hmg- coa reductase 1). November/1997

P16237 *schistosoma mansoni* (blood fluke). 3-hydroxy-3-methylglutaryl-coenzyme a reductase (ec 1.1.1.34) (hmg-coa reductase). July/1998

O28538 *archaeoglobus fulgidus*. 3-hydroxy-3-methylglutaryl-coenzyme a reductase (ec 1.1.1.34) (hmg-coa reductase). December/1998

M24015 *Pseudomonas mevalonii P.mevalonii* HMG-CoA reductase (mvaA) gene, complete cds; HMG-COA reductase (EC 1.1.1.88). April/1993

B. Steroid Pathway Enzymes

The present invention contemplates nucleic acid sequences encoding polypeptides having the enzyme activity of the steroid pathway enzymes squalene epoxidase, sterol methyl transferase I, sterol C4-demethylase, obtusifoliol C14α-demethylase, sterol C5-desaturase and sterol methyl transferase II.

i. Squalene Epoxidase

Squalene epoxidase (also called squalene monooxygenase) catalyzes the conversion of squalene to squalene epoxide (2,3-oxidosqualene), a precursor to the initial sterol molecule in phytosterol biosynthetic pathway, cycloartenol. This is the first reported step in the pathway where oxygen is required for activity. The formation of squalene epoxide is also the last common reported step in sterol biosynthesis of animals, fungi and plants. Recently, several homologues of Arabidopsis and Brassica squalene epoxidase genes were reported (Schafer, U. A., Reed, D. W., Hunter, D. G., Yao, K., Weninger, A. M., Tsang, E. W., Reaney, M. J., MacKenzie, S. L., and Covello, P. S. (1999). Plant Mol. Biol. 39(4): 721–728). The same authors also have a PCT application disclosing the use of antisense technology with squalene epoxidase to elevate squalene levels in plants (WO 97/34003). However, to date there are no reports on functional characterization of any plant squalene epoxidase gene or enzyme.

Squalene Epoxidase, also known as squalene monooxygenase is enzyme reference number 1.14.99.7, *Enzyme Nomenclature* 1992, p. 146.

Several squalene epoxidase enzymes are known to the art. These include Arabidopsis squalene epoxidase protein sequence Accession No. AC004786 (SEQ ID NO:1), Arabidopsis squalene epoxidase Accession No. N64916 (SEQ ID NO:2), and Arabidopsis squalene epoxidase Accession No. T44667 (SEQ ID NO:3). Japanese patent application No. 07194381 A discloses a DNA encoding a mammalian squalene epoxidase.

In order to facilitate the modifications to sterol biosynthesis and accumulation described herein, the present invention also provides an isolated DNA molecule, comprising a nucleotide sequence selected from the group consisting of:

(a) Arabidopsis squalene epoxidase from clone ID ATA506263 disclosure SEQ ID NO:4, clone ID ATA304243 disclosure SEQ ID NO:6, clone ID ATA102071 disclosure SEQ ID NO: 8, clone ATA504158 disclosure SEQ ID NO:10, or the complement thereof;

(b) a nucleotide sequence that hybridizes to said nucleotide sequence of (a) under a wash stringency equivalent to 0.5×SSC to 2×SSC, 0.1% SDS, at 55–65° C., and which encodes a polypeptide having squalene epoxidase enzymatic activity substantially similar to that of the disclosed squalene epoxidase;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

An additional aspect of the invention is the recombinant constructs and vectors (pMON48343, FIG. 30; pMON43844, FIG. 31) comprising nucleic acid sequences encoding the novel squalene epoxidase, as well as a method of producing the novel squalene epoxidase, comprising culturing a host cell transformed with the novel constructs or vectors for a time and under conditions conductive to the production of the squalene epoxidase, and recovering the squalene epoxidase produced thereby.

ii. Sterol Methyl Transferase I

S-adenosyl-L-methionine:sterol C-24 methyl transferases (SMT1 and SMT2) catalyze the transfer of a methyl group from a cofactor, S-adenosyl-L-methionine, to the C-24 center of the sterol side chain (Bach, T. J. and Benveniste, P. (1997), Prog. Lipid Res. 36: 197–226). SMT in higher plant cells are responsible for their capability to produce a mixture of 24-methyl and 24-ethyl sterols (Schaffer, A., Bouvier-Navé, Benveniste, P., Schaller, H. (2000) Lipids 35: 263–269). Functional characterization of the SMT using a yeast erg6 expression system demonstrated unambiguously that an SMT1 sequence encodes a cycloartenol-C24-methyltransferase and a SMT2 sequence encodes a 24-methylene lophenol-C24-methyltransferase in a given plant species (Bouvier-Navé, P., Husselstein, T., and Benveniste, P. (1998), Eur. J. Biochem. 246: 518–529). Several plant genes coding for SMT1 and SMT2 have been reported and reviewed (Schaffer, A., Bouvier-Navé, Benveniste, P., Schaller, H. (2000) Lipids 35: 263–269). Transgenic plants expressing homologues of either SMT1 or SMT2 have been studied (Schaffer, A., Bouvier-Navé, Benveniste, P., Schaller, H. (2000) Lipids 35: 263–269). The use of these genes to modify plant sterol composition are also covered by two Monsanto patent applications (WO 98/45457 and WO 00/61771).

Sterol methyl transferase I enzymes known in the art are useful in the present invention. Examplary sequences include the known Arabidopsis sterol methyl transferase I protein sequence Accession No. U71400 (disclosure SEQ ID NO:19), the known tobacco sterol methyl transferase I protein sequence Accession No. U81312 (disclosure SEQ ID NO:20) and *Ricinus communis* sterol-C-methyltransferase, *Eur. J. Biochem.*, 246(2), 518–529 (1997). (Complete cds, Accession No. g2246457).

S-Adenosyl-L-Methionine-Sterol-C24-Methyltransferase—A nucleic acid sequence encoding an *Arabidopsis thaliana* S-adenosyl-L-methionine-sterol-C24-methyltransferase has been published by Husselstein et al. (1996) *FEBS Letters* 381: 87–92. $\Delta^{24}$-sterol C-methyltransferase is enzyme number 2.1.1.41, *Enzyme Nomenclature* 1992, page 160.

iii. Sterol C4-Demethylase

Sterol C-4 demethylase catalyses the first of several demethylation reactions, which results in the removal of the two methyl groups at C-4. While in animals and fungi the removal of the two C-4 methyl groups occurs consecutively, in plants it has been reported that there are other steps between the first and second C-4 demethylations (Bach, T. J. and Benveniste, P. (1997), Prog. Lipid Res. 36: 197–226). The C-4 demethylation is catalyzed by a complex of microsomal enzymes consisting of a monooxygenase, an NAD$^+$-dependent sterol 4-decarboxylase and an NADPH-dependent 3-ketosteroid reductase.

iv. Obtusifoliol C14α-Demethylase

Sterol C-14 demethylase catalyzes demethylation at C-14 which removes the methyl group at C-14 and creates a double bond at that position. In both fungi and animals, this is the first step in the sterol synthesis pathway. However, in higher plants, the 14α-methyl is removed after one C-4 methyl has disappeared. Thus, while lanosterol is the substrate for C-14 demethylase in animal and fungal cells, the plants enzyme uses obtusifoliol as substrate. Sterol 14-demethylation is mediated by a cytochrome P-450 complex. The mechanism of 14α-methyl removal involves two oxidation steps leading to an alcohol, then an aldehyde at C-29 and a further oxidative step involving a deformylation leading to formic acid and the sterol product with a typical 8,14-diene (Aoyama, Y., Yoshida, Y., Sonoda, Y., and Sato, Y. (1989) J. Biol. Chem. 264: 18502–18505). Obtusifoliol 14α-demethylase from Sorghum bicolor (L) Moench has been cloned using a gene-specific probe generated using PCR primers designed from an internal 14 amino acid sequence and was functionally expressed in *E. coli* (Bak, S, Kahn, R. A., Olsen, C. E. and Halkier, B. A. (1997) The Plant Journal 11(2): 191–201). Also, *Saccharomyces cerevisiae* CYP51A1 encoding lanosterol-14-demethylase was functionally expressed in tobacco (Grausem, B., Chaubet, N., Gigot, C., Loper, J. C., and Benveniste, P. (1995) The Plant Journal 7(5): 761–770).

Sterol C-14 demethylase enzymes and sequences are known in the art. For example Sorghum bicolor obtusifoliol 14α-demethylase CYP51 mRNA, described in *Plant J.*, 11(2):191–201 (1997) (complete cds Acession No. U74319). In order to facilitate the modifications to sterol biosynthesis and accumulation described herein, the present invention also provides an isolated DNA molecule, having a nucleotide sequence selected from the group consisting of:

(a) obtusifoliol C14α-demethylase from clone ID: ATA101105 disclosure SEQ ID NO:14, clone ID ATA202967 disclosure SEQ ID NO:15, clone ID ATA403931 disclosure SEQ ID NO:17, or the complement thereof;

(b) a nucleotide sequence that hybridizes to said nucleotide sequence of (a) under a wash stringency equivalent to 0.5×SSC to 2×SSC, 0.1% SDS, at 55–65° C., and which encodes a polypeptide having obtusifoliol C14α-demethylase enzymatic activity substantially similar to that of the disclosed obtusifoliol C14α-demethylase;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

An additional aspect of the invention is the recombinant constructs and vectors (pMON43842, FIG. 29) comprising nucleic acid sequences encoding the novel obtusifoliol C14α-demethylase, as well as a method of producing the novel obtusifoliol C14α-demethylase, comprising culturing a host cell transformed with the novel constructs or vectors for a time and under conditions conductive to the production of the obtusifoliol C14α-demethylase, and recovering the obtusifoliol C14α-demethylase produced thereby.

V. Sterol C5-Desaturase

Sterol C-5 desaturase catalyzes the insertion of the $\Delta^5$-double bond that normally occurs at the $\Delta^7$-sterol level, thereby forming a $\Delta^{5,7}$-sterol (Parks et al., *Lipids* 30:227–230 (1995)). The reaction has been reported to involve the stereospecific removal of the 5α and 6α hydrogen atoms, biosynthetically derived from the 4 pro-R and 5 pro-S hydrogens of the (+) and (−) R-mevalonic acid, respectively (Goodwin, T. W. (1979) Annu. Rev. Plant Physiol. 30: 369–404). The reaction is obligatorily aerobic and requires NADPH or NADH. The desaturase has been reported to be a multienzyme complex present in microsomes. It consists of the desaturase itself, cytochrome $b_5$ and a pyridine nucleotide-dependent flavoprotein. The $\Delta^5$-desaturase is reported to be a mono-oxygenase that utilizes electrons derived from a reduced pyridine nucleotide via cytochrome$_b$ (Taton, M., and Rahier, A. (1996) Arch. Biochem. Biophys. 325: 279–288). An *Arabidopsis thaliana* cDNA encoding a sterol-C5-desaturase was cloned by functional complementation of a yeast mutant, erg3 defective in ERG3, the gene encoding the sterol C5-desaturase required for ergosterol biosynthesis (Gachotte D., Husselstein, T., Bard, M., Lacroute F., and Benveniste, P. (1996) The Plant Journal 9(3): 391–398). Known sterol C5-desaturase enzymes are useful in the present invention, including Arabidopsis sterol C5-desaturase protein sequence Accession No. X90454, disclosure SEQ ID NO:22, and the *Arabidopsis thaliana* mRNA for sterol-C5-desaturase described in *Plant J.* 9(3):391–398 (1996) (complete cds Accession No. g1061037).

The NCBI (National Center for Biotechnology Information) database shows 37 sequences for sterol desaturase that are useful in the present invention. The following are exemplary of such sequences. From yeast: C5 sterol desaturase NP_013157 (*Saccharomyces cerevisiae*); hypothetical C5 sterol desaturase-fission T40027 (*Schizosaccharomyces pombe*); C5 sterol desaturase-fission T37759 (*Schizosaccharomyces pombe*); C5 sterol desaturase JQ1146 (*Saccharomyces cerevisiae*); C5 sterol desaturase BAA21457 (*schizosaccharomyces pombe*); C5 sterol desaturase CAA22610 (*Schizosaccharomyces pombe*); putative C5 sterol desaturase CAA16898 (*Schizosaccharomyces pombe*); probable C5 sterol desaturase 013666 (erg3_schpo); C5 sterol desaturase P50860 (Erg3_canga); C5 sterol desaturase P32353 (erg3_yeast); C5,6 desaturase AAC99343 (*Candida albicans*); C5 sterol desaturase BAA20292 (*Saccharomyces cerevisiae*); C5 sterol desaturase AAB39844 (*Saccharomyces cerevisiae*); C5 sterol desaturase AAB29844 (*Saccharomyces cerevisiae*); C5 sterol desaturase CAA64303 (*Saccharomyces cerevisiae*); C5 sterol desaturase AAA34595 (*Saccharomyces cerevisiae*); C5 sterol desaturase AAA34594 (*Saccharomyces cerevisiae*). From plants: C5 sterol desaturase S71251 (*Arabidopsis thaliana*); putative sterol-C5-desaturase AAF32466 (*Arabidopsis thaliana*); sterol-C5-desaturase AAF32465 (*Arabidopsis thaliana*); putatuve sterol desaturase AAF22921 (*Arabidopsis thaliana*); delta7 sterol C5 desaturase (*Arabidopsis thaliana*); sterol C5(6) desaturase homolog AAD20458 (*Nicotiana tabacum*); sterol C5 desaturase AAD12944 (*Arabidopsis thaliana*); sterol C5,6 desaturase AAD04034 (*Nicotiana tabacum*); sterol C5 desaturase CAA62079 (*Arabidopsis thaliana*). From mammals: sterol-C5-desaturase (*Mus musculus*) BAA33730; sterol-C5-desaturase BAA33729 (*Homo sapiens*); lathosterol oxidase CAB65928 (*Leishmania major*); lathosterol oxidase (lathosterol 5-desaturase) 088822 (*Mus musculus*); lathosterol 5-desaturase 075845 (*Homo sapiens*); delta7 sterol C5 desaturase AAF00544 (*Homo sapiens*). Others: fungal sterol C5 desaturase homolog BAA18970 (*Homo sapiens*).

For DNA sequences encoding a sterol-C5-desaturase useful in the present invention, the NCBI_nucleotide search for "sterol desaturase" came up with 110 sequences. The following are exemplary of such sequences. NC_001139 (*Saccharomyces cerevisiae*); NC_001145 (*Saccharomyces cerevisiae*); NC_001144 (*Saccharomyces cerevisiae*); AW700015 (*Physcomitrella patens*); AB004539 (*Schizosaccharomyces pombe*); and AW596303 (*Glycine max*); AC012188 (*Arabidopsis thaliana*).

vi. Sterol Methyl Transferase II

The combination of introduction of an HMG-COA reductase gene along with a sterol methyl transferase II gene into a cell serves to reduce steroid pathway intermediate compound accumulation in addition to reducing the accumulation of 24-methyl sterols such as campesterol.

Known sterol methyl transferase II enzymes are useful in the present invention, including Arabidopsis sterol methyl transferase II protein sequence (complete mRNA cds from *FEBS Lett.* 381(12):87–92 (1996) Accession No. X89867), disclosure SEQ ID NO:21.

Recombinant constructs encoding any of the forgoing enzymes affecting the steroid biosynthetic pathway can be incorporated into recombinant vectors comprising the recombinant constructs comprising the isolated DNA molecules. Such vectors can be bacterial or plant expression vectors.

IV. Recombinant Constructs and Vectors

The present invention contemplates a recombinant construct that contains a DNA sequence encoding a polypeptide exhibiting 3-hydroxy-3-methylfluaryl-Coenzyme A (HMG-CoA) reductase activity and a DNA sequence encoding a polypeptide exhibiting the activity of a steroid pathway enzyme. Each polypeptide-encoding DNA sequence is operably linked in the 5' to 3' direction independent of the other sequence. Each DNA sequence in the 5' to 3' direction comprises a promoter, then the DNA sequence encoding the polypeptide then a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme.

Preferably, the promoters in the recombinant construct are seed-specific promoters. In one embodiment, the promoter is derived from a species in a different order from the host cell. In other embodiments, the encoded HMG CoA reductase and/or steroid pathway enzymes is(are) from a species in a different order from the order that of the host cell.

It is contemplated that a construct comprises more than one of the DNA sequences encoding a steroid pathway enzyme.

The invention also contemplates a recombinant vector comprising the above-described recombinant construct, wherein that vector is preferably a plant expression vector.

A recombinant DNA molecule of the present invention can be produced by operatively linking a vector to a useful DNA segment discussed herein to form a plasmid. A vector capable of directing the expression of a polypeptide having HMG-COA reductase activity is referred to herein as an HMG-COA reductase "plant integrating vector".

Figure 5:
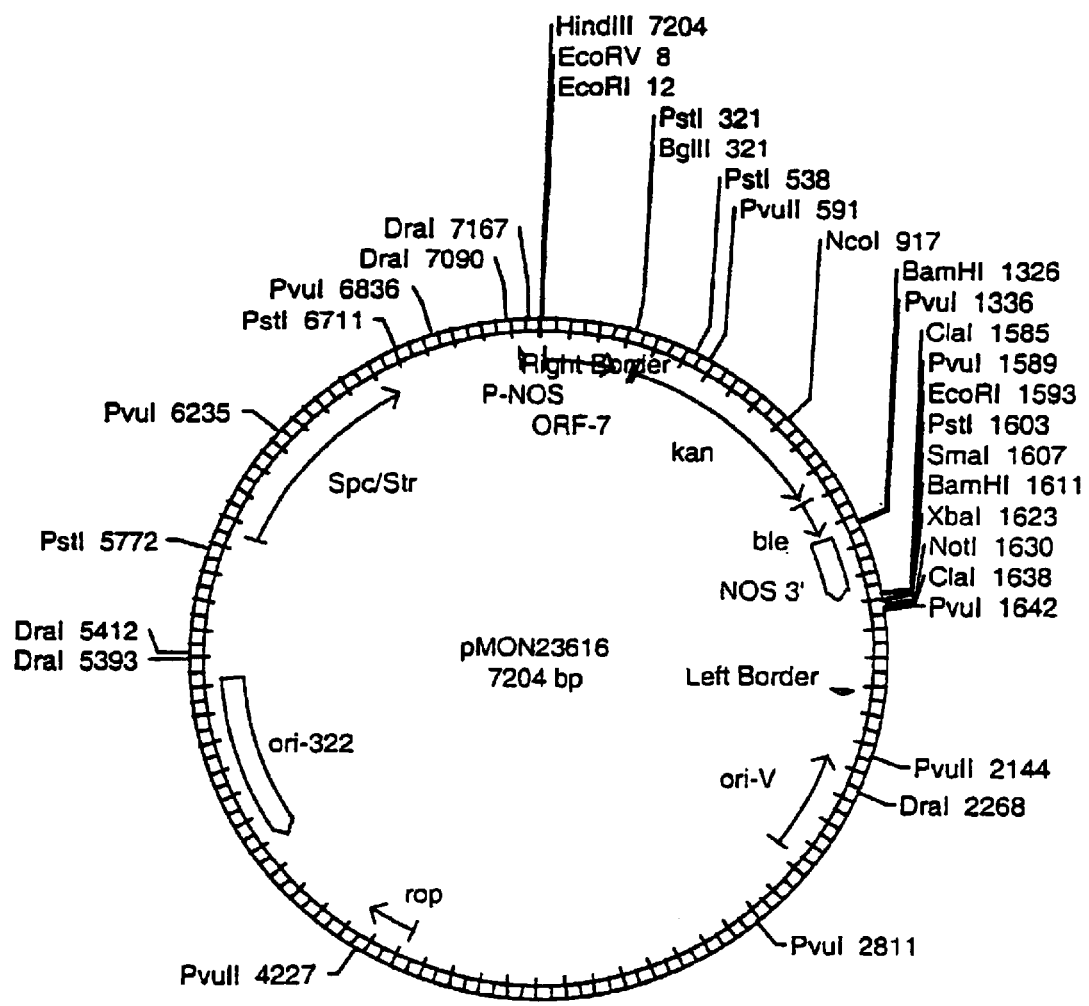
FIG. 5 is a map showing the structure of construct pMON23616. pMON23616 is a plant expression vector containing P-NOS/ORF-7/KAN/NOS-3' cassette. P-NOS: NOS promoter from Agrobacterium tumefaciens pTiT37; ORF-7: a short open reading frame that attenuates expression of KAN in plants; KAN: coding sequence of NPTII gene that confers resistance to kanamycin and neomycin; ble: confers resistance to bleomycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

Such plant integrating vectors contain control elements that direct and regulate expression, including a promoter, a marker, a terminator and insertion sequence (e.g. FIG. 5). The polypeptide coding genes are operatively linked to the plant integrating vector to allow the promoter sequence to direct RNA polymerase binding and expression of the desired polypeptide coding gene.

Useful in expressing the polypeptide coding gene are promoters that are inducible, viral, synthetic, constitutive as described by Poszkowski et al., *EMBO J.*, 3:2719 (1989) and Odell et al., *Nature*, 313:810 (1985), and temporally regulated, spatially regulated and spatiotemporally regulated as given in Chau et al., *Science*, 244:174–181 (1989). The promoter preferably comprises a promoter sequence whose function in regulating expression of the structural gene is substantially unaffected by the amount of sterol or squalene in the cell. As used herein, the term "substantially unaffected" means that the promoter is not responsive to direct feedback control by the sterols or squalene accumulated in transformed cells or transgenic plants.

A promoter is also selected for its ability to direct the transformed plant cell's or transgenic plant's transcriptional activity to the structural gene encoding a polypeptide having HMG-COA reductase activity. Structural genes can be driven by a variety of promoters in plant tissues. Promoters can be near-constitutive, such as the CaMV 35S promoter, or tissue specific or developmentally specific promoters affecting dicots or monocots.

As exemplified and discussed in detail herein, where the near-constitutive promoter CaMV 35S is used to transform tobacco plants, increases in total sterol and squalene accumulation are found in a variety of transformed plant tissues (e.g. callus, leaf, seed and root). Alternatively, the effects of transformation (e.g. increased amount of a gene coding for HMG-CoA reductase, increased total sterol accumulation and increased squalene accumulation) can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Lel) that is only expressed during seed maturation and accounts for about 2 to about 5 percent of total seed mRNA. The Lectin gene and seed-specific promoter have been fully characterized and used to direct seed specific expression in transgenic tobacco plants. See, e.g., Vodkin et al., *Cell*, 34:1023 (1983) and Lindstrom et al., *Developmental Genetics*, 11:160 (1990).

A plant integrating vector containing a structural gene coding for a polypeptide having HMG-COA reductase activity is engineered to be under control of the Lectin promoter and that vector is introduced into soybean plants using a protoplast transformation method. E. G. Dhir et al., *Plant Cell Reports*, 10:97 (1991). The expression of the polypeptide having HMG-CoA reductase activity is directed specifically to the seeds of the transgenic plant. In this way, a transgenic soybean seed having increased squalene accumulation is produced. Such seeds can then be used to extract oil containing enhanced levels of squalene. As set forth hereinafter, such squalene-enhanced oil is characterized by a greater thermal stability when compared to non-squalene-enhanced oil.

In the present invention, a plant has an exogenously provided structural gene for HMG-COA reductase and at least one of the six enumerated steroid pathway enzymes, a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. The plant or seed thus containing these added genes is contemplated, while the methods to arrive at a plant or seed according to the invention are open to the multitude of methods contemplated by a person of ordinary skill in the art. In particular, all of the added structural genes do not have to have been added at the same time, or by the same route. Thus, for example, the HMG-CoA reductase activity may result from a cross with a plant made according to a process of U.S. Pat. No. 5,349,126, while a steroid pathway enzyme is added by nucleic acid bombardment to that plant. Further, when more than one nucleotide sequence encoding a steroid pathway enzyme is present in a contemplated plant, the expression of the gene does not have to be under the control of the same promoter, or even the same type of promoter.

The choice of which plant integrating vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene, i.e., the gene encoding HMG-CoA reductase activity, included in the DNA segment to which it is operatively linked.

Typical vectors useful for expression of genes in higher plants are well known in the art and include vectors derived from the tumor-inducing (Ti) plasmid of *Agrobacterium tumefaciens*, described by Rogers et al., *Meth. Enzymol.*, 153:253–277 (1987). However, several other plant integrating vector systems are known to function in plants including pCaMVCN transfer control vector described by Fromm et al. *Proc. Nat. Acad. Sci. USA*, 82:5824 (1985). Plasmid pCaMVCN (available from Pharmacia, Piscataway, N.J.) includes the cauliflower mosaic virus CaMV 35S promoter.

The use of retroviral plant integrating vectors to form the recombinant DNAs of the present invention is also contemplated. As used herein, the term "retroviral plant integrating vector" refers to a DNA molecule that includes a promoter sequence derived from the long terminal repeat (LTR) region of a retrovirus genome.

In preferred embodiments, the vector used to express the polypeptide coding gene includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods for Plant Molecular Biology*, A. Weissbach and H. Weissbach eds., Academic Press Inc., San Diego, Calif. (1988).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the plant integrating vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into a plant integrating vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above-described recombinant DNA molecules.

A preferred recombinant DNA molecules utilized in accordance with the present invention are pMON53733-pMON53740 (FIGS. 13–20).

A. Promoters and Target Tissues

Promoters useful in the present invention include those that confer appropriate cellular and temporal specificity of expression. Such promoters include those that are constitutive or inducible, environmentally- or developmentally-regulated, or organelle-, cell-, or tissue-specific. Preferred promoters for use with the present invention promote expression of the introduced enzymes in the seed in the cytosol, although expression in plasids or organelles of the seeds is also contemplated.

Often-used constitutive promoters include the CaMV 35S promoter (Odell et al. (1985) *Nature* 313: 810), the enhanced CaMV 35S promoter, the Figwort Mosaic Virus (FMV) promoter (Richins et al. (1987) NAR 20: 8451), the mannopine synthase (mas) promoter, the nopaline synthase (nos) promoter, and the octopine synthase (ocs) promoter.

Useful inducible promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651).

Examples of useful tissue-specific, developmentally-regulated promoters include fruit-specific promoters such as the E4 promoter (Cordes et al. (1989) *Plant Cell* 1:1025), the E8 promoter (Deikman et al. (1988) *EMBO J.* 7: 3315), the kiwifruit actinidin promoter (Lin et al. (1993) *PNAS* 90: 5939), the 2A11 promoter (Houck et al., U.S. Pat. 4,943,674), and the tomato pZ130 promoter (U.S. Pat. Nos. 5,175,095 and 5,530,185); the β-conglycinin 7S promoter (Doyle et al. (1986) *J. Biol. Chem.* 261: 9228; Slighton and Beachy (1987) *Planta* 172: 356), and seed-specific promoters (Knutzon et al. (1992) *Proc. Natl. Acad. Sci. USA* 89: 2624; Bustos et al. (1991) *EMBO J.* 10: 1469; Lam and Chua (1991) *J. Biol. Chem.* 266: 17131; Stayton et al. (1991) *Aust. J. Plant. Physiol.* 18: 507). Fruit-specific gene regulation is discussed in U.S. Pat. No. 5,753,475. Other useful seed-specific promoters include, but are not limited to, the napin, phaseolin, zein, soybean trypsin inhibitor, 7S, ADR12, ACP, stearoyl-ACP desaturase, oleosin, Lasquerella hydroxylase, and barley aldose reductase promoters (Bartels (1995) *Plant J.* 7: 809–822), the EA9 promoter (U.S. Pat. No. 5,420,034), and the Bce4 promoter (U.S. Pat. No. 5,530,194). Useful embryo-specific promoters include the corn globulin 1 and oleosin promoters. Useful endosperm-specific promoters include the rice glutelin-1 promoter, the promoters for the low-pI—amylase gene (Amy32b) (Rogers et al. (1984) *J. Biol. Chem.* 259: 12234), the high-pI—amylase gene (Amy 64) (Khurseed et al. (1988) *J. Biol. Chem.* 263: 18953), and the promoter for a barley thiol protease gene ("Aleurain") (Whittier et al. (1987) *Nucleic Acids Res.* 15: 2515).

Appropriate target tissues of plants for enhanced production of sterol compounds such as sitosterol, sitosterol esters, sitostanol, sitostanol esters, and tocopherols, and reduced production of campesterol, campestanol, and esters thereof, include, but are not limited to, fruits, flowers, seeds, roots, tubers, leaves, stems, buds, and other vegetable parts of plants. Within seeds, appropriate organ compartments include the embryo, the endosperm, and the aleurone layer. Within any of the noted target tissues, appropriate cellular compartments include, but are not limited to, the cell cytoplasm and plastids (e.g., proplastids, chloroplasts, chromoplasts, leucoplasts, amyloplasts, etc.).

B. Vectors

In plants, transformation vectors capable of introducing encoding DNAs involved in sterol compound and tocopherol biosynthesis are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding the protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (1988) *Vectors: A Survey of Molecular Cloning Vectors and Their Uses*, Butterworths, Boston; Glick et al. (1993) *Methods in Plant Molecular Biology and Biotechnology* CRC Press, Boca Raton, Fla.; and Croy (1993) *In Plant Molecular Biology Labfax*, Hames and Rickwood, Eds., BIOS Scientific Publishers Limited, Oxford, UK.

The use of transit peptides, e.g. translational fusion peptides, are not preferred for use in conjunction with the enzymes of the present invention, where the sterol synthethic compounds are present primarily in the cellular cytosol.

V. Cell Transformation and Plant Regeneration

The amount of a gene coding for a polypeptide having HMG-CoA reductase activity is increased by transforming a desired plant cell with a suitable vector that contains that added exogenous structural gene. Expression of that gene in the transformed plant cell and transgenic plants developed from that transformed plant cell enhances the activity of HMG-CoA reductase.

Methods for transforming polypeptide-coding genes into plant cells include Agrobacterium-mediated plant transformation, protoplast transformation, gene transfer into pollen, injection into reproductive organs and injection into immature embryos. Each of these methods has distinct advantages and disadvantages. Thus, one particular methods of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology*, 3:629 (1984) and Rogers et al., *Methods in Enzymology*, 153:253–277 (1987). Further the integration of the T8-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al, *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Meth. Enzymol.*, 153:253 (1987), have convenient multi-linker regions flanked by a promoter and a polyadenylation site for directed expression inserted polypeptide conding genes and are suitable for present purposes.

In addition, Agrobacteria containing both armed and disarmed Ti genes can be used for the transformations. Both types of transforming systems are illustrated herein. Transformants from the former system result in callus from which the desired squalene or sterol can be obtained, whereas transformants obtained from the latter, disarmed Ti genes can be regenerated into complete transgenic plants from whose tissues, e.g. leaf, seed and root, the desired chemicals can be obtained.

In those plant strains where Agrobacterium-mediated transformation is efficient, it is the method of choice because of the facile and defined nature of the gene transfer.

Agrobacterium-mediated transformation of leaf disks and other tissues, such as cotyledons and hypocotyls, appears to be limited to plant strains that Agrobacaterium naturally infects. Agrobacterium-mediated transformation is the most efficient in dicotyledonous plants. Few monocots appear to be natural hosts for Agrobacterium, although transgenic plants have been produced in the monocot, asparagus, using Agrobacterium vectors as described by Bytebier et al., *Proc. Natl. Acad. Sci. USA*, 84:5345 (1987). Therefore, commercially important cereal grains such as rice, corn, and wheat must usually be transformed using alternative methods. However, as mentioned above, the transformation of asparagus using Agrobacteriuim can also be achieved.

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one more than one added gene as here, it is believed that a more accurate name for such a plant is an independent segregant, because the added, exogenous gene segregates independently during mitosis and meiosis. A transgenic plant containing a single structural gene that encodes a polypeptide having HMG-CoA reductase activity and at least one of the enumerated 6 steroid pathway enzymes; i.e., and independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains the added genes according to the invention, germinating some of the seed produced and analyzing the resulting plants produced for enhanced HMG-CoA reductase activity, steroid pathway product accumulation or both, relative to a control (native, non-transgenic) or an independent segregant transgenic plant.

A homozygous transgenic plant exhibits enhanced HMG-COA reductase activity as compared to a native, non-transgenic plant and an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide having HMG-CoA reductase activity. Backcrossing to a parental plant and outcrossing with a non-transgenic plant are also contemplated.

A. Host Cells and Transformed Plant Cells

Cells modified according to the present invention are contemplated at each stage of the processes of the invention. As a result of the invention comprising at least two genes, there are several means to accomplish that end. In some embodiments of the invention, the intermediate steps include transformation of nucleic acids comprising some or all of the genes into host cells.

The nucleic acid sequence encoding a polypeptide exhibiting HMGR activity does not have to be in the same orientation as a nucleic acid sequence encoding a polypeptide exhibiting the activity of a steroid pathway enzyme. The coding nucleic acids can be under the control of different promoters or be in different orientations. For the host plant cell useful in carrying out the steroid compound biosynthesis according to the invention, the minimum that is required is the coding nucleic acids be in the same host cell. As long as the HMGR and a steroid pathway enzyme coding sequences are present in the same host cell, they do not have to be on the same DNA molecule or under the control of the same promoter, nor do they have to be derived from the same vector or construct.

Host cells are useful for making, storing, reproducing or manipulating nucleic acid constructs of the invention. Contemplated host cells are eukaryotic cells, such as yeast or plant cells. Any plant cells can be utilized with the present invention. Some particularly useful agriculturally significant plant cells are canola, soybean, corn, maize, tobacco, cotton, rape, tomato and alfalfa. Other common plant varieties are carrot, barley, arabidopsis, guayule and petunia. Prokaryotic host cells containing constructs and/or vectors according to the invention are also contemplated (e.g. *E. coli*).

One embodiment of the invention is a transformed host cell containing inter alia a recombinant construct that encodes both a DNA sequence encoding a polypeptide exhibiting 3-hydroxy-3-methylglutaryl-Coenzyme A reductase enzyme activity and a DNA sequence encoding a steroid pathway enzyme, where the steroid pathway enzyme is as described in detail above. In a preferred embodiment, those coding DNA sequences are operably linked to a promoter and a transcription termination signal sequence. In the coding sense direction of the construct, the components of the construct are operably linked in the 5' to 3' direction as a promoter, the DNA sequence encoding sequence and a transcription termination signal sequence.

Another embodiment of the invention is host cell that has been transformed with a recombinant vector that has such a construct. As discussed herein, in one embodiment of the invention, such a recombinant vector is a plant expression vector. Preferably such a host cell is a plant cell.

Methods of culturing various eukaryotic and prokaryotic cell cultures are well known in the art. The present invention contemplates cell cultures of transformed host cells. Transformed plant cells include transformed protoplasts and other types of host cell intermediates as well as plant cell cultures.

Non-limiting examples of plants that can be used in the practice of the invention include, acacia, alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, ornamental plants, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, watermelon, wheat, yam, and zucchini.

Plants particularly attractive for the steroid pathway modifications described herein include those that produce carbon substrates which can be employed for synthesis of these compounds. Non-limiting examples of such plants include various monocots and dicots, including high oil seed plants such as high oil seed Brassica (e.g., *Brassica nigra, Brassica napus, Brassica hirta, Brassica rapa, Brassica campestris, Brassica carinata,* and *Brassica juncea*), soybean (*Glycine max*), castor bean (*Ricinus communis*), cotton, safflower (*Carthamus tinctorius*), sunflower (*Helianthus annuus*), flax (*Linum usitatissimum*), corn (*Zea mays*), coconut (*Cocos nucifera*), palm (*Elaeis guineensis*), oilnut trees such as olive (*Olea europaea*), sesame, and peanut (*Arachis hypogaea*), as well as Arabidopsis, tobacco, wheat, barley, oats, amaranth, potato, rice, tomato, and legumes (e.g., peas, beans, lentils, alfalfa, etc.)

Enhancement of sitostanol compound production by the methods discussed herein is expected to result in yields of sitostanol, sitostanol esters, or mixtures thereof in an amount of at least about 57% by weight, preferably from about 57% to about 90% by weight, and more preferably from about 57% to about 65% by weight of the total sterol compounds present in seed oil. Expressed on a seed dry weight basis, sitostanol, sitostanol esters, or mixtures thereof are expected to be present in an amount of at least about 0.08%, preferably from about 0.08% to about 0.8%, and more preferably from about 0.08% to about 0.4% of seed dry weight.

B. Processes of Transformation

A variety of different methods can be employed to introduce transformation/expression vectors into plant protoplasts, cells, callus tissue, leaf discs, meristems, etc., to generate transgenic plants. These methods include, for example, Agrobacterium-mediated transformation, particle gun delivery, microinjection, electroporation, polyethylene glycol-mediated protoplast transformation, liposome-mediated transformation, etc. (reviewed in Potrykus (1991) *Ann. Rev. Plant Physiol. Plant Mol. Biol.* 42: 205).

In general, transgenic plants comprising cells containing and expressing nucleic acids encoding enzymes facilitating the modifications in sterol compound and tocopherol biosynthesis and accumulation described herein can be produced by transforming plant cells with a DNA construct as described above via any of the foregoing methods; selecting plant cells that have been transformed on a selective medium; regenerating plant cells that have been transformed to produce differentiated plants; and selecting a transformed plant that expresses the enzyme-encoding nucleotide sequence(s) at a level such that the amount of sitosterol, sitosterol esters, sitostanol, sitostanol esters, tocopherol compound(s), and campesterol/campestanol and their esters is within the ranges described herein.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the desired combination of enzymes into a single plant, and to produce hybrid progeny of the invention plants.

Specific methods for transforming a wide variety of dicots and obtaining transgenic plants are well documented in the literature (Gasser and Fraley (1989) *Science* 244: 1293; Fisk and Dandekar (1993) *Scientia Horticulturae* 55: 5; Christou (1994) *Agro Food Industry Hi Tech*, p. 17; and the references cited therein).

Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucellus, 2) diplospory where the embryo develops from an unreduced egg in an embryo sac derived from the megaspore mother cell, and 3) adventitious embryony where the embryo develops directly from a somatic cell. In most forms of apomixis, psuedogamy or fertilization of the polar nuclei to produce endosperm is necessary for seed viability. In apospory, a "nurse" cultivar can be used as a pollen source for endosperm formation in seeds. The nurse cultivar does not affect the genetics of the aposporous apomictic cultivar since the unreduced egg of the cultivar develops parthenogenetically, but makes possible endosperm production.

Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636 and references cited therein which are herein incorporated by reference.

The present invention also encompasses uniform populations of any of the plants discussed herein.

Successful transformation and plant regeneration have been achieved in the monocots as follows: asparagus (*Asparagus officinalis*; Bytebier et al. (1987) *Proc. Natl. Acad. Sci. USA* 84: 5345); barley (*Hordeum vulgarae*; Wan and Lemaux (1994) *Plant Physiol.* 104: 37); maize (*Zea mays*; Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa*; Somers et al. (1992) *Bio/Technology* 10: 1589); orchardgrass (*Dactylis glomerata*; Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); sorghum (*Sorghum bicolor*; Cassas et al. (1993) *Proc. Natl. Acad. Sci. USA* 90: 11212); sugar cane (*Saccharum spp.*; Bower and Birch (1992) *Plant J.* 2: 409); tall fescue (*Festuca arundinacea*; Wang et al. (1992) *Bio/Technology* 10: 691); turfgrass (*Agrostis palustris*; Zhong et al. (1993) *Plant Cell Rep.* 13: 1); and wheat (*Triticum aestivum*; Vasil et al. (1992) *Bio/Technology* 10: 667; Weeks et al. (1993) *Plant Physiol.* 102: 1077; Becker et al. (1994) *Plant J.* 5: 299).

Plant transformation vectors capable of delivering DNAs (genomic DNAS, plasmid DNAS, cDNAs, or synthetic DNAs) encoding plant-derived or other enzymes that affect the biosynthesis and accumulation of sterol compounds and tocopherols in plants for optimizing the pools of sitosterol, sitostanol, esters of either, and tocopherols, and for reducing the levels of campesterol, campestanol, and/or their esters, can be easily designed by art-recognized methods. Various strategies can be employed to introduce these encoding DNAs into plants to produce transgenic plants that biosynthesize and accumulate desirable levels of various sterol compounds and tocopherols, including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.
2. Sequentially transforming plants with plasmids containing each of the encoding DNAs of interest, respectively.
3. Simultaneously cotransforming plants with plasmids containing each of the encoding DNAs, respectively.
4. Transforming plants with a single plasmid containing two or more encoding DNAs of interest.
5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al. (1994) *Proc. Natl. Acad. Sci. USA* 91: 12760; PCT International Publication WO 93/02187), or to produce hybrid offspring.

In methods 2 and 3, the use of vectors containing different selectable marker genes to facilitate selection of plants containing two or more different encoding DNAs is advantageous. Examples of useful selectable marker genes include those conferring resistance to kanamycin, hygromycin, sulphonamides, glyphosate, bialaphos, and phosphinothricin.

C. Processes of Regeneration

Processes of regeneration of plants from transformed protoplasts are known in the art.

D. Transgenic Plants and Progeny

The present invention contemplates the plants that contain the exogenous constructs according to the present invention, such that a plant comprises at least one transformed plant cell comprising a nucleic acid construct. The nucleic acid construct, as described above has as operably linked components in the 5' to 3' direction, a promoter, a DNA sequence encoding a polypeptide exhibiting 3-hydroxy-3-methylglutaryl-Coenzyme A reductase enzyme activity, and a transcription termination signal sequence. The plant also comprises a nucleic acid construct that has as operably linked components in the 5' to 3' direction, a promoter, a DNA sequence encoding a steroid pathway enzyme, and a transcription termination signal sequence. The steroid pathway enzyme is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. In one embodiment, the nucleic acid constructs are recombinant constructs.

In one embodiment of the present invention a transgenic plant can be produced in accordance with the processes discussed elsewhere herein. One method to arrive at the above construct-containing plant is to transform the plant cell with a recombinant vector harboring such a construct. Other methods involve direct transfer of the exogenous construct into the plant cell. The methods of arriving at a plant cell having exogenous nucleic acids are well known in art and are applicable to the present invention. In one embodiment, the nucleic acid constructs are recombinant constructs. In a preferred embodiment, the recombinant vector is a plant expression vector.

The present invention contemplates a plant, the genome of which comprises introduced DNA. That introduced DNA has at least two components. One component is a DNA encoding a 3-hydroxy-3-methyulglutaryl-Coenzyme A reductase enzyme. The other component is DNA encoding a steroid pathway enzyme that is a squalene epoxidase enzyme, a sterol methyl transferase I enzyme, a sterol C4-demethylase enzyme, a obtusifoliol C14α-demethylase enzyme, a sterol C5-desaturase enzyme, or a sterol methyl transferase II enzyme. The storage organs, preferably seeds, of such a plant contain an elevated level of total accumulated sterol, compared to storage organs of an otherwise identical plant, the genome of which does not comprise the introduced DNA. The introduced DNAs are operatively linked to regulatory signals, preferably that cause seed-specific expression of said introduced DNAs. The seeds of such a plant contain a reduced level of squalene, cycloartenol, 24-methylene cycloartenol, obtusifoliol, stigmasta-7-enol, or campesterol compared to the seeds of an otherwise identical plant or compared to a plant comprising an introduced DNA encoding a HMG CoA reductase enzyme without the contemplated steroid pathway enzyme.

Also contemplated is a plant with introduced DNA, as described above, that produces seed having an elevated level of a steroid pathway product, compared to a corresponding transgenic or non-transgenic plant that does not contain said introduced DNA.

The invention also contemplates a plant comprising introduced DNA encoding (i) an HMGR enzyme and (ii) a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixtures thereof, wherein said plant that produces a storage organ (preferably a seed) having an elevated level of a sterol pathway product compared to a corresponding transgenic or non-transgenic plant that does not contain said introduced DNA.

The invention also contemplates a plant having introduced DNA, as described above, that produces a storage organ (preferably a seed) having a reduced level of squalene, cycloartenol, 24-methylene cycloartenol, obtusifoliol, stigmasta-7-enol, campesterol, or mixtures thereof, compared to a corresponding transgenic plant that comprises introduced DNA encoding an HMGR enzyme but that does not contain introduced DNA encoding a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixtures thereof.

For any of the above plants, an embodiment is contemplated wherein the introduced nucleic acid has regulatory signals that cause seed-specific expression of said introduced DNAs.

The progeny of the above-described plants are also considered an embodiment of the present invention, as are plant cells or transformed plant cells. Cultures of those plant cells are also contemplated. Plants produced from seeds having introduced DNA are also embodiments of the present invention.

A further embodiment of the present invention is a method of producing a plant that accumulates an elevated level of sterol pathway products, in seed of said plant compared to seed of a corresponding plant comprising no introduced DNA encoding a peptide, polypeptide, or protein that affects the biosynthesis and accumulation of a sterol pathway product, comprising sexually crossing a plant having introduced nucleic acid with the corresponding plant having no introduced DNA. Plants, including apomictic plants produced by this method are contemplated.

Another embodiment is a seed resulting from a cross of a plant having introduced DNA, described above, with a nurse cultivar. Also contemplated are seeds of any of the above-described plants. Also part of the present invention plant parts, other than a seed of any of the above-described plants.

Uniform populations of the above-described plants are also contemplated.

E. Stability of Transgene Expression

As several overexpressed enzymes may be required to produce optimal levels of substrates for the biosynthesis of sterol compounds and tocopherols, the phenomenon of co-suppression may influence transgene expression in transformed plants. Several strategies can be employed to avoid this potential problem (Finnegan and McElroy (1994) *Bio/Technology* 12: 883).

One commonly employed approach is to select and/or screen for transgenic plants that contain a single intact copy of the transgene or other encoding DNA (Assaad et al. (1993) *Plant Mol. Biol.* 22: 1067; Vaucheret (1993) *C.R. Acad. Sci. Paris, Science de la vie/Life Sciences* 316: 1471; McElroy and Brettell (1994) *TIBTECH* 12: 62). Agrobacterium-mediated transformation technologies are preferred in this regard.

Inclusion of nuclear scaffold or matrix attachment regions (MAR) flanking a transgene has been shown to increase the level and reduce the variability associated with transgene expression in plants (Stief et al. (1989) *Nature* 341: 343; Breyne et al. (1992) *Plant Cell* 4: 463; Allen et al. (1993) *Plant Cell* 5: 603); Mlynarova et al. (1994) *Plant Cell* 6: 417; Spiker and Thompson (1996) *Plant Physiol.* 110: 15). Flanking a transgene or other encoding DNA with MAR elements may overcome problems associated with differential base composition between such transgenes or encoding DNAs and integrations sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs (Register et al. (1994) *Plant Mol. Biol.* 25: 951). Site-specific recombination in which the endogenous copy of a gene is replaced by the same gene, but with altered expression characteristics, should obviate this problem (Yoder and Goldsbrough (1994) *Bio/Technology* 12: 263).

Any of the foregoing methods, alone or in combination, can be employed in order to insure the stability of transgene expression in transgenic plants of the present invention.

F. Hybrid Plants

The invention contemplates a plant having introduced DNA encoding an HMGR and at least one of the six steroid pathway enzymes, as described in detail above. It is contemplated that a transgenic plant having DNA encoding an HMGR, as is known in the art, might be crossed with a transgenic plant having DNA encoding at least one of the six steroid pathway enzymes.

Also contemplated as a hybrid plant according to the invention is a plant that is a hybrid of a transgenic plant having introduced DNA encoding an HMGR and at least one of the six steroid pathway enzymes wherein the plant has been hybridized with another strain, yet still retains the introduced DNA.

G. Storage Organs

The term "storage organ" as used herein, refers to the seeds, fruits or vegetable parts of a plant. Most often the seed is important for use in the present invention. However, there are consumable embodiments, such as with potatoes or carrots, where the vegetable parts are preferred.

A contemplated embodiment of the present invention is a storage organ comprising at least one transformed host cell. The transformed host cell has at a minimum a construct according the invention as described above. Also contemplated are the embodiments when the construct has plant promoters, when the construct is recombinant, when the construct is part of a vector, and when the vector is a plant expression vector.

The invention contemplates a transgenic plant seed transformed with a vector comprising a DNA segment that encodes a polypeptide having HMG-CoA reductase activity, and a DNA segment that encodes a polypeptide having a steroid pathway enzyme, wherein the transgenic plant seed is capable of germinating into a transgenic plant that overaccumulates steroid pathway products relative to a native, non-transgenic plant of the same strain; and mutants, recombinants, genetically engineered derivatives thereof and hybrids derived therefrom, wherein said mutants, recombinants, genetically engineer derivatives thereof and hybrids derived therefrom maintain the ability to overaccumulate steroid pathway products.

Seed from a transgenic plant is grown in the field or greenhouse, and resulting sexually mature transgenic plants are self-pollinated to generate true breeding plants. The progeny from these plants become true breeding lines that are evaluated for steroid compound or squalene accumulation, preferably in the field under a range of environmental conditions.

The commercial value of a transgenic plant with increased steroid compound or squalene accumulation is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, steroid compound or squalene accumulation is preferably bred into a large number of parental lines so that many hybrid combinations can be produced.

Adding an enhanced steroid compound or squalene accumulation trait to an agronomically elite line is accomplished by a variety of techniques well known to those of skill in the art. For example, parent transgenic plants that are either homozygous or contain a single independent segregatable gene that encodes a polypeptide having HMG-CoA activity and thus for enhanced sterol or squalene accumulation are crossed with lines having other desirable traits such as herbicide resistance (U.S. Pat. No. 4,761,373) produce hybrids. Preferably, transgenic plants homozygous for enhanced sterol or squalene accumulation are used to generate hybrids.

For example, a transgenic plant homozygous for enhance sterol accumulation is crossed with a parent plant having other desired traits. The progeny, which are heterozygous or independently segregatable for enhanced sterol accumulation and their other desired traits. The backcrossing of progeny with the parent may have to be repeated more than once to obtain a transgenic plant that possesses all desirable traits.

Alternatively, transgenic plants with an enhanced sterol or squalene accumulation trait are made multiply transgenic by introducing into such plants other genes that encode and express other desirable traits, or are mutated as with radiation, e.g. X-rays or gamma rays, as in U.S. Pat. No. 4,616,099, whose disclosures are incorporated by reference. Thus, the present invention also contemplates mutants and genetically engineered derivatives of transgenic plants having enhanced sterol or squalene accumulation.

VI. Harvest

Besides seed, elevated levels of sterols, phytosterols, such as sitosterol, phytostanols, such as sitostanol, and esters thereof, can be found in other parts of the plants encompassed herein. While the seed-specific promoters contemplated in the present invention function preferentially in seed tissues, expression in other plant parts can be expected, depending upon the specificity of the particular promoter. In this case, promoters functional in plant plastids are less desirable than those primarily directing expression in the cellular cytosol, though it may be desirable to use promoters to drive expression of the recombinant constructs or expression cassettes disclosed herein in tissues and organs other than seeds. For example, elevated levels of sterols, phytosterols, etc., can be expected in fruits, as well as vegetable parts of plants other than seeds. Vegetable parts of plants include, for example, pollen, inflorescences, terminal buds, lateral buds, stems, leaves, tubers, and roots. Thus, the present invention also encompasses these and other parts of the plants disclosed herein that contain elevated levels of desirable phytosterol, and phytostanol.

Of course, a significant effect of introducing into plants the coding sequences disclosed herein will be on the content of phytosterols/phytostanols and their esters of seed oil. Therefore, additional aspects of the present invention include oil obtainable from the seed of the plants described herein, and methods for producing such plants and oil. Methods for extracting and processing seed oils are well known in the art.

Oils produced by the cells, plants, and methods disclosed herein are superior in phytosterol/phytostanol composition to conventional oils in a variety of ways. Oil of the present invention can contain an elevated level of at least one sterol, at least one phytosterol, at least one phytosterol ester, at least one phytostanol, at least one phytostanol ester, or mixtures thereof. Preferred compounds include sitosterol, sitostanol, and their esters.

Oil from seed of plants containing and expressing introduced DNA encoding a sterol methyltransferase II enzyme advantageously contains a reduced level of campesterol, at least one campesterol ester, campestanol, at least one campestanol ester, or mixtures thereof. The sterol methyltransferase II-encoding DNA can be introduced alone, or in combination with other introduced DNA sequences encoding enzymes affecting the biosynthesis of steroid compounds as discussed herein. Campesterol/campestanol and their esters are considered to be undesirable because they are readily absorbed in the intestine, while their safety in the blood is unknown. Employing the plants and methods disclosed herein, one can obtain seed oil comprising about 0% to about 19%, preferably about 0% to about 12%, more preferably about 5% to about 9% campesterol, at least one campesterol ester, campestanol, at least one campestanol ester, or mixtures thereof by weight of the total sterol compounds of the oil. (The levels of these compounds are difficult to express on a percent seed dry weight basis because different seeds contain different percentages of these compounds expressed on this basis) These values represent a reduction of about 10% to about 100% in the amount of these compounds compared to those in conventional oils.

Introduction into plant cells of the enzyme-encoding DNA sequences discussed above modifies the biosynthesis of sterol compounds carried out by the methods, and in the cells, plants, and seeds, disclosed herein. In particular, the expression of an HMG CoA reductase in conjunction with DNA sequences for a steroid pathway enzyme is expected to result in alteration of the steroid pathway product profiles in oil as the enhanced steroid pathway throughput produces substrates for the enhanced enzyme activity. The novel phytostanol ester compositions, e.g., sitostanol ester compositions, thus produced constitute another aspect of the present invention.

A. Harvest of Steroid Compounds

Methods for the derivation of steroid compounds from cells are well known in the art. The invention contemplates the recovery of biosynthesized steroid compounds from the leaves and/or stems of plants, from plant seeds, from plant's vegetative organs, from callouses, and from cell cultures of plants, yeasts or eukaryotic cells.

Different sources of steroid compounds are preferred for various plants. For use as a food or a food component as discussed later, the steroid compounds need not be isolated or purified to 100 percent purity. Steroid compound-enriched plants may be utilized directly.

For example, from tobacco or Arabidopsis, it may be preferable to extract a pulp of the leaves and stems. From tomato, potato, or corn, it may be preferable to use the tomato, potato or corn in the form of the familiar storage organs that are typically consumed either directly, or a derivative thereof, such as tomato paste, potato flakes, vegetable oil and many more that are well known in the food science arts.

If desired, after cultivation, the transgenic plant is harvested to recover the sterol or squalene product. This harvesting step can consist of harvesting a callus culture, the entire plant, or only the leaves, or roots of the plant. This step can either kill the plant or, if only a non-essential portion of the transgenic plant is harvested, can permit the remainder of the plant to continue to grow.

In preferred embodiments, this harvesting step further comprises the steps of:

(i) homogenizing at least a sterol-containing or a squalene-containing portion of the transgenic plant to produce a plant pulp and using the sterol-or squalene-containing pulp directly, as in dried pellets or tablets as where an animal food is contemplated; or (ii) extracting the squalene or sterol(s) from the plant pulp with an appropriate solvent such as an organic solvent or by supercritical extraction [Favati, et al., *J. Food Sci.* 53:1532 (1988) and the citations therein] to produce a sterol-or squalene-containing liquid solution or suspension; and (iii) isolating the squalene or sterol(s) from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of squalene or the sterol of interest, residual amounts of precursors, cellular particles and cytosol contents. This pulp can be dried and compressed into pellets or tablets and eaten or otherwise used to derive the benefits, or the pulp can be subjected to extraction procedures.

The sterol or squalene can be extracted from the plant pulp produced above to form a sterol-or-squalene-containing solution or suspension. Such extraction processes are common and well known to one skilled in this art. For example, the extracting step can consist of soaking or immersing the plant pulp in a suitable solvent. This suitable solvent is capable of dissolving or suspending the squalene or sterol present in the plant pulp to produce a sterol-or squalene-containing solution or suspension. Solvents useful for such an extraction process are well known to those skilled in the art and included several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction as can steam distillation.

A whole plant or callus culture with an added, exogenous structural gene for a polypeptide having HMG-CoA reductase activity is grown under suitable conditions for a period of time sufficient for squalene or sterols to be synthesized and accumulated. The sterol-squalene-containing plant cells, preferably in dried form, are then lysed chemically or mechanically, and the squalene or sterol is extracted from the lysed cells using a liquid organic solvent or steam distillation, as described before, to form a sterol- or squalene-containing liquid solution or suspension by usual means such as chromatography.

The squalene or sterol is isolated from the solution or suspension produced above using methods that are well known to those skilled in the art of squalene and sterol isolation. These methods include, but are not limited to, purification procedures based on solubility in various liquid media, chromatographic techniques such as column chromatography and the like.

The invention contemplates a sitosterol or sitostanol ester composition extracted from the seed of a transgenic plant of the invention. The invention also contemplates such a sitosterol or sitostanol ester wherein an esterifying fatty acid has 2 to 22 carbon atoms in the main chain.

B. Harvest of Oil

The novel biosynthetic composition of the oil in the transgenic plants is contemplated. Thus, the present invention contemplates oil containing at least one sterol pathway product, extracted from seed of a described transgenic plant. Preferably, sitosterol, at least one sitosterol ester, or mixtures thereof, comprise at least about 50% by weight of the total sterol compounds of the oil. Preferably, sitosterol, at least one sitosterol ester, or mixtures thereof, comprise at least about 0.08% of the dry weight of a contemplated seed. Preferably, the oil has a reduced amount of squalene, cycloartenol, 24-methylene cycloartenol, obtusifoliol, stigmasta-7-enol, campesterol, or mixtures thereof, compared to oil from a corresponding transgenic plant that does not contain introduced DNA encoding a squalene epoxidase enzyme, a sterol methyl transferase I enzyme, a sterol C4-demethylase enzyme, a obtusifoliol C14α-demethylase enzyme, a sterol C5-desaturase enzyme, a sterol methyl transferase II enzyme, or mixture thereof, and that reduction is in the range of from about 10% to about 100%.

Oil is extracted from transgenic plant seeds of the present invention by method well known in the art. By way of example, oil can be extracted from plant seeds using extraction methods set forth above for harvesting sterols and squalene from transgenic plants. Alternatively, oil can be extracted from transgenic plant seeds by usually used methods for obtaining seed oils such as by crushing he seeds to produced a pulp and then pressing the pulp to obtain oil. The pulp can also be extracted with appropriate solvents (e.g. benzene) to obtain the oil. *Industrial Chemistry: A Manual for the Student and Manufacturer*, ed. By A. Rogers and A. B. Aubert, D. Van Nostrand Co., New York, pages 547–548 (1912).

C. Uses of Oil

As discussed in the "Description of Related Art," phytostanols such as sitostanol are beneficial for lowering serum cholesterol (Ling et al. (1995) *Life Sciences* 57: 195–206) and preventing cardiac disease. Tocopherols act as antioxidants, and play a major role in protecting cells from damage caused by free radicals (Halliwell (1997) *Nutrition Review* 55: 44–60). As the amount of sitostanol in conventional vegetable and bran oils is low relative to that of other sterol compounds, the oils of the present invention are particularly useful for reducing the concentration of low density lipoprotein cholesterol in plasma.

Thus, further aspects of the present invention include the following:

Cholesterol-lowering compositions comprising the oils and sitostanol ester compositions disclosed herein. Such cholesterol-lowering compositions can take the form of, or be used in, foods, food products, processed foods, food ingredients, food additive compositions, or dietary supplements that contain oils and/or fats. Non-limiting examples include margarines; butters; shortenings; cooking oils; frying oils; dressings, such as salad dressings; spreads; mayonnaises; and vitamin/mineral supplements. Patent documents relating to such compositions include U.S. Pat. Nos. 4,588,717 and 5,244,887, and PCT International Publication Nos. WO 96/38047, WO 97/42830, WO 98/06405, and WO 98/06714. Additional non-limiting examples include toppings; dairy products such as cheese and processed cheese; processed meat; pastas; sauces; cereals; desserts, including frozen and shelf-stable desserts; dips; chips; baked goods; pastries; cookies; snack bars; confections; chocolates; beverages; unextracted seed; and unextracted seed that has been ground, cracked, milled, rolled, extruded, pelleted, defatted, dehydrated, or otherwise processed, but which still contains the oils, etc., disclosed herein.

Food additive compositions of the present invention can be made by a method comprising obtaining oil containing a phytostanol or phytostanol ester selected from sitostanol, at least one sitostanol ester, or mixtures thereof, from cultured cells, or seeds of a plant, of the present invention, and evenly distributing the oil or desired phytostanol compound in finely divided form throughout the food product or food additive composition to which it is added by dissolution or by suspension in an emulsion. For example, the oil or phytostanol compound can be dissolved in an edible solubilizing agent, or can be mixed with an edible solubilizing agent, an effective amount of a dispersant, and optionally, an effective amount of an antioxidant. Examples of useful edible solubilizing agents include, but are not limited to, monoglycerides, diglycerides, triglycerides, vegetable oils, tocopherols, alcohols, polyols, or mixtures thereof. Examples of useful antioxidants include, but are not limited to, tocopherols, such as -tocopherol, ascorbic acid, inexpensive synthetic antioxidants, and mixtures thereof. Effective carriers for preparing emulsions or suspensions include water, alcohols, polyols, other edible compounds in which the oil or phytostanol compound is soluble or insoluble, and mixtures thereof. Examples of useful dispersants include, but are not limited to, lecithin, other phospholipids, sodium lauryl sulfate, fatty acids, salts of fatty acids, fatty acid esters, other detergent-like molecules, and mixtures thereof. Alternatively, the food additive composition can be made by a method comprising obtaining oil containing at least one tocopherol, and a phytostanol or phytostanol ester selected from sitostanol, at least one sitostanol ester, and mixtures thereof, from cultured cells, or seed of a plant, of the present invention, and mixing the oil with an edible solubilizing agent and an effective amount of a dispersant. Again, the edible solubilizing agent can include, but is not limited to, monoglycerides, diglycerides, triglycerides, vegetable oils, tocopherols, alcohols, polyols, or mixtures thereof, and the dispersant can include, but is not limited to, lecithin, other phospholipids, sodium lauryl sulfate, fatty acids, salts of fatty acids, fatty acid esters, other detergent-like molecules, and mixtures thereof.

The cholesterol-lowering compositions can also take the form of pharmaceutical compositions comprising a cholesterol-lowering effective amount of the oils or sitostanol ester compositions disclosed herein, along with a pharmaceutically acceptable carrier, excipient, or diluent. These pharmaceutical compositions can be in the form of a liquid or a solid. Liquids can be solutions or suspensions; solids can be in the form of a powder, a granule, a pill, a tablet, a gel, or an extrudate. U.S. Pat. No. 5,270,041 relates to sterol-containing pharmaceutical compositions.

Any of the foregoing cholesterol-lowering compositions can be used alone or in combination in methods to lower the risk of developing an elevated plasma concentration of low density lipoprotein cholesterol, to lower the plasma concentration of low density lipoprotein cholesterol, or to treat or prevent an elevated plasma concentration of low density lipoprotein cholesterol. Such methods comprise orally administering to a human or animal subject an effective amount of cholesterol-lowering composition. What constitutes an effective amount of cholesterol-lowering composition can be determined empirically, and depends in part on a variety of factors, including the age, weight, sex, diet, general medical condition of the subject, and the severity of hypercholesterolemia. Subjects undergoing treatment with the cholesterol-lowering combinations disclosed herein can be monitored by routine measurement of serum cholesterol levels to determine the effectiveness of therapy. Continuous analysis of the data obtained in this way permits modification of the treatment regimen during therapy so that optimal effective amounts of the cholesterol-lowering compositions of this invention are administered, and so that the duration of treatment can be determined as well. In this way, the treatment regimen/dosing schedule can be rationally modified over the course of treatment so as to achieve the lowest cholesterol-lowering effective amount of the present compositions which results in satisfactory anti-cholesterolemic effectiveness, and so that administration of these compositions is continued only so long as is necessary to successfully treat this condition. In general, an effective amount of a cholesterol-lowering composition of the present invention in the form of a phytostanol- or phytostanol ester-containing composition is in the range of from about 0.1 gm/day to about 4.5 gm/day. By way of example, a phytostanol ester composition, for example a sitostanol ester composition, can be administered in an amount in the range of from about 0.1 gm/day to about 4.5 gm/day, preferably from about 1 gm/day to about 4.5 gm/day, more preferably from about 2 gm/day to about 4.5 gm/day. A phytostanol composition, for example a sitostanol composition, can be administered in an amount in the range of from about 0.1 gm/day to about 3 gm/day, preferably from about 1 gm/day to about 3 gm/day, more preferably from about 2 gm/day to about 3 gm/day.

The cholesterol-lowering compositions of the present invention can be administered daily to patients in accordance with a number of different regimens. Fundamentally, these compositions should be administered in a cholesterol-lowering effective amount for a period of time effective to exert their anti-hypercholesterolemic preventing, reducing, or reversing action. Administration of the present cholesterol-lowering compositions should be continued until the hypercholesterolemic condition has been controlled or eliminated.

Another method encompassed by the present invention is that of achieving or improving effective absorption of sitostanol into a host, comprising producing at least one sitostanol ester by any of the methods disclosed herein, and administering this sitostanol ester to a host, which can be a human or animal. The sitostanol ester can be administered by a route selected from oral route, parenteral route, or topical route. The dose, which can be administered daily, can be up to about 10 milligrams of the sitostanol ester per kilogram of body weight. U.S. Pat. No. 5,202,045 relates to the use of stanol fatty acid esters to reduce serum cholesterol.

Also envisioned are plants which in addition to having increased levels of phytosterols and phytostanols due to the presence of constructs comprising sequences encoding 3-hydroxy-3-methylglutaryl-Coenzyme A reductase and at least one other sterol synthesis pathway enzyme, have increase levels of tocopherol due to the presence of constructs comprising sequences allowing the overexpression of enzymes in the tocopherol biosynthetic pathway.

Tocopherol levels vary in different plants, tissues, and developmental stages, indicating a highly regulated biosynthetic pathway. The production of homogentisic acid by p-hydroxyphenylpyruvate dioxygenase is likely to be a regulatory point for bulk flow through the pathway because of irreversible enzyme action and because homogentisic acid production is the first committed step in tocopherol biosynthesis (Norris et al., 1995, *Plant Cell* 7: 2139–2149). The other key regulatory step in tocopherol biosynthesis is the availability of the phytylpyrophosphate pool. Feeding studies (Furuya et al., 1987, *Phytochem.*, 26: 2741–2747) in safflower callus culture demonstrated 1.8-fold and 18-fold increases in tocopherol synthesis by feeding homogentisate and phytol, respectively. In meadow rescue leaf, vitamin E increases in the initial phase of foliar senescence when phytol is cleaved off from the chlorophylls and when free phytol is available (Peskier et al., 1989, *J. Plant Physiol.* 135: 428–432). These reports suggest tight coupling of tocopherol biosynthesis to the availability of homogentisic acid and phytol.

Transformation of plants with nucleic acid constructs that increase the biosynthetic activity of the tocopherol pathway can lead to increased production of particular tocopherol isomers, for example, α-tocopherol, are known in the art and can be found, for example, in PCT International publication WO 00/61771 which is incorporated herein by reference. Formation of α-tocopherol from other tocopherols occurs due to S-adenosylmethionine (SAM)-dependent methylases such as γ-tocopherol methyl transferase. Overexpression of methyl transferases in combination with 3-hydroxy-3-methylglutaryl-Coenzyme A reductase and at least one other sterol synthesis pathway enzyme as described herein is also contemplated in the present methods. Thus, any of the DNAs encoding enzymes of the tocopherol biosynthetic pathway, discussed above, are useful in the present invention. Transformation of plants with an early tocopherol biosynthesis gene is sufficient to produce plants having an elevated level of tocopherols. By "early tocopherol biosynthesis gene" is meant DNA encoding geranylgeranylpyrophosphate synthase, geranylgeranylpyrophosphate hydrogenase, 4-hydroxyphenylpyruvate dioxygenase, and phytyl/prenyl transferase. DNA encoding enzymes active in later steps of tocopherol biosynthesis ("secondary tocopherol biosynthesis genes") can be expressed to enhance carbon flux through the tocopherol pathway even further, and to produce specific tocopherol isomers. In this way, the tocopherol biosynthetic pathway can be modified to enhance production of any tocopherol compound of interest, such as α-tocopherol. As noted above, a variety of sources are available for the early tocopherol biosynthesis genes (and other tocopherol biosynthesis genes), and a gene from any of these sources can be utilized. If co-suppression occurs when a plant gene native to the target host plant is used to increase expression of a particular enzyme, a coding sequence from another source can be used as an alternative.

Preferred genes for introduction into plants to alter tocopherol quantity/quality include 3-deoxy-D-arabino-heptulosonate-7-P synthas (DAHP synthase), shikimate kinase, either or both of the prephenate dehydrogenases, 1-deoxy-d-xylulose 5-phosphate synthetase (DXS), 1-deoxy-d-xylulose 5-phosphate reductoisomerase (DXR), 4-diphosphocytidyl-2C-methyl-d-erythritol synthase (YgbP), 4-diphosphocytidyl-2C-methyl-d-erythritol kinase (YchB), 2C-methyl-d-erythritol 2,4-cyclodiphosphate synthase (YgbB), the gene product of GcpE, LytB (Altincicek et al., 2001, *J. Bacteriol.*, 183:2411–2416; Altincicek et al., 2001, *J. Immunol.*, 166:3655–3658; Campos et al., 2001, *FEBS Lett.*, 488:170–173), geranylgeranylpyrophosphate synthase (GGPPS), geranylgeranylpyrophosphate hydrogenase (GGH), phytyl/prenyltransferase (PPT), 4-hydroxyphenylpyruvate dioxygenase (HPPD), 2-methyl-6-phytylplastoquinol tocopherol methyltransferase I (MTI), tocopherol cyclase, γ-tocopherol methyltransferase (GMT) a plant sir 1736 gene (see Cyanobase http://www.kazusa.or.jp/cyanbase), a plant sir 1737 gene (see Cyanobase http://www.kazusa.or.jp/cyanbase), an ATPT2 gene (Smith et al., *Plant J.*, 11:83–92, 1977), and an AANT1 gene (Saint Guily et al., *Plant Physiol.*, 100:1069–1071, 1992).

4-hydroxy-phenylpyruvate dioxygenase and geranylgeranylpyrophosphate hydrogenase will increase the homogentisate and phytol pools, respectively. Enzymes that control fluxes through pathways are well known to be regulated in higher organisms such as plants. Therefore, 4-hydroxyphenylpyruvate dioxygenase and geranylgeranylpyrophosphate hydrogenase genes of microbial origin which are not subject to regulation in plants, or those from higher organisms (plants, algae, fungi, etc.) that are deregulated, are especially attractive in this regard. A non-limiting example is the microbial enzyme 4-amino-4-deoxyprephenate dehydrogenase (TyrA from *Erwinia herbicola*) which can replace prephenate aminotransferase, arogenate dehydrogenase and aminotransferase. Overexpression of enzymes such as 3-deoxy-arabino-heptulosonate 7-P (DAHP) synthase, prephenate dehydrogenase, and shikimate kinase would lead to increases in the levels of homogentisate. DNA encoding any of the tocopherol biosynthetic enzymes discussed herein can be introduced alone or in various combinations to enhance tocopherol quantity and/or alter tocopherol quality. When introduction of multiple enzymes is desirable, preferred combinations include, but are not limited to, 4-hydroxyphenylpyruvate dioxygenase (HPPD) plus geranylgeranylpyro-phosphate hydrogenase (GGH), geranylgeranylpyrophosphate synthase (GGPP synthase) plus geranylgeranylpyrophosphate hydrogenase (GGH), 4-amino-4-deoxyprephenate dehydrogenase (TyrA) plus phytylprenyltransferase (PPT), geranylgeranylpyrophosphate hydrogenase (GGH) plus phytylprenyltransferase (PPT), geranylgeranylpyrophosphate synthase (GGPP synthase) plus phytylprenyltransferase (PPT), 2-methyl-6-phytylplastoquinol tocopherol methyltransferase I (MTI) plus phytylprenyltransferase (PPT), or 2-methyl-6-phytylplastoquinol tocopherol methyltransferase I (MTI), phytylprenyltransferase (PPT), 4-hydroxyphenylpyruvate dioxygenase (HPPD) and geranylgeranylpyrophosphate synthase (GGPP synthase).

Plants characterized by increase levels of sterol and tocopherol production can be produced by transforming plant cells or tissues genetically altered for increased sterol production by the methods described herein with additional nucleic acid constructs encoding tocopherol biosynthetic enzymes. Introduction of constructs encoding tocopherol pathway enzymes can be accomplished using standard methods in molecular biology such as those described herein or those described in PCT International Publication WO 00/61771. Introduction of constructs encoding 3-hydroxy-3-methylglutaryl-Coenzyme A reductase, at least one other sterol synthesis pathway enzyme, and at least one tocopherol synthesis pathway enzyme can be accomplished in a single transformation or in a series of transformations. For example, and without limitation, plant cells transformed with constructs encoding 3-hydroxy-3-methylglutaryl-Coenzyme A reductase, at least one other sterol synthesis pathway enzyme as described herein could be selected and then further transformed with additional constructs encoding one or more tocopherol synthesis pathway enzymes and in particular S-adenosylmethionine-dependent γ-tocopherol methyltransferase enzyme. Successfully transformed cells can then be selected and used to regenerate plants having increased levels of phytosterols and/or phytostanols as well as increased levels of tocopherol. Plants produced can then be "selfed", a technique well known in the art, to produce uniform populations of plants.

Alternatively, plants characterized by increased levels of tocopherols and phytosterols and/or phytostanols can be produced by traditional plant breeding methods. For example, plants transformed with nucleic acid constructs encoding 3-hydroxy-3-methylglutaryl-Coenzyme A reductase and at least one other sterol synthesis pathway enzyme can be sexually crossed with high tocopherol plants. Any plant transformed to produce increased levels of tocopherols and in particular a-tocopherols can be used. Non-limiting examples include plants produced by the methods described above and in PCT International publication WO 00/61771.

If desired, the plants produced can be selfed to produce homozygous, uniform populations of plants.

Seed obtained from the transgenic, progeny, hybrid, etc., plants disclosed herein can be used in methods for obtaining oil containing phytosterols, phytosterol esters, phytostanols, phytostanol esters, or mixtures thereof along with tocopherols employing extraction and processing procedures known in the art. Note, in this regard, Kochhar (1983) *Prog. Lipid Res.* 22: 161–188. Alternatively, seeds with increased levels of tocopherols and phytosterols, phytosterol esters, phytostanols, phytostanol esters, or mixtures thereof; or fruits and vegetables with increased levels of tocopherols and phytosterols, phytosterol esters, phytostanols, phytostanol esters, or mixtures thereof, can be used directly.

Tocopherols and phytosterols and/or phytostanols can then be obtained from deodorized distillates of oil seed extracts and in particular soybean oil extracts. Such deodorized distillates are expected to contain increased levels of both tocopherols and phytosterols and/or phytostanol extracts. Oil extracts from plants and seed of the present invention are particularly valuable in that they allow the production of high sterol/tocopherol oils in a single process thus resulting in reduced purification costs, processing time and waste stream. Methods for the isolation of tocopherols and sterols from plant oils are well known in the art and can be found, for example, in U.S. Pat. Nos. 4,454,329; 5,097,012; 5,594,437; and 5,981,781.

EXAMPLES

The following examples are intended to provide illustrations of the application of the present invention. The following examples are not intended to completely define or otherwise limit the scope of the invention.

Example 1

Figure 4:
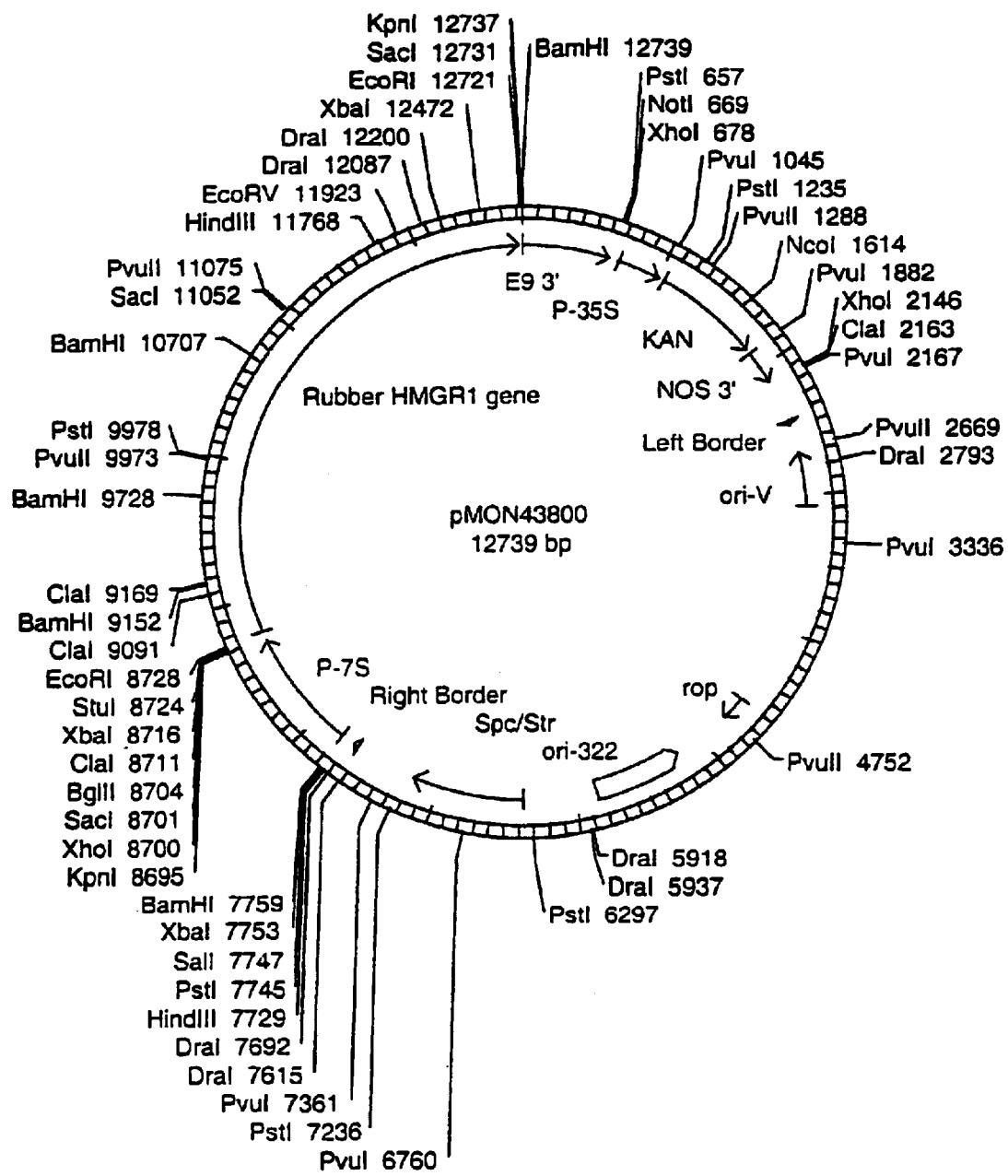
FIG. 4 is a map showing the structure of construct pMON43800. pMON43800 is a recombinant binary vector for Agrobacterium-mediated transformation, carrying the rubber HMGR1 gene cassette. The HMGR1 gene is driven by the 7S alpha' beta conglycinin promoter from soybean. P-7S: 7S promoter, rubber HMGR1 gene: coding sequence for 3-hydroxy-3-methylglutaryl reductase from Hevea brasiliensis; E9 3': 3' end of pea rbcS E9 gene; P-35S: 35S promoter from cauliflower mosaic virus; KAN: coding region for NPTII gene conferring resistance for kanamycin; NOS 3': 3' termination end of nopaline synthase coding region: Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycinand streptomycin.
Figure 6:
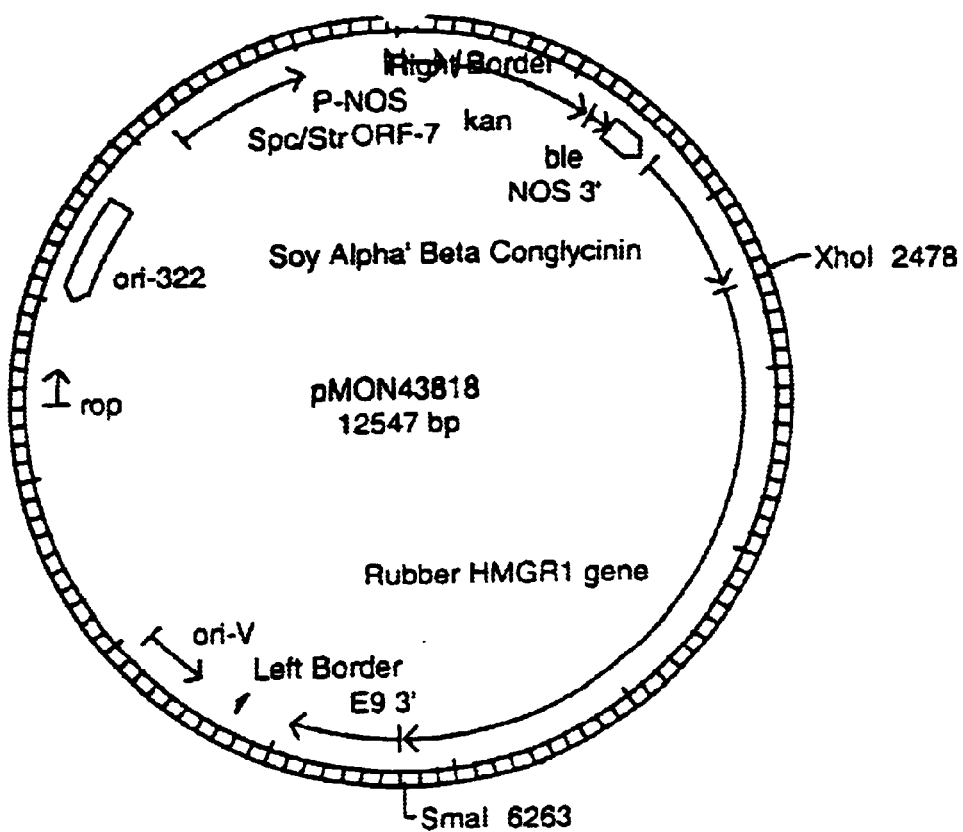
FIG. 6 is a map showing the structure of construct pMON43818. pMON43818 is a recombinant binary vector carrying the gene encoding rubber hydroxymethyl glutaryl CoA reductase1 (HMGR1) in sense orientation driven by the soybean alpha' beta conglycinin promoter. P-NOS: nopaline synthase gene promoter; kan: coding region for neomycin phospho transferase protein to confer resistance to kanamycin; NOS 3': 3' termination end of nopaline synthase coding region; Soy Alpha' Beta Conglycinin: 7S alpha' beta conglycinin gene promoter from soybean; Rubber HMGR1 gene: coding sequence for HMGR1 gene from *Hevea brasiliensis*; E9 3': 3' end of pea rbcS E9 gene; Left border: octopine left border, sequence essential for transfer of T-DNA into Agrobacterium; ori-V: plasmid origin of replication in Agrobacterium; rop: coding sequence for repressor of primer; Ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium.

Enhancement of Phytosterol content in seeds of transgenic plants by seed-specific overexpression of full-length HMG-CoA reductase (HMGR) In order to examine the ability of HMGR overexpression for increasing sterol compound levels in seeds, the following experiment was performed in Glycine max. A full-length HMGR gene from rubber genomic DNA was expressed in developing *Glycine max* seeds using the 7S promoter. This was achieved by excising the rubber HMGR gene from the plasmid pHEV15 (Schaller et al., (1995) *Plant Physiol.*, 109: 761–770) using EcoRI. The 3.8 Kb fragment was inserted into the EcoRI site of pMON29920 (FIG. 3) such that the HMGR gene is flanked by the 7S promoter on the 5' end and the E9 3' terminator to create pMON43800 (FIG. 4). This was next digested with SalI and NotI to release a 7.7 Kb fragment that was then blunt-ended at the Sal I end before ligating to pMON23616 (FIG. 5) that was first cut with SmaI and NotI. This created the pMON43818 binary vector that contains the rubber HMGR gene driven by 7S promoter and the NPTII gene selection marker driven by the NOS promoter and 3' NOS terminator. PMON43818 (FIG. 6) was used to transform *Agrobacterium tumefaciens* and transform *Glycine max* cotyledon explants as described in Example 2.

Seeds from 15 transgenic plants and one nontransgenic control plant were harvested at maturity. Sterol extraction and analysis on ten individual seeds per plant were performed as described in Example 2. Results are presented in Table 2.

TABLE 2

Sterol profile of transgenic soybean plants expressing rubber HMGR gene driven by 7s promoter.

| Event | Campesterol ug/g | Stigasterol ug/g | Sitosterol ug/g | Sitotanol ug/g | Others (Pathway intermediates) ug/g | Total ug/g | Intermediate accumulation (% of total sterol) |
|---|---|---|---|---|---|---|---|
| 1 | 161.9 | 148.2 | 551.3 | 36.8 | 264.8 | 1163 | 22.8 |
| 2 | 241.6 | 287.9 | 1128.8 | 96.6 | 1489.8 | 3244.5 | 46 |
| 3 | 442.4 | 320.1 | 1876.6 | 117.3 | 1728.4 | 4484.8 | 38.5 |
| 4 | 311.2 | 345.6 | 1645.6 | 113.8 | 1307.5 | 3723.6 | 35 |
| 5 | 395.5 | 323.0 | 1592.1 | 83.1 | 933.8 | 3327.5 | 28 |
| 6 | 370.5 | 301.6 | 1735.8 | 97.2 | 990.5 | 3495.6 | 28.3 |
| 7 | 351.0 | 307.0 | 1457.3 | 101.1 | 885.3 | 3101.7 | 28.5 |
| 8 | 248 | 172.4 | 1270.1 | 74.3 | 428.8 | 2193.6 | 19.5 |
| 9 | 221.1 | 140.7 | 1149 | 76.7 | 652.6 | 2240.1 | 29.1 |
| 10 | 234.2 | 184.8 | 1306.8 | 64.1 | 669.4 | 2459.3 | 27.2 |
| 11 | 156.5 | 125.4 | 679.2 | 38.8 | 142.3 | 1142.2 | 12.4 |
| 12 | 311.2 | 242.9 | 1457.3 | 67 | 418.6 | 2497 | 16.7 |
| 13 | 165.4 | 135.4 | 1320.1 | 59.7 | 1645.8 | 3326.4 | 49.4 |
| 14 | 190.8 | 152 | 1121.3 | 51.4 | 1040.7 | 2556.2 | 40.7 |
| 15 | 182.9 | 157.4 | 1118.5 | 55.2 | 376.6 | 1890.6 | 20 |
| 16 | 197.9 | 151.7 | 946.6 | 61.7 | 225.3 | 1583.2 | 14.2 |

Event 1: control, events 2–16:15 transgenic plants generated by 15 independent events using *Agrobacterium* mediated transformation.

Total sterols increased by 3.2- and 3.9-fold in the best performing plants (transgenic events 3 and 4). These two events also showed the highest increases of individual sterols. Campesterol increased by 2.7-fold, sitosterol by 3.4-fold, sitostanol by 3.2-fold and other sterols by 6.5-fold in event 3 while stigmasterol increased by 2.3-fold in event 4. The other sterols, which account for the highest increase in total sterols were pathway intermediates that included squalene, cycloartenol, 24-methylene cycloartenol, obtusifoliol, isofucosterol, and stigmasta-7-enol. These pathway intermediates normally form minor constituents in the sterol composition of seeds. However, in the transgenic seeds, probably due to increased carbon flux through the pathway, they accumulate in significant amounts. This suggests additional control points for sterol biosynthesis in plants such as squalene epoxidase, C-24 sterol methyltransferase, and C-14 obtusifoliol demethylase.

Example 2

Enhance phytosterol biosynthesis in seeds of transgenic soybean plants by seed-specific expression of catalytic domain of HMG-CoA Reductase (HMGR) alone and in combination with sterol methyl transferase II (SMTII)

Figure 11:
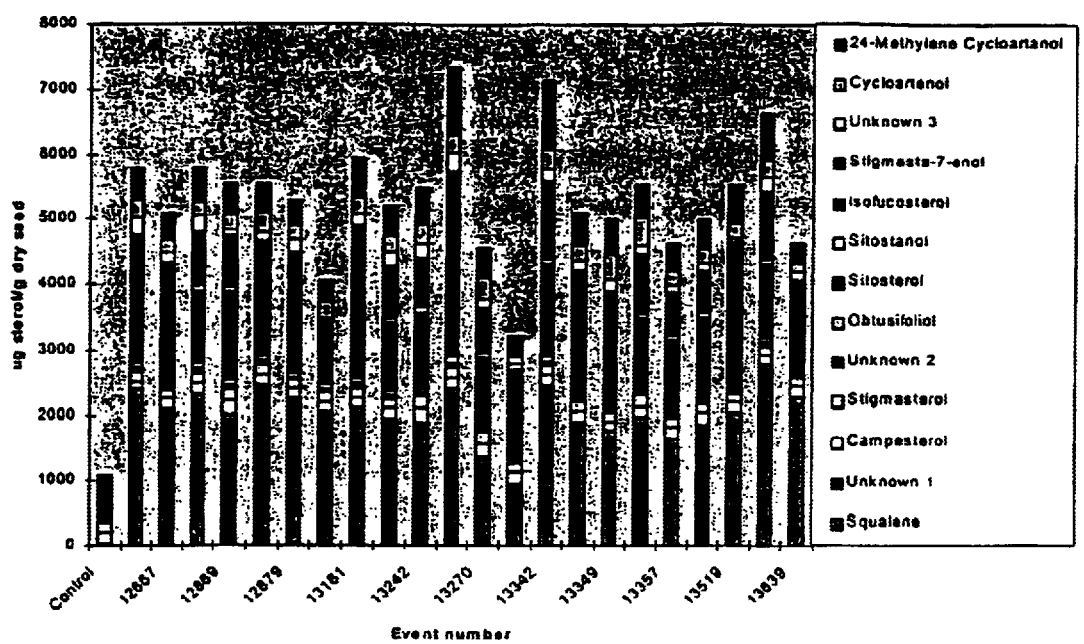
FIG. 11 is profile (histogram) of the sterol composition of R1 transgenic soybean seeds when Arabidopsis truncated HMGR (catalytic domain without linker) was overexpressed using seed-specific 7S promoter (data from pMON43057:p7S::At HMGR truncated).
Figure 12:
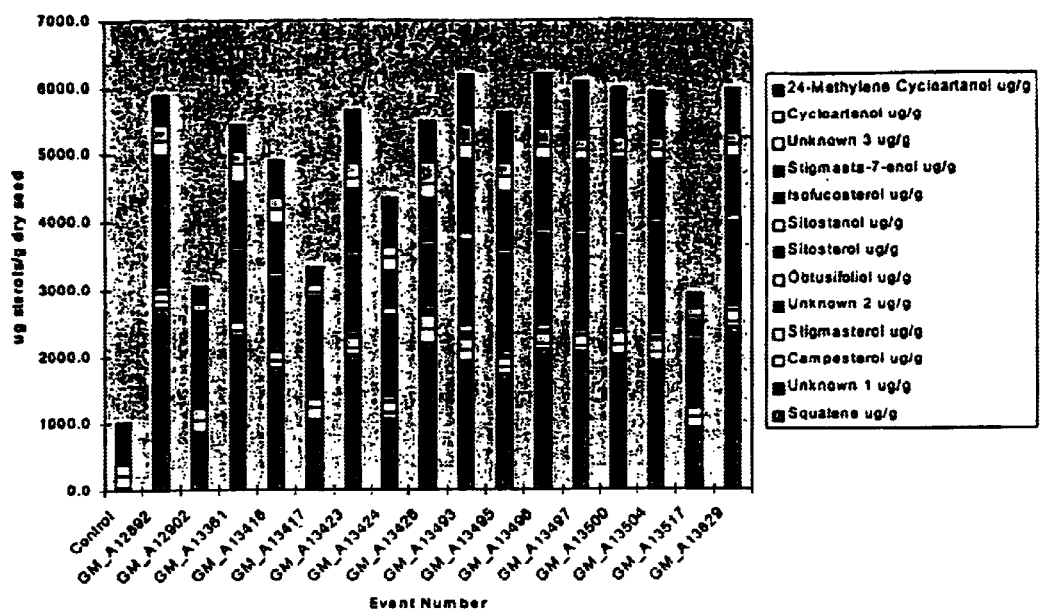
FIG. 12 is a profile (histogram) of the sterol composition of R1 transgenic soybean seeds when Arabidopsis truncated HMGR (catalytic domain without linker) and Arabidopsis SMTII were overexpresed (data from pMON43058:p7S::At HMGR truncated and p7S::At SMTII). The expression of the genes is controlled by the seed-specific 7S promoter.
Figure 13:
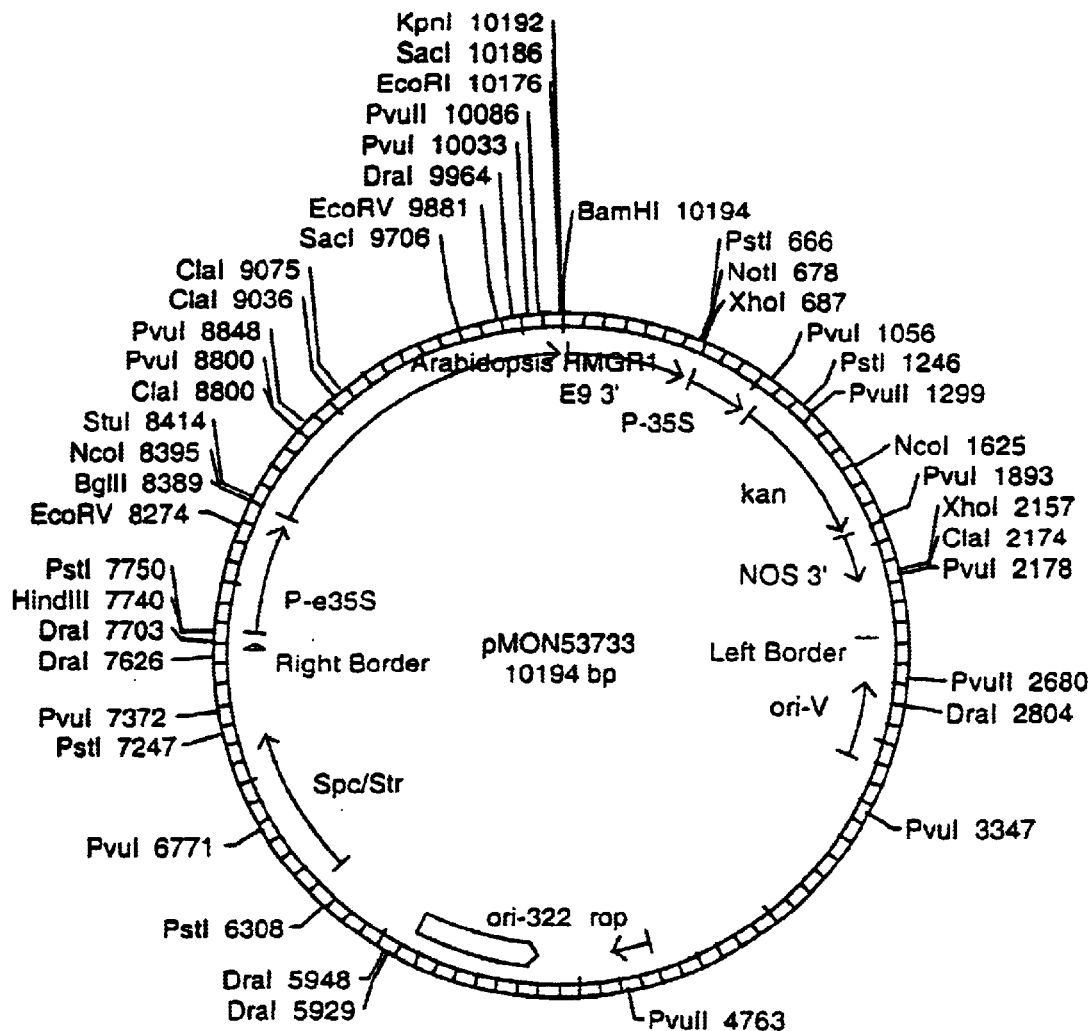
FIG. 13 is a map showing the structure of construct pMON53733. pMON53733 is a recombinant binary vector carrying the cDNA encoding full-length form of Arabidopsis hydroxymethyl glutaryl CoA reductase1(HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium; P-e35S: enhanced cauliflower mosaic virus promoter; Arabidopsis HMGR1: cDNA sequence encoding full-length form of Arabidopsis HMGR1; E9 3': 3' end of pea rbcS E9 gene.
Figure 14:
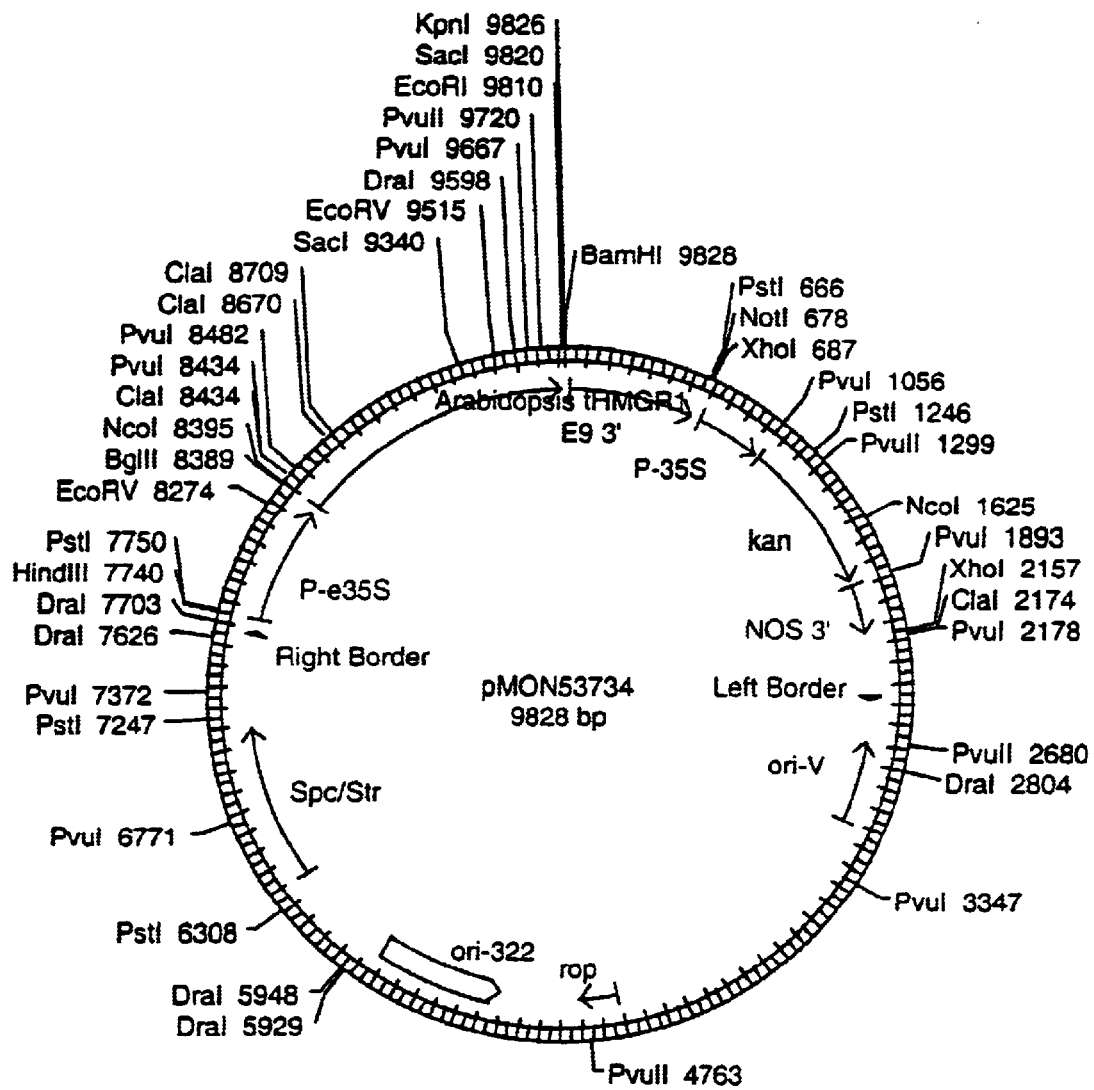
FIG. 14 is a map showing the structure of construct pMON53734. pMON53734 is a recombinant binary vector carrying the cDNA encoding catalytic domain with linker region of Arabidopsis hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium; P-e35S: enhanced cauliflower mosaic virus promoter; Arabidopsis tHMGR1: cDNA sequence encoding catalytic domain with linker region of Arabidopsis HMGR1; E9 3': 3' end of pea rbcS E9 gene.
Figure 15:
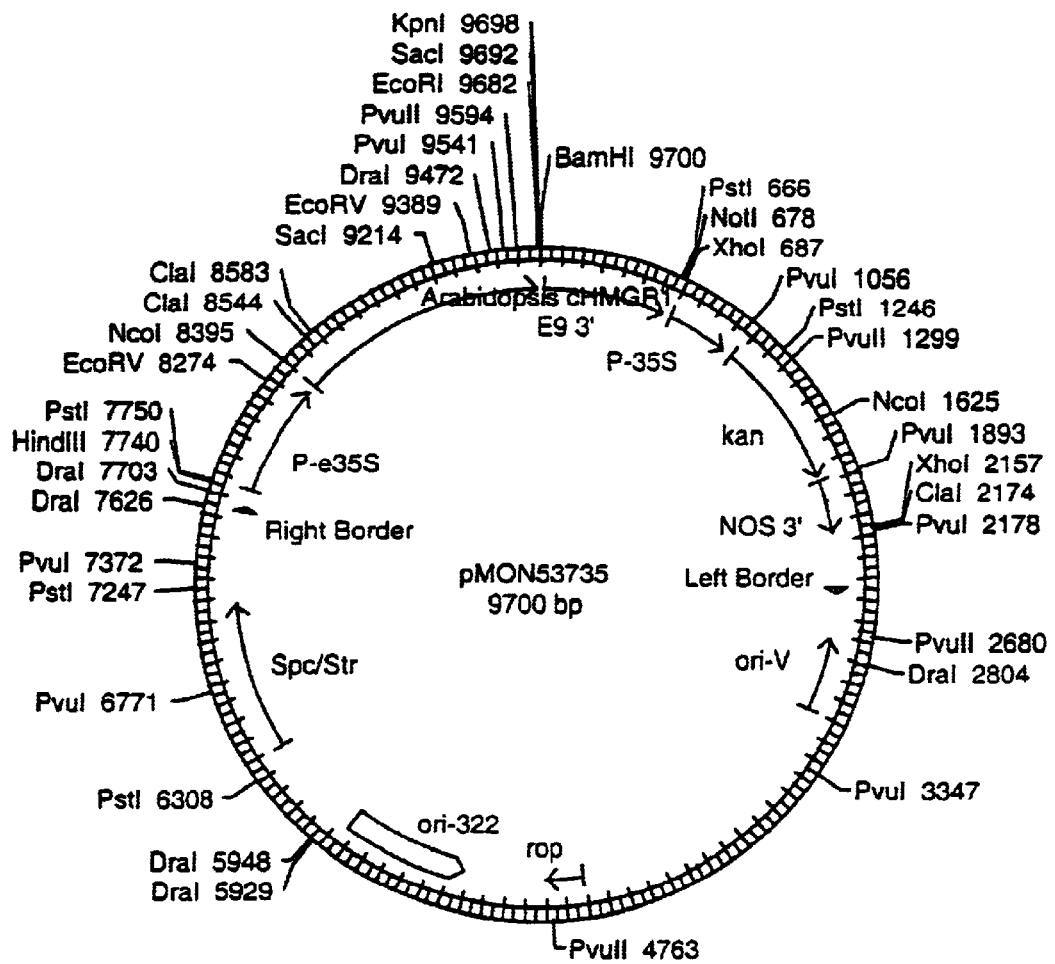
FIG. 15 is a map showing the structure of construct pMON53735. pMON53735 is a recombinant binary vector carrying the cDNA encoding catalytic domain without the linker region of Arabidopsis hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium; P-e35S: enhanced cauliflower mosaic virus promoter; Arabidopsis cHMGR1: cDNA sequence encoding catalytic domain without the linker region of Arabidopsis HMGR1; E9 3': 3' end of pea rbcS E9 gene.
Figure 16:
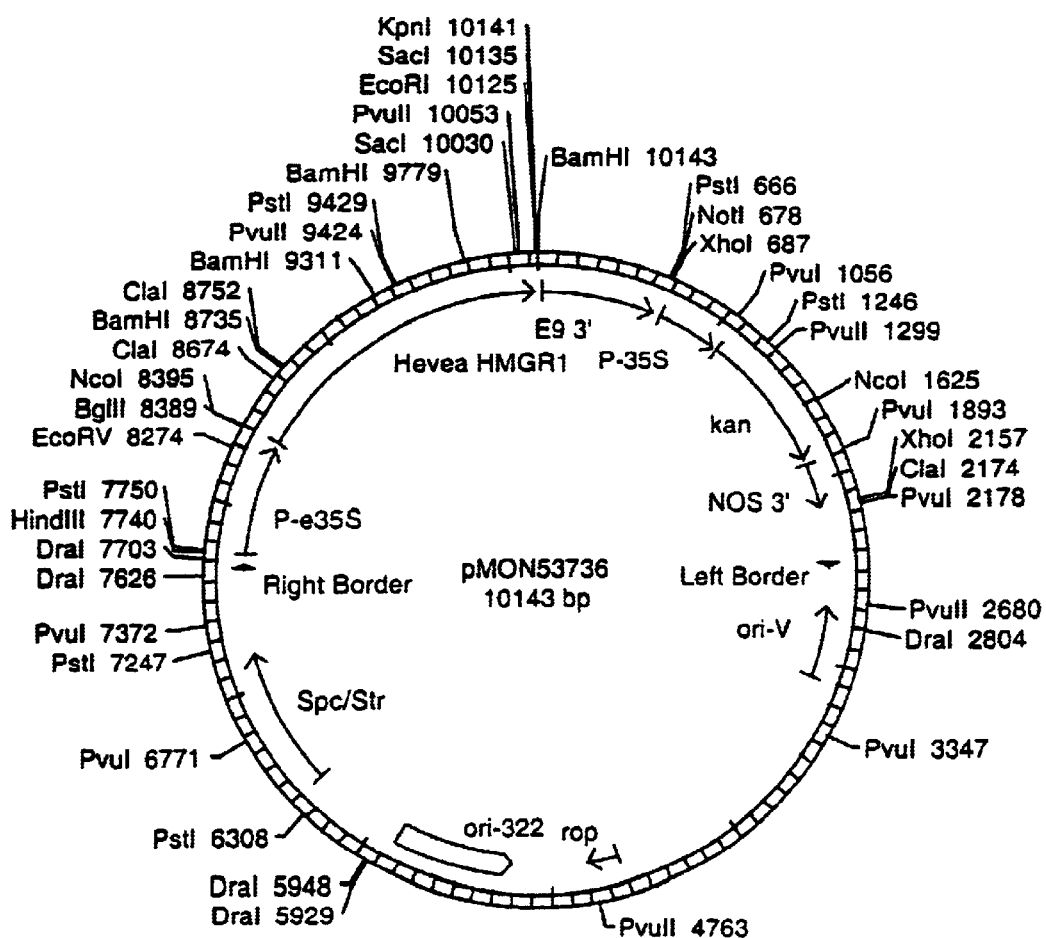
FIG. 16 is a map showing the structure of construct pMON53736. pMON53736 is a recombinant binary vector carrying the cDNA encoding full-length form of rubber (*Hevea brasiliensis*) hydroxymethyl glutaryl CoA reductase1 (HMGR1) in sense orientation driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium; P-e35S: enhanced cauliflower mosaic virus promoter; Hevea HMGR1: cDNA sequence encoding full-length form of rubber HMGR1; E9 3': 3" end of pea rbcS E9 gene.
Figure 17:
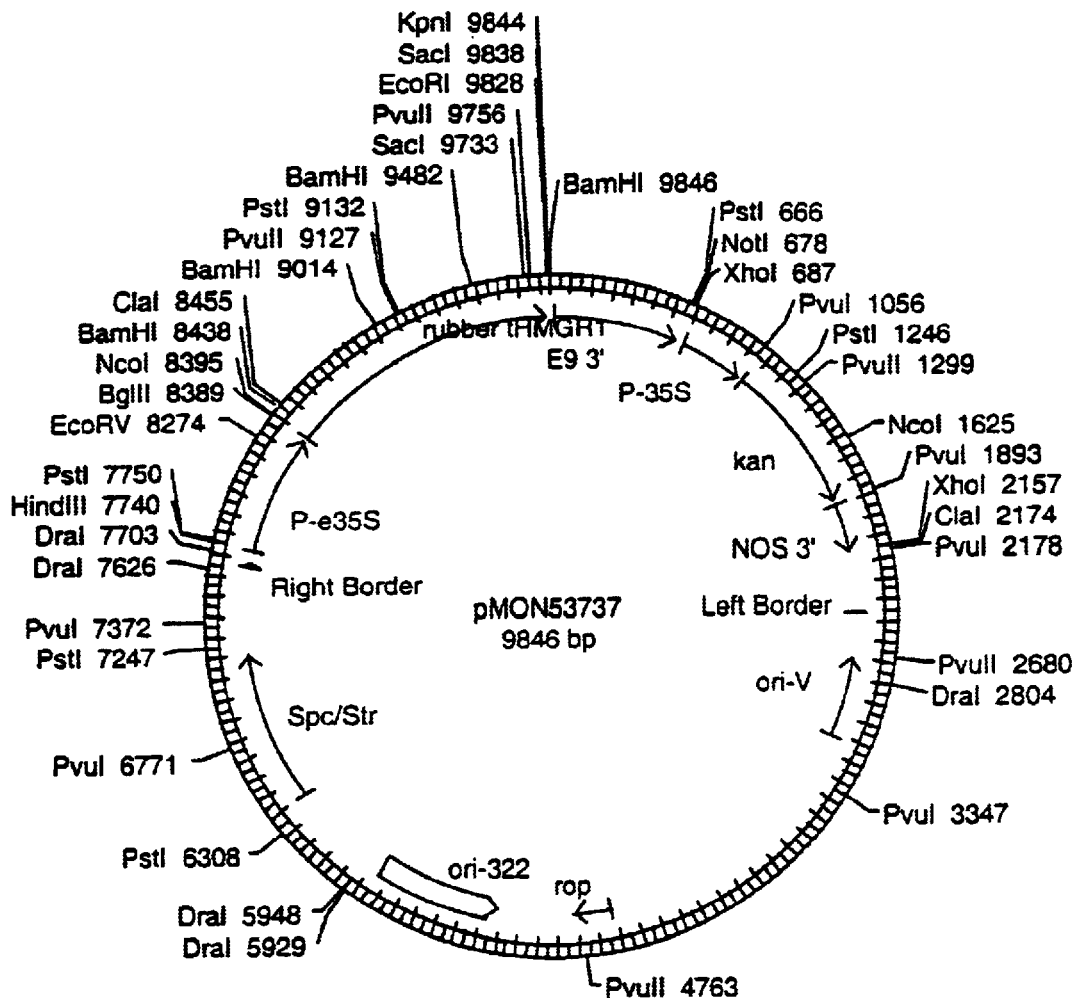
FIG. 17 is a map showing the structures of construct pMON53737. pMON53737 is a recombinant binary vector carrying the cDNA encoding catalytic domain with linker region of rubber (*Hevea brasiliensis*) hydroxymethyl glutaryl CoA reductase1 (HMGR1) in sense orientation_driven by the enhanced cauliflower mosaic virus 35S promoter. P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD (3")) conferring resistance to spectinomycin and streptomycin; Right Border: right border sequence of T-DNA essential for integration into Agrobacterium; P-e35S: enhanced cauliflower mosaic virus promoter; rubber tHMGR1: cDNA sequence encoding catalytic domain with linker region of rubber HMGR1; E9 3': 3" end of pea rbcS E9 gene.
Figure 18:
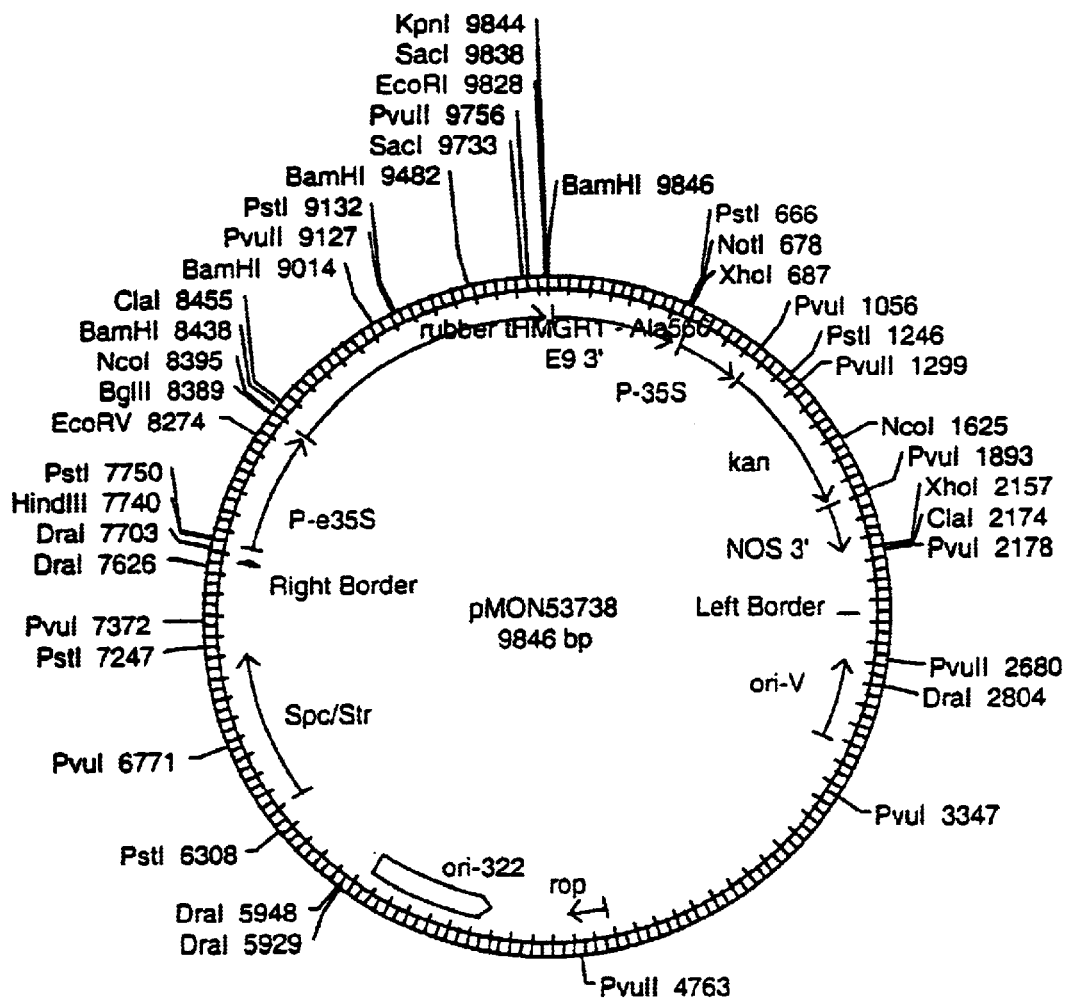
FIG. 18 is a map showing the structure of construct pMON53738. pMON53738 is a recombinant binary vector carrying the cDNA encoding mutant form of rubber (*Hevea brasiliensis*) hydroxymethyl glutaryl CoA reductase1 (HMGR1) in sense orientation driven by the enhanced cauliflower mosaic virus 35S promoter. In the mutant rubber HMGR1 the putative phosphorylation site, the serine amino acid residue at position 566 is changed to alanine amino acid residue (SEQ ID 23). P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium; P-e35S: enhanced cauliflower mosaic virus promoter; rubber tHMGR1 Ala 566: cDNA sequence encoding catalytic domain with linker region of rubber HMGR1 in which serine amino acid residue at position 566 is changed to alanine amino acid residue using site directed mutagenesis; E9 3': 3' end of pea rbcS E9 gene.
Figure 19:
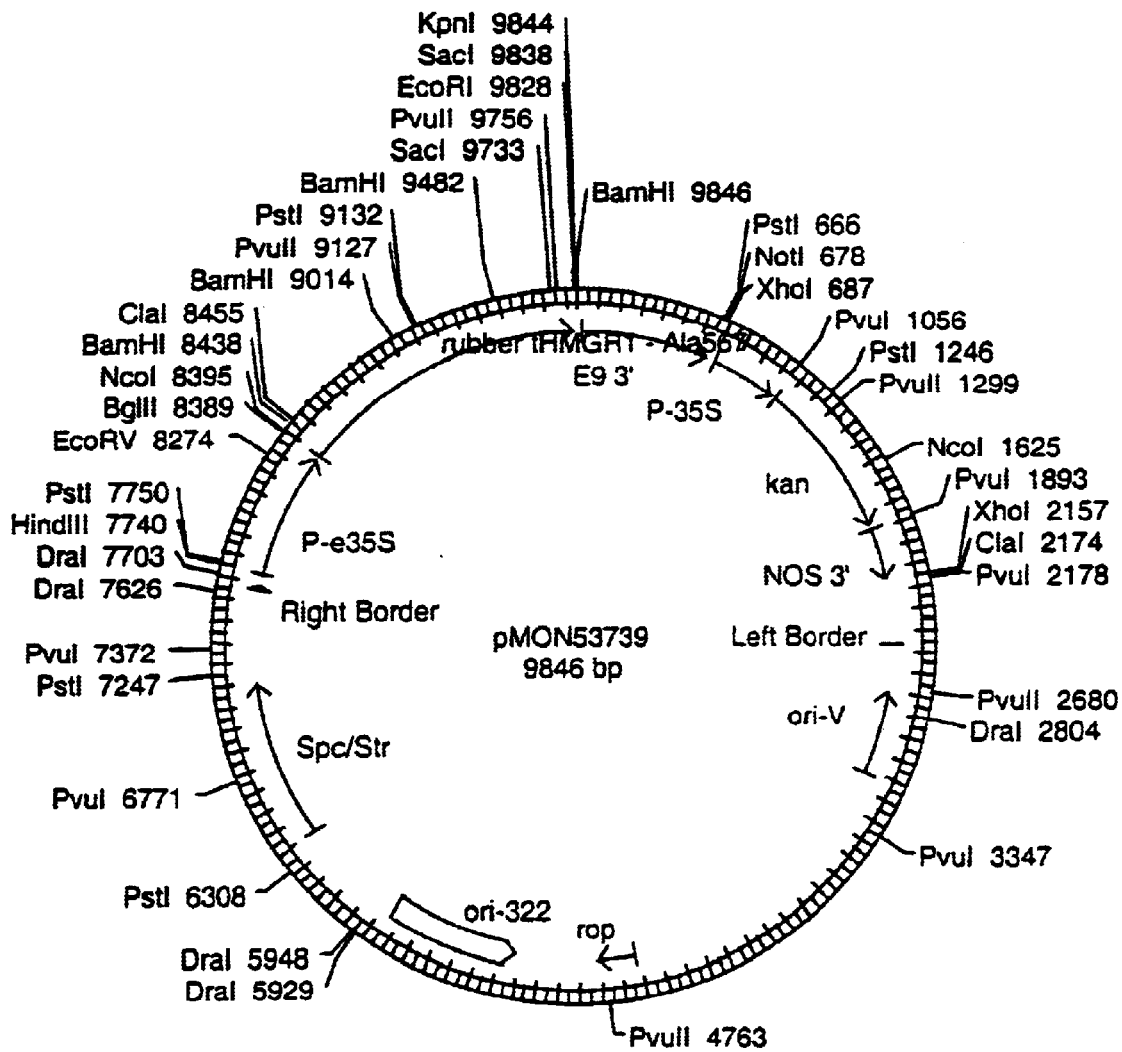
FIG. 19 is a map showing the structure of construct pMON53739. pMON53739 is a recombinant binary vector carrying the cDNA encoding mutant form of rubber (Hevea brasiliensis) hydroxymethyl glutaryl CoA reductase1 (HMGR1) in sense orientation driven by the enhanced cauliflower mosaic virus 35S promoter. In the mutant rubber HMGR1 the putative phosphorylation site, the serine amino acid residue at position 567 is changed to alanine amino acid residue (SEQ ID 24). P-35S: 35S promoter from cauliflower mosaic virus; kan: confers resistance to neomycin and kanamycin; NOS 3': 3' termination end of nopaline synthase coding region; Left border: octopine left border, sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium; P-e35S: enhanced cauliflower mosaic virus promoter; rubber tHMGR1 Ala 567: cDNA sequence encoding catalytic domain with linker region of rubber HMGR1 in which serine amino acid residue at position 567 is changed to alanine amino acid residue using site directed mutagenesis; E9 3': 3' end of pea rbcS E9 gene.
Figure 20:
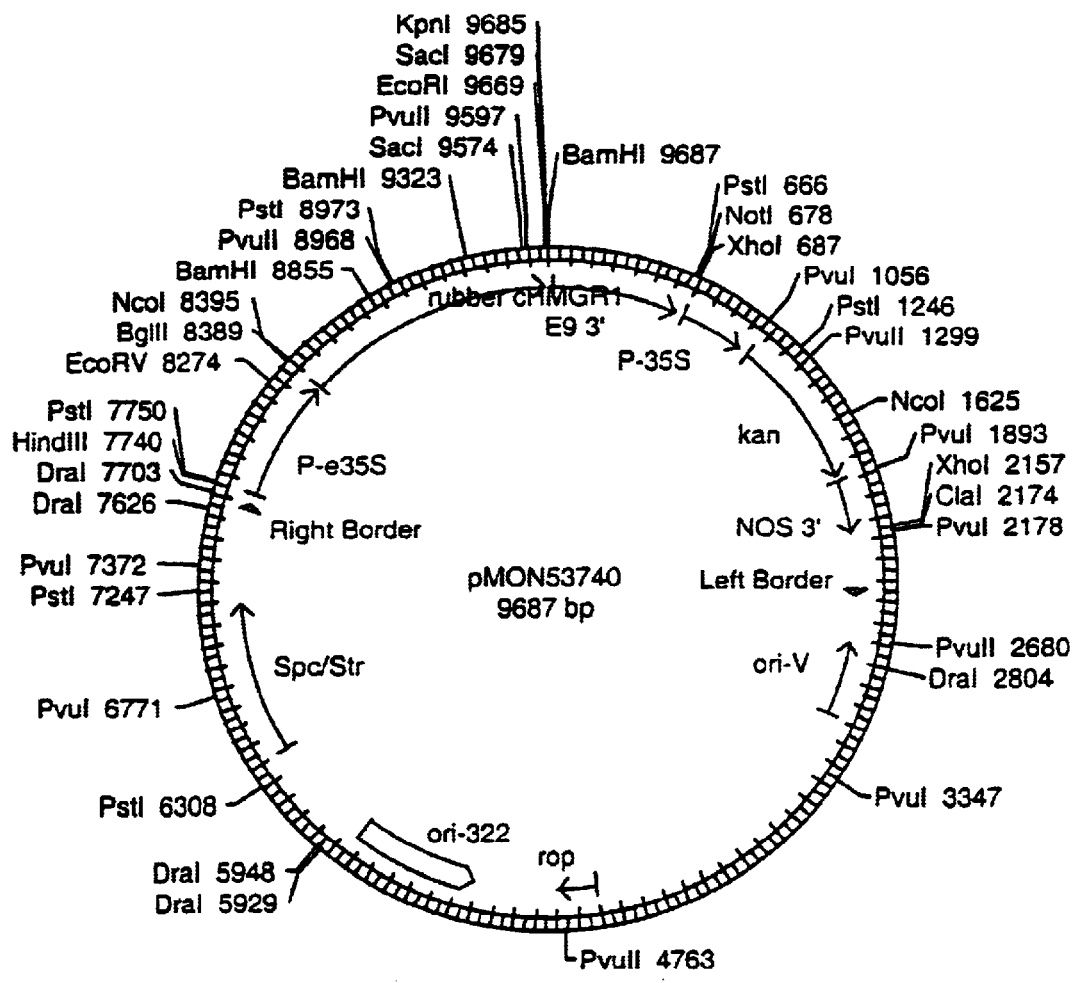
FIG. 20 is a map showing the structure of construct pMON53740. pMON53740 is a recombinant binary vector carrying the cDNA encoding catalytic domain without linker region of rubber (*Hevea brasiliensis*) hydroxymethyl glutaryl CoA reductase1 (HMGR1) in sense orientation driven by the enhanced cauliflower mosaic virus 35S promoter. P-35S: 35S promoter from cauliflower mosaic virus; kan.

In another embodiment of the present invention, the levels of sterol compounds, including sitosterol, sitostanol, campesterol, stigmasterol and at least one ester for each of the sterol compounds and mixture there of, can be elevated in plant seeds by overexpression of catalytic domain of plant-HMG-CoA reductases. One can transform a plant of interest using an expression cassette or vector comprising DNA encoding a polypeptide exhibiting 3-hydroxy-3-methylglutaryl-Coenzyme A reductase (HMG-CoA reductase or HMGR) activity. HMGR cDNAs from rubber have been successfully used to increase plant sterol levels in plant tissues (Schallet et al. (1995) *Plant Physiol.* 109: 761–770). Full-length and truncated forms of HMGR CDNAs encoding full-length and catalytic domain of HMGR, respectively, from Arabidopsis have also been used to overproduce sterols in transgenic Arabidopsis plants (Gonzalez et al. (1997) *Third Terpnet Meeting of the European Network on Plant Isoprenoids Abstracts*, Abstract No. 33, page 33). In the above examples however, the genes have not been specifically targeted to increase sterol levels in seeds. Another approach to enhance the nutritionally beneficial 24-ethyl sterols (sitosterol, sitostanol) and reduce the accumulation of 24-methyl sterols (campesterol) in seeds one can co-express two genes encoding the enzymes HMGR and sterol methyl transferse II (SMTII), each under the control of seed-specific promoter. Here we present evidence for such approaches: sterol composition of transgenic soybean seeds haboring truncated form (catalytic domain of HMGR without linker) of Arabidopsis HMGR1 is presented in FIG. 11 and Table 3. Sterol composition of transgenic soybean seeds haboring Arabidopsis HMGR1 (catalytic domain of HMGR without linker) and Arabidopsis SMTII is presented in FIG. 12 and Table 4.

Figure 7:
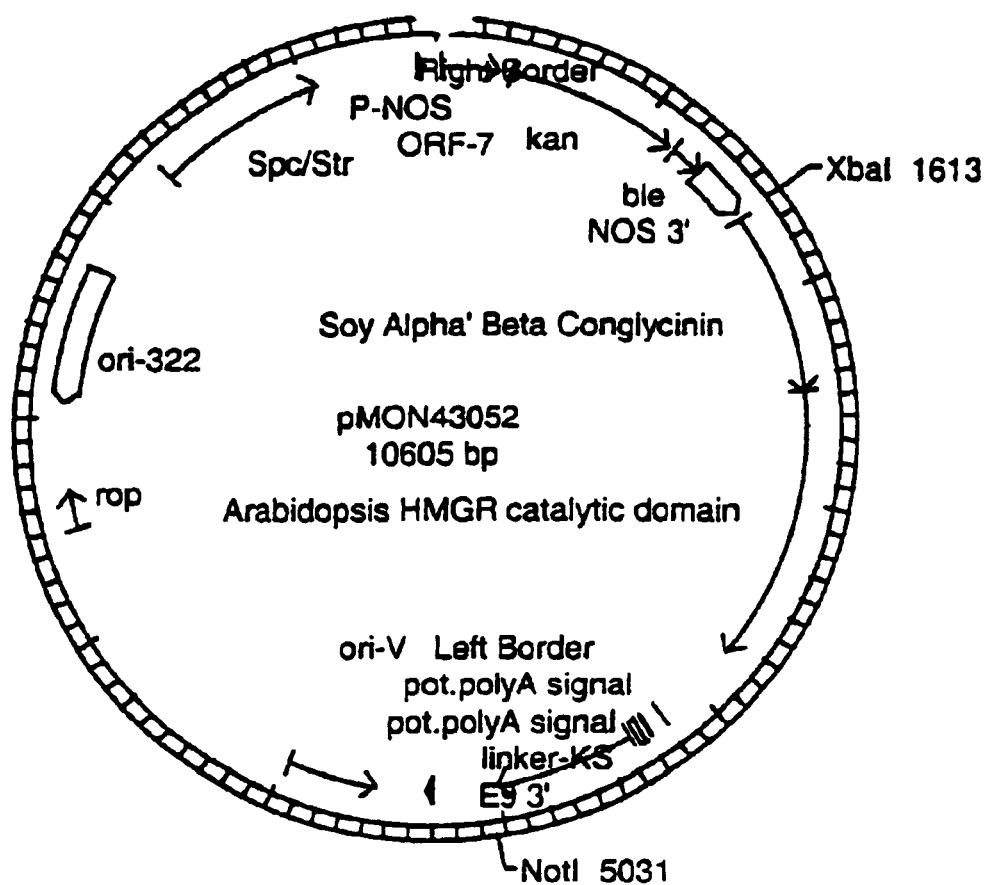
FIG. 7 is a map showing the structure of construct pMON43052. pMON43052 is a recombinant shuttle vector, carrying the cDNA fragment encoding the catalytic domain of Arabidopsis HMGR1 in sense orientation driven by the soybean alpha' beta conglycinin promoter. P-NOS: nopaline synthase gene promoter; kan: coding region for neomycin phosphotransferase protein to confer resistance to kanamycin; NOS 3': 3' termination end of nopaline synthase coding region; Soy Alpha' Beta Conglycinin: 7S alpha' beta conglycinin gene promoter from soybean; Arabidopsis HMGR catalytic domain: coding sequence for the catalytic domain of Arabidopsis HMGR1 protein; E9 3': 3' end of pea rbcS E9 gene; Left border: octopine left border, sequence essential for transfer of T-DNA into Agrobacterium; ori-V: plasmid origin of replication in Agrobacterium; rop: coding sequence for repressor of primer; Ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium.
Figure 8:
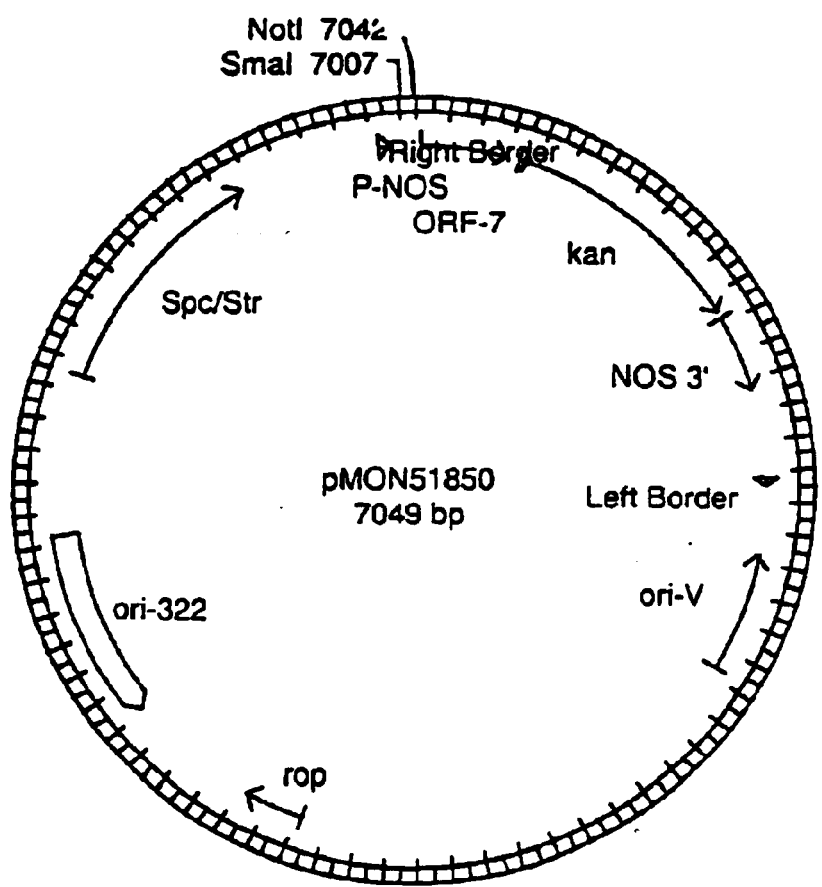
FIG. 8 is a map showing the structure of construct pMON51850. pMON51850 is a binary vector for Agrobacterium mediated transformation of soybean. P-NOS: nopaline synthase gene promoter; kan: coding region for neomycin phosphotransferase protein to confer resistance to kanamycin; NOS 3': 3' termination end of nopaline synthase coding region; Left border: octopine left border sequence essential for transfer of T-DNA into Agrobacterium; ori-v: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence of T-DNA essential for integration into Agrobacterium.
Figure 9:
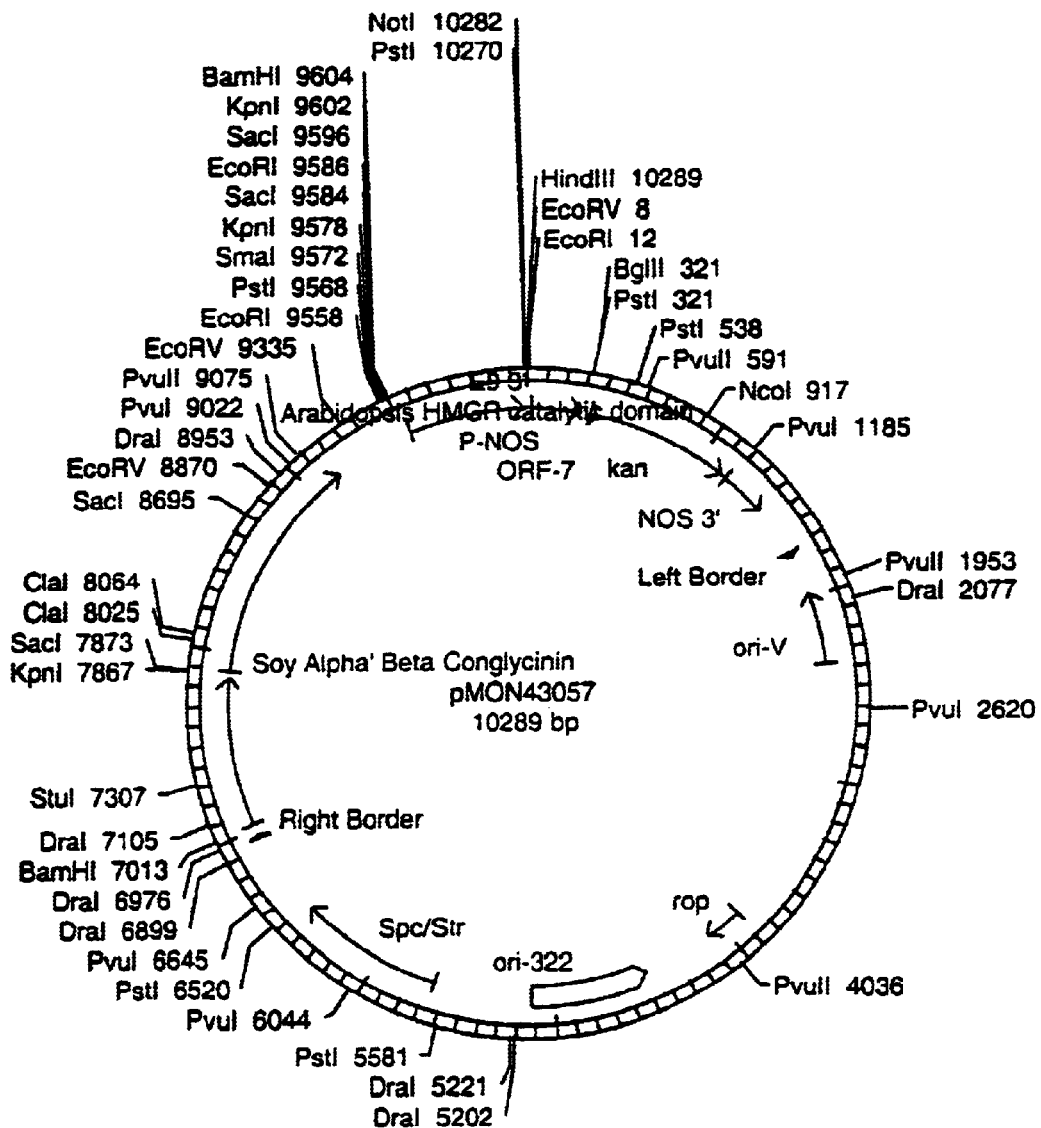
FIG. 9 is a map showing the structure of construct pMON43057. pMON43057 is a recombinant binary vector for Agrobacterium mediated transformation of soybean, carrying the gene cassette for expressing catalytic domain of HMGR1 from *Arabidopsis thaliana*. The catalytic domain of the HMGR1 cDNA is driven by soybean 7S alpha' beta conglycinin promoter. P-NOS: nopaline synthase gene promoter; kan: coding region for neomycin phosphotransferase protein to confer resistance to kanamycin; NOS 3': 3' termination end of nopaline synthase coding region; Left border: octopine left border sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD (3")) conferring resistance to spectinomycin and streptomycin; Right Border: right border sequence essential for transfer of T-DNA into Agrobacterium; Soy Alpha' Beta Conglycinin: soybean 7S alpha' beta conglycinin gene promoter; Arabidopsis HMGR catalytic domain: coding sequence for Arabidopsis HMGR1 catalytic domain; E9 3': 3' end of pea rbcS E9 gene.
Figure 10:
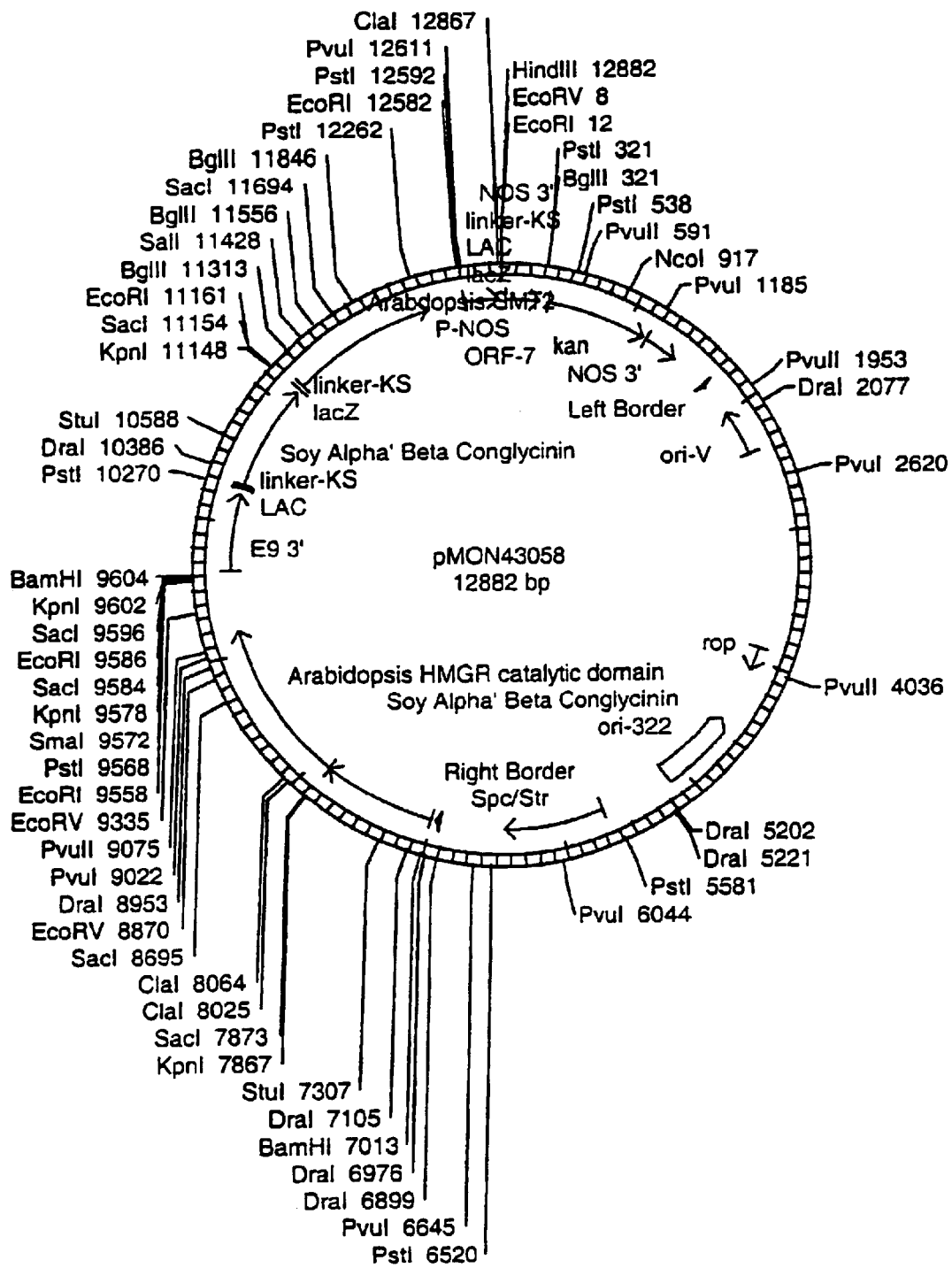
FIG. 10 is a map showing the structure of construct pMON43058. pMON43058 is a recombinant binary vector for Agrobacterium-mediated soybean transformation, carrying gene expression cassettes for catalytic domain of HMGR1 from *Arabidopsis thaliana* and SMTII from *Arabidopsis thaliana*. P-NOS: nopaline synthase gene promoter; kan: coding region for neomycin phosphotransferase protein to confer resistance to kanamycin; NOS 3': 3' termination end of nopaline synthase coding region; Left border: octopine left border sequence essential for transfer of T-DNA into Agrobacterium; ori-V: plasmid origin of replication in Agrobacterium; rop: coding sequence for repressor of primer; ori-322: origin of replication in *E. coli*; Spc/Str: coding region for Tn7 adenylyltransferase (AAD(3")) conferring resistance to spectinomycin and streptomycin; Right Border: right border sequence essential for transfer of T-DNA into Agrobacterium; Soy Alpha' Beta Conglycinin: 7S alpha' beta conglycinin gene promoter from soybean; Arabidopsis HMGR catalytic domain: sequence encoding the catalytic domain of Arabidopsis HMGR1; E9 3': 3' end of pea rbcS E9 gene; Soy Alpha' Beta Conglycinin: soybean 7S alpha' beta conglycinin gene promoter; Arabidopsis SMT2: cDNA encoding sterol methyl transferase II enzyme from *Arabidopsis thaliana* (accession no: X89867); NOS 3': 3' termination end of nopaline synthase coding region.

In order to examine whether overexpression of the catalytic domain of HMGR increases sterol levels in the seeds of transgenic soybean, the following experiment was performed in *Glycine max*. A truncated form of HMGR1 cDNA encoding only the catalytic domain of HMGR from Arabidopsis was expressed in developing seeds of *Glycine max* using the seed-specific 7S promoter. This was achieved by excising the cDNA fragment (HMGR1cd) encoding the HMGR1 catalytic domain from the plasmid pHMGR1cd (Dale et al., (1995) *Eur. J. Biochem.* 233: 506–513) using NdeI and SmaI enzymes resulting in the isoloation of a 1.9 Kb fragment. The NdeI overhang was filled-in and the 1.9 Kb fragment was blunt-end ligated to vector pMON43818 (FIG. 6), previously XhoI (XhoI overhang was filled-in) and SmaI digested such that the HMGRlcd was flanked by the 7S promoter on the 5' end and the E9 3' terminator to create a recombinant vector pMON43052 (FIG. 7). This was next digested with XbaI and blunt-ended and then digested with NotI to release a 3.4 Kb fragment and ligated to pMON51850 (FIG. 8) that was digeted with SmaI and NotI. The ligation created a recombinant binary vector pMON43057 (FIG. 9) that contained the cDNA fragment encoding the catalytic domain of Arabidopsis HMGR1, driven by 7S promoter and E9 3' terminator and the NPTII selectable marker gene driven by the NOS promoter and 3' NOS terminator. The pMON43057 was used for *Agrobacterium tumefaciens* mediated transformation of *Glycine max* cotyledon explants. The pMON43058 (FIG. 10) construct carrying both the catalytic domain of Arabidopsis HMGR1 and Arabidopsis SMTII, both driven by the 7S promoter, was also used for *Agrobacterium temefaciens*-mediated transformation of *Glycine max* in a similar manner described below.

Explants for transformation were prepared as follows: sterilized seeds were germinated on germination medium under light at 28° C. for 5–6 days. Germinated seeds were placed in the dark at 4° C. for 24 hours prior to excision. Seed coats were removed and hypocotyls of each seedling trimmed to a length of 0.5 cm to 1.0 cm in length. The cotyledons were then split open such that the hypocotyl was split down in the middle. The primary leaves and apical region of each cotyledon was removed to expose the wounding region. Wounding was performed with 3–7 shallow, scalpel scores in line with the embryo axis, ensuring that the apical bud was damaged. Wounded explants were incubated in the culture of *Agrobacterium tumefaciens* containing pMON43057. Incubation was for 1 hour at room temperature. Inoculated explants were then transferred to a co-culture medium and placed under light at 23° C. for 3–4 days. At this time explants were transferred to shooting medium without kanamycin selection and placed in a 25° C. light growth room for 4 days.

After 4 days on delay, explants were transferred to a 186 ppm kanamycin selection medium and placed in a 25° C. light growth room for 2 weeks. At the end of two weeks explants were transferred to 186 ppm Woody Plant medium and placed again in a 25° C. light growth room for another 2 weeks. Cultures were transferred every 2 weeks to fresh medium for approximately 18–21 weeks. At the 6 week transfer, the cotyledons and any dead material were removed from the explants, and the petiole was cut. At each subsequent 2 week transfer, the petiole was cut to expose fresh cells to the medium.

Transgenic shoots that were approximately ½" in length, with 2 nodes, 1 open trifoliate and an active growing point were selected, cut and transferred to rooting medium. Once a good root system was developed, the plants were sent to the greenhouse to grow up in soils in pots.

Seeds from the 15 transgenic plants and one nontransgenic control plant were harvested at maturity. Ten individual seeds from each plant were weighed and ground into fine powder using an electric grinder. A known amount of cholestane (usually 100 $\mu$g in 100 $\mu$l ethanol) was added to each approximately 50 mg powder sample. Sterol compounds were hydrolyzed directly from the ground tissue by saponification with 2 ml of 10% KOH in methanol by refluxing the material at 60° C. for 30 minutes. The refluxed samples were cooled to room temperature and filtered through glass wool. An equal volume of water was added to each filtrate, and the nonsaponifiables were extracted by partitioning three times with equal volumes of hexane. The hexane phases were pooled and evaporated. The residues were resuspended in 1 ml of acetone, and quantatively transferred to glass GC vials that were immediately capped. Sterols were analyzed by Gas Chromatography-Flame Ionizing Detector using the following conditions: Inlet temperature of 220° C., detector temperature of 320° C., and column oven temperature programmed from 220° C. to 320° C. with initial temperature for 1 minute and final temperature for 16 minutes and ramp rate of 8°/min. The column used was a glass capillary DB-5 column of 50 m length, 320 $\mu$m diameter, and a film thickness of 0.25 $\mu$m. The carrier gas was helium at a flow rate of 1.0 ml/min. Results are presented in Table 3 and Table 4.

TABLE 3

| Construct | Plant/Seed ID | Squalene μg/g | Unknown 1 μg/g | Campesterol μg/g | Stigmasterol μg/g | Unknown 2 μg/g | Obtusifoliol μg/g | Sitosterol μg/g | Sitostanol μg/g | Isofucosterol μg/g | Stigmasta-7-enol μg/g | Unknown 3 μ/g |
|---|---|---|---|---|---|---|---|---|---|---|---|---|
| Control | Control | 33.4 | 18.5 | 152.0 | 153.6 | 0.0 | 0.0 | 547.1 | 34.6 | 15.8 | 34.6 | 24.9 |
| pMON43057 | OM_A12666 | 2385.2 | 17.7 | 119.5 | 130.4 | 98.4 | 52.3 | 866.9 | 40.5 | 164.8 | 900.4 | 273.6 |
| pMON43057 | OM_A12667 | 2083.9 | 13.5 | 149.0 | 129.2 | 95.9 | 11.9 | 973.6 | 26.3 | 118.8 | 738.4 | 136.9 |
| pMON43057 | OM_A12783 | 2282.3 | 20.6 | 178.3 | 140.0 | 89.7 | 64.2 | 1119.0 | 75.0 | 164.5 | 670.5 | 249.9 |
| pMON43057 | OM_A12869 | 1981.3 | 19.1 | 200.4 | 170.3 | 65.3 | 71.7 | 1357.7 | 66.1 | 123.8 | 882.3 | 83.5 |
| pMON43057 | OM_A12870 | 2433.0 | 13.5 | 153.5 | 153.9 | 78.5 | 75.8 | 939.2 | 44.7 | 181.3 | 600.0 | 121.3 |
| pMON43057 | OM_A12879 | 2244.6 | 2.2 | 146.7 | 120.8 | 44.3 | 41.9 | 1150.0 | 42.8 | 120.3 | 549.0 | 186.2 |
| pMON43057 | OM_A12986 | 2038.8 | 9.2 | 131.9 | 152.1 | 41.5 | 79.3 | 593.7 | 13.7 | 210.5 | 157.7 | 55.5 |
| pMON43057 | OM_A13181 | 2100.1 | 13.6 | 137.1 | 138.7 | 85.7 | 64.7 | 1180.0 | 56.7 | 181.1 | 935.0 | 175.7 |
| pMON43057 | OM_A13241 | 1945.6 | 11.9 | 145.7 | 118.7 | 89.0 | 80.1 | 1054.4 | 65.0 | 149.2 | 662.9 | 200.9 |
| pMON43057 | OM_A13242 | 1870.4 | 21.3 | 199.7 | 176.4 | 65.9 | 53.5 | 1177.8 | 69.6 | 124.2 | 636.5 | 218.2 |
| pMON43057 | OM_A13265 | 2383.6 | 7.8 | 155.6 | 149.5 | 84.7 | 114.6 | 1470.1 | 58.7 | 239.2 | 1074.3 | 276.4 |
| pMON43057 | OM_A13270 | 1329.8 | 27.6 | 192.2 | 179.0 | 79.5 | 47.0 | 1022.5 | 69.0 | 118.1 | 572.9 | 139.0 |
| pMON43057 | OM_A13341 | 950.9 | 7.4 | 170.6 | 130.7 | 41.6 | 35.6 | 807.0 | 34.4 | 88.1 | 408.7 | 36.8 |
| pMON43057 | OM_A13342 | 2437.9 | 0.0 | 158.3 | 141.8 | 74.0 | 38.2 | 1420.5 | 50.4 | 184.2 | 1016.8 | 177.3 |
| pMON43057 | OM_A13348 | 1875.7 | 17.9 | 162.3 | 133.0 | 71.2 | 21.8 | 1059.2 | 42.2 | 145.2 | 679.3 | 153.4 |
| pMON43057 | OM_A13349 | 1740.1 | 19.0 | 133.4 | 137.8 | 73.1 | 20.1 | 953.1 | 54.1 | 123.7 | 638.4 | 176.7 |
| pMON43057 | OM_A13350 | 1934.4 | 26.5 | 152.9 | 174.7 | 81.4 | 41.8 | 1073.5 | 61.9 | 143.6 | 777.9 | 109.1 |
| pMON43057 | OM_A13357 | 1604.4 | 21.1 | 175.1 | 130.9 | 57.1 | 41.6 | 1103.6 | 51.4 | 137.0 | 541.3 | 107.5 |
| pMON43057 | OM_A13427 | 1817.3 | 23.8 | 192.5 | 132.4 | 54.4 | 36.9 | 1227.2 | 70.2 | 132.7 | 501.5 | 128.9 |
| pMON43057 | OM_A13518 | 2013.5 | 10.7 | 151.9 | 130.1 | 61.8 | 27.4 | 1304.9 | 54.3 | 128.2 | 736.7 | 80.0 |
| pMON43057 | OM_A13634 | 2755.8 | 18.1 | 135.1 | 126.8 | 80.2 | 75.1 | 1111.5 | 77.4 | 190.3 | 863.2 | 201.8 |
| pMON43057 | OM_A13639 | 2248.8 | 19.8 | 184.3 | 128.0 | 29.1 | 30.0 | 912.8 | 33.6 | 78.5 | 426.9 | 110.0 |
| 43057 average | | 1161 | 17 | 173 | 136 | 40 | 31 | 911 | 42 | 85 | 388 | 93 |
| 43057 average/high expressing | | 2020 | 15 | 160 | 142 | 69 | 54 | 1058 | 53 | 147 | 671 | 157 |

| Construct | Plant/Seed ID | Cycloartenol μg/g | 24 Methylene Cycloartenol μg/g | Total sterol μg/g | Total End Product μg/g | Total Intermediates μg/g | Total Ethyl Sterols μg/g | Total Methyl Sterols μg/g | Ratio of methyl/ethyl | Total Unknowns μg/g | % Intermediates (of Total Sterols) |
|---|---|---|---|---|---|---|---|---|---|---|---|
| Control | Control | 28.5 | 47.5 | 1088.9 | 922.1 | 125.4 | 785.5 | 152.9 | 0.06 | 41.4 | 11.5 |
| pMON43057 | OM_A12666 | 274.5 | 485.8 | 5770.0 | 2057.8 | 3322.5 | 2103.0 | 119.5 | 0.06 | 389.7 | 57.6 |
| pMON43057 | OM_A12667 | 186.4 | 429.3 | 5094.0 | 2016.5 | 2830.1 | 1986.1 | 149.0 | 0.08 | 247.4 | 55.6 |
| pMON43057 | OM_A12783 | 203.9 | 521.8 | 5779.3 | 2182.6 | 3236.6 | 2169.0 | 178.3 | 0.05 | 360.4 | 56.0 |
| pMON43057 | OM_A12869 | 223.2 | 486.3 | 5531.1 | 2478.9 | 2886.9 | 2400.1 | 200.4 | 0.08 | 187.9 | 52.2 |
| pMON43057 | OM_A12870 | 321.6 | 441.0 | 5537.3 | 1891.3 | 3432.7 | 1899.1 | 153.5 | 0.08 | 213.3 | 62.0 |
| pMON43057 | OM_A12879 | 205.2 | 411.2 | 5285.0 | 2009.1 | 3043.2 | 1982.8 | 146.7 | 0.07 | 232.7 | 57.6 |
| pMON43057 | OM_A12986 | 237.7 | 315.6 | 4035.2 | 1049.1 | 2879.9 | 1127.7 | 131.9 | 0.12 | 100.2 | 71.4 |
| pMON43057 | OM_A13181 | 243.1 | 633.9 | 5944.6 | 2447.4 | 3222.2 | 2491.5 | 137.1 | 0.06 | 275.0 | 54.2 |
| pMON43057 | OM_A13241 | 220.5 | 451.1 | 5185.0 | 2046.6 | 2856.5 | 2050.1 | 145.7 | 0.07 | 261.8 | 55.1 |
| pMON43057 | OM_A13242 | 288.7 | 572.9 | 5475.0 | 2259.8 | 2909.8 | 2184.2 | 199.7 | 0.09 | 305.5 | 53.1 |
| pMON43057 | OM_A13265 | 272.1 | 1039.6 | 7333.1 | 2911.1 | 4055.0 | 2991.6 | 158.6 | 0.05 | 369.0 | 55.3 |
| pMON43057 | OM_A13270 | 313.7 | 455.7 | 4543.9 | 2035.7 | 2262.2 | 1059.5 | 192.2 | 0.10 | 246.1 | 49.8 |
| pMON43057 | OM_A13341 | 137.0 | 303.5 | 3202.2 | 1551.5 | 1515.1 | 1468.9 | 170.8 | 0.12 | 135.6 | 47.3 |
| pMON43057 | OM_A13342 | 324.3 | 1055.3 | 7129.1 | 278.8 | 4069.9 | 2813.6 | 158.3 | 0.06 | 251.3 | 57.4 |
| pMON43057 | OM_A13348 | 235.2 | 482.4 | 5078.7 | 2076.1 | 2760.2 | 2059.0 | 162.3 | 0.08 | 242.4 | 54.3 |
| pMON43057 | OM_A13349 | 363.3 | 564.7 | 4999.6 | 1916.9 | 2611.9 | 1907.2 | 133.4 | 0.07 | 270.8 | 56.2 |
| pMON43057 | OM_A13350 | 443.8 | 498.8 | 5520.5 | 2240.9 | 3062.4 | 2235.7 | 152.9 | 0.07 | 217.2 | 55.5 |
| pMON43057 | OM_A13357 | 212.9 | 409.4 | 4808.2 | 2017.3 | 2405.3 | 1979.1 | 175.1 | 0.09 | 185.6 | 52.2 |
| pMON43057 | OM_A13427 | 199.5 | 476.6 | 4993.7 | 2123.6 | 2662.9 | 2064.0 | 192.5 | 0.09 | 206.9 | 53.3 |
| pMON43057 | OM_A13518 | 225.9 | 591.9 | 5517.3 | 2377.9 | 2987.0 | 2354.2 | 151.9 | 0.06 | 152.5 | 54.1 |
| pMON43057 | OM_A13634 | 264.4 | 750.3 | 8647.6 | 2343.9 | 4035.7 | 2369.0 | 135.1 | 0.08 | 298.1 | 60.7 |
| pMON43057 | OM_A13639 | 137.2 | 309.9 | 4626.8 | 1865.7 | 2802.5 | 1579.9 | 164.3 | 0.10 | 158.7 | 60.8 |
| 43057 average | | 151 | 314 | 3541 | 1650 | 1741 | 1562 | 173 | 0 14 | 150 | 49 2 |
| 43057 average/high expressing | | 252 | 532 | 5356 | 2112 | 3003 | 2099 | 160 | 0 | 242 | 56 1 |

TABLE 4

| Construct | Plant/Seed ID | Squalene μg/g | Unknown 1 μg/g | Campesterol μg/g | Stigmasterol μg/g | Unknown 2 μg/g | Obtusifoliol μg/g | Sitosterol μg/g | Sitostanol μg/g | Isofucosterol μg/g | Stigmasta-7-enol μg/g | Unknown 3 μ/g |
|---|---|---|---|---|---|---|---|---|---|---|---|---|
| Control | Control | 51.0 | 12.5 | 164.6 | 174.1 | 0.0 | 0.0 | 529.6 | 11.2 | 2.7 | 22.5 | 5.3 |
| pMON43058 | OM_A12892 | 2714.6 | 20.8 | 78.0 | 133.2 | 30.3 | 80.7 | 1149.8 | 70 3 | 61.3 | 675.4 | 193.5 |
| pMON43058 | OM_A12902 | 862.6 | 16.6 | 163.0 | 169.0 | 9.9 | 19.1 | 1039.6 | 36 2 | 24.0 | 286.5 | 39.7 |
| pMON43058 | OM_A13361 | 2314.7 | 15.0 | 51.4 | 125.3 | 7.1 | 47.5 | 988.3 | 59 4 | 70.4 | 928.8 | 248.5 |
| pMON43058 | OM_A13416 | 1619.2 | 23.6 | 89.3 | 136.5 | 28.7 | 50.6 | 1033.1 | 69 1 | 61.8 | 674.9 | 187.3 |
| pMON43058 | OM_A13417 | 1045.3 | 24.1 | 160.1 | 149.9 | 26.6 | 28.8 | 887.5 | 39 0 | 45.4 | 495.4 | 52.7 |
| pMON43058 | OM_A13423 | 1999.2 | 21.9 | 103.1 | 159.2 | 34.8 | 69.0 | 1089.7 | 63 2 | 78.9 | 858.1 | 173.1 |

TABLE 4-continued

| Construct | Plant/Seed ID | | | | | | | | | | | |
|---|---|---|---|---|---|---|---|---|---|---|---|---|
| pMON43058 | OM_A13424 | 1055.4 | 13.2 | 92.9 | 144.0 | 21.4 | 86.5 | 1198.0 | 92.2 | 59.5 | 497.7 | 196.6 |
| pMON43058 | OM_A13426 | 2179.8 | 29.4 | 197.9 | 135.8 | 81.2 | 60.1 | 910.5 | 75.5 | 153.6 | 485.4 | 191.1 |
| pMON43058 | OM_A13493 | 1900.1 | 31.2 | 149.9 | 172.4 | 104.0 | 91.5 | 1286.6 | 94.8 | 280.0 | 826.4 | 213.9 |
| pMON43058 | OM_A13495 | 1695.8 | 24.7 | 87.6 | 154.3 | 27.7 | 79.9 | 1425.2 | 84.6 | 75.1 | 788.0 | 213.2 |
| pMON43058 | OM_A13496 | 2089.5 | 20.6 | 77.5 | 157.6 | 39.0 | 77.8 | 1350.2 | 68.8 | 88.6 | 957.6 | 172.7 |
| pMON43058 | OM_A13497 | 2051.3 | 20.4 | 74.3 | 151.7 | 19.5 | 66.8 | 1409.4 | 57.2 | 65.0 | 989.3 | 137.6 |
| pMON43058 | OM_A13500 | 2004.7 | 30.1 | 123.5 | 174.9 | 25.8 | 65.4 | 1347.9 | 50.9 | 73.4 | 1029.9 | 101.5 |
| pMON43058 | OM_A13504 | 1914.8 | 24.6 | 102.6 | 178.5 | 32.7 | 85.3 | 1619.4 | 70.4 | 77.3 | 800.1 | 131.8 |
| pMON43058 | OM_A13517 | 902.2 | 21.1 | 151.1 | 151.0 | 8.2 | 17.6 | 984.6 | 61.9 | 16.6 | 199.1 | 63.6 |
| pMON43058 | OM_A13629 | 2392.3 | 22.5 | 56.6 | 145.6 | 7.9 | 62.7 | 1290.4 | 63.3 | 58.6 | 839.7 | 173.2 |
| pMON43058 | 43058 aver hi ex | 1806.9 | 22.5 | 111.8 | 155.8 | 31.7 | 61.9 | 1188.1 | 66.1 | 80.8 | 708.3 | 155.6 |

| Construct | Plant/Seed ID | Cyclo-artenol μg/g | 24 Methylene Cycloartenol μg/g | Total sterol μg/g | Total End Product μg/g | Total Inter-mediates μg/g | Total Ethyl Sterols μg/g | Total Methyl Sterols μg/g | Ratio of methyl/ethyl | Total Un-knowns μg/g | % Inter-mediates (of Total Sterols) |
|---|---|---|---|---|---|---|---|---|---|---|---|
| Control | Control | 10.5 | 43.4 | 1027.7 | 902.2 | 107.7 | 740.4 | 164.6 | 0.22 | 17.8 | 10.5 |
| pMON43058 | OM_A12892 | 216.1 | 467.3 | 5891.6 | 2106.7 | 3540.2 | 2090.0 | 78.0 | 0.04 | 244.6 | 60.1 |
| pMON43058 | OM_A12902 | 118.5 | 267.6 | 3052.2 | 1694.3 | 1291.7 | 1555.3 | 163.0 | 0.10 | 66.2 | 42.3 |
| pMON43058 | OM_A13361 | 192.4 | 386.3 | 5437.2 | 2153.2 | 3013.4 | 2172.2 | 51.4 | 0.02 | 270.6 | 55.4 |
| pMON43058 | OM_A13416 | 186.0 | 560.5 | 4920.6 | 2002.9 | 2678.1 | 1975.4 | 89.3 | 0.05 | 239.5 | 54.4 |
| pMON43058 | OM_A13417 | 105.7 | 266.6 | 3331.8 | 1731.8 | 1494.7 | 1620.1 | 160.1 | 0.10 | 105.4 | 44.9 |
| pMON43058 | OM_A13423 | 212.0 | 796.0 | 5657.9 | 2273.2 | 3155.0 | 2249.0 | 103.1 | 0.05 | 220.7 | 55.8 |
| pMON43058 | OM_A13424 | 155.0 | 730.9 | 4343.7 | 2024.8 | 2087.8 | 1991.4 | 92.9 | 0.05 | 231.1 | 48.1 |
| pMON43058 | OM_A13426 | 323.3 | 627.3 | 5500.8 | 1855.0 | 3344.2 | 1810.7 | 197.9 | 0.11 | 301.6 | 60.8 |
| pMON43058 | OM_A13493 | 277.4 | 752.4 | 6180.5 | 2530.0 | 3301.5 | 2660.1 | 149.9 | 0.06 | 349.0 | 53.4 |
| pMON43058 | OM_A13495 | 191.1 | 783.2 | 5630.5 | 2539.7 | 2825.2 | 2527.3 | 87.6 | 0.03 | 232.4 | 50.2 |
| pMON43058 | OM_A13496 | 265.7 | 827.5 | 6193.4 | 2611.7 | 3349.3 | 2623.0 | 77.5 | 0.03 | 232.4 | 54.1 |
| pMON43058 | OM_A13497 | 161.8 | 876.9 | 6081.2 | 2682.0 | 3221.7 | 2672.7 | 74.3 | 0.03 | 177.5 | 53.0 |
| pMON43058 | OM_A13500 | 187.3 | 761.0 | 5976.4 | 2727.1 | 3091.8 | 2677.0 | 123.5 | 0.05 | 157.5 | 51.7 |
| pMON43058 | OM_A13504 | 181.7 | 711.3 | 5930.4 | 2771.0 | 2970.4 | 2745.7 | 102.6 | 0.04 | 189.1 | 50.1 |
| pMON43058 | OM_A13517 | 102.2 | 264.6 | 2943.7 | 1547.7 | 1303.2 | 1413.1 | 151.1 | 0.11 | 92.8 | 44.3 |
| pMON43058 | OM_A13629 | 155.0 | 692.5 | 5990.6 | 2425.8 | 3361.1 | 2397.9 | 86.6 | 0.04 | 203.6 | 56.1 |
| pMON43058 | 43058 aver hi ex | 189.5 | 610.9 | 5191.4 | 2229.6 | 2751.8 | 2198.8 | 111.8 | 0.1 | 209.8 | 52.2 |

To fully characterize the sterol compounds present in the transgenic seeds, a representative sample was also analyzed by Gas Chromatograpy-Mass Spectrometry (GC-MS) for confirmation of the sterol compounds present. The GC-MS conditions were as follows: inlet temp. 250° C., detector 320° C., oven programmed from 180° C. to 325° C. with initial equilibration time of 1.0 min, ramping to 310° C. at 4°/min at then 20°/min to 325° C. The column was a DB-5 capillary glass column similar to the one used for GC-FID.

Majority of the transgenic lines harboring pMON43057 showed 3 to 5-fold increase in total sterols. The best performing transgenic lines, GM_A13342 and GM_A13634, showed 6.5- and 6.1-fold increase in total sterols, respectively. These lines showed 2- to 2.6-fold increase in sitosterol, 1.5 to 2.2-fold increase in sitostanol and no significant change in the campesterol levels. Hence the major proportion of the total sterol increase was accounted by the accumulation of pathway intermediates which include squalene, cycloartenol, 24-methylene cycloartenol, obtusifoliol, isofucosterol, and stigmasta-7-enol. The best performing transgenic lines, GM_A13342 and GM_A13634, showed 32.6- and 32.2-fold increase in pathway intermediates accumulation, respectively, as compared to the control. In all the transgenic lines harboring the pMON43057, 50–70% of the total increase was accounted by the increase in the pathway intermediates accumulation as compared to the control. The pathway intermediates include squalene, cycloartenol, 24-methylene cycloartenol, obtusifoliol, isofucosterol, and stigmasta-7-enol.

Six transgenic lines haboring pMON43058 produced 5.8- to 6-fold increase in total sterols and the rest of the 10 transgenic lines with the pMON43058 showed 3- to 5-fold increase in total sterols. The best performing transgenic lines showed about 2- to 3-fold increase in sitosterol and 4.5- to 6-fold increase in sitostanol levels. However, the campesterol accumulation was reduced by 50% in these lines. This was due to overexpression of the Arabidopsis SMTII enzyme which enhances the carbon flux towards the synthesis of 24-ethyl sterols thereby reducing the carbon flux through the pathway leading to the synthesis of 24-methyl sterols. As seen in pMON43057 transgenic lines, all of the transgenic lines harboring the pMON43058 also accumulated 50–60% of the total sterols in the form of pathway intermediates which are squalene, cycloartenol, 24-methylene cycloartenol, obtusifoliol, isofucosterol, and stigmasta-7-enol. These pathway intermediates normally form minor constituents in the sterol composition of seeds. However, in the transgenic seeds, probably due to increased carbon flux through the pathway, they accumulate in significant amounts. The pathway intermediates accumulation is highly significant when the truncated from of HMGR is overexpressed as compared to the full length form of HMGR suggesting that the overexpression of the truncated form of HMGR creates even greater increase in carbon flux through the pathway. This provides further evidence for additional control points for sterol biosynthesis in plants such as squalene epoxidase, sterol methyltransferase I, sterol C4-demethylase, obtusifoliol C14α-demethylase, sterol C5-desaturase, and sterol methyl transferase II.

Example 3

Enhancement of phytosterol biosynthesis in seeds of Arabidopsis transgenic plants by constitutive expression of different forms of Arabidopsis and rubber HMGR enzymes.

Arabidopsis transgenic plants were generated using Agrobacterium mediated transformation of constructs (pMON53733, pMON53734, pMON53735, pMON53736, pMON53737, pMON53738, pMON53739, pMON53740) carrying cDNA encoding different forms of Arabidopsis and rubber HMGR enzymes driven by CaMV enhanced 35S promoter (FIGS. 13–20). The transformed Arabidopsis seeds carrying each of the above constructs were selected on kanamycin (50 µg/ml) medium to select for transformants expressing the selectable marker, the NPTII gene driven by CaMV 35S promoter. Kanamycin resistant Arabidopsis transgenic plants were grown in green house for maturity and seeds were collected from each of the transgenic lines for sterol analysis. About 50 mg of seeds from each transgenic line were weighed, homogenized and used for saponification to extract sterols as described in Example 2.

FIGS. 21–26 describe the sterol analysis data obtained from the transgenic lines carrying each of the above constructs. FIG. 27 shows the effect on different sterol end products and pathway intermediate accumulation when different forms of rubber HMGR cDNAs were expressed constitutively in transgenic Arabidopsis plants. When truncated rubber HMGR (with or without linker region) was overexpressed the total sterol accumulation in seeds increased by 2.9 to 3.7-fold as compared with the wild type control plants. The sterol end products such as campesterol and sitosterol showed 1.5 to 2-fold increase in the lines expressing truncated form of rubber HMGR (with and without linker). However the sitostanol end product accumulation in the transgenic lines harboring the truncated form of rubber HMGR (with and without linker) was enhanced by 2.8 to 7-fold. There is a significant accumulation of pathway intermediates such as cycloartenol and 24-methylene cycloartenol in the seeds of the transgenic lines transformed with the truncated form of rubber HMGR (with and without linker region). The wild type control plants used in the experiment do not accumulate both of the pathway intermediates.

Example 4

Comparison of Steroid Compounds from HMGR Constructs in a Yeast HMGR1 Knockout Mutant The effects on the sterol levels of the expression of various HMGR constructs expressed in a yeast HMGR1 knockout mutant were compared. Constructs containing a nucleic acid encoding the full length HMGR polypeptides from Arabidopsis and rubber were compared to those encoding a truncated Arabidopsis or rubber HMGR polypeptide that were lacking both the membrane binding and linker region of HMGR. The control yeast cells were transformed with a similar construct lacking a polypeptide encoding any form of HMGR.

Yeast cells transformed with Arabidopsis HMGR and rubber HMGR constructs accumulated approximately the same amounts of zymosterol and ergosterol, but more squalene than the control yeast.

Transformed yeast cells having rubber HMGR constructs accumulated about the same amount of ergosterol, but about twice as much squalene and zymosterol than the control yeast.

Transformed yeast cells having Arabidopsis tHMGR constructs accumulated three times as much squalene, twice as much zymosterol, and about 30 percent more ergosterol than the control yeast.

Transformed yeast cells having rubber tHMGR constructs accumulated three times as much squalene, four times as much zymosterol, and about 50 percent more ergosterol than the control yeast.

The data are shown in a FIG. 28, "Plant HMGR1 Contructs in Yeast HMGR1 Knockout Mutant".

Example 5

Gene sequences for all genes listed in the application

The sequences obtained from the NCBI public database are SEQ ID NO.: 1,2,3,20,21,22,23. These sequences are included in the appendix and denoted as follows:

Appendix A=SEQ ID NO. 1,
Appendix B=SEQ ID NO. 2,
Appendix C=SEQ ID NO. 3,
Appendix D=SEQ ID NO. 20,
Appendix E=SEQ ID NO. 21,
Appendix F=SEQ ID NO. 22,
Appendix G=SEQ ID NO. 23.

SEQ ID 1=Arabidopsis squalene epoxidase protein sequence (Accession NO: AC004786) See Appendix A SEQ ID 2=Arabidopsis squalene epoxidase (Accession NO: N64916) See Appendix B SEQ ID 3=Arabidopsis squalene epoxidase (Accession NO: T44667) See Appendix C SEQ ID 4=Arabidopsis squalene epoxidase (clone ID: ATA506263) nucleotide sequence

```
GAATTCCCGGGTCGACCCACGCGTCCGCTTATAGATAAGGATATGGCCTT

TACGAACGTTTGCCTATGGACGCTACTCGCCTTCATGCTGACTTGGACAG

TGTTCTACGTCACAAACAGGGGAAGAAGGCGACGCAGTTGGCGGATGCG

GTGGTTGAAGAGCGAGAAGACGGTGCTACTGACGTTATCATCGTTGGGGC

TGGAGTAGGCGGCTCGGCTCTCGCATATGCTCTTGCTAAGGACGGGCGTC

GAGTCCATGTAATAGAGAGGGACCTGAGAGAACCAGAGAGAATCATGGGT

GAGTTTATGCAACCAGGAGGACGACTCATGCTCTCTAAGCTTGGTCTTGA

AGATTGTTTGGAGGGAATAGATGCCCAAAAAGCCACGGGCATGACAGTTT

ATAAGGACGGAAAAGAAGCAGTCGCATCTTTTCCCGTGGACAACAACAAT

TTTCCTTTTGATCCTTCGGCTCGATCTTTTCACAATGGCCGATTCGTCCA

ACGATTGCGGCAAAAGGCTTCTTCTCTTCCCAATGTGCGCCTGGAAGAAG

GAACGGTGAAGTCTTTGATAGAAGAAAAAGGAGTGATCAAAGGAGTGACA

TACAAAAATAGCGCAGGCGAAGAAACAACAGCCTTGGCACCTCTCACTGT

AGTATGCGACGGTTGCTACTCAAACCTTCGCCGGTCTCTTAATGACAACA

ATGCGGAGGTTCTGTCATACCAAGTTGGTTTTATCTCAAAGAACTGTCAG

CTTGAAGAACCCGAAAAGTTAAAGTTGATAATGTCTAAACCCTCCTTCAC

CATGTTGTATCAAATCAGCAGCACCGACGTTCGTTGTGTTTTTGAAGTTC

TCCCCAACAACATTCCTTCTATTTCAAATGGTGAAATGGCTACTTTCGTG

AAGAACACTATTGCTCCTCAGGTACCTTTAAAACTCCGCAAAATATTTTT

GAAAGGGATTGATGAAGGAGAACATATAAAAGCCATGCCAACAAAGAAGA

TGACAGCTACTTTGAGCGAGAAGAAAGGAGTGATTTTATTGGGAGATGCA

TTCAACATGCGTCATCCAGCAATCGCATCTGGAATGATGGTTTTATTATC

TGACATTCTCATTTTACGCCGTCTTCTCCAGCCATTAAGCAACCTTGGCA
```

-continued

ATGCGCAAAAAATCTCACAAGTTATCAAGTCCTTTTATGATATCCGCAAG
CCAATGTCAGCGACAGTTAACACGTTAGGAAATGCATTCTCTCAAGTGCT
AGTTGCATCGACGGACGAAGCAAAAGAGGCAATGAGACAAGGTTGCTATG
ATTACCTCTCTAGTGGTGGGTTTCGCACGTCAGGGATGATGGCTTTGCTA
GGCGGCATGAACCCTCGTCCGATCTCTCTCATCTATCATCTATGTGCTAT
CACTCTATCCTCCATTGGCCATCTACTCTCTCCATTTCCCTCTCCCCTTG
GCATTTGGCATAGCCTTCGACTTTTTGGTTTGGCTATGAAAATGTTGGTT
CCCCATCTCAAGGCTGAAGGAGTTAGCCAAATGTTGTTTCCAGTCAACGC
CGCCGCGTATAGCAAAAGCTATATGGCTGCAACGGCTCTTTAAAACACTG
GTGCTTTAAACTGCAAAATATAACACATATATAAATCCCGAATCTTTGTG
ATTCTGCATATATTGTGTTCTACAATTATTCTCATATAAATGAAAATTGT
TCTACGTAAAAGTAAAAAGAAGGAATTGTAATACTAATAAAACGAGTTTT
TAATTCTGTTGAATGCTTGTGTATATTGGTGAAAAAAAAAAAAAAAAAA
AAAAAAAAAAAAAAAAAAAAAAGGGCGGCCGC

SEQ ID 5=Arabidopsis squalene epoxidase (clone ID: ATA506263) amino acid translation EFPGRPTRPLIDKDMAFTNVCLWTLLAFMLTWTVFYVTNRGKKATQLADA
VVEEREDGATDVIIVGAGVGGSALAYALAKDGRRVHVIERDLREPERIMG
EFMQPGGRLMLSKLGLEDCLEGIDAQKATGMTVYKDGKEAVASFPVDNNN
FPFDPSARSFHNGRFVQRLRQKASSLPNVRLEEGTVKSLIEEKGVIKGVT
YKNSAGEETTALAPLTVVCDGCYSNLRRSLNDNNAEVLSYQVGFISKNCQ
LEEPEKLKLIMSKPSFTMLYQISSTDVRCVFEVLPNNIPSISNGEMATFV
KNTIAPQVPLKLRKIFLKGIDEGEHIKAMPTKKMTATLSEKKGVILLGDA
FNMRHPAIASGMMVLLSDILILRRLLQPLSNLGNAQKISQVIKSFYDIRK
PMSATVNTLGNAFSQVLVASTDEAKEAMRQGCYDYLSSGGFRTSGMMALL
GGMNPRPISLIYHLCAITLSSIGHLLSPFPSPLGIWHSLRLFGLAMKMLV
PHLKAEGVSQMLFPVNAAAYSKSYMAATAL*

SEQ ID 6=Arabidopsis squalene epoxidase (clone ID: ATA304243) nucleotide sequence GAATTCCCGGGTCGACCCACGCGTCCGCGGACGCGTGGGATTGAGAACAA
ATAGATTTGGTTATATATGGCTTTTACGCACGTTTGTTTATGGACGTTAG
TCGCCTTCGTGCTGACGTGGACGGTGTTCTACCTTACCAACATGAAGAAG
AAGGCGACGGATTTGGCTGATACGGTGGCTGAGGATCAAAAAGACGGTGC
TGCTGACGTCATTATCGTCGGGGCTGGTGTAGGTGGTTCGGCTCTCGCAT
ATGCTCTTGCTAAGGATGGGCGTCGAGTACATGTGATCGAGAGGGACATG
AGAGAACCAGAAAGAATGATGGGTGAGTTTATGCAACCTGGCGGACGACT
CATGCTTTCTAAACTTGGCCTTCAAGATTGCTTGGAAGACATAGATGCAC
AGAAAGCCACGGGTTTGGCAGTTTATAAAGATGGAAAAGAAGCAGACGCA
CCTTTTCCAGTGGATAACAACAATTTTTCTTATGAACCTTCTGCTCGATC -continued TTTTCACAATGGCCGATTCGTCCAACAACTGCGTCGAAAGGCTTTTTCTC
TTTCCAATGTGCGCCTGGAAGAAGGAACGGTGAAGTCTTTACTAGAAGAA
AAAGGAGTGGTCAAAGGAGTGACATACAAGAATAAAGAAGGCGAAGAAAC
AACAGCCTTGGCACCTCTCACTGTGGTATGCGACGGTTGCTACTCAAACC
TTCGTCGGTCTCTTAATGATGACAACAATGCTGAGATTATGTCGTACATA
GTTGGTTACATCTCAAAGAATTGTCGGCTTGAAGAACCCGAAAAGCTACA
CTTGATATTGTCTAAACCATCTTTCACCATGGTATACCAAATAAGCAGCA
CTGACGTTCGTTGTGGTTTTGAGGTTCTCCCCGAAAATTTTCCTTCTATT
GCAAATGGTCAAATGTCTACTTTCATGAAGAATACTATAGTTCCTCAGGT
ACCTCCAAAACTCCGCAAAATATTTTTGAAAGGTATAGATGAGGGAGCAC
ACATAAAAGTGGTGCCGGCAAAGCGCATGACATCTACTTTAAGCAAGAAG
AAAGGTGTGATTGTATTGGGAGATGCATTCAATATGCGTCATCCAGTTGT
TGCATCTGGAATGATGGTTTTACTGTCGGACATTCTCATTCTACGCCGTC
TTCTTCAGCCATTAAGCAACCTCGGCGATGCAAACAAAGTCTCAGAAGTT
ATCAATTCCTTTTATGATATCCGCAAGCCAATGTCGGCGACGGTTAACAC
ATTGGGAAATGCATTTTCTCAAGTACTAATTGGATCAACGGATGAAGCAA
AAGAGGCAATGAGACAGGGTGTCTATGATTACCTTTGTAGTGGCGGGTTT
CGTACGTCAGGGATGATGGCTCTGCTCGGCGGCATGAATCCTCGTCCTCT
CTCTCTCGTCTATCATCTTTGTGCCATCACTCTATCCTCCATTGGCCAAC
TGCTCTCTCCATTTCCCTCTCCCCTTCGCATTTGGCATAGCCTCAAGCTT
TTTGGTTTGGCCATGAAAATGTTGGTTCCCAATCTCAAAGCTGAAGGAGT
TAGCCAAATGTTGTTTCCAGCAAATGCAGCCGCGTATCACAAAAGCTATA
TGGCTGCAACCACTCTCTAAACTTTGATGCTCTCAATCGCAATATATATG
GAGCACGAATCTATGTGATTGTGCATTTGGTAAACGTGTATTGCAGTGCT
TATAATTATTAGTATGTAACGGGAAAAGTTCTAAACACAAAAAAATAAA
CTTTTGAATGTTATATGTGTGAATTATTTTTGTTGTTACAAGTAATGCTC
TTTTTTTTTAGCTTCACACATGTATTATTGGAGCTAATTTTTTGTTTCTC
TGTTCTTTTATTTTTGTTTTCTTACTGTATTTACTTTGAAAAGTTTCGTT
TTATACATATTGGACATTTTTAAAAAAAAAAAAAAAAAAAAAAAAAAAA
AAAAAAAAAAAAAAAAAAAAAAAAAAAAAAAAAAAAAAAAAAAAAAAA
AAAAAAAAAAAAAAAAAAAAAAAAAGGGCGGCCGC SEQ ID 7=Arabidopsis squalene epoxidase (clone ID: ATA304243) amino acid translation MAFTHVCLWTLVAFVLTWTVFYLTNMKKKATDLADTVAEDQKDGAADVII
VGAGVGGSALAYALAKDGRRVHVIERDMREPERMMGEFMQPGGRLMLSKL
GLQDCLEDIDAQKATGLAVYKDGKEADAPFPVDNNNFSYEPSARSFHNGR
FVQQLRRKAFSLSNVRLEEGTVKSLLEEKGVVKGVTYKNKEGEETTALAP
LTVVCDGCYSNLRRSLNDDNNAEIMSYIVGYISKNCRLEEPEKLHLILSK -continued

PSFTMVYQISSTDVRCGFEVLPENFPSIANGEMSTFMKNTIVPQVPPKLR

KIFLKGIDEGAHIKVVPAKRMTSTLSKKKGVIVLGDAFNMRHPVVASGMM

VLLSDILILRRLLQPLSNLGDANKVSEVINSFYDIRKPMSATVNTLGNAF

SQVLIGSTDEAKEAMRQGVYDYLCSGGFRTSGMMALLGGMNPRPLSLVYH

LCAITLSSIGQLLSPFPSPLRIWHSLKLFGLAMKMLVPNLKAEGVSQ ML

FPANAAAYHKSYMAATTL*

SEQ ID 8=Arabidopsis squalene epoxidase (clone ID: ATA102071) nucleotide sequence

AAATCATATTGAGAACAAATAGATTTGGTTATATATGGCTTTTACGCACG

TTTGTTTATGGACGTTAGTCGCCTTCGTGCTGACGTGGACGGTGTTCTAC

CTTACCAACATGAAGAAGAAGGCGACGGATTTGGCTGATACGGTGGCTGA

GGATCAAAAAGACGGTGCTGCTGACGTCATTATCGTCGGGGCTGGTGTAG

GTGGTTCGGCTCTCGCATATGCTCTGCTAAGTGTGCGCCTGGAAGAAGGA

ACGGTGAAGTCTTTACTAGAAGAAAAAGGAGTGGTCAAAGGAGTGACATA

CAAGAATAAAGAATGCGAACAAACAACAGCCTTGGCACCTCTCACTGTGG

TATGCGACGGTTGCTAATCAAACCTTCGTCGGTCTCTTAATG

SEQ ID 9=Arabidopsis squalene epoxidase (clone ID: ATA102071) amino acid translation

MAFTHVCLWTLVAFVLTWTVFYLTNMKKKATDLADTVAEDQKDGAADVII

VGAGVGGSALAYALLSVRLEEGTVKSLLEEKGVVKGVTYKNKECEQTTAL

APLTVVCDGC

SEQ ID 10=Arabidopsis squalene epoxidase (clone ID: ATA504158) nucleotide sequence

CACAAAGCAAAAAAATCTCTGTAAAAGCAGAACGATAATGGAGTCACAAT

TATGGAATTGGATCTTACCTCTTTTGATCTCTTCTCCTCATCTCCTTC

GTCGCTTTCTATGGATTCTTCGTCAAACCGAAGCGGAACGGTCTCCGTCA

CGATCGGAAAACTGTTTCTACCGTCACCTCCGACGTCGGATCTGTTAATA

TTACCGGAGATACTGTCGCTGATGTCATTGTTGTTGGAGCTGGTGTTGCT

GGTTCTGCTCTTGCTTATACTCTTGGAAAGGGGAAATTTAAACGCCGAGT

TCATGTGATTGAAAGAGATTTATCGGAGCCTGATCGTATTGTTGGGGAGT

TGTTACAGCCTGNGGGTTACCTCAAGTTACTGGAGTGTGGAATTGGAGAT

TGTGTGGAAGAAATAGATGCTCAGCNTGTGTATGGTTATGCACTTTTTAA

AAATGGG

SEQ ID 11=Arabidopsis squalene epoxidase (clone ID: ATA504158) amino acid translation

TKQKNLCKSRTIMESQLWNWILPLLISSLLISFVAFYGFFVKPKRNGLRH

DRKTVSTVTSDVGSVNITGDTVADVIVVGAGVAGSALAYTLGKGKFKRRV

-continued

HVIERDLSEPDRIVGELLQPXGYLKLLECGIGDCVEEIDAQXVYGYALFK

NG

SEQ ID 12=Arabidopsis obtusifoliol C14α-demethylase nucleotide sequence (Accession NO: complement, join AC002329:37461 . . . 38456, AC002329:39121 . . . 39546) (homolog of sorghum obtusifoliol C14α-demethylase) nucleotide sequence

CGTGTTTTACAAATTTCCTTTGTTGGTTTTCCACAGATTTAAAGAACCCT

AACGAGAGAAAAAAATGGACTGGGATTACTATACGCTGTTGAAGACGAGT

GTGGCTATTATTATAGTGTTTGTTGTGGCCAAACTCATAACCTCCTCCAA

ATCCAAGAAGAAAACAAGTGTCGTCCCACTCCCTCCAGTTCTTCAAGCGT

GGCCTCCATTTATCGGATCCCTAATCCGCTTCATGAAAGGTCCAATAGTG

CTACTTAGAGAGGAATATCCTAAGCTTGGAAGTGTTTTCACAGTGAAGCT

TCTTCACAAAAACATCACTTTTCTCATCGGTCCCGAAGTCTCGTCCCACT

TTTTCAACGCTTATGAATCTGAACTCAGCCAGAAAGAAATTTACAAATTT

AATGTGCCTACTTTTGGCCCCGGAGTTGTGTTTGATGTTGACTATCCCGT

TCGGATGGAGCAGTTCCGATTCTTCTCCAGCGCTCTCAAGGATTACTTCT

CAAAATGGGGAGAAAGTGGGGAAGTGGATCTAAAGGCCGAGTTAGAGCGT

CTAATCACCTTGACTGCTAGTAGATGTCTATTGGGTCGAGAAGTCCGTGA

CCAACTTTTTGATGATGTTGCTCCATTGTTCCATGACCTTGATAAAGGCA

TGCAACCCATAAGTGTCATCTTCCCAAAGCTCCCCATTCCAGCTCACAAT

TGTCGTGACCGTGCTCGCGGAAAGATTGCAAAAATCTTTTCAAACATCAT

AGCAACAAGAAAACGCTCTGGTGACAAATCAGAGAACGACATGCTACAAT

GTTTCATCGACTCAAAGTACAAAGACGGTAGAGAGACAACTGAATCTGAA

GTAACTGGTTTGCTCATTGCTGGTTTGTTTGCAGGACAACATACAAGCTC

TATCACTGCCACATGGACCGGTGCTTATCTAATTCAAAACAAACACTGGT

GGTCCGCGGCTTTGGACGAGCAGAAGAAACTGATTGGAAAACATGGGGAC

AAGATCGACTACGATGTTTTGTCTGAGATGGATTTTCTGTTTCGCAGTGC

AAAAGAAGCTTTAAGGCTTCACCCTCCAAAGATCTTACTGCTGAGAACAG

TACACAGTGATTTCACCGTGACAACTCGAGAAGGAAAGCAATATGAGATA

CCAAAGGGTCATATCGTTGCAACTTCTCCTGCATTCGCCAACCGCTTACC

TCATGTCTACAAAGATCCGGAAAATTTTGATCCGGATAGATTTTCAAAGG

AAAGAGAAGAGGATAAAGCAGCTGGTTCGTGTTCATACATCTCTTTGGGA

GCTGGTAGGCACGAGTGTCCTGGTGGATCATTTGCGTTCTTGCAGATCAA

AGCCGTATGGTGTCACTTATTGAGAAACTTTGAGCTTGAGTTAGTGTCAC

SEQ ID 13=Arabidopsis obtusifoliol C14α-demethylase nucleotide sequence (Accession NO: complement, join AC002329:37461 . . . 38456, AC002329:39121 . . . 39546) (homolog of sorghum obtusifoliol C14α-demethylase) amino acid translation MDWDYYTLLKTSVAIIIVFVVAKLITSSKSKKKTSVVPLPPVLQAWPPFI
GSLIRFMKGPIVLLREEYPKLGSVFTVKLLFHKNITFLIGPEVSSHFFNA
YESELSQKEIYKFNVPTFGPGVVFDVDYPVRMEQFRFFSSALKDYFSKWG
ESGEVDLKAELERLITLTASRCLLGREVRDQLFDDVAPLFHDLDKGMQPI
SVIFPKLPIPAHNCRDRARGKIAKIFSNIIATPRKRSGDKSENDMLQCFI
DSKYKDGRETTFSEVTGLLIAGLFAGQHTSSITATWTGAYLIQNKHWWSA
ALDEQKKLIGKHGDKIDYDVTLSEMDFLFRSAKEALRLHPPKILLLRTVH
SDFTVTTREGKQYEIPKGHIVATSPAFANRTLPHVYKDPENFDPDRFSKE
REEDKAAGSCSYISLGAGRHECPGGSFAFLQIKAVWCHLLRNFELELVSP
FPEINWNALVVGAKGNVMVRYKRRPFS*

SEQ ID 14=Arabidopsis obtusifoliol C14α-demethylase (clone ID: ATA101105) nucleotide sequence GACACTATAGAAGAGCTATGACGTCGCATGCACGCGTACGTAAGCTCGGA
ATTCGGCTCGAGCTTGTTCACAAAAAGATTACTTTTCTTATTGGTCCTGA
AGTCTCTGCTCATTTTTTCAAAGCTTCTGAATCTGATCTTAGTCAGCAGG
AAGTGTATCAGTTCAATGTCCCTACTTTTGGTCCTGGAGTTGTTTTCGAT
GTTGATTATTCTGTTTCGTCAGGAGCAGTTCGGTTCTTCACTGAGGCACT
TAGAGTTAACAAGTTGAAGGGTTATGTGGATATGATGGTTACTGAAGCTG
AGGATTACTTCTCTAAATGGGAGAGAGTGGTGAAGTTGATATTAAGGTT
GAGCTAGAGAGGCTCATCATCTTGACTGCAAGTGATGTTTACTGGGTCGA
GAAGTTCGTGATCAGCTTTTTGATGATGTCTCTGCTTTGTTCCATGACCT
TGACAATGGAATGCTTCCCATCAGTGCTTCCCATCAGTGTTCTCTTCCCA
TATCTCCCAATTCCAGCTCACCG SEQ ID 15=Arabidopsis obtusifoliol C14α-demethylase (clone ID: ATA101105) amino acid translation HYRRAMTSHARVRKLGIRLELVHKKITFLIGPEVSAHFFKASESDLSQQE
VYQFNVPTFGPGVVFDVDYSVRQEQFGSSLRHLELTS SEQ ID 16=Arabidopsis obtusifoliol C14α-demethylase (clone ID: ATA202967) nucleotide sequence TCGACCCCGCGTCCGCGGACGCGTGGGATCAGCTTCAAGCTTAAGAGAGC
TTCGAAAGCGAAAGCGACGATTTCTTCTCCATCGTGAGAGCAAATCTCCA
GAGCCGTTTTCTCTTCTTCTTCTTCCTCCTCGCGCCGTCTCTGAAACTCC
ATCATCGTATCAATCAAATTGCTTCCTCCTCCAAATTGAAAAACAATGGA
ATTGGATTCGGAGAACAAATTGTTGAAGACGGGTTTGGTTATAGTGGCGA
CACTTGTTATAGCCAAACTCATCTTCTCTTTCTTCACTTCTGATTCTAAG
AAGAAGCGTCTTCCTCCTACTCTTAAAGCTTGGCCTCCATTGGTTGGAAG
TCTTATCAAATTCTTGAAAGGACCTATTATTATGCTTAGAGAGGAATACC
CTAAGCTTGGAAGTGTGTTTACTGTTAATCTTGTTCACAAAAAGATTACT
TTTCTTATTGGTCCTGAAGTCTCTGCTCATTTTTTCAAAGCTTCTGAATC
TGATCTTAGTCAGCAGGAAGTGTATCAGTTCAATGTCCCTACTTTTGGTC
CTGGAGTTGTTTTCGATGTTGATTATTCTGTTCGTCAGGAGCAGTTTCGG
TTCTTCACTGAGGCACTTAGAGTTAACAAGTTGAAGGGTTATGTGGATAT
GATGGTTACTGAAGCTGAGGATTACTTCTCTAAATGGGAGAGAGTGGTG
AAGTTGATATTAAGGTTGAGCTAGAGAGGCTCATCATCTTGACTGCAAGT
AGATGTTTACTGGGTCGAGAAGTTCGTGATCAGCTTTTTGATGATGTCTC
TGCTTTGTTCCATGACCTTGACAATGGAATGCTTCCCATCAGTGTTCTCT
TCCCATATCTCCCAATTCCAGCTCACCGCCGTCGTGACCGTGCCCGAGAA
AAGCTTTCGGAGATTTTCGCAAAAATCATTGGGTCGAGAAAACGCTCTGG
AAAAACAGAGAACGACATGCTGCAGTGTTTCATCGAATCAAAGTACAAG
ATGGTAGACAGACAACCGAATCTGAAGTCACTGGTTTGCTCATTGCTGCT
CTGTtTGCAGGACAACACACGAGCTCTATCACTTCCACCTGGACCGGTGC
TTATCTGATGCGATACAAAGAGTACTTCTCAGCTGCTCTTGATGAGCAGA
AGAACCTGATTGCGAAACATGGAGACAAGATCGATCATGATATCTTATCC
GAGATGGATGTTCTCTACCGCTGCATTAAGGAAGCGTTGAGGCTTCACCC
TCCACTCATCATGTTAATGAGAGCCTCGCACAGTGATTTCAGCGTGACAG
CTCGGGATGGAAAAACTTACGATATCCCAAAGGGTCACATCGTTGCAACC
TCCCCTGCATTTGCCAACCGCTTACCGCACATCTTCAAAGACCCCGACAC
CTACGACCCAGAAAGATTCTCCCCTGGAAGAGAAGAGGACAAAGCCGCAG
GGGCATTCTCGTACATTGCATTCGGAGGGGGAAGGCACGGGTGCCTTGGA
GAGCCGTTTGCTTACCTGCAGATCAAAGCCATATGGAGTCATTTGTTGAG
GAACTTCGAGCTTGAGCTAGTTTCACCGTTCCCTGAGATTGACTGGAACG
CTATGGTGGTTGGAGTTAAAGGCAATGTGATGGTGCGTTACAAGAGGCgc
CAGCTTTCTTAAAGACAAGTTTAAGGTTATTGCAGCTTTGGATTTTTCTC
TCTGGTTTCTGCTTTGCTTTTGTCCCTCTCTGGTTTTAGTTTTGTTGTTG
AATAATTCTTCTGTTTTTATAAACTGTTGTTACTCTTTAATTGACATTTA
TTTTTAAGCTTCCTAAGTTTGTGGTTCAAAAAAAAAAAAAGGCGGCGTTA
CT SEQ ID 17=Arabidopsis obtusifoliol C14α-demethylase (clone ID: ATA202967) amino acid translation MELDSENKLLKTGLVIVATLVIAKLIFSFFTSDSKKKRLPPTLKAWPPLV
GSLIKFLKGPIIMLREEYPKLGSVFTVNLVHKKITFLIGPEVSAHFFKAS

ESDLSQQEVYQFNVPTFGPGVVFDVDYSVRQEQFRFFTEALRVNKLKGYV

DMMVTEAEDYFSKWGESGEVDIKVELERLIILTASRCLLGREVRDQLFDD

VSALFHDLDNGMLPISVLFPYLPIPAHRRRDRAREKLSEIFAKIIGSRKR

SGKTENDMLQCFIESKYKDGRQTTESEVTGLLIAALFAGQHTSSITSTWT

GAYLMRYKEYFSAALDEQKNLIAKHGDKIDHDILSEMDVLYRCIKEALRL

HPPLIMLMRASHSDFSVTARDGKTYDIPKGHIVATSPAFANRLPHIFKDP

DTYDPERFSPGREEDKAAGAFSYIAFGGGRHGCLGEPFAYLQIKAIWSHL

LRNFELELVSPFPEIDWNAMVVGVKGNVMRYKRRQLS*

SEQ ID 18=Arabidopsis obtusifoliol C14α-demethylase (clone ID: ATA403931) nucleotide sequence

TCGACCCCGCGTCCGCGGACGCGTGGGATCAGCTTCAAGCTTAAGAGAGC

TTCGAAAGCGAAAGCGACGATTTCTTCTCCATCGTGAGAGCAAATCTCCA

GAGCCGTTTTCTCTTCTTCTTCTTCCTCCTCGCGCCGTCTCTGAAACTCC

ATCATCGTATCAATCAAATTGCTTCCTCCTCCAAATTGAAAAACAATGGA

ATTGGATTCGGAGAACAAATTGTTGAAGACGGGTTTGGTTATAGTGGCGA

CACTTGTTATAGCCAAACTCATCTTCTCTTTCTTCACTTCTGATTCTAAG

AAGAAGCGTCTTCCTCCTACTCTTAAAGCTTGGCCTCCATTGGTTGGAAG

TCTTATCAAATTCTTGAAAGGACCTATTATTATGCTTAGAGAGGAATACC

CTAAGCTTGGAAGTGTGTTTACTGTTAATCTTGTTCACAAAAAGATTACT

TTTCTTATTGGTCCTGAAGTCTCTGCTCATTTTTTCAAAGCTTCTGAATC

TGATCTTAGTCAGCAGGAAGTGTATCAGTTCAATGTCCCTACTTTTGGTC

CTGGAGTTGTTTTCGATGTTGATTATTCTGTTCGTCAGGAGCAGTTTCGG

TTCTTCACTGAGGCACTTAGAGTTAACAAGTTGAAGGGTTATGTGGATAT

GATGGTTACTGAAGCTGAGGATTACTTCTCTAAATGGGGAGAGAGTGGTG

AAGTTGATATTAAGGTTGAGCTAGAGAGGCTCATCATCTTGACTGCAAGT

AGATGTTTACTGGGTCGAGAAGTTCGTGATCAGCTTTTTGATGATGTCTC

TGCTTTGTTCCATGACCTTGACAATGGAATGCTTCCCATCAGTGTTCTCT

TCCCATATCTCCCAATTCCAGCTCACCGCCGTCGTGACCGTGCCCGAGAA

AAGCTTTCGGAGATTTTCGCAAAAATCATTGGGTCGAGAAAACGCTCTGG

AAAAACAGAGAACGACATGCTGCAGTGTTTCATCGAATCAAAGTACAAAG

ATGGTAGACAGACAACCGAATCTGAAGTCACTGGTTTGCTCATTGCTGCT

CTGTtTGCAGGACAACACACGAGCTCTATCACTTCCACCTGGACCGGTGC

TTATCTGATGCGATACAAAGAGTACTTCTCAGCTGCTCTTGATGAGCAGA

AGAACCTGATTGCGAAACATGGAGACAAGATCGATCATGATATCTTATCC

GAGATGCATGTTCTCTACCGCTGCATTAAGGAAGCGTTGAGGCTTCACCC

TCCACTCATCATGTTAATGAGAGCCTCGCACAGTGATTTCAGCGTGACAG

CTCGGGATGGAAAAACTTACGATATCCCAAAGGGTCACATCGTTGCAACC

TCCCCTGCATTTGCCAACCGCTTACCGCACATCTTCAAAGACCCCGACAC

CTACGACCCAGAAAGATTCTCCCCTGGAAGAGAAGAGGACAAAGCCGCAG

GGGCATTCTCGTACATTGCATTCGGAGGGGGAAGGCACGGGTGCCTTGGA

GAGCCGTTTGCTTACCTGCAGATCAAAGCCATATGGAGTCATTTGTTGAG

GAACTTCGAGCTTGAGCTAGTTTCACCGTTCCCTGAGATTGACTGGAACG

CTATGGTGGTTGGAGTTAAAGGCAATGTGATGGTGCGTTACAAGAGGCgc

CAGCTTTCTTAAAGACAAGTTTAAGGTTATTGCAGCTTTGGATTTTTCTC

TCTGGTTTCTGCTTTGCTTTTGTCCCTCTCTGGTTTTAGTTTTGTTGTTG

AATAATTCTTCTGTTTTTATAAACTGTTGTTACTCTTTAATTGACATTTA

TTTTTAAGCTTCCTAAGTTTGTGGTTCAAAAAAAAAAAAAGGCGGCGTTA

CT

SEQ ID 19=Arabidopsis obtusifoliol C14α-demethylase (clone ID: ATA403931) amino acid translation

MELDSENKLLKTGLVIVATLVIAKLIFSFFTSDSKKKRLPPTLKAWPPLV

GSLIKFLKGPIIMLREEYPKLGSVFTVNLVHKKITFLIGPEVSAHFFKAS

ESDLSQQEVYQFNVPTFGPGVVFDVDYSVRQEQFRFFTEALRVNKLKGYV

DMMVTEAEDYFSKWGESGEVDIKVELERLIILTASRCLLGREVRDQLFDD

VSALFHDLDNGMLPISVLFPYLPIPAHRRRDRAREKLSEIFAKIIGSRKR

SGKTENDMLQCFIESKYKDGRQTTESEVTGLLIAALFAGQHTSSITSTWT

GAYLMRYKEYFSAALDEQKNLIAKHGDKIDHDILSEMDVLYRCIKEALRL

HPPLIMLMRASHSDFSVTARDGKTYDIPKGHIVATSPAFANRLPHIFKDP

DTYDPERFSPGREEDKAAGAFSYIAFGGGRHGCLGEPFAYLQIKAIWSHL

LRNFELELVSPFPEIDWNAMVVGVKGNVMVRYKRRQLS*

SEQ ID 20=Arabidopsis sterol methyl transferase I protein sequence (Accession NO: U71400) See Appendix D SEQ ID 21=Tobacco sterol methyl transferase I protein sequence (from Prof. Pierre Benveniste Accession NO: U81312) See Appendix E SEQ ID 22=Arabidopsis sterol methyl transferase II protein sequence (Accession NO: X89867) (from Prof. Pierre Benveniste) See Appendix F SEQ ID 23=Arabidopsis sterol C5-desaturase protein sequence (Accession NO: X90454) See Appendix G SEQ ID 24=Rubber truncated HMGR1m1 (S566 to A) nucleotide sequence

ATGGCACGCGCCTCCCATGACGTGTGGGACCTCGAAGATACGGATCCCAA

CTACCTCATCGATGAAGATCACCGTCTCGTTACTTGCCCTCCCGCTAATA

TATCTACTAAGACTACCATTATTGCCGCACCTACCAAATTGCCTACCTCG

GAACCCTTAATTGCACCCTTAGTCTCGGAGGAAGACGAAATGATCGTCAA

CTCCGTCGTGGATGGGAAGATACCCTCCTATTCTCTGGAGTCGAAGCTCG

GGGACTGCAAACGAGCGGCTGCGATTCGACGCGAGGCTTTGCAGAGGATG

ACAAGGAGGTCGCTGGAAGGCTTGCCAGTAGAAGGGTTCGATTACGAGTC

GATTTTAGGACAATGCTGTGAAATGCCAGTGGGATACGTGCAGATTCCGG

TGGGGATTGCGGGGCCGTTGTTGCTGAACGGGCGGGAGTACTCTGTTCCA

ATGGCGACCACGGAGGGTTGTTTGGTGGCGAGCACTAATAGAGGGTGTAA

-continued

```
GGCGATTTACTTGTCAGGTGGGGCCACCAGCGTCTTGTTGAAGGATGGCA

TGACAAGAGCGCCTGTTGTAAGATTCGCGTCGGCGACTAGAGCCGCGGAG

TTGAAGTTCTTCTTGGAGGATCCTGACAATTTTGATACCTTGGCCGTAGT

TTTTAACAAGTCCAGTAGATTTGCGAGGCTCCAAGGCATTAAATGCTCAA

TTGCTGGTAAGAATCTTTATATAAGATTCAGCTGCAGCACTGGCGATGCA

ATGGGGATGAACATGGTTTCTAAAGGGGTTCAAAACGTTCTTGAATTTCT

TCAAAGTGATTTTTCTGATATGGATGTCATTGGAATCTCAGGAAATTTTT

GTTCGGATAAGAAGCCTGCTGCTGTAAATTGGATTGAAGGACGTGGCAAA

TCAGTTGTTTGTGAGGCAATTATCAAGGAAGAGGTGGTGAAGAAGGTGTT

GAAAACCAATGTGGCCTCCCTAGTGGAGCTTAACATGCTCAAGAATCTTG

CTGGTTCTGCTGTTGCTGGTGCTTTGGGTGGATTTAATGCCCATGCAGGC

AACATCGTATCTGCAATCTTTATTGCCACTGGCCAGGATCCAGCACAGAA

TGTTGAGAGTTCTCATTGCATTACCATGATGGAAGCTGTCAATGATGGAA

AGGATCTCCATATCTCTGTGACCATGCCCTCCATTGAGGTGGGTACAGTC

GGAGGTGGAACTCAACTTGCATCTCAGTCTGCTTGTCTCAATTTGCTTGG

GGTGAAGGGTGCAAACAAAGAGTCGCCAGGATCAAACTCAAGGCTCCTTG

CTGCCATCGTAGCTGGTTCAGTTTTGGCTGGTGAGCTCTCCTTGATGTCT

GCCATTGCAGCTGGGCAGCTTGTCAAGAGTCACATGAAGTACAACAGAGC

CAGCAAAGATATGTCTAAAGCTGCATCTTAG
```

SEQ ID 25=Rubber truncated HMGR1m1 (S566 to A) amino acid translation

```
MARASHDVWDLEDTDPNYLIDEDHRLVTCPPANISTKTTIIAAPTKLPTS

EPLIAPLVSEEDEMIVNSVVDGKIPSYSLESKLGDCKRAAAIRREALQRM

TRRSLEGLPVEGFDYESILGQCCEMPVGYVQIPVGIAGPLLLNGREYSVP

MATTEGCLVASTNRGCKAIYLSGGATSVLLKDGMTRAPVVRFASATRAAE

LKFFLEDPDNFDTLAVVFNKSSRFARLQGIKCSIAGKNLYIRFSCSTGDA

MGMNMVSKGVQNVLEFLQSDFSDMDVIGISGNFCSDKKPAAVNWIEGRGK

SVVCEAIIKEEVVKKVLKTNVASLVELNMLKNLAGSAVAGALGGFNAHAG

NIVSAIFIATGQDPAQNVESSHCITMMEAVNDGKDLHISVTMPSIEVGTV

GGGTQLASQSACLNLLGVKGANKESPGSNSRLLAAIVAGSVLAGELSLMS

AIAAGQLVKSHMKYNRASKDMSKAAS
```

SEQ ID. 26=Rubber truncated HMGR1m2 (S567 to A) nucleotide sequence

```
ATGGCACGCGCCTCCCATGACGTGTGGGACCTCGAAGATACGGATCCCAA

CTACCTCATCGATGAAGATCACCGTCTCGTTACTTGCCCTCCCGCTAATA

TATCTACTAAGACTACCATTATTGCCGCACCTACCAAATTGCCTACCTCG

GAACCCTTAATTGCACCCTTAGTCTCGGAGGAAGACGAAATGATCGTCAA
```

```
CTCCGTCGTGGATGGGAAGATACCCTCCTATTCTCTGGAGTCGAAGCTCG

GGGACTGCAAACGAGCGGCTGCGATTCGACGCGAGGCTTTGCAGAGGATG

ACAAGGAGGTCGCTGGAAGGCTTGCCAGTAGAAGGGTTCGATTACGAGTC

GATTTTAGGACAATGCTGTGAAATGCCAGTGGGATACGTGCAGATTCCGG

TGGGGATTGCGGGGCCGTTGTTGCTGAACGGGCGGGAGTACTCTGTTCCA

ATGGCGACCACGGAGGGTTGTTTGGTGGCGAGCACTAATAGAGGGTGTAA

GGCGATTTACTTGTCAGGTGGGGCCACCAGCGTCTTGTTGAAGGATGGCA

TGACAAGAGCGCCTGTTGTAAGATTCGCGTCGGCGACTAGAGCCGCGGAG

TTGAAGTTCTTCTTGGAGGATCCTGACAATTTTGATACCTTGGCCGTAGT

TTTTAACAAGTCCAGTAGATTTGCGAGGCTCCAAGGCATTAAATGCTCAA

TTGCTGGTAAGAATCTTTATATAAGATTCAGCTGCAGCACTGGCGATGCA

ATGGGGATGAACATGGTTTCTAAAGGGGTTCAAAACGTTCTTGAATTTCT

TCAAAGTGATTTTTCTGATATGGATGTCATTGGAATCTCAGGAAATTTTT

GTTCGGATAAGAAGCCTGCTGCTGTAAATTGGATTGAAGGACGTGGCAAA

TCAGTTGTTTGTGAGGCAATTATCAAGGAAGAGGTGGTGAAGAAGGTGTT

GAAAACCAATGTGGCCTCCCTAGTGGAGCTTAACATGCTCAAGAATCTTG

CTGGTTCTGCTGTTGCTGGTGCTTTGGGTGGATTTAATGCCCATGCAGGC

AACATCGTATCTGCAATCTTTATTGCCACTGGCCAGGATCCAGCACAGAA

TGTTGAGAGTTCTCATTGCATTACCATGATGGAAGCTGTCAATGATGGAA

AGGATCTCCATATCTCTGTGACCATGCCCTCCATTGAGGTGGGTACAGTC

GGAGGTGGAACTCAACTTGCATCTCAGTCTGCTTGTCTCAATTTGCTTGG

GGTGAAGGGTGCAAACAAAGAGTCGCCAGGATCAAACTCAAGGCTCCTTG

CTGCCATCGTAGCTGGTTCAGTTTTGGCTGGTGAGCTCTCCTTGATGTCT

GCCATTGCAGCTGGGCAGCTTGTCAAGAGTCACATGAAGTACAACAGATC

CGCCAAAGATATGTCTAAAGCTGCATCTTAG
```

SEQ ID 27=Rubber truncated HMGR1m2 (S567 to A) amino acid translation

```
MARASHDVWDLEDTDPNYLIDEDHRLVTCPPANISTKTTIIAAPTKLPTS

EPLIAPLVSEEDEMIVNSVVDGKIPSYSLESKLGDCKRAAAIRREALQRM

TRRSLEGLPVEGFDYESILGQCCEMPVGYVQIPVGIAGPLLLNGREYSVP

MATTEGCLVASTNRGCKAIYLSGGATSVLLKDGMTRAPVVRFASATRAAE

LKFFLEDPDNFDTLAVVFNKSSRFARLQGIKCSIAGKNLYIRFSCSTGDA

MGMNMVSKGVQNVLEFLQSDFSDMDVIGISGNFCSDKKPAAVNWIEGRGK

SVVCEAIIKEEVVKKVLKTNVASLVELNMLKNLAGSAVAGALGGFNAHAG

NIVSAIFIATGQDPAQNVESSHCITMMEAVNDGKDLHISVTMPSIEVGTV

GGGTQLASQSACLNLLGVKGANKESPGSNSRLLAAIVAGSVLAGELSLMS

AIAAGQLVKSHMKYNRSAKDMSKAAS
```

Example 6

Arabidopsis obtusifoliol C14α-demethylase constructs

The Arabidopsis obtusifoliol C14α-demethylase gene was amplified from two separate Arabidopsis mRNA samples (SIN 2 and Keto-10) through use of primers BXK33 and BXK34, as described below.

```
BXK33
(SEQ ID 28): 5'-GAGATCTGAACCCTAACGAGAG-3'

BXK34
(SEQ ID 29): 5'-GGAGCTCTTAAGAAAAGGGACGACGC-3'
```

The primer BXK33 has a Bgl II cleavage site shown in bold. The primer BXK34 has a Sac I cleavage site shown in bold. The actual size of the structural gene is 1.445 Kb.

The Arabidopsis mRNA was amplified using a Perkin Elmer GeneAmp RT-PCR kit. The reverse transcription reaction used 25 mM MgCl$_2$ (4 μl; 5 mM final), 10× PCR buffer (2 μl), di DEPC water (1 μl), 2 μl each of 1 mM solution of each of four dNTPs (dGTP, DATP, dUTP, dCTP), RNase inhibitor (1 μl of 10 units per μl stock), MMLV reverse transcriptase (1 μl of a 2.5 U/μl stock), Oligo d(T)16 Primer (1 μl of a 2.5 μM stock), and 2 μl of an Arabidopsis polyA RNA sample. The reaction mix was incubated at room temperature (about 20° C.) for 10 minutes, then in a PCR machine for one cycle (15 min. at 42° C., 5 min. at 99° C. and 5 min. at 4° C.).

Separate primer-mediated amplification reactions were carried out using Taq DNA polymerase and Vent DNA polymerase to obtain Arabidopsis obtusifoliol C14α-demethylase cDNA from the amplified mRNA sample.

| Taq PCR Reaction | Vent PCR Reaction |
|---|---|
| 4 μl 25 mM MgCl$_2$ | 4 μl 25 mM MgCl$_2$ |
| 8 μl 10X PCR buffer II | 8 μl 10X Vent PCR buffer |
| 65.5 μl di DEPC water | 65.5 μl di DEPC water |
| 0.5 μl AmpliTaq polymerase | 0.5 μl Vent polymerase |

After 1 minute and 35 seconds at 95° C., 1 μl each of 15 μM stocks of the upstream and downstream primers (BXK33 and BXK34) were added to the PCR reaction (100 μl total PCR reaction volume) and the PCR reaction solutions were subjected to 35 cycles (95° C. for 15 seconds, then 60° C. for 30 seconds). The amplified PCR reaction was then maintained at 72° C. for 7 minutes and then stored at 4° C. An amplification positive control reaction was carried out under the same conditions with DM151 and DM152 primers.

```
DM151
(SEQ ID 30): 5'-GTCTCTGAATCAGAAATCCTTCTATC-3'

DM152
(SEQ ID 31): 5'-CATGTCAAATTTCACTGCTTCATCC-3'
```

Electrophoresis of the nucleic acid solutions after PCR amplification displayed an amplification product corresponding approximately to the size of the desired 1.445 Kb structural gene. The fragment was cloned into an M13 vector. A representative sequencing reaction consisted of: 10 μl of plasmid DNA (200–500 ng), 2 μl of M13 Forward or Reverse primer (15 picomoles) and 8 μl of Big Dye Terminator Reaction Mix (PE Applied Biosci.). The clone copy of ATA101105 was called CPR17398. The sequence of the selected clone (Arabidopsis obtusifoliol C14α-demethylase) is identified as SEQ ID NO:9.

The predicted polypeptide sequence for the cloned Arabidopsis obtusifoliol C14α-demethylase sequence was subjected to a BLAST search in the public database and found to align with the sorghum obtusifoliol 14-alpha demethylase polypeptide (ATA101105/U74319/g1658192; and g1216657/U74319) exhibiting 75–78% sequence identity and 87–90% sequence homology. The cloned nucleic acid encoding Arabidopsis obtusifoliol C14α-demethylase (SEQ ID No:9) is missing the 5' end.

The 5' terminal portion of the structural gene was obtained by the RACE (Rapid Amplification of cDNA Ends) PCR using primers BXK39 and BXK40 per manufacturer's instructions (Clontech).

```
BXK39
(SEQ ID 32): 5'-GAGATCTCCACAGATTTAAAGAACCCTAACG-3'

BXK40
(SEQ ID 33): 5'-GGAGCTCGGTTTTTAAGAAAAGGGACGACGC-3'
```

The cloned nucleic acid encoding full length Arabidopsis obtusifoliol C14α-demethylase is identified as SEQ ID No:8. The amplified Arabidopsis obtusifoliol C14α-demethylase structural gene is useful for making constructs that express Arabidopsis obtusifoliol C14α-demethylase in transgenic plants.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A recombinant construct comprising:
   (a) a DNA sequence encoding a polypeptide having 3-hydroxy-3-methylglutaryl-Coenzyme A reductase enzyme activity, and
   (b) a DNA sequence encoding a polypeptide having squalene epoxidase enzyme activity.

2. The recombinant construct of claim 1, further comprising at least one promoter operably linked to said coding regions.

3. The recombinant construct of claim 1, further comprising a first promoter operably linked to said DNA sequence encoding a polypeptide having 3-hydroxy-3-methylglutaryl-Coenzyme A reductase enzyme activity and a second promoter operably linked to said DNA sequence encoding squalene epoxidase enzyme activity, wherein said first and second promoters may or may not be the same.

4. The recombinant construct of claim 2 or 3 further comprising an operably linked transcription termination sequence located 3' to each coding region.

5. A recombinant construct according to claim 3 wherein the promoters are selected from the group consisting of seed-specific promoters, organ specific promoters and constitutive promoters.

6. A recombinant vector comprising operably linked in the 5' to 3' direction,
- a promoter, a DNA sequence encoding a polypeptide having a 3-hydroxy-3-methylglutaryl-Coenzyme A reductase enzyme activity, and a transcription termination signal sequence;
- a promoter, a DNA sequence encoding squalene epoxidase enzyme activity, and a transcription termination signal sequence.

7. The recombinant vector of claim 6 wherein said vector is a plant expression vector.

8. A transformed host cell comprising a recombinant construct of claim 1.

9. The transformed host cell of claim 8 wherein said cell is a plant cell.

10. A transformed host cell comprising a recombinant vector of claim 6.

11. The transfonued host cell according to claim 10 wherein said host cell is a plant cell.

12. A transformed host cell comprising a plant expression vector comprising,
  (a) as operably linked components in the 5' to 3' direction, a promoter, a DNA sequence encoding a polypeptide having a 3-hydroxy-3-methylglutaryl-Coenzyme A reductase enzyme activity, and a transcription termination signal sequence; and
  (b) as operably linked components in the 5' to 3' direction, a promoter, a DNA sequence encoding squalene epoxidase enzyme activity, and a transcription termination signal sequence.

13. The transformed host cell according to claim 12 wherein said host cell is a plant cell.

14. A cell culture comprising transformed host cells according to any one of claims 8–13.

15. A transformed plant comprising at least one transformed host cell of any one of claim 9 or 11.

16. A transformed plant storage organ, comprising at least one transformed host cell according to any one of claim 9 or 11.

17. A transformed plant storage organ including at least one transformed plant host cell containing a recombinant vector comprising:
  (a) As operably linked components in the 5' to 3' direction, a promoter, a DNA sequence encoding at least one polypeptide having 3-hydroxy-3-methylglutaryl-Coenzyme A reductase enzyme activity, and a transcription termination signal sequence; and
  (b) as operably linked components in the 5' to 3' direction, a promoter, a DNA sequence encoding a polypeptide having squalene epoxidase activity, and a transcription termination signal sequence.

18. A process of increasing the formation of steroid pathway products in a transformed plant as compared to an otherwise identical non-transformed plant comprising:
  (1) transforming a host plant cell with a recombinant vector comprising
    (a) as operably linked components in the 5' to 3' direction, a promoter, a DNA sequence encoding a first polypeptide having 3-hydroxy-3-methylglutaryl-Coenzyme A reductase enzyme activity, and a transcription termination signal sequence; and
    (b) as operably linked components in the 5' to 3' direction, a promoter, a DNA sequence encoding at least one polypeptide having squalene epoxidase enzyme activity, and a transcription termination signal sequence, and
  (2) regenerating the transformed host plant cell into said transgenic plant.

* * * * *

UNITED STATES PATENT AND TRADEMARK OFFICE
CERTIFICATE OF CORRECTION

| | |
|---|---|
| PATENT NO. | : 6,822,142 B2 |
| APPLICATION NO. | : 09/885723 |
| DATED | : November 23, 2004 |
| INVENTOR(S) | : Karunanandaa et al. |

Page 1 of 1

It is certified that error appears in the above-identified patent and that said Letters Patent is hereby corrected as shown below:

In claim 15, column 134, line 8, please delete "9 or 11" and insert --9 and 11--.

In claim 16, column 134, line 10, please delete "9 or 11" and insert --9 and 11--.

Signed and Sealed this

Twenty-fourth Day of April, 2007

JON W. DUDAS
*Director of the United States Patent and Trademark Office*

SEQUENCE LISTING

<160> NUMBER OF SEQ ID NOS: 33

<210> SEQ ID NO 1
<211> LENGTH: 585
<212> TYPE: PRT
<213> ORGANISM: Arabidopsis thaliana

<400> SEQUENCE: 1

```
Met Lys Pro Phe Val Ile Arg Asn Leu Pro Arg Phe Gln Ser Thr Leu
1               5                   10                  15

Arg Ser Ser Leu Leu Tyr Thr Asn His Arg Pro Ser Ser Arg Phe Ser
            20                  25                  30

Leu Ser Thr Arg Arg Phe Thr Thr Gly Ala Thr Tyr Ile Arg Arg Trp
        35                  40                  45

Lys Ala Thr Ala Ala Gln Thr Leu Lys Leu Ser Ala Val Asn Ser Thr
50                  55                  60

Val Met Met Lys Pro Ala Lys Ile Ala Leu Asp Gln Phe Ile Ala Ser
65                  70                  75                  80

Leu Phe Thr Phe Leu Leu Leu Tyr Ile Leu Arg Arg Ser Ser Asn Lys
                85                  90                  95

Asn Lys Lys Asn Arg Gly Leu Val Val Ser Gln Asn Asp Thr Val Ser
            100                 105                 110

Lys Asn Leu Glu Thr Glu Val Asp Ser Gly Thr Asp Val Ile Ile Val
        115                 120                 125

Gly Ala Gly Val Ala Gly Ser Ala Leu Ala His Thr Leu Gly Lys Glu
130                 135                 140

Gly Arg Arg Val His Val Ile Glu Arg Asp Phe Ser Glu Gln Asp Arg
145                 150                 155                 160

Ile Val Gly Glu Leu Leu Gln Pro Gly Gly Tyr Leu Lys Leu Ile Glu
                165                 170                 175

Leu Gly Leu Glu Asp Cys Val Lys Lys Ile Asp Ala Gln Arg Val Leu
            180                 185                 190

Gly Tyr Val Leu Phe Lys Asp Gly Lys His Thr Lys Leu Ala Tyr Pro
        195                 200                 205

Leu Glu Thr Phe Asp Ser Asp Val Ala Gly Arg Ser Phe His Asn Gly
    210                 215                 220

Arg Phe Val Gln Arg Met Arg Glu Lys Ala Leu Thr Leu Ser Asn Val
225                 230                 235                 240

Arg Leu Glu Gln Gly Thr Val Thr Ser Leu Leu Glu Glu His Gly Thr
                245                 250                 255

Ile Lys Gly Val Arg Tyr Arg Thr Lys Glu Gly Asn Glu Phe Arg Ser
            260                 265                 270

Phe Ala Pro Leu Thr Ile Val Cys Asp Gly Cys Phe Ser Asn Leu Arg
        275                 280                 285

Arg Ser Leu Cys Lys Pro Lys Val Asp Val Pro Ser Thr Phe Val Gly
    290                 295                 300

Leu Val Leu Glu Asn Cys Glu Leu Pro Phe Ala Asn His Gly His Val
305                 310                 315                 320

Val Leu Gly Asp Pro Ser Pro Ile Leu Met Tyr Pro Ile Ser Ser Ser
                325                 330                 335

Glu Val Arg Cys Leu Val Asp Val Pro Gly Gln Lys Leu Pro Pro Ile
            340                 345                 350

Ala Asn Gly Glu Met Ala Lys Tyr Leu Lys Thr Arg Val Ala Pro Gln
```

```
            355                 360                 365
Val Pro Thr Lys Val Arg Glu Ala Phe Ile Thr Ala Val Glu Lys Gly
    370                 375                 380

Asn Ile Arg Thr Met Pro Asn Arg Ser Met Pro Ala Asp Pro Ile Pro
385                 390                 395                 400

Thr Pro Gly Ala Leu Leu Gly Asp Ala Phe Asn Met Arg His Pro
                405                 410                 415

Leu Thr Gly Gly Gly Met Thr Val Ala Leu Ala Asp Ile Val Val Leu
                420                 425                 430

Arg Asp Leu Leu Arg Pro Ile Arg Asn Leu Asn Asp Lys Glu Ala Leu
                435                 440                 445

Ser Lys Tyr Ile Glu Ser Phe Tyr Thr Leu Arg Lys Pro Val Ala Ser
    450                 455                 460

Thr Ile Asn Thr Leu Ala Asp Ala Leu Tyr Lys Val Phe Leu Ala Ser
465                 470                 475                 480

Ser Asp Glu Ala Arg Thr Glu Met Arg Glu Ala Cys Phe Asp Tyr Leu
                485                 490                 495

Ser Leu Gly Gly Val Phe Ser Ser Gly Pro Val Ala Leu Leu Ser Gly
                500                 505                 510

Leu Asn Pro Arg Pro Leu Ser Leu Val Leu His Phe Ala Val Ala
                515                 520                 525

Ile Tyr Ala Val Cys Arg Leu Met Leu Pro Phe Pro Ser Ile Glu Ser
    530                 535                 540

Phe Trp Leu Gly Ala Arg Ile Ile Ser Ser Ala Ser Ser Ile Ile Phe
545                 550                 555                 560

Pro Ile Ile Lys Ala Glu Gly Val Arg Gln Met Phe Phe Pro Arg Thr
                565                 570                 575

Ile Pro Ala Ile Tyr Arg Ala Pro Pro
                580                 585

<210> SEQ ID NO 2
<211> LENGTH: 418
<212> TYPE: DNA
<213> ORGANISM: Arabidopsis thaliana
<220> FEATURE:
<221> NAME/KEY: Unsure
<222> LOCATION: (1)..(418)
<223> OTHER INFORMATION: n=a, c, g or t

<400> SEQUENCE: 2
cttacgcgtg gttatngacg cttctcgcct ttgttctgac atggatgatt tttcacctca      60
tcaagatgaa gaaggcggca accggagatt tagaggccga ggcagaagca agaagagatg     120
gtgcaacgga tgtcatcatt gtngggcgg gtgttgcagg cgcttctctt gcttatgcnt      180
tagctaagga tngacgacga gtacatgtga tagagangga cttaaaagag ccacaaagat     240
tcatgggaga nctgatgcaa ncggaggtc gctttcatgt taagcccagc ttggcctcga     300
agattgttnt ggaggacatn gacgcacaag aatncgaaan cctttggcat atnccaagnn    360
tggaaacacg cgaaatggcc tttccanatg aaaagaantt tcctcatgag ccagtagg      418

<210> SEQ ID NO 3
<211> LENGTH: 354
<212> TYPE: DNA
<213> ORGANISM: Arabidopsis thaliana
<220> FEATURE:
<221> NAME/KEY: Unsure
<222> LOCATION: (1)..(354)
<223> OTHER INFORMATION: n=a, c, g or t
```

<400> SEQUENCE: 3

```
gcaatgactt acgcgtggtt atggacgctt ctngcctttn tnctgacatg gatggttttt        60
cacctcanca agatgaagaa ggcggcaacc ggagatttag aggccgaggc agaagcaaga       120
agagatggtg caacggatgt natcattgtt ggggcgggtn ttgcaggcgc ttctnttgct       180
tatncttttag ctaaggatgg acgacgagta catgtgatag agagggactt aaaagagcca      240
caaagattca tgggaganct gatgcaagcg gggaggtcgc ttcatgttag cccagnttgg       300
cctcgaagat ttttttttgna gggcataaga cgnaccaana agcggaatnc cttt            354
```

<210> SEQ ID NO 4
<211> LENGTH: 1829
<212> TYPE: DNA
<213> ORGANISM: Arabidopsis thaliana

<400> SEQUENCE: 4

```
gaattcccgg gtcgacccac gcgtccgctt atagataagg atatggcctt tacgaacgtt        60
tgcctatgga cgctactcgc cttcatgctg acttggacag tgttctacgt cacaaacagg       120
gggaagaagg cgacgcagtt ggcggatgcg gtggttgaag agcgagaaga cggtgctact       180
gacgttatca tcgttgggc tggagtaggc ggctcggctc tcgcatatgc tcttgctaag       240
gacgggcgtc gagtccatgt aatagagagg gacctgagag aaccagagag aatcatgggt       300
gagtttatgc aaccaggagg acgactcatg ctctctaagc ttggtcttga agattgtttg       360
gagggaatag atgcccaaaa agccacgggc atgacagttt ataaggacgg aaaagaagca       420
gtcgcatctt ttcccgtgga caacaacaat tttccttttg atccttcggc tcgatctttt       480
cacaatggcc gattcgtcca acgattgcgg caaaaggctt cttctcttcc caatgtgcgc       540
ctggaagaag gaacggtgaa gtctttgata gaagaaaaag gagtgatcaa aggagtgaca       600
tacaaaaata gcgcaggcga agaaacaaca gccttggcac ctctcactgt agtatgcgac       660
ggttgctact caaaccttcg ccggtctctt aatgacaaca atgcggaggt tctgtcatac       720
caagttggtt ttatctcaaa gaactgtcag cttgaagaac ccgaaaagtt aaagttgata       780
atgtctaaac cctccttcac catgttgtat caaatcagca gcaccgacgt tcgttgtgtt       840
tttgaagttc tccccaacaa cattccttct atttcaaatg gtgaaatggc tactttcgtg       900
aagaacacta ttgctcctca ggtaccttta aaactccgca aaatattttt gaaagggatt       960
gatgaaggag aacatataaa agccatgcca acaaagaaga tgacagctac tttgagcgag      1020
aagaaaggag tgattttatt gggagatgca ttcaacatgc gtcatccagc aatcgcatct      1080
ggaatgatgg ttttattatc tgacattctc attttacgcc gtcttctcca gccattaagc      1140
aaccttggca atgcgcaaaa aatctcacaa gttatcaagt cctttatga tatccgcaag      1200
ccaatgtcag cgacagttaa cacgttagga aatgcattct ctcaagtgct agttgcatcg      1260
acggacgaag caaaagaggc aatgagacaa ggttgctatg attacctctc tagtggtggg      1320
tttcgcacgt cagggatgat ggcttttgcta ggcggcatga accctcgtcc gatctctctc      1380
atctatcatc tatgtgctat cactctatcc tccattggcc atctactctc tccattccc       1440
tctcccctttg gcatttggca tagccttcga ctttttggtt tggctatgaa aatgttggtt      1500
ccccatctca aggctgaagg agttagccaa atgttgtttc cagtcaacgc cgccgcgtat      1560
agcaaaagct atatggctgc aacggctctt taaaacactg gtgcttttaaa ctgcaaaata      1620
taacacatat ataaatcccg aatctttgtg attctgcata tattgtgttc tacaattatt      1680
```

```
ctcatataaa tgaaaattgt tctacgtaaa agtaaaaaga aggaattgta atactaataa    1740
aacgagtttt taattctgtt gaatgcttgt gtatattggt gaaaaaaaaa aaaaaaaaaa    1800
aaaaaaaaaa aaaaaaaaag ggcggccgc                                     1829
```

<210> SEQ ID NO 5
<211> LENGTH: 530
<212> TYPE: PRT
<213> ORGANISM: Arabidopsis thaliana

<400> SEQUENCE: 5

```
Glu Phe Pro Gly Arg Pro Thr Arg Pro Leu Ile Asp Lys Asp Met Ala
1               5                   10                  15

Phe Thr Asn Val Cys Leu Trp Thr Leu Leu Ala Phe Met Leu Thr Trp
            20                  25                  30

Thr Val Phe Tyr Val Thr Asn Arg Gly Lys Lys Ala Thr Gln Leu Ala
        35                  40                  45

Asp Ala Val Val Glu Glu Arg Glu Asp Gly Ala Thr Asp Val Ile Ile
    50                  55                  60

Val Gly Ala Gly Val Gly Gly Ser Ala Leu Ala Tyr Ala Leu Ala Lys
65                  70                  75                  80

Asp Gly Arg Arg Val His Val Ile Glu Arg Asp Leu Arg Glu Pro Glu
                85                  90                  95

Arg Ile Met Gly Glu Phe Met Gln Pro Gly Gly Arg Leu Met Leu Ser
            100                 105                 110

Lys Leu Gly Leu Glu Asp Cys Leu Glu Gly Ile Asp Ala Gln Lys Ala
        115                 120                 125

Thr Gly Met Thr Val Tyr Lys Asp Gly Lys Glu Ala Val Ala Ser Phe
    130                 135                 140

Pro Val Asp Asn Asn Phe Pro Phe Asp Pro Ser Ala Arg Ser Phe
145                 150                 155                 160

His Asn Gly Arg Phe Val Gln Arg Leu Arg Gln Lys Ala Ser Ser Leu
                165                 170                 175

Pro Asn Val Arg Leu Glu Glu Gly Thr Val Lys Ser Leu Ile Glu Glu
            180                 185                 190

Lys Gly Val Ile Lys Gly Val Thr Tyr Lys Asn Ser Ala Gly Glu Glu
        195                 200                 205

Thr Thr Ala Leu Ala Pro Leu Thr Val Val Cys Asp Gly Cys Tyr Ser
    210                 215                 220

Asn Leu Arg Arg Ser Leu Asn Asp Asn Ala Glu Val Leu Ser Tyr
225                 230                 235                 240

Gln Val Gly Phe Ile Ser Lys Asn Cys Gln Leu Glu Glu Pro Glu Lys
                245                 250                 255

Leu Lys Leu Ile Met Ser Lys Pro Ser Phe Thr Met Leu Tyr Gln Ile
            260                 265                 270

Ser Ser Thr Asp Val Arg Cys Val Phe Glu Val Leu Pro Asn Asn Ile
        275                 280                 285

Pro Ser Ile Ser Asn Gly Glu Met Ala Thr Phe Val Lys Asn Thr Ile
    290                 295                 300

Ala Pro Gln Val Pro Leu Lys Leu Arg Lys Ile Phe Leu Lys Gly Ile
305                 310                 315                 320

Asp Glu Gly Glu His Ile Lys Ala Met Pro Thr Lys Met Thr Ala
                325                 330                 335

Thr Leu Ser Glu Lys Lys Gly Val Ile Leu Leu Gly Asp Ala Phe Asn
            340                 345                 350
```

```
Met Arg His Pro Ala Ile Ala Ser Gly Met Met Val Leu Leu Ser Asp
        355                 360                 365

Ile Leu Ile Leu Arg Arg Leu Leu Gln Pro Leu Ser Asn Leu Gly Asn
        370                 375                 380

Ala Gln Lys Ile Ser Gln Val Ile Lys Ser Phe Tyr Asp Ile Arg Lys
385                 390                 395                 400

Pro Met Ser Ala Thr Val Asn Thr Leu Gly Asn Ala Phe Ser Gln Val
                405                 410                 415

Leu Val Ala Ser Thr Asp Glu Ala Lys Glu Ala Met Arg Gln Gly Cys
                420                 425                 430

Tyr Asp Tyr Leu Ser Ser Gly Phe Arg Thr Ser Gly Met Met Ala
        435                 440                 445

Leu Leu Gly Gly Met Asn Pro Arg Pro Ile Ser Leu Ile Tyr His Leu
        450                 455                 460

Cys Ala Ile Thr Leu Ser Ser Ile Gly His Leu Leu Ser Pro Phe Pro
465                 470                 475                 480

Ser Pro Leu Gly Ile Trp His Ser Leu Arg Leu Phe Gly Leu Ala Met
                485                 490                 495

Lys Met Leu Val Pro His Leu Lys Ala Glu Gly Val Ser Gln Met Leu
                500                 505                 510

Phe Pro Val Asn Ala Ala Ala Tyr Ser Lys Ser Tyr Met Ala Ala Thr
        515                 520                 525

Ala Leu
    530

<210> SEQ ID NO 6
<211> LENGTH: 2038
<212> TYPE: DNA
<213> ORGANISM: Arabidopsis thaliana

<400> SEQUENCE: 6
gaattcccgg gtcgacccac gcgtccgcgg acgcgtggga ttgagaacaa atagatttgg    60
ttatatatgg cttttacgca cgtttgttta tggacgttag tcgccttcgt gctgacgtgg   120
acggtgttct accttaccaa catgaagaag aaggcgacgg atttggctga tacggtggct   180
gaggatcaaa aagacggtgc tgctgacgtc attatcgtcg gggctggtgt aggtggttcg   240
gctctcgcat atgctcttgc taaggatggg cgtcgagtac atgtgatcga gagggacatg   300
agagaaccag aaagaatgat gggtgagttt atgcaacctg gcggacgact catgctttct   360
aaacttggcc ttcaagattg cttggaagac atagatgcac agaaagccac gggtttggca   420
gtttataaag atgaaaagaa agcagacgca ccttttccag tggataacaa caattttttct  480
tatgaacctt ctgctcgatc ttttcacaat ggccgattcg tccaacaact gcgtcgaaag   540
gcttttttctc tttccaatgt gcgcctggaa gaaggaacgg tgaagtcttt actagaagaa   600
aaaggagtgg tcaaaggagt gacatacaag aataaagaag gcgaagaaac aacagccttg   660
gcacctctca ctgtggtatg cgacggttgc tactcaaacc ttcgtcggtc tcttaatgat   720
gacaacaatg ctgagattat gtcgtacata gttggttaca tctcaaagaa ttgtcggctt   780
gaagaacccg aaaagctaca cttgatattg tctaaaccat ctttcaccat ggtataccaa   840
ataagcagca ctgacgttcg ttgtggtttt gaggttctcc ccgaaaattt tccttctatt   900
gcaaatggtg aaatgtctac tttcatgaag aatactatag ttcctcaggt acctccaaaa   960
ctccgcaaaa tattttgaa aggtatagat gagggagcac acataaaagt ggtgccggca  1020
```

-continued

```
aagcgcatga catctacttt aagcaagaag aaaggtgtga ttgtattggg agatgcattc    1080
aatatgcgtc atccagttgt tgcatctgga atgatggttt tactgtcgga cattctcatt    1140
ctacgccgtc ttcttcagcc attaagcaac ctcggcgatg caaacaaagt ctcagaagtt    1200
atcaattcct tttatgatat ccgcaagcca atgtcggcga cggttaacac attgggaaat    1260
gcattttctc aagtactaat tggatcaacg gatgaagcaa aagaggcaat gagacagggt    1320
gtctatgatt acctttgtag tggcgggttt cgtacgtcag ggatgatggc tctgctcggc    1380
ggcatgaatc ctcgtcctct ctctctcgtc tatcatcttt gtgccatcac tctatcctcc    1440
attggccaac tgctctctcc atttccctct ccccttcgca tttggcatag cctcaagctt    1500
tttggtttgg ccatgaaaat gttggttccc aatctcaaag ctgaaggagt tagccaaatg    1560
ttgtttccag caaatgcagc cgcgtatcac aaaagctata tggctgcaac cactctctaa    1620
actttgatgc tctcaatcgc aatatatatg gagcacgaat ctatgtgatt gtgcatttgg    1680
taaacgtgta ttgcagtgct tataattatt agtatgtaac ggggaaaagt tctaaacaca    1740
aaaaaataaa cttttgaatg ttatatgtgt gaattatttt tgttgttaca agtaatgctc    1800 tttttttta gcttcacaca tgtattattg gagctaattt tttgtttctc tgttcttta    1860 tttttgtttt cttactgtat ttactttgaa aagtttcgtt ttatacatat tggacatttt    1920
ttaaaaaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaaaaaaaaa aaaaaaaagg gcggccgc     2038
```

<210> SEQ ID NO 7
<211> LENGTH: 517
<212> TYPE: PRT
<213> ORGANISM: Arabidopsis thaliana

<400> SEQUENCE: 7

```
Met Ala Phe Thr His Val Cys Leu Trp Thr Leu Val Ala Phe Val Leu
1               5                   10                  15

Thr Trp Thr Val Phe Tyr Leu Thr Asn Met Lys Lys Ala Thr Asp
            20                  25                  30

Leu Ala Asp Thr Val Ala Glu Asp Gln Lys Asp Gly Ala Ala Asp Val
        35                  40                  45

Ile Ile Val Gly Ala Gly Val Gly Ser Ala Leu Ala Tyr Ala Leu
    50                  55                  60

Ala Lys Asp Gly Arg Arg Val His Val Ile Glu Arg Asp Met Arg Glu
65                  70                  75                  80

Pro Glu Arg Met Met Gly Glu Phe Met Gln Pro Gly Gly Arg Leu Met
                85                  90                  95

Leu Ser Lys Leu Gly Leu Gln Asp Cys Leu Glu Asp Ile Asp Ala Gln
            100                 105                 110

Lys Ala Thr Gly Leu Ala Val Tyr Lys Asp Gly Lys Glu Ala Asp Ala
        115                 120                 125

Pro Phe Pro Val Asp Asn Asn Phe Ser Tyr Glu Pro Ser Ala Arg
    130                 135                 140

Ser Phe His Asn Gly Arg Phe Val Gln Gln Leu Arg Arg Lys Ala Phe
145                 150                 155                 160

Ser Leu Ser Asn Val Arg Leu Glu Glu Gly Thr Val Lys Ser Leu Leu
                165                 170                 175

Glu Glu Lys Gly Val Val Lys Gly Val Thr Tyr Lys Asn Lys Glu Gly
            180                 185                 190

Glu Glu Thr Thr Ala Leu Ala Pro Leu Thr Val Val Cys Asp Gly Cys
```

```
                195              200              205
Tyr Ser Asn Leu Arg Arg Ser Leu Asn Asp Asp Asn Ala Glu Ile
    210              215              220
Met Ser Tyr Ile Val Gly Tyr Ile Ser Lys Asn Cys Arg Leu Glu Glu
225              230              235              240
Pro Glu Lys Leu His Leu Ile Leu Ser Lys Pro Ser Phe Thr Met Val
                245              250              255
Tyr Gln Ile Ser Ser Thr Asp Val Arg Cys Gly Phe Glu Val Leu Pro
            260              265              270
Glu Asn Phe Pro Ser Ile Ala Asn Gly Glu Met Ser Thr Phe Met Lys
            275              280              285
Asn Thr Ile Val Pro Gln Val Pro Pro Lys Leu Arg Lys Ile Phe Leu
        290              295              300
Lys Gly Ile Asp Glu Gly Ala His Ile Lys Val Val Pro Ala Lys Arg
305              310              315              320
Met Thr Ser Thr Leu Ser Lys Lys Lys Gly Val Ile Val Leu Gly Asp
                325              330              335
Ala Phe Asn Met Arg His Pro Val Val Ala Ser Gly Met Met Val Leu
            340              345              350
Leu Ser Asp Ile Leu Ile Leu Arg Arg Leu Leu Gln Pro Leu Ser Asn
        355              360              365
Leu Gly Asp Ala Asn Lys Val Ser Glu Val Ile Asn Ser Phe Tyr Asp
    370              375              380
Ile Arg Lys Pro Met Ser Ala Thr Val Asn Thr Leu Gly Asn Ala Phe
385              390              395              400
Ser Gln Val Leu Ile Gly Ser Thr Asp Glu Ala Lys Glu Ala Met Arg
                405              410              415
Gln Gly Val Tyr Asp Tyr Leu Cys Ser Gly Phe Arg Thr Ser Gly
            420              425              430
Met Met Ala Leu Leu Gly Gly Met Asn Pro Arg Pro Leu Ser Leu Val
            435              440              445
Tyr His Leu Cys Ala Ile Thr Leu Ser Ser Ile Gly Gln Leu Leu Ser
        450              455              460
Pro Phe Pro Ser Pro Leu Arg Ile Trp His Ser Leu Lys Leu Phe Gly
465              470              475              480
Leu Ala Met Lys Met Leu Val Pro Asn Leu Lys Ala Glu Gly Val Ser
                485              490              495
Gln Met Leu Phe Pro Ala Asn Ala Ala Tyr His Lys Ser Tyr Met
            500              505              510
Ala Ala Thr Thr Leu
        515

<210> SEQ ID NO 8
<211> LENGTH: 392
<212> TYPE: DNA
<213> ORGANISM: Arabidopsis thaliana

<400> SEQUENCE: 8
aaatcatatt gagaacaaat agatttggtt atatatggct tttacgcacg tttgtttatg     60
gacgttagtc gccttcgtgc tgacgtggac ggtgttctac cttaccaaca tgaagaagaa    120
ggcgacggat ttggctgata cggtggctga ggatcaaaaa gacggtgctg ctgacgtcat    180
tatcgtcggg gctggtgtag gtggttcggc tctcgcatat gctctgctaa gtgtgcgcct    240
ggaagaagga acggtgaagt ctttactaga agaaaaagga gtggtcaaag gagtgacata    300
```

```
caagaataaa gaatgcgaac aaacaacagc cttggcacct ctcactgtgg tatgcgacgg      360
ttgctaatca aaccttcgtc ggtctcttaa tg                                    392
```

<210> SEQ ID NO 9
<211> LENGTH: 110
<212> TYPE: PRT
<213> ORGANISM: Arabidopsis thaliana

<400> SEQUENCE: 9

```
Met Ala Phe Thr His Val Cys Leu Trp Thr Leu Val Ala Phe Val Leu
  1               5                  10                  15

Thr Trp Thr Val Phe Tyr Leu Thr Asn Met Lys Lys Ala Thr Asp
             20                  25                  30

Leu Ala Asp Thr Val Ala Glu Asp Gln Lys Asp Gly Ala Ala Asp Val
         35                  40                  45

Ile Ile Val Gly Ala Gly Val Gly Gly Ser Ala Leu Ala Tyr Ala Leu
     50                  55                  60

Leu Ser Val Arg Leu Glu Glu Gly Thr Val Lys Ser Leu Leu Glu Glu
 65                  70                  75                  80

Lys Gly Val Val Lys Gly Val Thr Tyr Lys Asn Lys Glu Cys Glu Gln
                 85                  90                  95

Thr Thr Ala Leu Ala Pro Leu Thr Val Val Cys Asp Gly Cys
                100                 105                 110
```

<210> SEQ ID NO 10
<211> LENGTH: 457
<212> TYPE: DNA
<213> ORGANISM: Arabidopsis thaliana
<220> FEATURE:
<221> NAME/KEY: Unsure
<222> LOCATION: (1)..(457)
<223> OTHER INFORMATION: n=a, c, g or t

<400> SEQUENCE: 10

```
cacaaagcaa aaaatctct gtaaaagcag aacgataatg gagtcacaat tatggaattg       60
gatcttacct cttttgatct cttctctcct catctccttc gtcgctttct atggattctt     120
cgtcaaaccg aagcggaacg gtctccgtca cgatcggaaa actgtttcta ccgtcacctc     180
cgacgtcgga tctgttaata ttaccggaga tactgtcgct gatgtcattg ttgttggagc     240
tggtgttgct ggttctgctc ttgcttatac tcttggaaag gggaaattta aacgccgagt     300
tcatgtgatt gaaagagatt tatcggagcc tgatcgtatt gttggggagt tgttacagcc     360
tgngggttac ctcaagttac tggagtgtgg aattggagat tgtgtggaag aaatagatgc     420
tcagcntgtg tatggttatg cactttttaa aaatggg                              457
```

<210> SEQ ID NO 11
<211> LENGTH: 152
<212> TYPE: PRT
<213> ORGANISM: Arabidopsis thaliana
<220> FEATURE:
<221> NAME/KEY: UNSURE
<222> LOCATION: (1)..(152)
<223> OTHER INFORMATION: X=any amino acid

<400> SEQUENCE: 11

```
Thr Lys Gln Lys Asn Leu Cys Lys Ser Arg Thr Ile Met Glu Ser Gln
  1               5                  10                  15

Leu Trp Asn Trp Ile Leu Pro Leu Leu Ile Ser Ser Leu Leu Ile Ser
             20                  25                  30
```

Phe Val Ala Phe Tyr Gly Phe Val Lys Pro Lys Arg Asn Gly Leu
     35                  40                  45

Arg His Asp Arg Lys Thr Val Ser Thr Val Thr Ser Asp Val Gly Ser
 50                  55                  60

Val Asn Ile Thr Gly Asp Thr Val Ala Asp Val Ile Val Val Gly Ala
 65                  70                  75                  80

Gly Val Ala Gly Ser Ala Leu Ala Tyr Thr Leu Gly Lys Gly Lys Phe
                 85                  90                  95

Lys Arg Arg Val His Val Ile Glu Arg Asp Leu Ser Glu Pro Asp Arg
                100                 105                 110

Ile Val Gly Glu Leu Leu Gln Pro Xaa Gly Tyr Leu Lys Leu Leu Glu
                115                 120                 125

Cys Gly Ile Gly Asp Cys Val Glu Glu Ile Asp Ala Gln Xaa Val Tyr
130                 135                 140

Gly Tyr Ala Leu Phe Lys Asn Gly
145                 150

<210> SEQ ID NO 12
<211> LENGTH: 1486
<212> TYPE: DNA
<213> ORGANISM: Arabidopsis thaliana

<400> SEQUENCE: 12
cgtgttttac aaatttcctt tgttggtttt ccacagattt aaagaaccct aacgagagaa      60
aaaaatggac tgggattact atacgctgtt gaagacgagt gtggctatta ttatagtgtt     120
tgttgtggcc aaactcataa cctcctccaa atccaagaag aaaacaagtg tcgtcccact     180
ccctccagtt cttcaagcgt ggcctccatt tatcggatcc ctaatccgct tcatgaaagg     240
tccaatagtg ctacttagag aggaatatcc taagcttgga agtgttttca cagtgaagct     300
tcttcacaaa aacatcactt ttctcatcgg tcccgaagtc tcgtcccact tttcaacgc      360
ttatgaatct gaactcagcc agaaagaaat ttacaaattt aatgtgccta cttttggccc     420
cggagttgtg tttgatgttg actatcccgt tcggatggag cagttccgat tcttctccag     480
cgctctcaag gattacttct caaaatgggg agaaagtggg gaagtggatc taaaggccga     540
gttagagcgt ctaatcacct tgactgctag tagatgtcta ttgggtcgag aagtccgtga     600
ccaactttt gatgatgttg ctccattgtt ccatgacctt gataaaggca tgcaacccat     660
aagtgtcatc ttcccaaagc tccccattcc agctcacaat tgtcgtgacc gtgctcgcgg     720
aaagattgca aaaatctttt caaacatcat agcaacaaga aaacgctctg gtgacaaatc     780
agagaacgac atgctacaat gtttcatcga ctcaaagtac aaagacggta gagagacaac     840
tgaatctgaa gtaactggtt tgctcattgc tggtttgttt gcaggacaac atacaagctc     900
tatcactgcc acatggaccg gtgcttatct aattcaaaac aaaactggtg gtccgcggc     960
tttggacgag cagaagaaac tgattggaaa acatgggac aagatcgact acgatgtttt    1020
gtctgagatg gattttctgt tcgcagtgc aaaagaagct taaggcttc accctccaaa    1080
gatcttactg ctgagaacag tacacagtga tttcaccgtg acaactcgag aaggaaagca    1140
atatgagata ccaaagggtc atatcgttgc aacttctcct gcattcgcca accgcttacc    1200
tcatgtctac aaagatccgg aaaattttga tccggataga ttttcaaagg aaagagaaga    1260
ggataaagca gctggttcgt gttcatacat ctctttggga gctggtaggc acgagtgtcc    1320
tggtggatca tttgcgttct tgcagatcaa agccgtatgg tgtcacttat tgagaaactt    1380

```
tgagcttgag ttagtgtcac ctttccctga aatcaactgg aatgctttgg tcgttggtgc   1440
taaaggaaat gtcatggttc gttacaagcg tcgtcccttt tcttaa               1486
```

<210> SEQ ID NO 13
<211> LENGTH: 473
<212> TYPE: PRT
<213> ORGANISM: Arabidopsis thaliana

<400> SEQUENCE: 13

```
Met Asp Trp Asp Tyr Tyr Thr Leu Leu Lys Thr Ser Val Ala Ile Ile
1               5                   10                  15

Ile Val Phe Val Val Ala Lys Leu Ile Thr Ser Ser Lys Ser Lys Lys
                20                  25                  30

Lys Thr Ser Val Val Pro Leu Pro Pro Val Leu Gln Ala Trp Pro Pro
            35                  40                  45

Phe Ile Gly Ser Leu Ile Arg Phe Met Lys Gly Pro Ile Val Leu Leu
        50                  55                  60

Arg Glu Glu Tyr Pro Lys Leu Gly Ser Val Phe Thr Val Lys Leu Leu
65                  70                  75                  80

His Lys Asn Ile Thr Phe Leu Ile Gly Pro Glu Val Ser Ser His Phe
                85                  90                  95

Phe Asn Ala Tyr Glu Ser Glu Leu Ser Gln Lys Glu Ile Tyr Lys Phe
            100                 105                 110

Asn Val Pro Thr Phe Gly Pro Gly Val Val Phe Asp Val Asp Tyr Pro
        115                 120                 125

Val Arg Met Glu Gln Phe Arg Phe Phe Ser Ser Ala Leu Lys Asp Tyr
130                 135                 140

Phe Ser Lys Trp Gly Glu Ser Gly Glu Val Asp Leu Lys Ala Glu Leu
145                 150                 155                 160

Glu Arg Leu Ile Thr Leu Thr Ala Ser Arg Cys Leu Leu Gly Arg Glu
                165                 170                 175

Val Arg Asp Gln Leu Phe Asp Asp Val Ala Pro Leu Phe His Asp Leu
            180                 185                 190

Asp Lys Gly Met Gln Pro Ile Ser Val Ile Phe Pro Lys Leu Pro Ile
        195                 200                 205

Pro Ala His Asn Cys Arg Asp Arg Ala Arg Gly Lys Ile Ala Lys Ile
    210                 215                 220

Phe Ser Asn Ile Ile Ala Thr Arg Lys Arg Ser Gly Asp Lys Ser Glu
225                 230                 235                 240

Asn Asp Met Leu Gln Cys Phe Ile Asp Ser Lys Tyr Lys Asp Gly Arg
                245                 250                 255

Glu Thr Thr Glu Ser Glu Val Thr Gly Leu Leu Ile Ala Gly Leu Phe
            260                 265                 270

Ala Gly Gln His Thr Ser Ser Ile Thr Ala Thr Trp Thr Gly Ala Tyr
        275                 280                 285

Leu Ile Gln Asn Lys His Trp Trp Ser Ala Ala Leu Asp Glu Gln Lys
    290                 295                 300

Lys Leu Ile Gly Lys His Gly Asp Lys Ile Asp Tyr Asp Val Leu Ser
305                 310                 315                 320

Glu Met Asp Phe Leu Phe Arg Ser Ala Lys Glu Ala Leu Arg Leu His
                325                 330                 335

Pro Pro Lys Ile Leu Leu Leu Arg Thr Val His Ser Asp Phe Thr Val
            340                 345                 350

Thr Thr Arg Glu Gly Lys Gln Tyr Glu Ile Pro Lys Gly His Ile Val
```

```
              355                 360                 365
Ala Thr Ser Pro Ala Phe Ala Asn Arg Leu Pro His Val Tyr Lys Asp
    370                 375                 380

Pro Glu Asn Phe Asp Pro Asp Arg Phe Ser Lys Glu Arg Glu Glu Asp
385                 390                 395                 400

Lys Ala Ala Gly Ser Cys Ser Tyr Ile Ser Leu Gly Ala Gly Arg His
                405                 410                 415

Glu Cys Pro Gly Gly Ser Phe Ala Phe Leu Gln Ile Lys Ala Val Trp
                420                 425                 430

Cys His Leu Leu Arg Asn Phe Glu Leu Glu Leu Val Ser Pro Phe Pro
            435                 440                 445

Glu Ile Asn Trp Asn Ala Leu Val Val Gly Ala Lys Gly Asn Val Met
    450                 455                 460

Val Arg Tyr Lys Arg Arg Pro Phe Ser
465                 470
```

<210> SEQ ID NO 14
<211> LENGTH: 523
<212> TYPE: DNA
<213> ORGANISM: Arabidopsis thaliana

<400> SEQUENCE: 14

```
gacactatag aagagctatg acgtcgcatg cacgcgtacg taagctcgga attcggctcg    60
agcttgttca caaaaagatt acttttctta ttggtcctga agtctctgct catttttca   120
aagcttctga atctgatctt agtcagcagg aagtgtatca gttcaatgtc cctacttttg   180
gtcctggagt tgttttcgat gttgattatt ctgtttcgtc aggagcagtt cggttcttca   240
ctgaggcact tagagttaac aagttgaagg gttatgtgga tatgatggtt actgaagctg   300
aggattactt ctctaaatgg ggagagagtg gtgaagttga tattaaggtt gagctagaga   360
ggctcatcat cttgactgca agtgatgttt actgggtcga aagttcgtg atcagctttt   420
tgatgatgtc tctgctttgt tccatgacct tgacaatgga atgcttccca tcagtgcttc   480
ccatcagtgt tctcttccca tatctcccaa ttccagctca ccg                    523
```

<210> SEQ ID NO 15
<211> LENGTH: 87
<212> TYPE: PRT
<213> ORGANISM: Arabidopsis thaliana

<400> SEQUENCE: 15

```
His Tyr Arg Arg Ala Met Thr Ser His Ala Arg Val Arg Lys Leu Gly
1               5                   10                  15

Ile Arg Leu Glu Leu Val His Lys Lys Ile Thr Phe Leu Ile Gly Pro
            20                  25                  30

Glu Val Ser Ala His Phe Phe Lys Ala Ser Glu Ser Asp Leu Ser Gln
        35                  40                  45

Gln Glu Val Tyr Gln Phe Asn Val Pro Thr Phe Gly Pro Gly Val Val
    50                  55                  60

Phe Asp Val Asp Tyr Ser Val Arg Gln Glu Gln Phe Gly Ser Ser Leu
65                  70                  75                  80

Arg His Leu Glu Leu Thr Ser
                85
```

<210> SEQ ID NO 16
<211> LENGTH: 1852
<212> TYPE: DNA

<213> ORGANISM: Arabidopsis thaliana

<400> SEQUENCE: 16

```
tcgaccccgc gtccgcggac gcgtgggatc agcttcaagc ttaagagagc ttcgaaagcg      60
aaagcgacga tttcttctcc atcgtgagag caaatctcca gagccgtttt ctcttcttct     120
tcttcctcct cgcgccgtct ctgaaactcc atcatcgtat caatcaaatt gcttcctcct     180
ccaaattgaa aacaatgga attggattcg agaacaaat tgttgaagac gggtttggtt       240
atagtggcga cacttgttat agccaaactc atcttctctt tcttcacttc tgattctaag     300
aagaagcgtc ttcctcctac tcttaaagct tggcctccat tggttggaag tcttatcaaa     360
ttcttgaaag gacctattat tatgcttaga gaggaatacc ctaagcttgg aagtgtgttt     420
actgttaatc ttgttcacaa aaagattact tttcttattg gtcctgaagt ctctgctcat     480
ttttcaaag cttctgaatc tgatcttagt cagcaggaag tgtatcagtt caatgtccct      540
actttggtc ctggagttgt tttcgatgtt gattattctg ttcgtcagga gcagtttcgg      600
ttcttcactg aggcacttag agttaacaag ttgaagggtt atgtggatat gatggttact     660
gaagctgagg attacttctc taaatgggga gagagtggtg aagttgatat taaggttgag    720
ctagagaggc tcatcatctt gactgcaagt agatgtttac tgggtcgaga agttcgtgat     780
cagcttttg atgatgtctc tgctttgttc catgaccttg acaatggaat gcttcccatc      840
agtgttctct tcccatatct cccaattcca gctcaccgcc gtcgtgaccg tgcccgagaa     900
aagctttcgg agattttcgc aaaaatcatt gggtcgagaa aacgctctgg aaaaacagag    960
aacgacatgc tgcagtgttt catcgaatca agtacaaag atggtagaca gacaaccgaa    1020
tctgaagtca ctggttttgct cattgctgct ctgtttgcag acaacacac gagctctatc   1080
acttccacct ggaccggtgc ttatctgatg cgatacaaag agtacttctc agctgctctt    1140
gatgagcaga gaacctgat tgcgaaacat ggagacaaga tcgatcatga tatcttatcc    1200
gagatggatg ttctctaccg ctgcattaag gaagcgttga ggcttcaccc tccactcatc    1260
atgttaatga gagcctcgca cagtgatttc agcgtgacag ctcgggatgg aaaaacttac   1320
gatatcccaa agggtcacat cgttgcaacc tcccctgcat tgccaaccg cttaccgcac    1380
atcttcaaag ccccgacac ctacgaccca gaaagattct ccctggaag agaagaggac    1440
aaagccgcag gggcattctc gtacattgca ttcggagggg aaggcacgg gtgccttgga    1500
gagccgtttg cttacctgca gatcaaagcc atatggagtc atttgttgag gaacttcgag    1560
cttgagctag tttcaccgtt ccctgagatt gactggaacg ctatggtggt tggagttaaa    1620
ggcaatgtga tggtgcgtta caagaggcgc cagcttctcttt aaagacaagt ttaaggttat   1680
tgcagctttg gatttttctc tctggttttct gctttgcttt tgtccctctc tggttttagt    1740
tttgttgttg aataattctt ctgtttttat aaactgttgt tactctttaa ttgacattta    1800
tttttaagct tccctaagttt gtggttcaaa aaaaaaaaaa ggcggcgtta ct            1852
```

<210> SEQ ID NO 17
<211> LENGTH: 488
<212> TYPE: PRT
<213> ORGANISM: Arabidopsis thaliana

<400> SEQUENCE: 17

Met Glu Leu Asp Ser Glu Asn Lys Leu Leu Lys Thr Gly Leu Val Ile
1               5                   10                  15

Val Ala Thr Leu Val Ile Ala Lys Leu Ile Phe Ser Phe Phe Thr Ser
            20                  25                  30

```
Asp Ser Lys Lys Arg Leu Pro Pro Thr Leu Lys Ala Trp Pro Pro
     35                  40                  45

Leu Val Gly Ser Leu Ile Lys Phe Leu Lys Gly Pro Ile Ile Met Leu
     50                  55                  60

Arg Glu Glu Tyr Pro Lys Leu Gly Ser Val Phe Thr Val Asn Leu Val
65                  70                  75                  80

His Lys Lys Ile Thr Phe Leu Ile Gly Pro Glu Val Ser Ala His Phe
                 85                  90                  95

Phe Lys Ala Ser Glu Ser Asp Leu Ser Gln Gln Glu Val Tyr Gln Phe
             100                 105                 110

Asn Val Pro Thr Phe Gly Pro Gly Val Val Phe Asp Val Asp Tyr Ser
             115                 120                 125

Val Arg Gln Glu Gln Phe Arg Phe Phe Thr Glu Ala Leu Arg Val Asn
         130                 135                 140

Lys Leu Lys Gly Tyr Val Asp Met Met Val Thr Glu Ala Glu Asp Tyr
145                 150                 155                 160

Phe Ser Lys Trp Gly Glu Ser Gly Glu Val Asp Ile Lys Val Glu Leu
                 165                 170                 175

Glu Arg Leu Ile Ile Leu Thr Ala Ser Arg Cys Leu Leu Gly Arg Glu
             180                 185                 190

Val Arg Asp Gln Leu Phe Asp Asp Val Ser Ala Leu Phe His Asp Leu
         195                 200                 205

Asp Asn Gly Met Leu Pro Ile Ser Val Leu Phe Pro Tyr Leu Pro Ile
         210                 215                 220

Pro Ala His Arg Arg Arg Asp Arg Ala Arg Glu Lys Leu Ser Glu Ile
225                 230                 235                 240

Phe Ala Lys Ile Ile Gly Ser Arg Lys Arg Ser Gly Lys Thr Glu Asn
                 245                 250                 255

Asp Met Leu Gln Cys Phe Ile Glu Ser Lys Tyr Lys Asp Gly Arg Gln
             260                 265                 270

Thr Thr Glu Ser Glu Val Thr Gly Leu Leu Ile Ala Ala Leu Phe Ala
         275                 280                 285

Gly Gln His Thr Ser Ser Ile Thr Ser Thr Trp Thr Gly Ala Tyr Leu
         290                 295                 300

Met Arg Tyr Lys Glu Tyr Phe Ser Ala Ala Leu Asp Glu Gln Lys Asn
305                 310                 315                 320

Leu Ile Ala Lys His Gly Asp Lys Ile Asp His Asp Ile Leu Ser Glu
                 325                 330                 335

Met Asp Val Leu Tyr Arg Cys Ile Lys Glu Ala Leu Arg Leu His Pro
             340                 345                 350

Pro Leu Ile Met Leu Met Arg Ala Ser His Ser Asp Phe Ser Val Thr
         355                 360                 365

Ala Arg Asp Gly Lys Thr Tyr Asp Ile Pro Lys Gly His Ile Val Ala
         370                 375                 380

Thr Ser Pro Ala Phe Ala Asn Arg Leu Pro His Ile Phe Lys Asp Pro
385                 390                 395                 400

Asp Thr Tyr Asp Pro Glu Arg Phe Ser Pro Gly Arg Glu Glu Asp Lys
                 405                 410                 415

Ala Ala Gly Ala Phe Ser Tyr Ile Ala Phe Gly Gly Arg His Gly
             420                 425                 430

Cys Leu Gly Glu Pro Phe Ala Tyr Leu Gln Ile Lys Ala Ile Trp Ser
         435                 440                 445
```

```
His Leu Leu Arg Asn Phe Glu Leu Glu Leu Val Ser Pro Phe Pro Glu
    450                 455                 460

Ile Asp Trp Asn Ala Met Val Val Gly Val Lys Gly Asn Val Met Val
465                 470                 475                 480

Arg Tyr Lys Arg Arg Gln Leu Ser
                485
```

<210> SEQ ID NO 18
<211> LENGTH: 1852
<212> TYPE: DNA
<213> ORGANISM: Arabidopsis thaliana

<400> SEQUENCE: 18

```
tcgaccccgc gtccgcggac gcgtgggatc agcttcaagc ttaagagagc ttcgaaagcg    60
aaagcgacga tttcttctcc atcgtgagag caaatctcca gagccgtttt ctcttcttct   120
tcttcctcct cgcgccgtct ctgaaactcc atcatcgtat caatcaaatt gcttcctcct   180
ccaaattgaa aaacaatgga attggattcg agaacaaat tgttgaagac gggtttggtt    240
atagtggcga cacttgttat agccaaactc atcttctctt tcttcacttc tgattctaag   300
aagaagcgtc ttcctcctac tcttaaagct tggcctccat tggttggaag tcttatcaaa   360
ttcttgaaag gacctattat tatgcttaga gaggaatacc ctaagcttgg aagtgtgttt   420
actgttaatc ttgttcacaa aaagattact tttcttattg gtcctgaagt ctctgctcat   480
tttttcaaag cttctgaatc tgatcttagt cagcaggaag tgtatcagtt caatgtccct   540
acttttggtc ctggagttgt tttcgatgtt gattattctg ttcgtcagga gcagtttcgg   600
ttcttcactg aggcacttag agttaacaag ttgaagggtt atgtggatat gatggttact   660
gaagctgagg attacttctc taaatgggga gagagtggtg aagttgatat taaggttgag   720
ctagagaggc tcatcatctt gactgcaagt agatgtttac tgggtcgaga agttcgtgat   780
cagcttttg atgatgtctc tgctttgttc catgaccttg acaatggaat gcttcccatc   840
agtgttctct tcccatatct cccaattcca gctcaccgcc gtcgtgaccg tgcccgagaa   900
aagcttttcgg agattttcgc aaaaatcatt gggtcgagaa acgctctgg aaaaacagag   960
aacgacatgc tgcagtgttt catcgaatca agtacaaag atggtagaca gacaaccgaa  1020
tctgaagtca ctggtttgct cattgctgct ctgtttgcag acaacacac gagctctatc  1080
acttccacct ggaccggtgc ttatctgatg cgatacaaag agtacttctc agctgctctt  1140
gatgagcaga gaacctgat tgcgaaacat ggagacaaga tcgatcatga tatcttatcc  1200
gagatggatg ttctctaccg ctgcattaag gaagcgttga ggcttcaccc tccactcatc  1260
atgttaatga gagcctcgca cagtgatttc agcgtgacag ctcgggatgg aaaaacttac  1320
gatatcccaa agggtcacat cgttgcaacc tcccctgcat tgccaaccg cttaccgcac  1380
atcttcaaag accccgacac ctacgaccca gaaagattct cccctggaag agaagaggac  1440
aaagccgcag gggcattctc gtacattgca ttcggagggg aaggcacgg gtgccttgga  1500
gagccgtttg cttacctgca gatcaaagcc atatggagtc atttgttgag gaacttcgag  1560
cttgagctag tttcaccgtt ccctgagatt gactggaacg ctatggtggt tggagttaaa  1620
ggcaatgtga tggtgcgtta caagaggcgc cagctttctt aaagacaagt ttaaggttat  1680
tgcagctttg gattttctc tctggtttct gctttgcttt tgtccctctc tggttttagt  1740
tttgttgttg aataattctt ctgttttat aaactgttgt tactctttaa ttgacattta  1800
tttttaagct tcctaagttt gtggttcaaa aaaaaaaaaa ggcggcgtta ct          1852
```

```
<210> SEQ ID NO 19
<211> LENGTH: 488
<212> TYPE: PRT
<213> ORGANISM: Arabidopsis thaliana

<400> SEQUENCE: 19

Met Glu Leu Asp Ser Glu Asn Lys Leu Leu Lys Thr Gly Leu Val Ile
1               5                   10                  15

Val Ala Thr Leu Val Ile Ala Lys Leu Ile Phe Ser Phe Phe Thr Ser
                20                  25                  30

Asp Ser Lys Lys Arg Leu Pro Pro Thr Leu Lys Ala Trp Pro Pro
            35                  40                  45

Leu Val Gly Ser Leu Ile Lys Phe Leu Lys Gly Pro Ile Ile Met Leu
        50                  55                  60

Arg Glu Glu Tyr Pro Lys Leu Gly Ser Val Phe Thr Val Asn Leu Val
65                  70                  75                  80

His Lys Lys Ile Thr Phe Leu Ile Gly Pro Glu Val Ser Ala His Phe
                85                  90                  95

Phe Lys Ala Ser Glu Ser Asp Leu Ser Gln Gln Glu Val Tyr Gln Phe
            100                 105                 110

Asn Val Pro Thr Phe Gly Pro Gly Val Val Phe Asp Val Asp Tyr Ser
        115                 120                 125

Val Arg Gln Glu Gln Phe Arg Phe Phe Thr Glu Ala Leu Arg Val Asn
    130                 135                 140

Lys Leu Lys Gly Tyr Val Asp Met Met Val Thr Glu Ala Glu Asp Tyr
145                 150                 155                 160

Phe Ser Lys Trp Gly Glu Ser Gly Glu Val Asp Ile Lys Val Glu Leu
                165                 170                 175

Glu Arg Leu Ile Ile Leu Thr Ala Ser Arg Cys Leu Leu Gly Arg Glu
            180                 185                 190

Val Arg Asp Gln Leu Phe Asp Asp Val Ser Ala Leu Phe His Asp Leu
        195                 200                 205

Asp Asn Gly Met Leu Pro Ile Ser Val Leu Phe Pro Tyr Leu Pro Ile
    210                 215                 220

Pro Ala His Arg Arg Asp Arg Ala Arg Glu Lys Leu Ser Glu Ile
225                 230                 235                 240

Phe Ala Lys Ile Ile Gly Ser Arg Lys Arg Ser Gly Lys Thr Glu Asn
                245                 250                 255

Asp Met Leu Gln Cys Phe Ile Glu Ser Lys Tyr Lys Asp Gly Arg Gln
            260                 265                 270

Thr Thr Glu Ser Glu Val Thr Gly Leu Leu Ile Ala Ala Leu Phe Ala
        275                 280                 285

Gly Gln His Thr Ser Ser Ile Thr Ser Thr Trp Thr Gly Ala Tyr Leu
    290                 295                 300

Met Arg Tyr Lys Glu Tyr Phe Ser Ala Ala Leu Asp Glu Gln Lys Asn
305                 310                 315                 320

Leu Ile Ala Lys His Gly Asp Lys Ile Asp His Asp Ile Leu Ser Glu
                325                 330                 335

Met Asp Val Leu Tyr Arg Cys Ile Lys Glu Ala Leu Arg Leu His Pro
            340                 345                 350

Pro Leu Ile Met Leu Met Arg Ala Ser His Ser Asp Phe Ser Val Thr
        355                 360                 365

Ala Arg Asp Gly Lys Thr Tyr Asp Ile Pro Lys Gly His Ile Val Ala
    370                 375                 380
```

```
Thr Ser Pro Ala Phe Ala Asn Arg Leu Pro His Ile Phe Lys Asp Pro
385                 390                 395                 400

Asp Thr Tyr Asp Pro Glu Arg Phe Ser Pro Gly Arg Glu Glu Asp Lys
            405                 410                 415

Ala Ala Gly Ala Phe Ser Tyr Ile Ala Phe Gly Gly Arg His Gly
        420                 425                 430

Cys Leu Gly Glu Pro Phe Ala Tyr Leu Gln Ile Lys Ala Ile Trp Ser
        435                 440                 445

His Leu Leu Arg Asn Phe Glu Leu Glu Leu Val Ser Pro Phe Pro Glu
        450                 455                 460

Ile Asp Trp Asn Ala Met Val Val Gly Val Lys Gly Asn Val Met Val
465                 470                 475                 480

Arg Tyr Lys Arg Arg Gln Leu Ser
            485
```

```
<210> SEQ ID NO 20
<211> LENGTH: 1249
<212> TYPE: DNA
<213> ORGANISM: Arabidopsis thaliana

<400> SEQUENCE: 20
ctttctccct gtgaaaaaat ggactcggtg gctctctact gcaccgctgg tctcattgcc     60
ggcgccgtct actggttcat atgcgtccta ggtccagcag aacgaaaagg caaacgagcc    120
tctgatctct ccggcggctc aatctccgca gaaaaagtca agacaacta taaccaatac     180
tggtctttct ccgcaaaacc aaaagagatc gaatcagccg agaaagtacc tgacttcgtc    240
gacacgttct acaatcttgt cactgatacc tacgagtggg gatggggaca atctttccat    300
ttctctcctc atgtccctgg aaaatccgac aaagacgcca caagaatcca cgaagaaatg    360
gccgtcgatc tcatcaaagt gaaaccggga caaaagattc ttgacgctgg ttgcggcgtg    420
ggtgggccga tgagagccat cgcggcccat tccaaggccc aagtcactgg aatcactatc    480
aacgagtacc aagtgcaacg agccaagctt cacaacaaga agctggact  tgattctctc    540
tgcaacgtcg tttgtggtaa cttttaaag  atgccgttcg atgaaaacac gtttgacgga    600
gcttactcga tcgaagctac gtgtcacgct cctaagctcg aagaagtata ctcggagatc    660
ttcagagtga tgaaaccagg atctttgttc gtgtcctacg aatgggtcac cactgaaaaa    720
tacagagacg atgacgaaga acacaaggac gtgattcaag gatcgagag aggagacgca     780
cttcctggac taagaagcta cgctgatata gccgtgacgg cgaagaaagt tgggtttgag    840
gtagtgaagg agaaagattt ggctaaacca ccgtctaaac cgtggtggaa ccggttaaag    900
atgggaagga ttgcttattg gagaaaccat gttgtggttg tgattctttc tgctattggg    960
gttgctccta aggaactgt tgatgttcat aagatgttgt ttaagactgc tgattatttg    1020
accagaggtg gtgagactgg aatcttctct ccgatgcata tgattctctg tagaaaacca   1080
gagaaagctt ctgaatgaat gattgagaat acttcttcct tgttctcgtt ttcttcttct   1140
ttctttctaa gttcatgttt ttccccttaa gaatctcttt gtccgtcgta ttaatgttat   1200
cactttgttg tttattgtat ttttttttt caatttgcta aattactcc               1249

<210> SEQ ID NO 21
<211> LENGTH: 1444
<212> TYPE: DNA
<213> ORGANISM: Nicotiana tabacum

<400> SEQUENCE: 21
```

```
gcacgagtac tctttcccat ttctctcttg aaaggtgaaa ggttctctcc aagaatacag      60
agatcctttc tctacataga ttttgtgtat atcttgtgat ttgggaaaga aatgtcaaaa     120
caagggctt ttgatctggc atctgggtt ggtggcaaaa ttaacaagga ggaagttctc      180
tctgctgttg acaagtatga gaagtaccat ggttattatg gaggtgaaga agaagagaga     240
aagaataact atactgacat ggttaacaaa tactatgatc tttgcactag cttctacgaa     300
tacggctggg gagagtcatt ccattttgca cccaggtgga aaggagaatc actccaagag     360
agcattaaaa ggcatgagca ctttcttgcc ttgcaactgg gattgaaacc aggacaaaag     420
gtcttggacg taggatgtgg aattggtggg ccgttaagag aaattgctcg attcagctct     480
acatcagtta caggcctcaa caataatgaa atcagatat ctaggggaca ggtgttgaac      540
cgcaaagtag gattggatca gacttgcaac tttgtaaagg gtgatttcat gaaaatgcca     600
ttccctgaca atagctttga tgcagtgtac gcaatagaag ctacctgcca tgcaccagat     660
ccattgggat gctataaaga gatttaccgg gtgctgaagc ctggtcaatg tttcgctgtg     720
tatgagtggt gcatgaccga ttcttacaac cccaataacg aagagcacaa caggatcaag     780
gccgaaattg agctcggaaa tggcctccct gaggttagat tgacaacaca gtgcctcgaa     840
gcagccaaac aagctggttt tgaagttgta tgggacaagg atctggctga tgactcacct     900
gttccatggt acttgccttt ggatacgagt cacttctcgc tcagtagctt ccgcctaaca     960
gcagttggca acttttcac cagaaatctg gtttcggcgc ttgaatacgt gggacttgct     1020
cctaaaggta gtcaaagggt tcaagctttc ttagagaaag ctgcagaagg tcttgtcggt     1080
ggtgccaaga aagggatttt cacaccaatg tacttcttcg tggttcgcaa gcccatttca     1140
gactctcagt aatatggagt ttagtcactt agcttttgc tttagctagc aaatctgtaa      1200
gattcttcgc acagaacttt acacattgaa tatgaccgcc ctaattaagg tgactacagt     1260
ttttggaggg cgttgtgggt ggagggtttc tttttctgtg ttgcttgtct ggcacaattt     1320
gatttcatgt cttgctattt ttgccattga tgtccttgtt ctaagatata tacctattga     1380
caagctcata aaggtgggca tttgctaata tatggtgttt caggtaaaaa aaaaaaaaaa     1440
aaaa                                                                 1444

<210> SEQ ID NO 22
<211> LENGTH: 1421
<212> TYPE: DNA
<213> ORGANISM: Arabidopsis thaliana

<400> SEQUENCE: 22
ctctctctct ctctctcttg gtcttcctca ctcttaacga aaatggactc tttaacactc      60
ttcttcaccg gtgcactcgt cgccgtcggt atctactggt tcctctgcgt tctcggtcca     120
gcagagcgta aagcaaacg agccgtagat ctctctggtg gctcaatctc cgccgagaaa     180
gtccaagaca actacaaaca gtactggtct ttcttccgcc gtccaaaaga aatcgaaacc     240
gccgagaaag ttccagactt cgtcgacaca ttctacaatc tcgtcaccga catatacgag     300
tggggatggg gacaatcctt ccacttctca ccatcaatcc ccggaaaatc tcacaaagac     360
gccacgcgcc tccacgaaga gatggcggta gatctgatcc aagtcaaacc tggtcaaaag     420
atcctagacg tcggatgcgg tgtcggcggt ccgatgcgag cgattgcatc tcactcgcga     480
gctaacgtag tcgggattac aataaacgag tatcaggtga acagagctcg tctccacaat     540
aagaaagctg gtctcgacgc gctttgcgag gtcgtgtgtg gtaacttcct ccagatgccg     600
```

-continued

| | | |
|---|---|---|
| ttcgatgaca acagtttcga cggagcttat tccatcgaag ccacgtgtca cgcgccgaag | 660 | |
| ctggaagaag tgtacgcaga gatctacagg gtgttgaaac ccggatctat gtatgtgtcg | 720 | |
| tacgagtggg ttacgacgga gaaatttaag gcggaggatg acgaacacgt ggaggtaatc | 780 | |
| caagggattg agagaggcga tgcgttacca gggcttaggg cttacgtgga tatagctgag | 840 | |
| acggctaaaa aggttggggtt tgagatagtg aaggagaagg atctggcgag tccaccggct | 900 | |
| gagccgtggt ggactaggct taagatgggt aggcttgctt attggaggaa tcacattgtg | 960 | |
| gttcagattt tgtcagcggt tggagttgct cctaaaggaa ctgttgatgt tcatgagatg | 1020 | |
| ttgtttaaga ctgctgattg tttgaccaga ggaggtgaaa ccggaatatt ctctccgatg | 1080 | |
| catatgattc tctgcagaaa accggagtca ccggaggaga gttcttgaga aggtagaaa | 1140 | |
| ggaaacatca ccgaaaaaag tatggagaat tttctcaatt tgtttttatt tttaagttaa | 1200 | |
| atcaacttgg ttattgtact attttttgtgt tttaatttgg tttgtgtttc aagaattatt | 1260 | |
| agttttttt tgttttgttg catatgagaa tcttactctt gatttctccg ccgtagagcc | 1320 | |
| ggcgagacat aggggattat tagtattttt aagtgtgttt aagattgatt aacaagttag | 1380 | |
| taaaataaaa tgtacttagg tgtcgaaaaa aaaaggaatt c | 1421 | |

<210> SEQ ID NO 23
<211> LENGTH: 1175
<212> TYPE: DNA
<213> ORGANISM: Arabidopsis thaliana

<400> SEQUENCE: 23

| | | |
|---|---|---|
| cagtgtgagt aatttagcat tactactgtt gacttgttca ataaaggtaa agtaagatca | 60 | |
| atccggcgca atcttctttc gttttccggc accgatctcg gtggatctcc gattcacatg | 120 | |
| gcggcggata atgcttatct gatgcagttt gttgacgaaa cctctttta caaccgaatc | 180 | |
| gttctgagtc atcttttgcc ggcgaatcta tgggaaccct tacctcattt tctccagaca | 240 | |
| tggctccgaa attacctcgc cggaaaccct ctatacatca tctccggttt cctctggtgc | 300 | |
| ttctacatct attaccgtaa atcaacgtt taccttccca agatgcaat tcctacaata | 360 | |
| aaggctatgc gtttgcaaat gtttgtggca atgaaggcta tgccatggta cactcttctt | 420 | |
| ccaactgtct ccgagagtat gattgaacgt ggttggacca atgttttgc tagcataggc | 480 | |
| gaattcggtt ggattctgta ttttgtttac atcgccatct atcttgtttt cgttgagttt | 540 | |
| ggtatttatt ggatgcacag agagcttcat gacattaagc ctctctataa gtatctccat | 600 | |
| gccacccatc atatctacaa caagcagaat acactctctc catttgccgg gcttgcattt | 660 | |
| cacccagtag acgggatact tcaggctgta ccgcatgtga tagcgctgtt tatagtgcca | 720 | |
| attcatttca caactcatat aggtcttttg ttcatggaag cgatatgggc ggcgaacatc | 780 | |
| catgactgca tccatggcaa catctggcca gtaatgggtg caggatacca tacgatacac | 840 | |
| cacacgacat acaagcataa ctatggtcat tataccatat ggatggattg gatgtttggc | 900 | |
| tctcttaggg atcctctctt agaagaagat gacaacaaag acagcttcaa gaaagcagag | 960 | |
| tgaggatgcc cacttggggg ttgttcttct gtgttgtctt gtgttgttgt tgtccaaagt | 1020 | |
| ttcagccttt cttgttcttt ttcttcttct tcttattcat gtgtctctct caacctttcc | 1080 | |
| aattatattg ttcaaacat ttgctgtcta gtttaaaaca tgtaaatgtt tgatgatctt | 1140 | |
| tccccaaaaa aaaaaaaact aaattactca cactg | 1175 | |

<210> SEQ ID NO 24
<211> LENGTH: 1431

<212> TYPE: DNA
<213> ORGANISM: Hevea brasiliensis

<400> SEQUENCE: 24

```
atggcacgcg cctcccatga cgtgtgggac ctcgaagata cggatcccaa ctacctcatc      60
gatgaagatc accgtctcgt tacttgccct cccgctaata tatctactaa gactaccatt     120
attgccgcac ctaccaaatt gcctacctcg gaacccttaa ttgcacccct tagtctcgga     180 
ggaagacgaa atgatcgtca actccgtcgt gatgggaaga tacctcctta ttctctggag     240
tcgaagctcg gggactgcaa acgagcggct gcgattcgac gcgaggcttt gcagaggatg     300
acaaggaggt cgctggaagg cttgccagta gaagggttcg attacgagtc gattttagga     360
caatgctgtg aaatgccagt gggatacgtg cagattccgg tggggattgc ggggccgttg     420
ttgctgaacg ggcgggagta ctctgttcca atggcgacca cggagggttg tttggtggcg     480
agcactaata gagggtgtaa ggcgatttac ttgtcaggtg gggccaccag cgtcttgttg     540
aaggatggca tgacaagagc gcctgttgta agattcgcgt cggcgactag agccgcggag     600
ttgaagttct tcttggagga tcctgacaat tttgatacct tggccgtagt ttttaacaag     660
tccagtagat ttgcgaggct ccaaggcatt aaatgctcaa ttgctggtaa gaatctttat     720
ataagattca gctgcagcac tggcgatgca atggggatga acatggtttc taaagggggtt     780
caaaacgttc ttgaatttct tcaaagtgat ttttctgata tggatgtcat tggaatctca     840
ggaaatttt gttcggataa gaagcctgct gctgtaaatt ggattgaagg acgtggcaaa     900
tcagttgttt gtgaggcaat tatcaaggaa gaggtggtga agaaggtgtt gaaaaccaat     960
gtggcctccc tagtggagct taacatgctc aagaatcttg ctggttctgc tgttgctggt    1020
gctttgggtg gatttaatgc ccatgcaggc aacatcgtat ctgcaatctt tattgccact    1080
ggccaggatc cagcacagaa tgttgagagt tctcattgca ttaccatgat ggaagctgtc    1140
aatgatggaa aggatctcca tatctctgtg accatgccct ccattgaggt gggtacagtc    1200
ggaggtggaa ctcaacttgc atctcagtct gcttgtctca atttgcttgg ggtgaagggt    1260
gcaaacaaag agtcgccagg atcaaactca aggctccttg ctgccatcgt agctggttca    1320
gttttggctg gtgagctctc cttgatgtct gccattgcag ctgggcagct tgtcaagagt    1380
cacatgaagt acaacagagc cagcaaagat atgtctaaag ctgcatctta g            1431
```

<210> SEQ ID NO 25
<211> LENGTH: 476
<212> TYPE: PRT
<213> ORGANISM: Hevea brasiliensis

<400> SEQUENCE: 25

```
Met Ala Arg Ala Ser His Asp Val Trp Asp Leu Glu Asp Thr Asp Pro
1               5                   10                  15

Asn Tyr Leu Ile Asp Glu Asp His Arg Leu Val Thr Cys Pro Pro Ala
            20                  25                  30

Asn Ile Ser Thr Lys Thr Thr Ile Ile Ala Ala Pro Thr Lys Leu Pro
        35                  40                  45

Thr Ser Glu Pro Leu Ile Ala Pro Leu Val Ser Glu Asp Glu Met
    50                  55                  60

Ile Val Asn Ser Val Val Asp Gly Lys Ile Pro Ser Tyr Ser Leu Glu
65                  70                  75                  80

Ser Lys Leu Gly Asp Cys Lys Arg Ala Ala Ala Ile Arg Arg Glu Ala
                85                  90                  95
```

Leu Gln Arg Met Thr Arg Arg Ser Leu Glu Gly Leu Pro Val Glu Gly
            100                 105                 110

Phe Asp Tyr Glu Ser Ile Leu Gly Gln Cys Cys Glu Met Pro Val Gly
            115                 120                 125

Tyr Val Gln Ile Pro Val Gly Ile Ala Gly Pro Leu Leu Leu Asn Gly
130                 135                 140

Arg Glu Tyr Ser Val Pro Met Ala Thr Thr Glu Gly Cys Leu Val Ala
145                 150                 155                 160

Ser Thr Asn Arg Gly Cys Lys Ala Ile Tyr Leu Ser Gly Gly Ala Thr
                165                 170                 175

Ser Val Leu Leu Lys Asp Gly Met Thr Arg Ala Pro Val Val Arg Phe
                180                 185                 190

Ala Ser Ala Thr Arg Ala Ala Glu Leu Lys Phe Phe Leu Glu Asp Pro
            195                 200                 205

Asp Asn Phe Asp Thr Leu Ala Val Val Phe Asn Lys Ser Ser Arg Phe
210                 215                 220

Ala Arg Leu Gln Gly Ile Lys Cys Ser Ile Ala Gly Lys Asn Leu Tyr
225                 230                 235                 240

Ile Arg Phe Ser Cys Ser Thr Gly Asp Ala Met Gly Met Asn Met Val
                245                 250                 255

Ser Lys Gly Val Gln Asn Val Leu Glu Phe Leu Gln Ser Asp Phe Ser
                260                 265                 270

Asp Met Asp Val Ile Gly Ile Ser Gly Asn Phe Cys Ser Asp Lys Lys
            275                 280                 285

Pro Ala Ala Val Asn Trp Ile Glu Gly Arg Gly Lys Ser Val Val Cys
            290                 295                 300

Glu Ala Ile Ile Lys Glu Val Val Lys Val Leu Lys Thr Asn
305                 310                 315                 320

Val Ala Ser Leu Val Glu Leu Asn Met Leu Lys Asn Leu Ala Gly Ser
                325                 330                 335

Ala Val Ala Gly Ala Leu Gly Gly Phe Asn Ala His Ala Gly Asn Ile
            340                 345                 350

Val Ser Ala Ile Phe Ile Ala Thr Gly Gln Asp Pro Ala Gln Asn Val
            355                 360                 365

Glu Ser Ser His Cys Ile Thr Met Met Glu Ala Val Asn Asp Gly Lys
370                 375                 380

Asp Leu His Ile Ser Val Thr Met Pro Ser Ile Glu Val Gly Thr Val
385                 390                 395                 400

Gly Gly Gly Thr Gln Leu Ala Ser Gln Ser Ala Cys Leu Asn Leu Leu
                405                 410                 415

Gly Val Lys Gly Ala Asn Lys Glu Ser Pro Gly Ser Asn Ser Arg Leu
                420                 425                 430

Leu Ala Ala Ile Val Ala Gly Ser Val Leu Ala Gly Glu Leu Ser Leu
            435                 440                 445

Met Ser Ala Ile Ala Ala Gly Gln Leu Val Lys Ser His Met Lys Tyr
450                 455                 460

Asn Arg Ala Ser Lys Asp Met Ser Lys Ala Ala Ser
465                 470                 475

<210> SEQ ID NO 26
<211> LENGTH: 1431
<212> TYPE: DNA
<213> ORGANISM: Hevea brasiliensis

<400> SEQUENCE: 26

```
atggcacgcg cctcccatga cgtgtgggac ctcgaagata cggatcccaa ctacctcatc      60
gatgaagatc accgtctcgt tacttgccct cccgctaata tatctactaa gactaccatt     120
attgccgcac ctaccaaatt gcctacctcg gaacccttaa ttgcacccct agtctcggag     180
gaagacgaaa tgatcgtcaa ctccgtcgtg gatgggaaga taccctccta ttctctggag     240
tcgaagctcg gggactgcaa acgagcggct gcgattcgac gcgaggcttt gcagaggatg     300
acaaggaggt cgctggaagg cttgccagta gaagggttcg attacgagtc gattttagga     360
caatgctgtg aaatgccagt gggatacgtg cagattccgg tggggattgc ggggccgttg     420
ttgctgaacg ggcgggagta ctctgttcca atggcgacca cggagggttg tttggtggcg     480
agcactaata gagggtgtaa ggcgatttac ttgtcaggtg gggccaccag cgtcttgttg     540
aaggatggca tgacaagagc gcctgttgta agattcgcgt cggcgactag agccgcggag     600
ttgaagttct tcttggagga tcctgacaat tttgatacct tggccgtagt ttttaacaag     660
tccagtagat ttgcgaggct ccaaggcatt aaatgctcaa ttgctggtaa gaatctttat     720
ataagattca gctgcagcac tggcgatgca atggggatga acatggtttc taaaggggtt     780
caaaacgttc ttgaatttct tcaaagtgat ttttctgata tggatgtcat tggaatctca     840
ggaaattttt gttcggataa gaagcctgct gctgtaaatt ggattgaagg acgtggcaaa     900
tcagttgttt gtgaggcaat tatcaaggaa gaggtggtga agaaggtgtt gaaaaccaat     960
gtggcctccc tagtggagct taacatgctc aagaatcttg ctggttctgc tgttgctggt    1020
gctttgggtg gatttaatgc ccatgcaggc aacatcgtat ctgcaatctt tattgccact    1080
ggccaggatc cagcacagaa tgttgagagt tctcattgca ttaccatgat ggaagctgtc    1140
aatgatggaa aggatctcca tatctctgtg accatgccct ccattgaggt gggtacagtc    1200
ggaggtggaa ctcaacttgc atctcagtct gcttgtctca atttgcttgg ggtgaagggt    1260
gcaaacaaag agtcgccagg atcaaactca aggctccttg ctgccatcgt agctggttca    1320
gttttggctg gtgagctctc cttgatgtct gccattgcag ctgggcagct tgtcaagagt    1380
cacatgaagt acaacagatc cgccaaagat atgtctaaag ctgcatctta g             1431
```

<210> SEQ ID NO 27
<211> LENGTH: 476
<212> TYPE: PRT
<213> ORGANISM: Hevea brasiliensis

<400> SEQUENCE: 27

```
Met Ala Arg Ala Ser His Asp Val Trp Asp Leu Glu Asp Thr Asp Pro
 1               5                  10                  15

Asn Tyr Leu Ile Asp Glu Asp His Arg Leu Val Thr Cys Pro Pro Ala
            20                  25                  30

Asn Ile Ser Thr Lys Thr Thr Ile Ala Ala Pro Thr Lys Leu Pro
        35                  40                  45

Thr Ser Glu Pro Leu Ile Ala Pro Leu Val Ser Glu Asp Glu Met
    50                  55                  60

Ile Val Asn Ser Val Val Asp Gly Lys Ile Pro Ser Tyr Ser Leu Glu
65                  70                  75                  80

Ser Lys Leu Gly Asp Cys Lys Arg Ala Ala Ile Arg Arg Glu Ala
                85                  90                  95

Leu Gln Arg Met Thr Arg Arg Ser Leu Glu Gly Leu Pro Val Glu Gly
            100                 105                 110

Phe Asp Tyr Glu Ser Ile Leu Gly Gln Cys Cys Glu Met Pro Val Gly
```

```
                115                 120                 125
Tyr Val Gln Ile Pro Val Gly Ile Ala Gly Pro Leu Leu Leu Asn Gly
            130                 135                 140

Arg Glu Tyr Ser Val Pro Met Ala Thr Thr Glu Gly Cys Leu Val Ala
145                 150                 155                 160

Ser Thr Asn Arg Gly Cys Lys Ala Ile Tyr Leu Ser Gly Gly Ala Thr
                165                 170                 175

Ser Val Leu Leu Lys Asp Gly Met Thr Arg Ala Pro Val Val Arg Phe
            180                 185                 190

Ala Ser Ala Thr Arg Ala Ala Glu Leu Lys Phe Phe Leu Glu Asp Pro
        195                 200                 205

Asp Asn Phe Asp Thr Leu Ala Val Val Phe Asn Lys Ser Ser Arg Phe
210                 215                 220

Ala Arg Leu Gln Gly Ile Lys Cys Ser Ile Ala Gly Lys Asn Leu Tyr
225                 230                 235                 240

Ile Arg Phe Ser Cys Ser Thr Gly Asp Ala Met Gly Met Asn Met Val
                245                 250                 255

Ser Lys Gly Val Gln Asn Val Leu Glu Phe Leu Gln Ser Asp Phe Ser
            260                 265                 270

Asp Met Asp Val Ile Gly Ile Ser Gly Asn Phe Cys Ser Asp Lys Lys
        275                 280                 285

Pro Ala Ala Val Asn Trp Ile Glu Gly Arg Gly Lys Ser Val Val Cys
    290                 295                 300

Glu Ala Ile Ile Lys Glu Val Val Lys Val Leu Lys Thr Asn
305                 310                 315                 320

Val Ala Ser Leu Val Glu Leu Asn Met Leu Lys Asn Leu Ala Gly Ser
                325                 330                 335

Ala Val Ala Gly Ala Leu Gly Gly Phe Asn Ala His Ala Gly Asn Ile
            340                 345                 350

Val Ser Ala Ile Phe Ile Ala Thr Gly Gln Asp Pro Ala Gln Asn Val
        355                 360                 365

Glu Ser Ser His Cys Ile Thr Met Met Glu Ala Val Asn Asp Gly Lys
370                 375                 380

Asp Leu His Ile Ser Val Thr Met Pro Ser Ile Glu Val Gly Thr Val
385                 390                 395                 400

Gly Gly Gly Thr Gln Leu Ala Ser Gln Ser Ala Cys Leu Asn Leu Leu
                405                 410                 415

Gly Val Lys Gly Ala Asn Lys Glu Ser Pro Gly Ser Asn Ser Arg Leu
            420                 425                 430

Leu Ala Ala Ile Val Ala Gly Ser Val Leu Ala Gly Glu Leu Ser Leu
        435                 440                 445

Met Ser Ala Ile Ala Ala Gly Gln Leu Val Lys Ser His Met Lys Tyr
450                 455                 460

Asn Arg Ser Ala Lys Asp Met Ser Lys Ala Ala Ser
465                 470                 475

<210> SEQ ID NO 28
<211> LENGTH: 22
<212> TYPE: DNA
<213> ORGANISM: Artificial sequence
<220> FEATURE:
<221> NAME/KEY: misc_feature
<222> LOCATION: (1)..(22)
<223> OTHER INFORMATION: Primer

<400> SEQUENCE: 28
```

-continued

```
gagatctgaa ccctaacgag ag                                        22
```

<210> SEQ ID NO 29
<211> LENGTH: 26
<212> TYPE: DNA
<213> ORGANISM: Artificial sequence
<220> FEATURE:
<221> NAME/KEY: misc_feature
<222> LOCATION: (1)..(26)
<223> OTHER INFORMATION: Primer

<400> SEQUENCE: 29

```
ggagctctta agaaaaggga cgacgc                                    26
```

<210> SEQ ID NO 30
<211> LENGTH: 26
<212> TYPE: DNA
<213> ORGANISM: Artificial sequence
<220> FEATURE:
<221> NAME/KEY: misc_feature
<222> LOCATION: (1)..(26)
<223> OTHER INFORMATION: Primer

<400> SEQUENCE: 30

```
gtctctgaat cagaaatcct tctatc                                    26
```

<210> SEQ ID NO 31
<211> LENGTH: 25
<212> TYPE: DNA
<213> ORGANISM: Artificial sequence
<220> FEATURE:
<221> NAME/KEY: misc_feature
<222> LOCATION: (1)..(25)
<223> OTHER INFORMATION: Primer

<400> SEQUENCE: 31

```
catgtcaaat ttcactgctt catcc                                     25
```

<210> SEQ ID NO 32
<211> LENGTH: 31
<212> TYPE: DNA
<213> ORGANISM: Artificial sequence
<220> FEATURE:
<221> NAME/KEY: misc_feature
<222> LOCATION: (1)..(31)
<223> OTHER INFORMATION: Primer

<400> SEQUENCE: 32

```
gagatctcca cagatttaaa gaaccctaac g                              31
```

<210> SEQ ID NO 33
<211> LENGTH: 31
<212> TYPE: DNA
<213> ORGANISM: Artificial sequence
<220> FEATURE:
<221> NAME/KEY: misc_feature
<222> LOCATION: (1)..(31)
<223> OTHER INFORMATION: Primer

<400> SEQUENCE: 33

```
ggagctcggt ttttaagaaa agggacgacg c                              31
```